United States Patent
Riddell et al.

(10) Patent No.: US 11,046,766 B2
(45) Date of Patent: **\*Jun. 29, 2021**

(54) TAGGED CHIMERIC EFFECTOR MOLECULES AND RECEPTORS THEREOF

(71) Applicant: Fred Hutchinson Cancer Research Center, Seattle, WA (US)

(72) Inventors: Stanley R. Riddell, Sammamish, WA (US); Lingfeng Liu, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/664,706

(22) Filed: Oct. 25, 2019

(65) Prior Publication Data

US 2020/0255517 A1  Aug. 13, 2020

Related U.S. Application Data

(63) Continuation of application No. 15/106,657, filed as application No. PCT/US2014/072007 on Dec. 22, 2014, now Pat. No. 10,494,434.

(60) Provisional application No. 61/919,201, filed on Dec. 20, 2013.

(51) Int. Cl.
| | |
|---|---|
| *A61K 38/17* | (2006.01) |
| *C07K 14/705* | (2006.01) |
| *C07K 19/00* | (2006.01) |
| *C07K 16/28* | (2006.01) |
| *A61K 35/17* | (2015.01) |
| *C07K 14/725* | (2006.01) |
| *A61K 38/20* | (2006.01) |
| *A61K 35/545* | (2015.01) |
| *C12N 5/0783* | (2010.01) |
| *G01N 33/569* | (2006.01) |
| *A61K 39/00* | (2006.01) |
| *A61K 35/12* | (2015.01) |

(52) U.S. Cl.
CPC .......... *C07K 16/2803* (2013.01); *A61K 35/17* (2013.01); *A61K 35/545* (2013.01); *A61K 38/1774* (2013.01); *A61K 38/2013* (2013.01); *A61K 38/2086* (2013.01); *C07K 14/705* (2013.01); *C07K 14/7051* (2013.01); *C07K 14/70521* (2013.01); *C07K 14/70578* (2013.01); *C07K 16/2818* (2013.01); *C07K 16/2878* (2013.01); *C12N 5/0637* (2013.01); *C12N 5/0638* (2013.01); *G01N 33/56972* (2013.01); *A61K 2035/124* (2013.01); *A61K 2039/505* (2013.01); *A61K 2039/507* (2013.01); *C07K 2317/622* (2013.01); *C07K 2317/64* (2013.01); *C07K 2319/03* (2013.01); *C07K 2319/20* (2013.01); *C07K 2319/22* (2013.01); *C07K 2319/33* (2013.01); *C07K 2319/95* (2013.01); *C12N 2501/2302* (2013.01); *C12N 2510/00* (2013.01)

(58) Field of Classification Search
CPC .............. A61K 38/177; A61K 38/1774; A61K 2035/124; C07K 14/705; C07K 14/7051; C07K 14/70521; C07K 14/7058; C07K 2319/22; C12N 5/0637; C12N 5/0638

See application file for complete search history.

(56) References Cited

U.S. PATENT DOCUMENTS

| | | | |
|---|---|---|---|
| 5,283,173 A | 2/1994 | Fields et al. | |
| 5,468,614 A | 11/1995 | Fields et al. | |
| 6,291,158 B1 | 9/2001 | Winter et al. | |
| 6,291,161 B1 | 9/2001 | Lerner et al. | |
| 6,303,373 B1 | 10/2001 | Bogan et al. | |
| 6,423,498 B1 | 7/2002 | Markland et al. | |
| 6,759,243 B2 | 7/2004 | Kranz et al. | |
| 7,575,925 B2 | 8/2009 | Schmitt et al. | |
| 7,776,562 B2 | 8/2010 | Busch et al. | |
| 7,981,632 B2 | 7/2011 | Schmidt | |
| 8,119,772 B2 | 2/2012 | Yang et al. | |
| 8,361,794 B2 | 1/2013 | Jakobsen | |
| 9,233,125 B2 | 1/2016 | Davila et al. | |
| 10,494,434 B2 * | 12/2019 | Riddell ................. | A61K 35/17 |
| 2003/0083474 A1 | 5/2003 | Schmidt | |
| 2007/0065431 A1 | 3/2007 | Coia et al. | |
| 2010/0105136 A1 | 4/2010 | Carter et al. | |
| 2013/0243779 A1 | 9/2013 | Nagy et al. | |

FOREIGN PATENT DOCUMENTS

| | | |
|---|---|---|
| WO | 99/42577 A2 | 8/1999 |
| WO | 2006/072620 A1 | 7/2006 |
| WO | 2006/095164 A1 | 9/2006 |
| WO | 2007/098934 A1 | 9/2007 |
| WO | 2008/045437 A2 | 4/2008 |
| WO | 2009/040338 A1 | 4/2009 |
| WO | 2010/040073 A1 | 4/2010 |
| WO | 2011/041093 A1 | 4/2011 |
| WO | 2011/089527 A1 | 7/2011 |
| WO | 2011/147890 A1 | 12/2011 |
| WO | 2012/127464 A2 | 9/2012 |
| WO | 2013/044225 A1 | 3/2013 |

(Continued)

OTHER PUBLICATIONS

Alder et al., "Antibody responses of variable lymphocyte receptors in the lamprey," *Nature Immunology* 9(3):319-327, 2008.

(Continued)

*Primary Examiner* — Jeffrey E. Russel
(74) *Attorney, Agent, or Firm* — Seed IP Law Group LLP

(57) ABSTRACT

The present disclosure relates to tagged chimeric effector molecules and receptor molecules thereof for genetically engineering a host cell, wherein the recombinant host cell can be identified, isolated, sorted, induced to proliferate, tracked or eliminated. For example, a T cell may be recombinantly modified for use in adoptive immunotherapy.

34 Claims, 97 Drawing Sheets

Specification includes a Sequence Listing.

(56) References Cited

FOREIGN PATENT DOCUMENTS

| WO | 2013/123061 A1 | 8/2013 |
|---|---|---|
| WO | 2013/124474 A2 | 8/2013 |
| WO | 2014/190273 A1 | 11/2014 |

OTHER PUBLICATIONS

Alexeev et al., "Recombinant DNA Technology in Emerging Modalities for Melanoma Immunotherapy," Chapter 6, in Duc (ed.), *Melanoma—From Early Detection to Treatment*, IntechOpen, 2013, pp. 175-196.
Baral et al., "Experimental therapy of African trypanosomiasis with a nanobody-conjugated human trypanolytic factor," *Nat. Med.* 12(5):580-584, 2006.
Barthelemy et al., "Comprehensive Analysis of the Factors Contributing to the Stability and Solubility of Autonomous Human $V_H$ Domains," *The Journal of Biological Chemistry* 283(6):3639-3654, 2008. (17 pages).
Beavil et al., "α-Helical coiled-coil stalks in the low-affinity receptor for IgE (FcεRII/CD23) and related C-type lectins," *Proc. Natl. Acad. Sci. USA* 89:753-757, 1992.
Besser et al., "Clinical Responses in a Phase II Study Using Adoptive Transfer of Short-term Cultured Tumor Infiltration Lymphocytes in Metastatic Melanoma Patients," *Clinical Cancer Research* 16(9):2646-2655, 2010. (11 pages).
Beste et al., "Small antibody-like proteins with prescribed ligand specificities derived from the lipocalin fold," *Proc. Natl. Acad. Sci. USA* 96:1898-1903, 1999.
Binz et al., "Designing Repeat Proteins: Well-expressed, Soluble and Stable Proteins from Combinatorial Libraries of Consensus Ankyrin Repeat Proteins," *J. Mol. Biol.* 332(2):489-503, 2003.
Binz et al., "Engineering novel binding proteins from nonimmunoglobulin domains," *Nat. Biotechnol.* 23(10):1257-1268, 2005.
Binz et al., "High-affinity binders selected from designed ankyrin repeat protein libraries," *Nat. Biotechnol.* 22(5):575-582, 2004.
Boersma et al., "DARPins and other repeat protein scaffolds: advances in engineering and applications," *Current Opinion in Biotechnology* 22:849-857, 2011.
Bowdish et al., "Conserved domains of the class A scavenger receptors: evolution and function," *Immunological Reviews* 277:19-31, 2009.
Boyington et al., "Structure of CD94 Reveals a Novel C-Type Lectin Fold: Implications for the NK Cell—Associated CD94/NKG2 Receptors," *Immunity* 10:75-82, 1999.
Capon et al., "Designing CD4 immunoadhesins for AIDS therapy," *Nature* 337:525-531, 1989.
Cartellieri et al., "A Novel Ex Vivo Isolation and Expansion Procedure for Chimeric Antigen Receptor Engrafted Human T Cells," *PLoS ONE* 9(4):e93745, 2014. (12 pages).
Clark, Jr. et al., "The Histogenesis and Biologic Behavior of Primary Human Malignant Melanomas of the Skin," *Cancer Research* 29:705-726, 1969. (23 pages).
Cortajarena et al., "Designed TPR Modules as Novel Anticancer Agents," *ACS Chem. Biol.* 3(3):161-166, 2008.
Cortez-Retamozo et al., "Efficient Cancer Therapy with a Nanobody-Based Conjugate," *Cancer Research* 64:2853-2857, 2004. (6 pages).
Darcy et al., "Expression in cytotoxic T lymphocytes of a single-chain anti-carcinoembryonic antigen antibody. Redirected Fas ligand-mediated lysis of colon carcinoma," *Eur. J. Immunol.* 28:1663-1672, 1998.
Dotti et al., "Design and Development of Therapies using Chimeric Antigen Receptor-Expressing T cells," *Immunol. Rev.* 257(1):107-126, 2014. (35 pages).
Dudley et al., "Cancer Regression and Autoimmunity in Patients After Clonal Repopulation with Antitumor Lymphocytes," *Science* 298(5594):850-854, 2002. (10 pages).
Ebersbach et al., "Affilin-Novel Binding Molecules Based on Human γ-B-Crystallin, an All β-Sheet Protein," *J. Mol. Biol.* 372(1):172-185, 2007.
Engels et al., "Retroviral Vectors for High-Level Transgene Expression in T Lymphocytes," *Human Gene Therapy* 14:1155-1168, 2003. (16 pages).
English Translation of Office Action, dated Mar. 27, 2020, of Chinese Patent Application No. 201480075007.8, 19 pages.
English Translation of Pre-Appeal Examination Report, dated Feb. 14, 2020, of Japanese Patent Application No. 2016-540620, 11 pages.
Examination Report, dated Mar. 7, 2020, of Indian Patent Application No. 201617021884, 11 pages. (w/ English Translation).
Figdor et al., "C-Type Lectin Receptors on Dendritic Cells and Langerhans Cells," *Nature Reviews Immunology* 2:77-84, 2002. (9 pages).
Frecha et al., "Advances in the Field of Lentivector-based Transduction of T and B Lymphocytes for Gene Therapy," *Molecular Therapy* 18(10):1748-1757, 2010.
Genosys Biotechnologies, Inc., "Strep-tag: Production of Recombinant Proteins," Product Brochure, Jul. 1998, 32 pages.
Ghahroudi et al., "Selection and identification of single domain antibody fragments from camel heavy-chain antibodies," *FEBS Letters* 414(3):521-526, 1997.
Hackel et al., "Picomolar Affinity Fibronectin Domains Engineered Utilizing Loop Length Diversity, Recursive Mutagenesis, and Loop Shuffling," *J. Mol. Biol.* 381(5):1238-1252, 2008. (27 pages).
Hamers-Casterman et al., "Naturally occurring antibodies devoid of light chains," *Nature* 363(6428):446-448, 1993.
Herrin et al., "Structure and specificity of lamprey monoclonal antibodies," *PNAS* 105(6):2040-2045, 2008.
Hoet et al., "Generation of high-affinity human antibodies by combining donor-derived and synthetic complementarity-determining-region diversity," *Nature Biotechnology* 23(3):344-348, 2005.
Huang et al., "Scorpion-Toxin Mimics of CD4 in Complex with Human Immunodeficiency Virus gp120: Crystal Structures, Molecular Mimicry, and Neutralization Breadth," *Structure* 13(5):755-768, 2005.
Hudecek et al., "The non-signaling extracellular spacer domain of chimeric antigen receptors is decisive for in vivo antitumor activity," *Cancer Immunol. Res.* 3(2):125-135, 2015. (20 pages).
International Search Report and Written Opinion, dated Apr. 21, 2015, of International Application No. PCT/US2014/072007, 22 pages.
Janeway, Jr. et al., *Immunobiology: The Immune System in Health and Disease*, 3rd ed., Current Biology Ltd., London, UK, 1997, Chapter 3, "Structure of the Antibody Molecule and Immunoglobulin Genes," 14 pages.
Jensen et al., "Design and implementation of adoptive therapy with chimeric antigen receptor-modified T cells," *Immunol. Rev.* 257(1):127-144, 2014. (32 pages).
Jespers et al., "Aggregation-resistant domain antibodies selected on phage by heat denaturation," *Nature Biotechnology* 22(9):1161-1165, 2004.
Jolly, "Emerging Viral Vectors," Chapter 9, in Friedmann (ed.), *The Development of Human Gene Therapy*, Cold Spring Harbor Laboratory Press, Cold Spring Harbor, New York, USA, 1999, pp. 209-240.
June, "Adoptive T cell therapy for cancer in the clinic," *The Journal of Clinical Investigation* 117(6):1466-1476, 2007.
Kitchen et al., "Engineering Antigen-Specific T Cells from Genetically Modified Human Hematopoietic Stem Cells in Immunodeficient Mice," *PLoS ONE* 4(12):e8208, 2009. (9 pages).
Kowolik et al., "CD28 Costimulation Provided through a CD19-Specific Chimeric Antigen Receptor Enhances In vivo Persistence and Antitumor Efficacy of Adoptively Transferred T Cells," *Cancer Res.* 66(22):10995-11004, 2006.
Krisky et al., "Development of herpes simplex virus replication-defective multigene vectors for combination gene therapy applications," *Gene Therapy* 5(11):1517-1530, 1998.
Lake et al., "Construction and binding analysis of recombinant single-chain TCR derived from tumor-infiltrating lymphocytes and a cytotoxic T lymphocyte clone directed against MAGE-1," *International Immunology* 11(5):745-751, 1999.

(56) References Cited

OTHER PUBLICATIONS

Ledbetter et al., "CD28 Ligation in T-Cell Activation: Evidence for Two Signal Transduction Pathways," *Blood* 75(7):1531-1539, 1990. (10 pages).
Liu et al., "Design of Novel Multifunctional Chimeric Antigen Receptors (Tag/CARs) for Cancer Immunotherapy," *Molecular Therapy* 22(Supplement 1):S164, 2014. (Abstract).
Luo et al., "Development of genetically engineered CD4+ and CD8+ T cells expressing TCRs specific for a *M. tuberculosis* 38-kDa antigen," *J. Mol. Med.* 89:903-913, 2011.
Madhurantakam et al., "Structure-based optimization of designed Armadillo-repeat proteins," *Protein Science* 21:1015-1028, 2012.
Main et al., "Design of Stable α-Helical Arrays from an Idealized TPR Motif," *Structure* 11:497-508, 2003.
Martin et al., "Rational design of a CD4 mimic that inhibits HIV-1 entry and exposes cryptic neutralization epitopes," *Nat. Biotechnol.* 21(1):71-76, 2003.
Maynard et al., "High-level bacterial secretion of single-chain αβ T-cell receptors," *J. Immunol. Methods* 306(1-2):51-67, 2005.
Molloy et al., "Soluble T cell receptors: novel immunotherapies," *Curr. Opin. Pharmacol.* 5(4):438-443, 2005.
Morgan et al., "Cancer Regression in Patients After Transfer of Genetically Engineered Lymphocytes," *Science* 314(5796):126-129, 2006. (10 pages).
Nguyen et al., "Heavy-chain antibodies in *Camelidae*; a case of evolutionary innovation," *Immunogenetics* 54(1):39-47, 2002.
Nguyen et al., "The Specific Variable Domain of Camel Heavy-chain Antibodies is Encoded in the Germline," *J. Mol. Biol.* 275(3):413-418, 1998.
Nord et al., "A combinatorial library of an α-helical bacterial receptor domain," *Protein Eng.* 8(6):601-608, 1995.
Nord et al., "Binding proteins selected from combinatorial libraries of an α-helical bacterial receptor domain," *Nat. Biotechnol.* 15(8):772-777, 1997.
Nord et al., "Recombinant human factor VIII-specific affinity ligands selected from phage-displayed combinatorial libraries of protein A," *Eur. J. Biochem.* 268(15):4269-4277, 2001.
Office Action, dated Nov. 14, 2019, of Mexican Patent Application No. MX/a/2016/007927, 8 pages. (w/ English Translation).
Official Communication, dated Aug. 2, 2019, of European Patent Application No. 14830770.5, 5 pages.
Parker et al., "Antibody mimics based on human fibronectin type three domain engineered for thermostability and high-affinity binding to vascular endothelial growth factor receptor two," *Protein Eng. Des. Sel.* 18(9):435-444, 2005.
Penman et al., "The Type I and Type II Bovine Scavenger Receptors Expressed in Chinese Hamster Ovary Cells Are Trimeric Proteins with Collagenous Triple Helical Domains Comprising Noncovalently Associated Monomers and Cys83-Disulfide-Linked Dimers," *J. Biol. Chem.* 266(35):23985-23993, 1991.
Pfeifer et al., "Gene Therapy: Promises and Problems," *Annu. Rev. Genomics Hum. Genet.* 2:177-211, 2001. (37 pages).
Richards et al., "Engineered Fibronectin Type III Domain with a RGDWXE Sequence Binds with Enhanced Affinity and Specificity to Human αvβ3 Integrin," *J. Mol. Biol.* 326(5):1475-1488, 2003.
Riddell et al., "The use of anti-CD3 and anti-CD28 monoclonal antibodies to clone and expand human antigen-specific T cells," *J. Immunol. Methods* 128(2):189-201, 1990.
Rossi et al., "Genetic therapies against HIV," *Nature Biotechnology* 25(12):1444-1454, 2007.
Roux et al., "Structural analysis of the nurse shark (new) antigen receptor (NAR): Molecular convergence of NAR and unusual mammalian immunoglobulins," *Proc. Natl. Acad. Sci. USA* 95:11804-11809, 1998.
Sandberg et al., "Human T-cell lines with well-defined T-cell receptor gene rearrangements as controls for the BIOMED-2 multiplex polymerase chain reaction tubes," *Leukemia* 21(2):230-237, 2007.
Sato et al., "Genes encoding putative natural killer cell C-type lectin receptors in teleostean fishes," *Proc. Natl. Acad. Sci. USA* 100(13):7779-7784, 2003.
Scatchard, "The Attractions of Proteins for Small Molecules and Ions," *Annals of the New York Academy of Sciences* 51(4):660-672, 1949.
Schmidt et al., "Adoptive T-Cell Therapy of Melanoma: Promises and Challenges," Chapter 8, in Murph (ed.), *Melanoma in the Clinic—Diagnosis, Management and Complications of Malignancy*, InTech, Shanghai, China, 2011, pp. 115-132. (19 pages).
Schmitt et al., "Induction of T cell development and establishment of T cell competence from embryonic stem cells differentiated in vitro," *Nat. Immunol.* 5(4):410-417, 2004.
Schmitt et al., "Induction of T Cell Development from Hematopoietic Progenitor Cells by Delta-like-1 In Vitro," *Immunity* 17(6):749-756, 2002.
Schmitt et al., "T Cell Receptor Gene Therapy for Cancer," *Hum. Gene Ther.* 20(11):1240-1248, 2009.
Scholten et al., "Codon modification of T cell receptors allows enhanced functional expression in transgenic human T cells," *Clin. Immunol.* 119(2):135-145, 2006.
Schönfeld et al., "An engineered lipocalin specific for CTLA-4 reveals a combining site with structural and conformational features similar to antibodies," *Proc. Natl. Acad. Sci. USA* 106(20):8198-8203, 2009.
Shi et al., "The role of PD-1 and PD-L1 in T-cell immune suppression in patients with hematological malignancies," *Journal of Hematology & Oncology* 6:74, 2013. (6 pages).
Stemberger et al., "Novel Serial Positive Enrichment Technology Enables Clinical Multiparameter Cell Sorting," *PLoS One* 7(4):e35798, 2012. (11 pages).
Stumpp et al., "Designing Repeat Proteins: Modular Leucine-rich Repeat Protein Libraries Based on the Mammalian Ribonuclease Inhibitor Family," *J. Mol. Biol.* 332(2):471-487, 2003.
Szymczak et al., "Correction of multi-gene deficiency in vivo using a single 'self-cleaving' 2A peptide-based retroviral vector," *Nat. Biotechnol.* 22(5):589-594, 2004.
Verhoeyen et al., "Lentiviral Vector Gene Transfer into Human T Cells," *Methods Mol. Biol.* 506:97-114, 2009. (19 pages).
Vincke et al., "General Strategy to Humanize a Camelid Single-domain Antibody and Identification of a Universal Humanized Nanobody Scaffold," *J. Biol. Chem.* 284(5):3273-3284, 2009.
Vita et al., "Scorpion toxins as natural scaffolds for protein engineering," *Proc. Natl. Acad. Sci. USA* 92(14):6404-6408, 1995.
Voss et al., "Mutagenesis of a flexible loop in streptavidin leads to higher affinity for the Strep-tag II peptide and improved performance in recombinant protein purification," *Protein Engineering* 10(8):975-982, 1997.
Wälchli et al., "A Practical Approach to T-Cell Receptor Cloning and Expression," *PLoS ONE* 6(11):e27930, 2011. (11 pages).
Wang et al., "A transgene-encoded cell surface polypeptide for selection, in vivo tracking, and ablation of engineered cells," *Blood* 118(5):1255-1263, 2011. (18 pages).
Weidle et al., "The Emerging Role of New Protein Scaffold-based Agents for Treatment of Cancer," *Cancer Genomics & Proteomics* 10(4):155-168, 2013.
Weisel et al., "A Model for Fibrinogen: Domains and Sequence," *Science* 230(4732):1388-1390, 1985. (4 pages).
Yam et al., "Design of HIV Vectors for Efficient Gene Delivery into Human Hematopoietic Cells," *Molecular Therapy* 5(4):479-484, 2002.
Yang et al., "Therapeutic Potential and Challenges of Targeting Receptor Tyrosine Kinase ROR1 with Monoclonal Antibodies in B-Cell Malignancies," *PLoS One* 6(6):e21018, 2011. (15 pages).
Yu et al., "Targeting Strategies for Multifunctional Nanoparticles in Cancer Imaging and Therapy," *Theranostics* 2(1):3-44, 2012.
Zelensky et al., "The C-type lectin-like domain superfamily," *FEBS J.* 272(24):6179-6217, 2005.
Zhang et al., "Transduction of Human T Cells with a Novel T-Cell Receptor Confers Anti-HCV Reactivity," *PLoS Pathogens* 6(7):e1001018, 2010. (13 pages).

(56) References Cited

OTHER PUBLICATIONS

Zhao et al., "Primary Human Lymphocytes Transduced With NY-ESO-1 Antigen-Specific TCR Genes Recognize and Kill Diverse Human Tumor Cell Lines," *J. Immunol.* 174(7):4415-4423, 2005. (25 pages).
Office Action, dated Nov. 20, 2020, for Canadian Application No. 2,933,707, 4 pages.
Office Action, dated Sep. 7, 2020, for Chinese Application No. 201480075007.8, 7 pages. (w/ English Translation).
Office Action, dated Mar. 7, 2020, for Indian Application No. 201617021884, 11 pages. (w/English Translation).
Office Action, dated Sep. 8, 2020, for Mexican Application No. MX/a/2016/007927, 10 pages. (w/ English Translation).

* cited by examiner

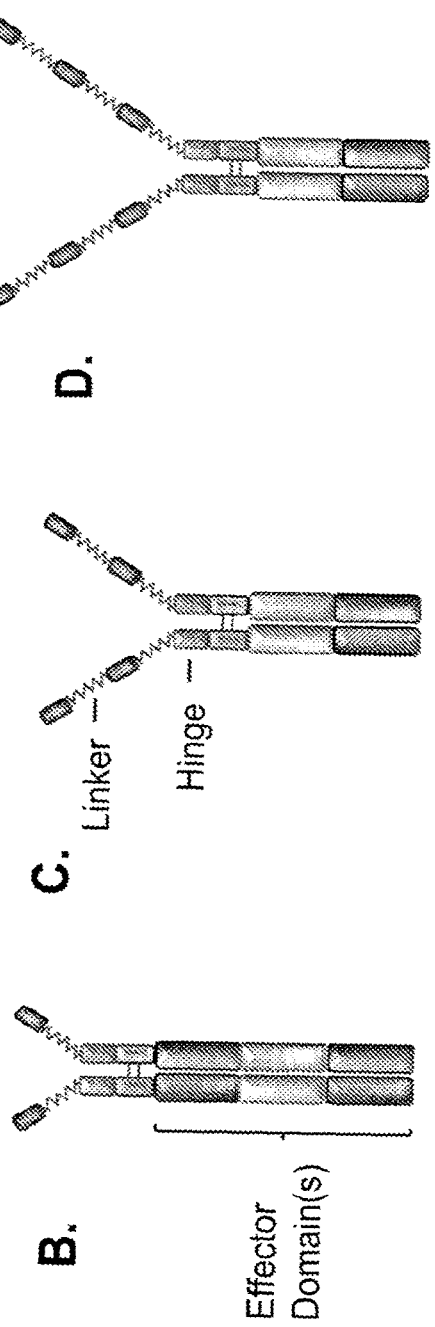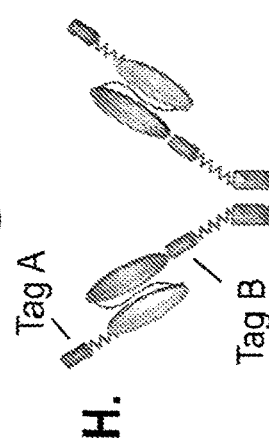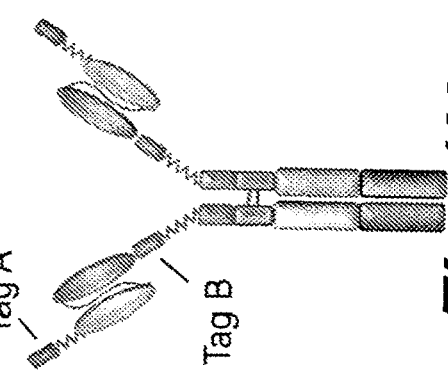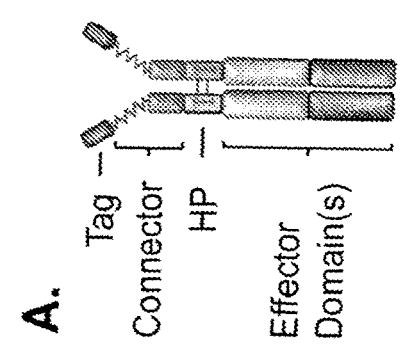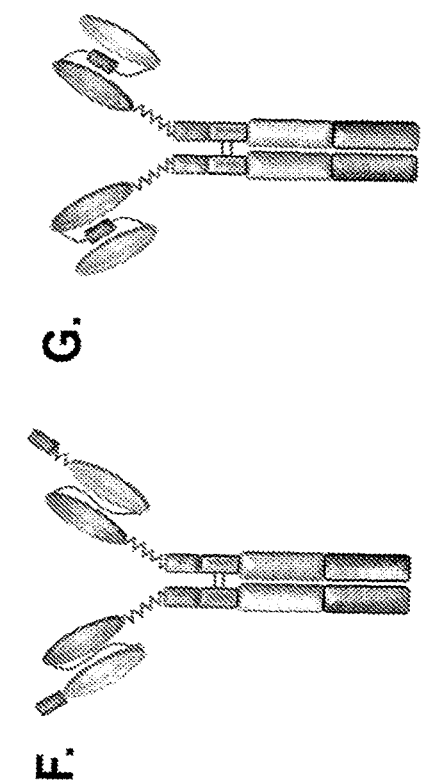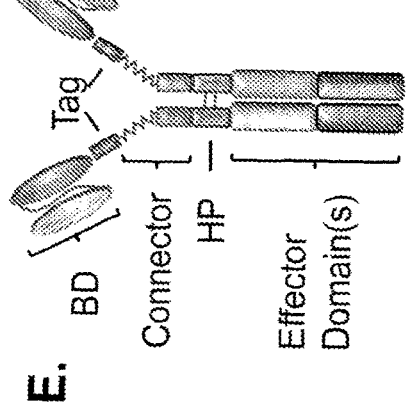

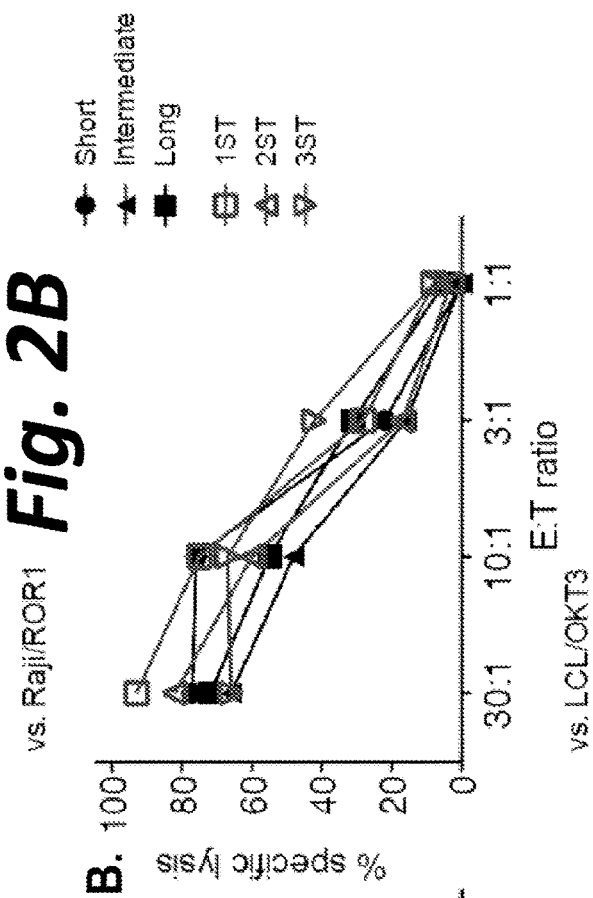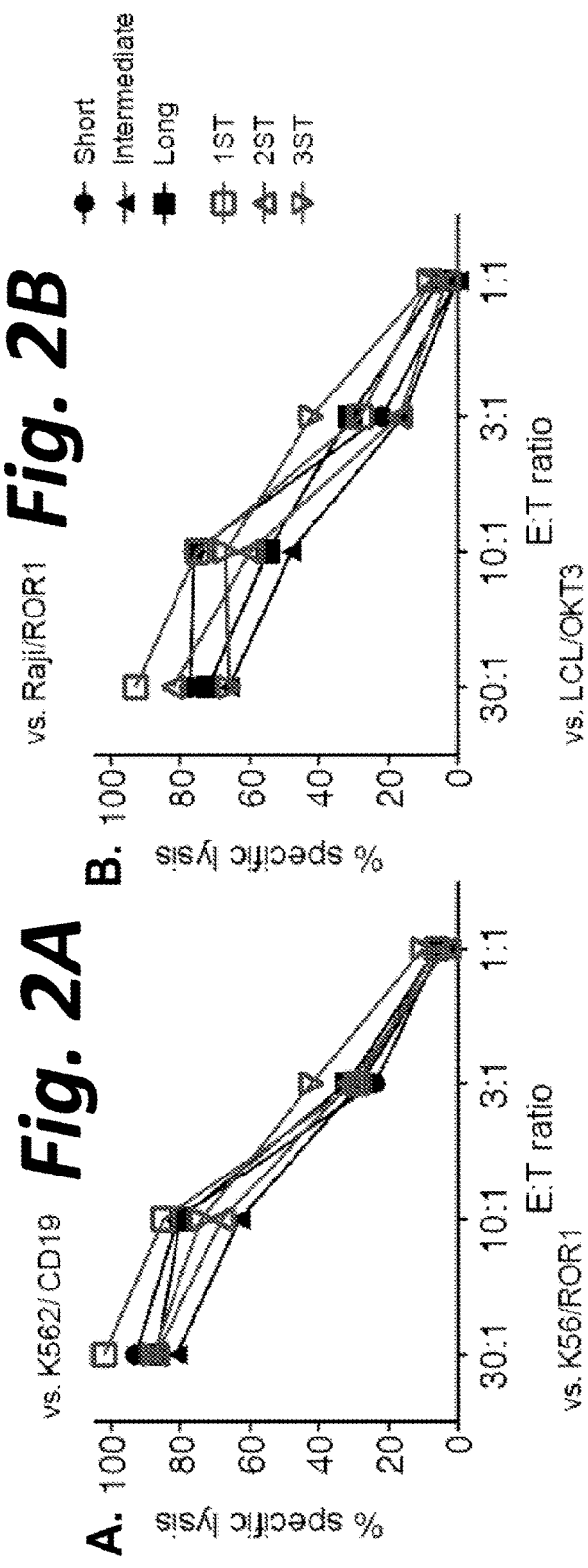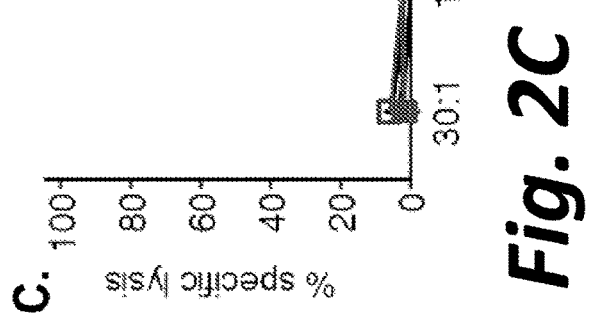

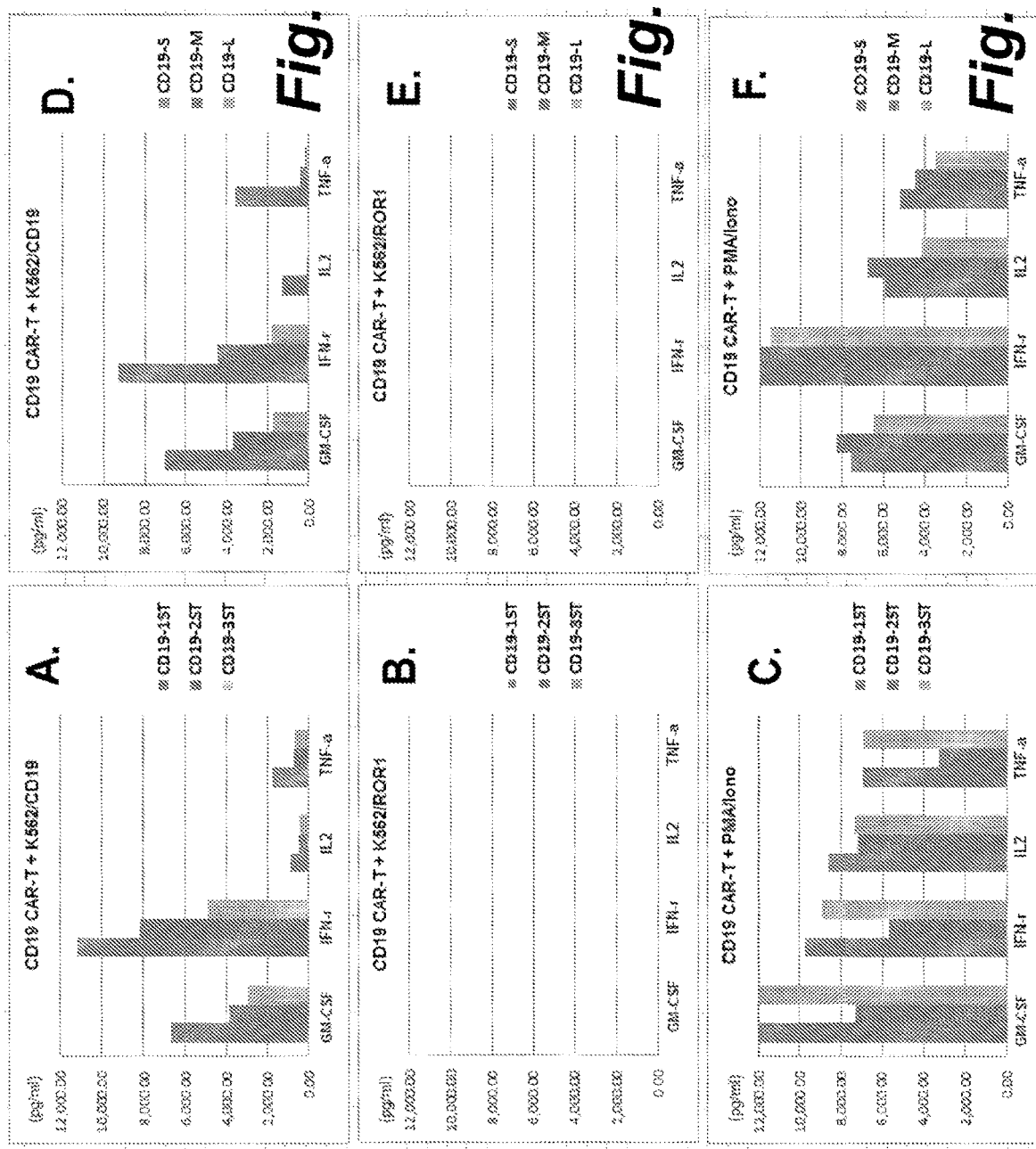

D6 after tumor
D0 after T cells
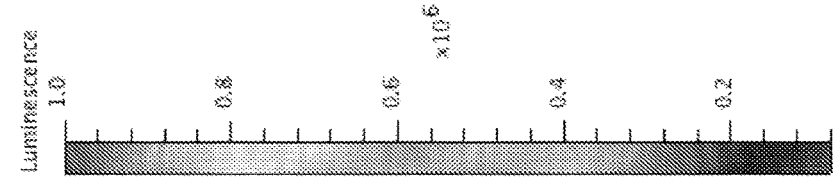
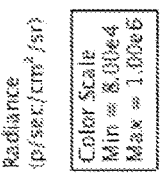
1. CAR(short)
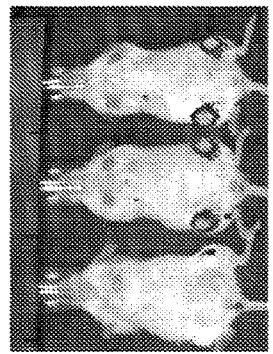
4. ChARM¹ beads+ LCL stim
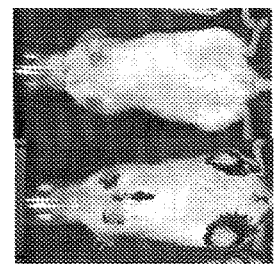
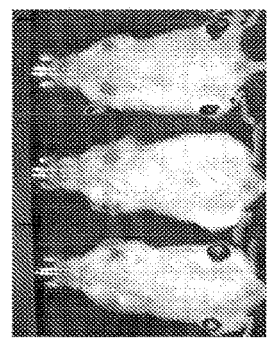
2. CAR(Medium)
5. ChARM² bead stim
3. CAR(long)
6. ChARM³ LCL stim
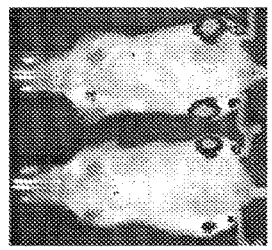
7. Untreated
*Fig. 6A*

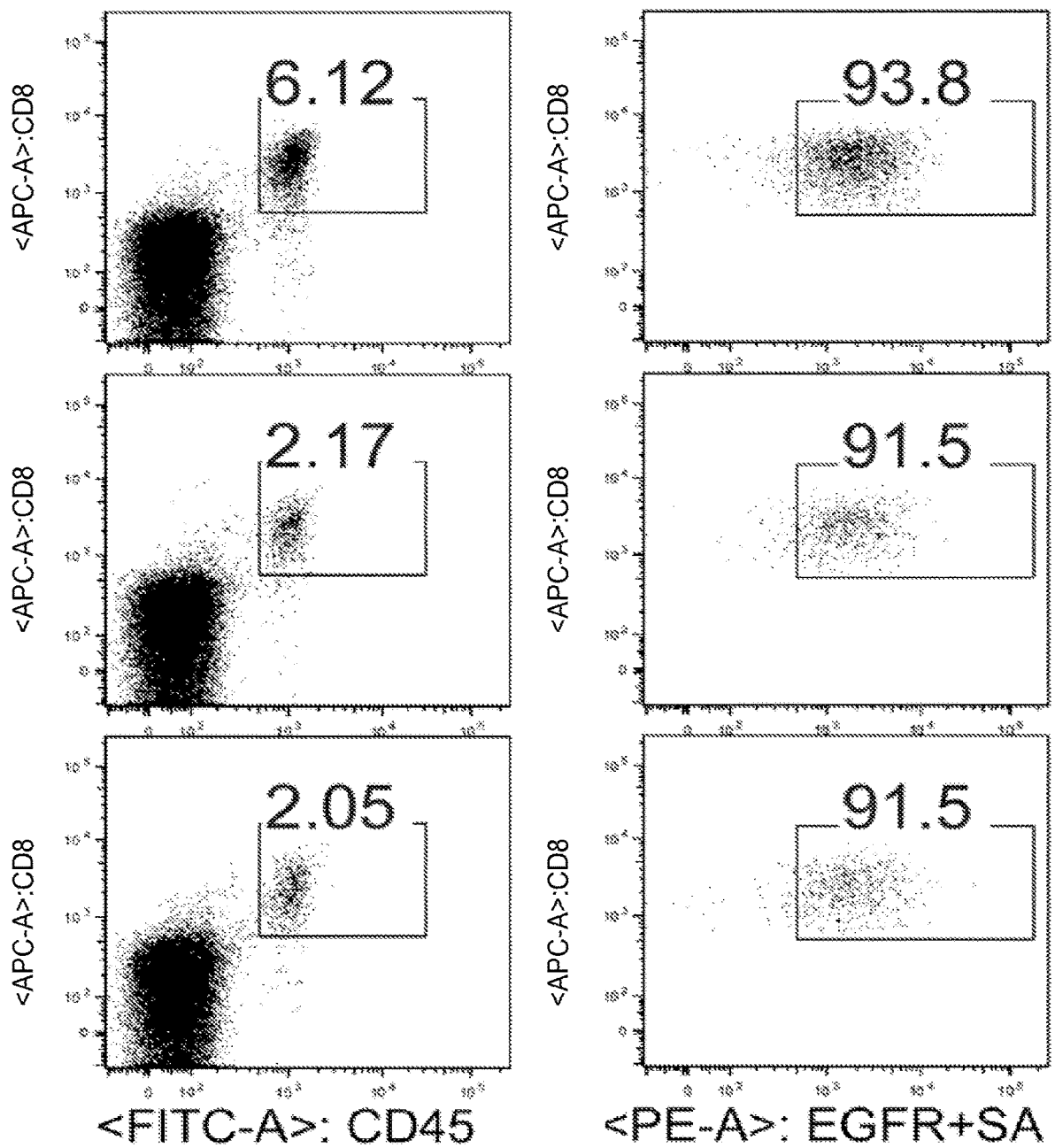
Fig. 7 *(Continued)*

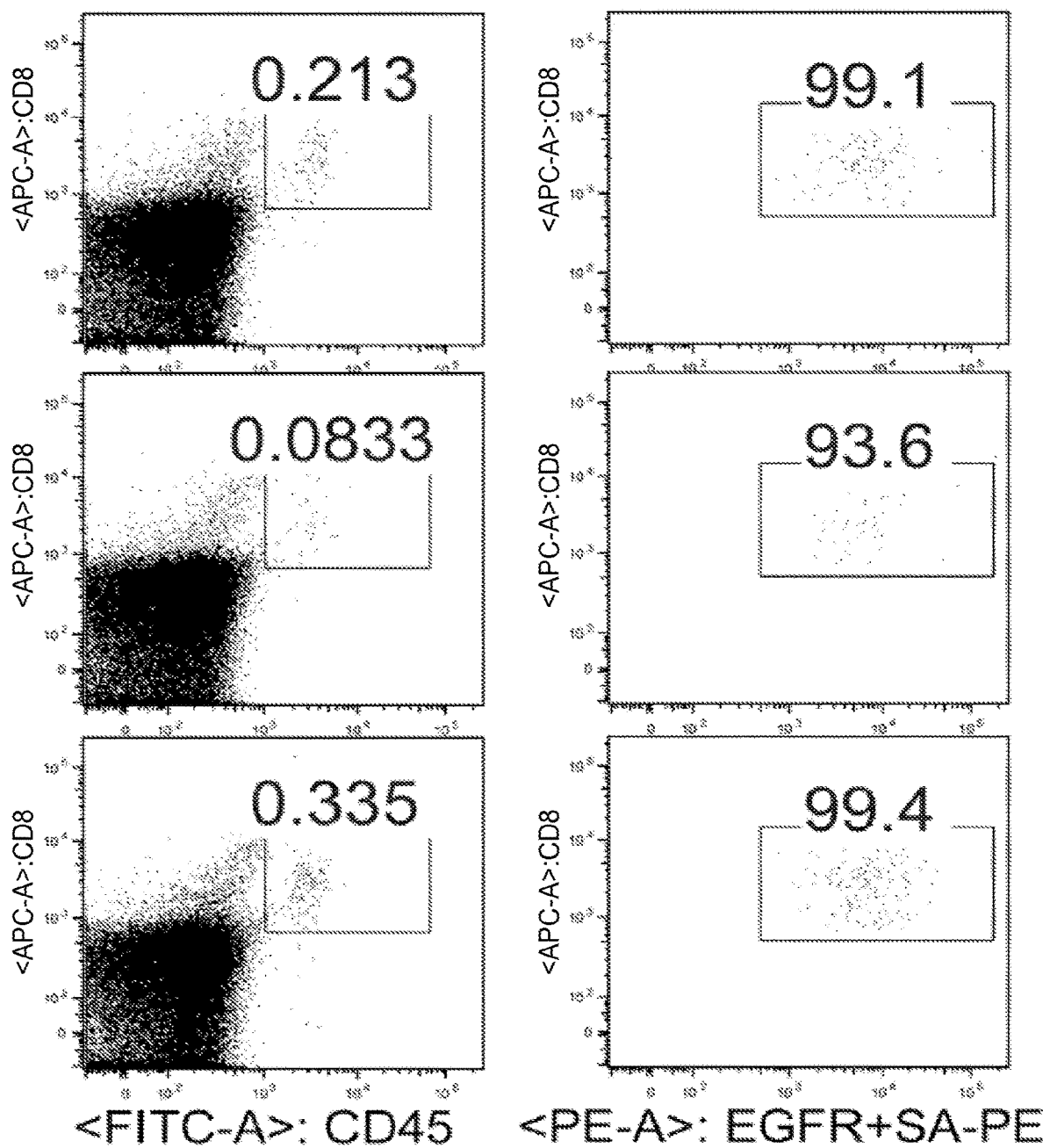
Fig. 7 *(Continued)*

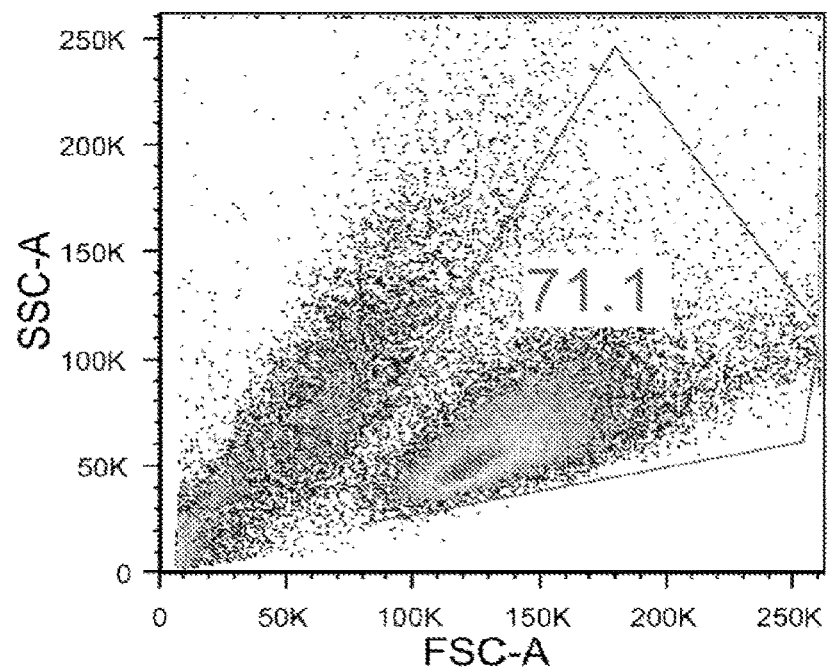
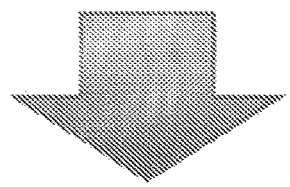
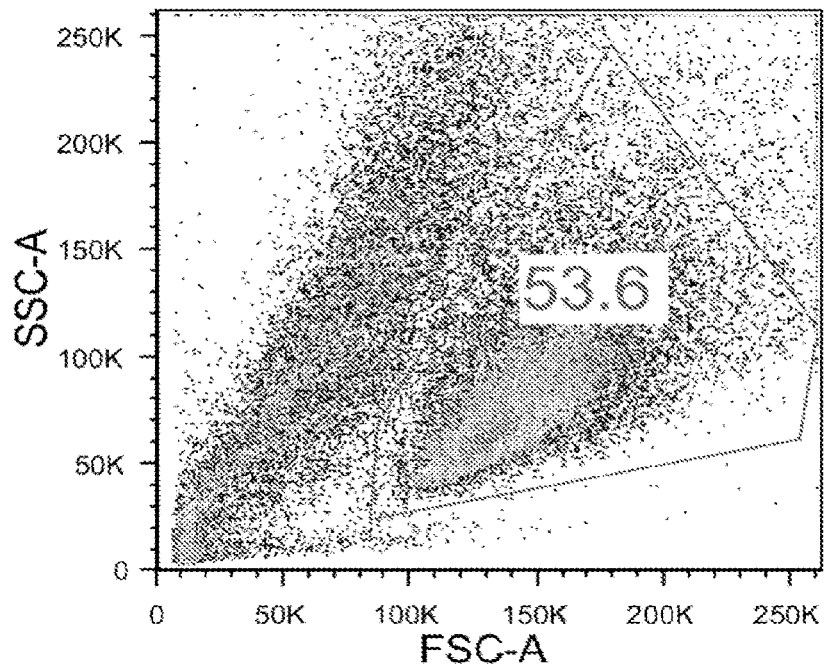
*Fig. 9*

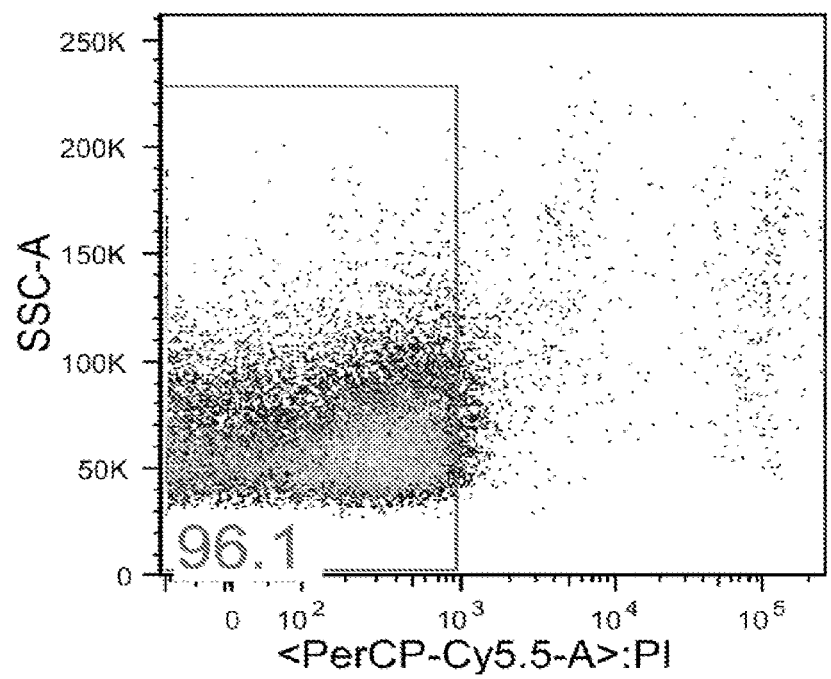
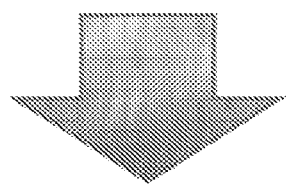
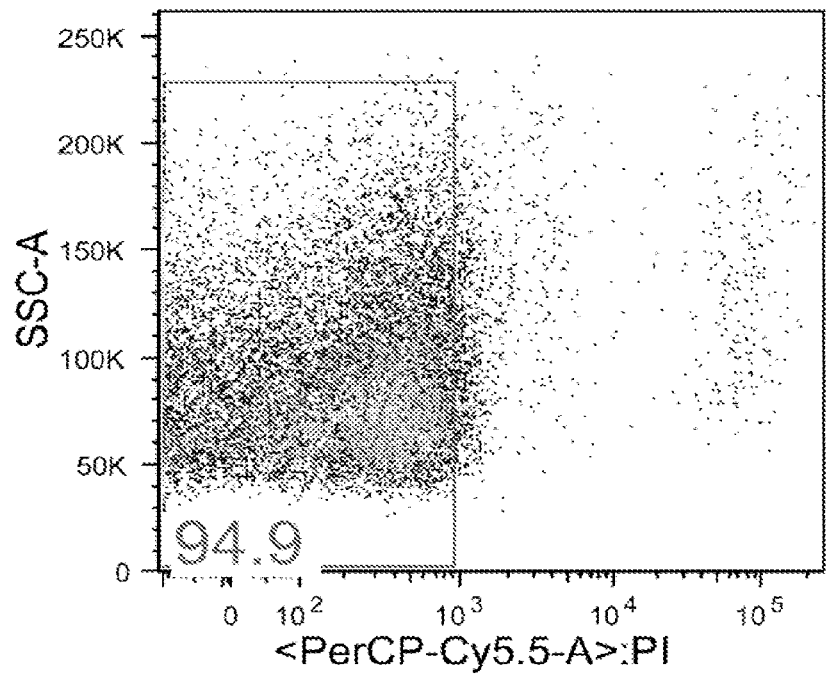
Fig. 9 *(Continued)*

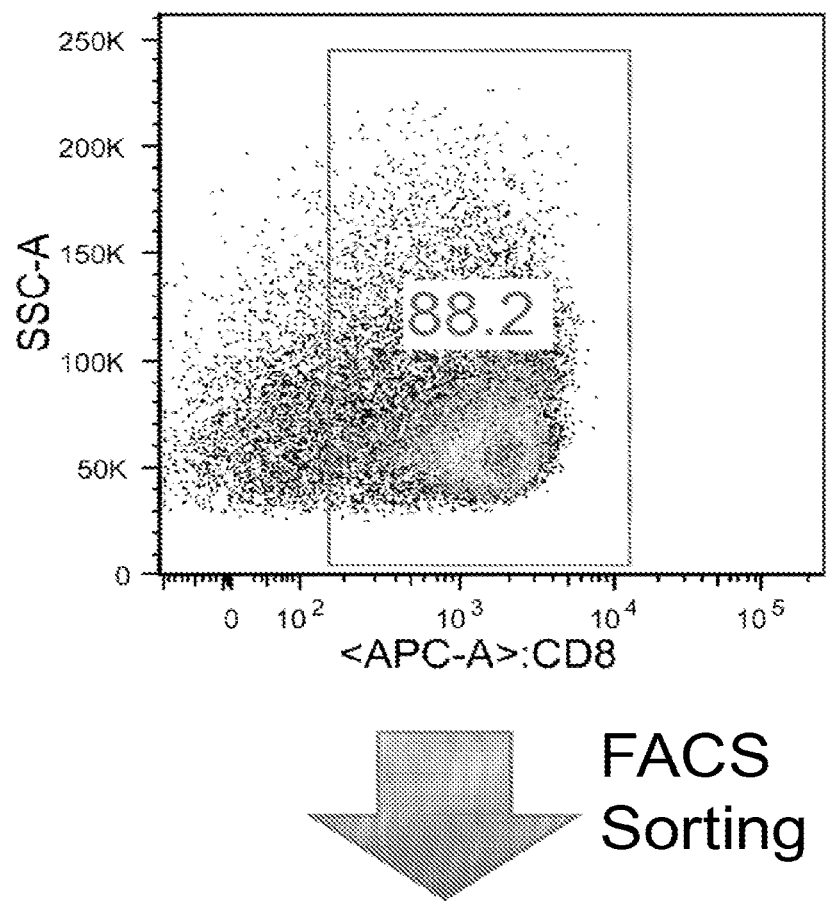
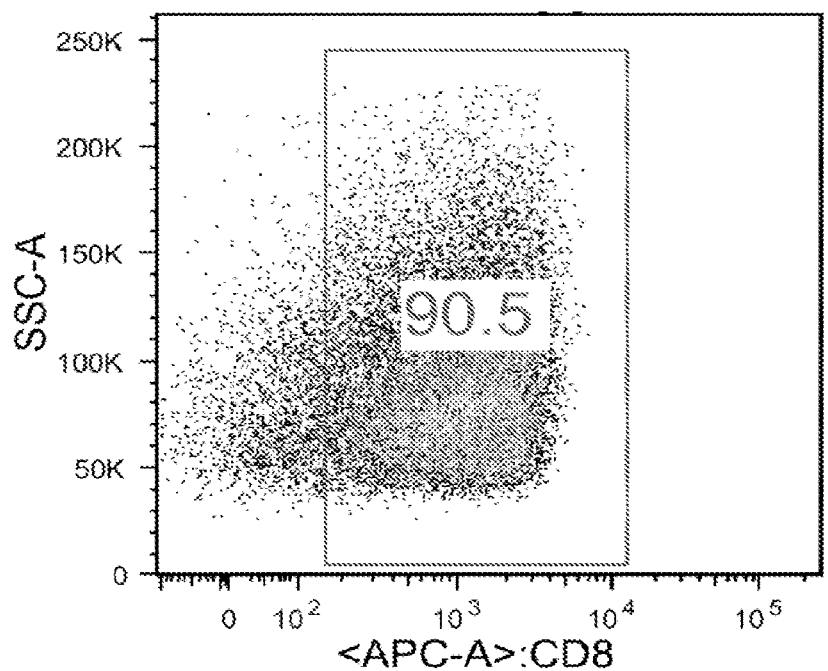
*Fig. 9* (Continued)

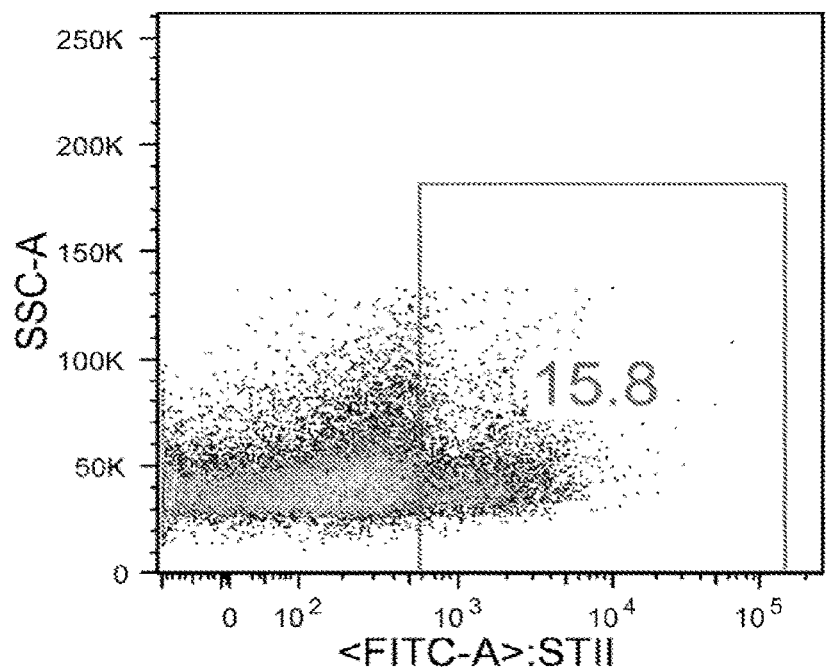
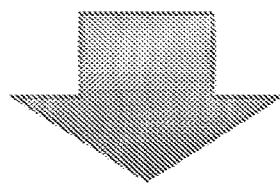
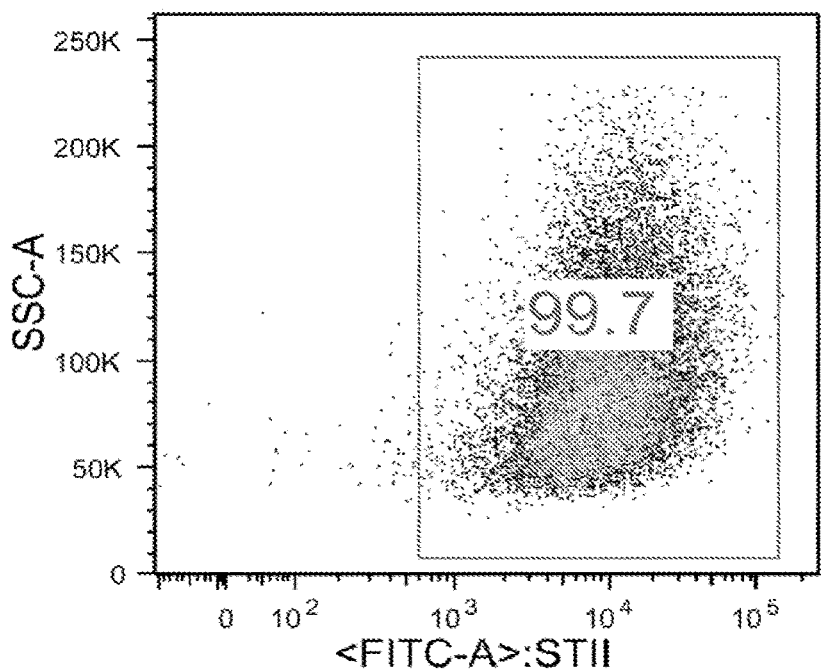
*Fig. 9* (Continued)

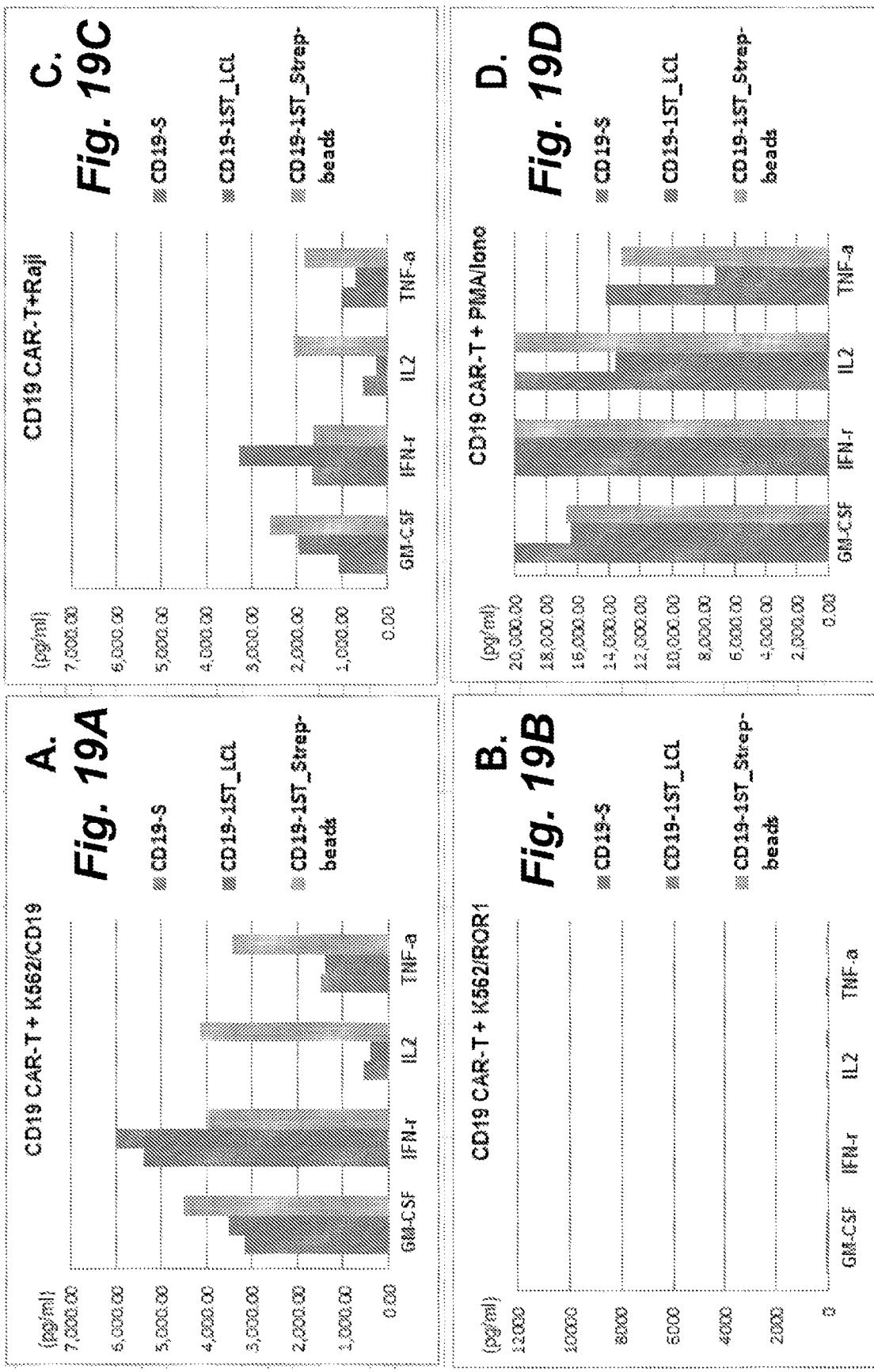

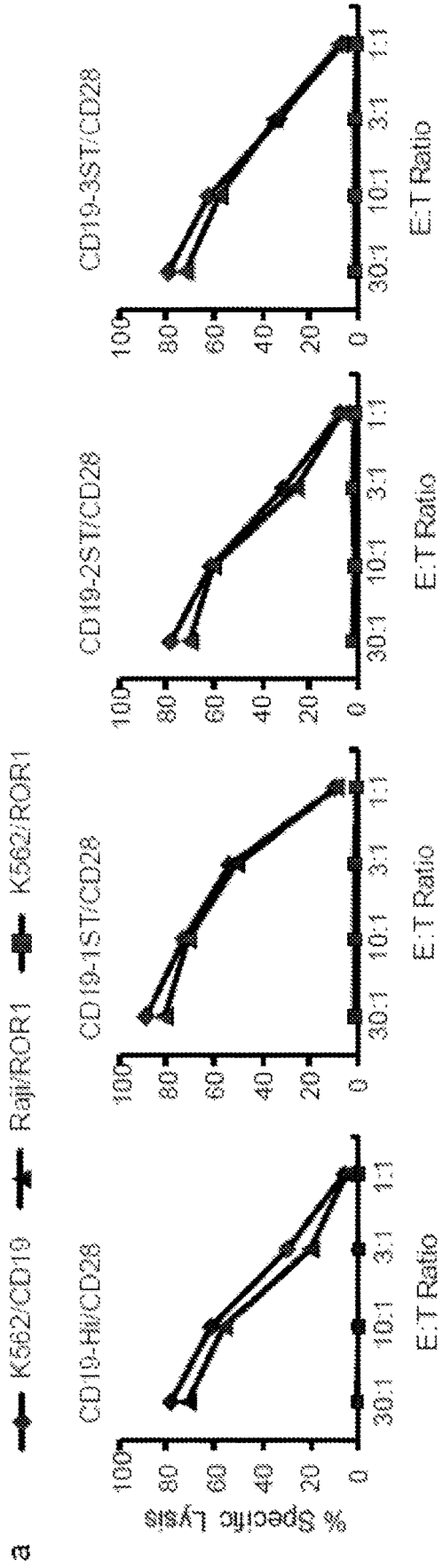
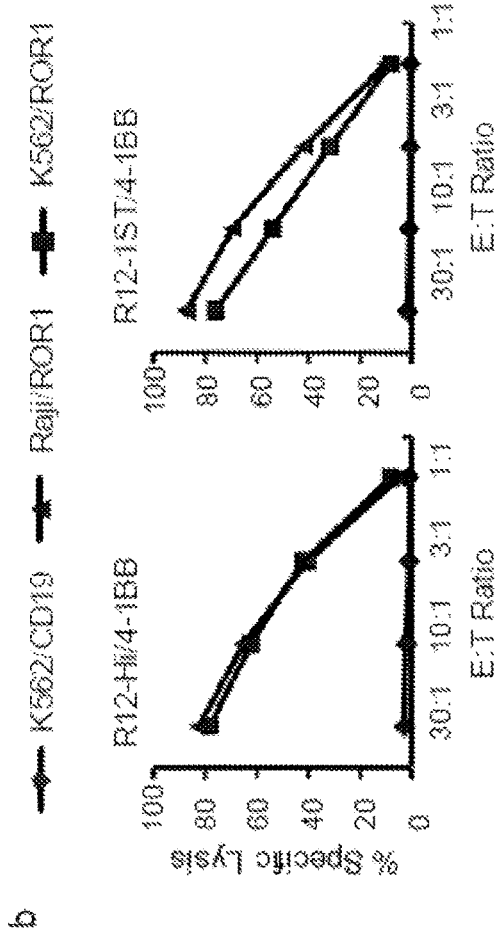
Fig. 23A
Fig. 23B

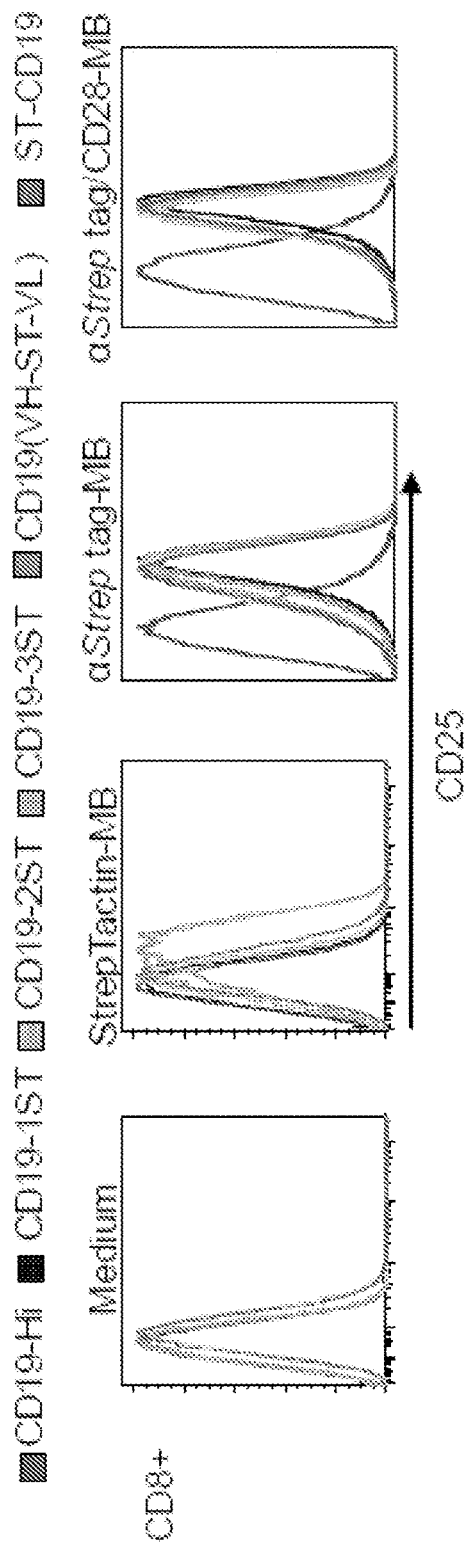
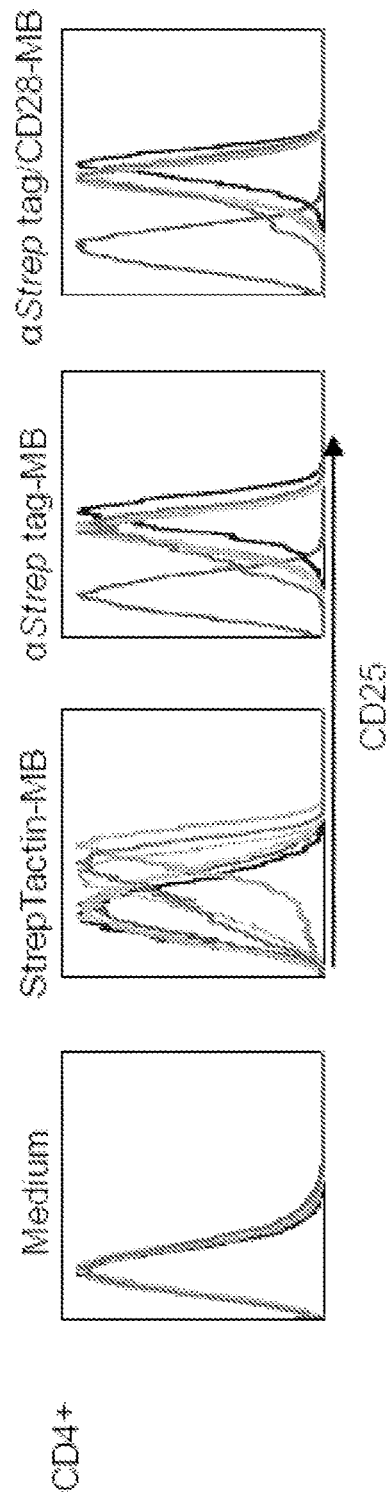
Fig. 27A
Fig. 27B

SEQUENCE LISTING

```
<160> NUMBER OF SEQ ID NOS: 73

<210> SEQ ID NO 1
<211> LENGTH: 8
<212> TYPE: PRT
<213> ORGANISM: Artificial Sequence
<220> FEATURE:
<223> OTHER INFORMATION: Strep-tag II

<400> SEQUENCE: 1

Trp Ser His Pro Gln Phe Glu Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Strep-tag

<400> SEQUENCE: 2

Trp Arg His Pro Gln Phe Gly Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Flag Tag

<400> SEQUENCE: 3

Asp Tyr Lys Asp Asp Asp Asp Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Xpress tag

<400> SEQUENCE: 4

Asp Leu Tyr Asp Asp Asp Asp Lys
1               5

<210> SEQ ID NO 5
<211> LENGTH: 15
<212> TYPE: PRT
<213> ORGANISM: Artificial Sequence
<220> FEATURE:
<223> OTHER INFORMATION: Avi tag

<400> SEQUENCE: 5

Gly Leu Asn Asp Ile Phe Glu Ala Gln Lys Ile Glu Trp His Glu
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: HA tag

<400> SEQUENCE: 6

Tyr Pro Tyr Asp Val Pro Asp Tyr Ala
1               5
```

<210> SEQ ID NO 7
<211> LENGTH: 10
<212> TYPE: PRT
<213> ORGANISM: Artificial Sequence
<220> FEATURE:
<223> OTHER INFORMATION: Myc tag

<400> SEQUENCE: 7

Glu Gln Lys Leu Ile Ser Glu Glu Asp Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: V5 tag

<400> SEQUENCE: 8

Gly Lys Pro Ile Pro Asn Pro Leu Leu Gly Leu Asp Ser Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Soft tag 1

<400> SEQUENCE: 9

Ser Leu Ala Glu Leu Leu Asn Ala Gly Leu Gly Gly Ser
1               5                   10

<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

Gly Gly Gly Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Gly Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: linker

<400> SEQUENCE: 12

Gly Gly Gly Ser Gly Gly Gly Ser Gly Gly Ser
1               5                   10

```
<210> SEQ ID NO 13
<211> LENGTH: 15
<212> TYPE: PRT
<213> ORGANISM: Artificial Sequence
<220> FEATURE:
<223> OTHER INFORMATION: linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: linker

<400> SEQUENCE: 14

Gly Gly Gly Ser Gly Gly Gly Ser Gly Gly Gly Ser Gly Gly Gly Ser
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: IgG4 Hinge

<400> SEQUENCE: 15

Glu Ser Lys Tyr Gly Pro Pro Cys Pro Pro Cys Pro
1               5                   10

<210> SEQ ID NO 16
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 16

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 17
<211> LENGTH: 42
<212> TYPE: PRT
<213> ORGANISM: Artificial Sequence
<220> FEATURE:
<223> OTHER INFORMATION: 4 1BB portion

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 18
<211> LENGTH: 112
<212> TYPE: PRT
<213> ORGANISM: Artificial Sequence
```

```
<220> FEATURE:
<223> OTHER INFORMATION: CD3 zeta portion

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65              70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 26
<212> TYPE: PRT
<213> ORGANISM: Artificial Sequence
<220> FEATURE:
<223> OTHER INFORMATION: Calmodulin tag

<400> SEQUENCE: 19

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 20
<211> LENGTH: 18
<212> TYPE: PRT
<213> ORGANISM: Artificial Sequence
<220> FEATURE:
<223> OTHER INFORMATION: linker+tag

<400> SEQUENCE: 20

Gly Gly Gly Gly Ser Gly Gly Gly Ser Trp Ser His Pro Gln Phe
1               5                   10                  15

Glu Lys

<210> SEQ ID NO 21
<211> LENGTH: 18
<212> TYPE: PRT
<213> ORGANISM: Artificial Sequence
<220> FEATURE:
<223> OTHER INFORMATION: linker+tag

<400> SEQUENCE: 21

Trp Ser His Pro Gln Phe Glu Lys Gly Gly Gly Ser Gly Gly Gly
1               5                   10                  15

Gly Ser

<210> SEQ ID NO 22
<211> LENGTH: 37
<212> TYPE: PRT
<213> ORGANISM: Artificial Sequence
<220> FEATURE:
<223> OTHER INFORMATION: linker tag
```

```
<400> SEQUENCE: 22

Gly Gly Gly Gly Ser Gly Gly Gly Ser Trp Ser His Pro Gln Phe
1               5                   10                  15

Glu Lys Gly Gly Gly Ser Gly Gly Gly Ser Gly Gly Ser Trp Ser His
            20                  25                  30

Pro Gln Phe Glu Lys
            35

<210> SEQ ID NO 23
<211> LENGTH: 37
<212> TYPE: PRT
<213> ORGANISM: Artificial Sequence
<220> FEATURE:
<223> OTHER INFORMATION: linker tag

<400> SEQUENCE: 23

Trp Ser His Pro Gln Phe Glu Lys Gly Gly Gly Ser Gly Gly Gly Ser
1               5                   10                  15

Gly Gly Ser Trp Ser His Pro Gln Phe Glu Lys Gly Gly Gly Ser
            20                  25                  30

Gly Gly Gly Gly Ser
            35

<210> SEQ ID NO 24
<211> LENGTH: 55
<212> TYPE: PRT
<213> ORGANISM: Artificial Sequence
<220> FEATURE:
<223> OTHER INFORMATION: linker tag

<400> SEQUENCE: 24

Gly Gly Gly Gly Ser Gly Gly Gly Ser Trp Ser His Pro Gln Phe
1               5                   10                  15

Glu Lys Gly Gly Gly Ser Gly Gly Gly Ser Gly Gly Ser Trp Ser His
            20                  25                  30

Pro Gln Phe Glu Lys Gly Gly Gly Ser Gly Gly Gly Ser Trp
            35                  40                  45

Ser His Pro Gln Phe Glu Lys
            50                  55

<210> SEQ ID NO 25
<211> LENGTH: 55
<212> TYPE: PRT
<213> ORGANISM: Artificial Sequence
<220> FEATURE:
<223> OTHER INFORMATION: linker tag

<400> SEQUENCE: 25

Trp Ser His Pro Gln Phe Glu Lys Gly Gly Gly Ser Gly Gly Gly
1               5                   10                  15

Gly Ser Trp Ser His Pro Gln Phe Glu Lys Gly Gly Ser Gly Gly
            20                  25                  30

Gly Ser Gly Gly Ser Trp Ser His Pro Gln Phe Glu Lys Gly Gly Gly
            35                  40                  45

Gly Ser Gly Gly Gly Ser
            50                  55

<210> SEQ ID NO 26
<211> LENGTH: 5
<212> TYPE: PRT
```

```
<213> ORGANISM: Artificial Sequence
<220> FEATURE:
<223> OTHER INFORMATION: core hinge region

<400> SEQUENCE: 26

Cys Pro Pro Cys Pro
1               5

<210> SEQ ID NO 27
<211> LENGTH: 36
<212> TYPE: DNA
<213> ORGANISM: Artificial Sequence
<220> FEATURE:
<223> OTHER INFORMATION: IgG4 Hinge

<400> SEQUENCE: 27
gagagcaagt acggaccgcc ctgcccccct tgccct                                 36

<210> SEQ ID NO 28
<211> LENGTH: 84
<212> TYPE: DNA
<213> ORGANISM: Artificial Sequence
<220> FEATURE:
<223> OTHER INFORMATION: CD28 transmembrane domain

<400> SEQUENCE: 28
atgttctggg tgctggtggt ggtcggaggc gtgctggcct gctacagcct gctggtcacc       60
gtggccttca tcatcttttg ggtg                                              84

<210> SEQ ID NO 29
<211> LENGTH: 126
<212> TYPE: DNA
<213> ORGANISM: Artificial Sequence
<220> FEATURE:
<223> OTHER INFORMATION: 4 1BB portion

<400> SEQUENCE: 29
aaacggggca gaaagaaact cctgtatata ttcaaacaac catttatgag accagtacaa       60
actactcaag aggaagatgg ctgtagctgc cgatttccag aagaagaaga aggaggatgt      120
gaactg                                                                126

<210> SEQ ID NO 30
<211> LENGTH: 336
<212> TYPE: DNA
<213> ORGANISM: Artificial Sequence
<220> FEATURE:
<223> OTHER INFORMATION: CD3 zeta  portion

<400> SEQUENCE: 30
cgggtgaagt tcagcagaag cgccgacgcc cctgcctacc agcagggcca gaatcagctg       60
tacaacgagc tgaacctggg cagaagggaa gagtacgacg tcctggataa gcggagaggc      120
cgggaccctg agatgggcgg caagcctcgg cggaagaacc cccaggaagg cctgtataac      180
gaactgcaga agacaagat ggccgaggcc tacagcgaga tcggcatgaa gggcgagcgg       240
aggcggggca gggccacga cggcctgtat cagggcctgt ccaccgccac caaggatacc       300
tacgacgccc tgcacatgca ggccctgccc ccaagg                                336

<210> SEQ ID NO 31
<211> LENGTH: 15
<212> TYPE: PRT
<213> ORGANISM: Artificial Sequence
<220> FEATURE:
```

<223> OTHER INFORMATION: S tag

<400> SEQUENCE: 31

Lys Glu Thr Ala Ala Ala Lys Phe Glu Arg Gln His Met Asp Ser
1               5                   10                  15

<210> SEQ ID NO 32
<211> LENGTH: 8
<212> TYPE: PRT
<213> ORGANISM: Artificial Sequence
<220> FEATURE:
<223> OTHER INFORMATION: Softag 3

<400> SEQUENCE: 32

Thr Gln Asp Pro Ser Arg Val Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Engineered tag of a minimal chelation site

<400> SEQUENCE: 33

His Gly Gly His His Gly
1               5

<210> SEQ ID NO 34
<211> LENGTH: 123
<212> TYPE: DNA
<213> ORGANISM: Artificial Sequence
<220> FEATURE:
<223> OTHER INFORMATION: CD28 effector domain

<400> SEQUENCE: 34
cggagcaagc ggagcagagg cggccacagc gactacatga acatgacccc cagacggcct      60
ggccccaccc ggaagcacta ccagccctac gccccaccca gggactttgc cgcctacaga     120
agc                                                                    123

<210> SEQ ID NO 35
<211> LENGTH: 41
<212> TYPE: PRT
<213> ORGANISM: Artificial Sequence
<220> FEATURE:
<223> OTHER INFORMATION: CD28 effector domain

<400> SEQUENCE: 35

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 36
<211> LENGTH: 735
<212> TYPE: DNA
<213> ORGANISM: Artificial Sequence
<220> FEATURE:
<223> OTHER INFORMATION: anti-CD19 scFv (VH-VL) from FMC63

<400> SEQUENCE: 36
gacatccaga tgacccagac cacctccagc ctgagcgcca gcctgggcga ccgggtgacc      60

```
atcagctgcc gggccagcca ggacatcagc aagtacctga actggtatca gcagaagccc    120
gacggcaccg tcaagctgct gatctaccac accagccggc tgcacagcgg cgtgcccagc    180
cggtttagcg gcagcggctc cggcaccgac tacagcctga ccatctccaa cctggaacag    240
gaagatatcg ccacctactt ttgccagcag ggcaacacac tgccctacac ctttggcggc    300
ggaacaaagc tggaaatcac cggcagcacc tccggcagcg gcaagcctgg cagcggcgag    360
ggcagcacca agggcgaggt gaagctgcag gaaagcggcc ctggcctggt ggcccccagc    420
cagagcctga gcgtgacctg caccgtgagc ggcgtgagcc tgcccgacta cggcgtgagc    480
tggatccggc agcccccag gaagggcctg aatggctgg gcgtgatctg gggcagcgag    540
accacctact acaacagcgc cctgaagagc cggctgacca tcatcaagga caacagcaag    600
agccaggtgt tcctgaagat gaacagcctg cagaccgacg acaccgccat ctactactgc    660
gccaagcact actactacgg cggcagctac gccatggact actggggcca gggcaccagc    720
gtgaccgtga gcagc                                                     735
```

<210> SEQ ID NO 37
<211> LENGTH: 245
<212> TYPE: PRT
<213> ORGANISM: Artificial Sequence
<220> FEATURE:
<223> OTHER INFORMATION: anti-CD19 scFv (VH-VL) from FMC63

<400> SEQUENCE: 37

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240
```

Val Thr Val Ser Ser
             245

<210> SEQ ID NO 38
<211> LENGTH: 24
<212> TYPE: DNA
<213> ORGANISM: Artificial Sequence
<220> FEATURE:
<223> OTHER INFORMATION: Strep-tag II

<400> SEQUENCE: 38
tggagccacc cgcagttcga aaaa                                            24

<210> SEQ ID NO 39
<211> LENGTH: 15
<212> TYPE: DNA
<213> ORGANISM: Artificial Sequence
<220> FEATURE:
<223> OTHER INFORMATION: G4S

<400> SEQUENCE: 39
ggaggtggag gttca                                                      15

<210> SEQ ID NO 40
<211> LENGTH: 15
<212> TYPE: DNA
<213> ORGANISM: Artificial Sequence
<220> FEATURE:
<223> OTHER INFORMATION: G4S

<400> SEQUENCE: 40
ggtggtggag gctct                                                      15

<210> SEQ ID NO 41
<211> LENGTH: 15
<212> TYPE: DNA
<213> ORGANISM: Artificial Sequence
<220> FEATURE:
<223> OTHER INFORMATION: G4S

<400> SEQUENCE: 41
ggtggcggag gctct                                                      15

<210> SEQ ID NO 42
<211> LENGTH: 30
<212> TYPE: DNA
<213> ORGANISM: Artificial Sequence
<220> FEATURE:
<223> OTHER INFORMATION: (G4S)2

<400> SEQUENCE: 42
ggaggtggag gttcaggtgg tggaggttca                                      30

<210> SEQ ID NO 43
<211> LENGTH: 33
<212> TYPE: DNA
<213> ORGANISM: Artificial Sequence
<220> FEATURE:
<223> OTHER INFORMATION: G3SG3SG2S

<400> SEQUENCE: 43
ggaggcggtt ctggaggtgg aagcggtggc tct                                  33

<210> SEQ ID NO 44
<211> LENGTH: 18

```
<212> TYPE: PRT
<213> ORGANISM: Artificial Sequence
<220> FEATURE:
<223> OTHER INFORMATION: variable domain linker

<400> SEQUENCE: 44

Gly Ser Thr Ser Gly Ser Gly Lys Pro Gly Ser Gly Glu Gly Ser Thr
1               5                   10                  15

Lys Gly

<210> SEQ ID NO 45
<211> LENGTH: 20
<212> TYPE: PRT
<213> ORGANISM: Artificial Sequence
<220> FEATURE:
<223> OTHER INFORMATION: variable domain linker + imbedded tag
<220> FEATURE:
<221> NAME/KEY: VARIANT
<222> LOCATION: (1)...(20)
<223> OTHER INFORMATION: Xaa = Any Amino Acid

<400> SEQUENCE: 45

Gly Gly Ser Gly Ser Gly Xaa Trp Ser His Pro Gln Phe Glu Lys Gly
1               5                   10                  15

Ser Gly Ser Gly
            20

<210> SEQ ID NO 46
<211> LENGTH: 18
<212> TYPE: PRT
<213> ORGANISM: Artificial Sequence
<220> FEATURE:
<223> OTHER INFORMATION: N-terminal tag + linker

<400> SEQUENCE: 46

Trp Ser His Pro Gln Phe Glu Lys Gly Gly Gly Ser Gly Gly Gly
1               5                   10                  15

Gly Ser

<210> SEQ ID NO 47
<211> LENGTH: 22
<212> TYPE: PRT
<213> ORGANISM: Artificial Sequence
<220> FEATURE:
<223> OTHER INFORMATION: secretory signal peptide

<400> SEQUENCE: 47

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 48
<211> LENGTH: 23
<212> TYPE: PRT
<213> ORGANISM: Artificial Sequence
<220> FEATURE:
<223> OTHER INFORMATION: secretory signal peptide
<220> FEATURE:
<221> NAME/KEY: VARIANT
<222> LOCATION: (1)...(23)
<223> OTHER INFORMATION: Xaa = Any Amino Acid

<400> SEQUENCE: 48

Met Leu Leu Leu Val Thr Ser Leu Leu Leu Cys Glu Leu Pro His Pro
1               5                   10                  15
```

Ala Phe Leu Leu Ile Pro Xaa
            20

<210> SEQ ID NO 49
<211> LENGTH: 13
<212> TYPE: PRT
<213> ORGANISM: Artificial Sequence
<220> FEATURE:
<223> OTHER INFORMATION: C-terminal junction amino acids

<400> SEQUENCE: 49

Glu Ser Lys Gly Gly Gly Gly Ser Gly Gly Gly Gly Ser
1               5                   10

<210> SEQ ID NO 50
<211> LENGTH: 4
<212> TYPE: PRT
<213> ORGANISM: Artificial Sequence
<220> FEATURE:
<223> OTHER INFORMATION: C-terminal junction amino acids

<400> SEQUENCE: 50

Gly Glu Ser Lys
1

<210> SEQ ID NO 51
<211> LENGTH: 107
<212> TYPE: PRT
<213> ORGANISM: Artificial Sequence
<220> FEATURE:
<223> OTHER INFORMATION: anti-CD19 VH domain

<400> SEQUENCE: 51

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 52
<211> LENGTH: 120
<212> TYPE: PRT
<213> ORGANISM: Artificial Sequence
<220> FEATURE:
<223> OTHER INFORMATION: anti-CD19 VL domain

<400> SEQUENCE: 52

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

```
Gly Val Ile Trp Gly Ser Glu Thr Thr Tyr Tyr Asn Ser Ala Leu Lys
     50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
            115                 120
```

<210> SEQ ID NO 53
<211> LENGTH: 263
<212> TYPE: PRT
<213> ORGANISM: Artificial Sequence
<220> FEATURE:
<223> OTHER INFORMATION: anti-CD19 scFv (Tag-VH-VL)

<400> SEQUENCE: 53

```
Trp Ser His Pro Gln Phe Glu Lys Gly Gly Gly Ser Gly Gly Gly
 1               5                  10                  15

Gly Ser Asp Ile Gln Met Thr Gln Thr Thr Ser Ser Leu Ser Ala Ser
                 20                  25                  30

Leu Gly Asp Arg Val Thr Ile Ser Cys Arg Ala Ser Gln Asp Ile Ser
             35                  40                  45

Lys Tyr Leu Asn Trp Tyr Gln Gln Lys Pro Asp Gly Thr Val Lys Leu
 50                  55                  60

Leu Ile Tyr His Thr Ser Arg Leu His Ser Gly Val Pro Ser Arg Phe
 65                  70                  75                  80

Ser Gly Ser Gly Ser Gly Thr Asp Tyr Ser Leu Thr Ile Ser Asn Leu
                 85                  90                  95

Glu Gln Glu Asp Ile Ala Thr Tyr Phe Cys Gln Gln Gly Asn Thr Leu
                100                 105                 110

Pro Tyr Thr Phe Gly Gly Gly Thr Lys Leu Glu Ile Thr Gly Ser Thr
            115                 120                 125

Ser Gly Ser Gly Lys Pro Gly Ser Gly Glu Gly Ser Thr Lys Gly Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser
            260
```

<210> SEQ ID NO 54

-continued

<211> LENGTH: 247
<212> TYPE: PRT
<213> ORGANISM: Artificial Sequence
<220> FEATURE:
<223> OTHER INFORMATION: anti-CD19 scFv (VH-Tag-VL)

<400> SEQUENCE: 54

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Ser Gly Ser
            100                 105                 110

Gly Asn Trp Ser His Pro Gln Phe Glu Lys Gly Ser Gly Ser Gly Glu
        115                 120                 125

Val Lys Leu Gln Glu Ser Gly Pro Gly Leu Val Ala Pro Ser Gln Ser
130                 135                 140

Leu Ser Val Thr Cys Thr Val Ser Gly Val Ser Leu Pro Asp Tyr Gly
145                 150                 155                 160

Val Ser Trp Ile Arg Gln Pro Pro Arg Lys Gly Leu Glu Trp Leu Gly
                165                 170                 175

Val Ile Trp Gly Ser Glu Thr Thr Tyr Tyr Asn Ser Ala Leu Lys Ser
            180                 185                 190

Arg Leu Thr Ile Ile Lys Asp Asn Ser Lys Ser Gln Val Phe Leu Lys
        195                 200                 205

Met Asn Ser Leu Gln Thr Asp Asp Thr Ala Ile Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Ser Val Thr Val Ser Ser
                245

<210> SEQ ID NO 55
<211> LENGTH: 121
<212> TYPE: PRT
<213> ORGANISM: Artificial Sequence
<220> FEATURE:
<223> OTHER INFORMATION: anti-ROR1 R12 VH domain

<400> SEQUENCE: 55

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp

```
                  65                  70                  75                  80
Leu Gln Met Asn Ser Leu Thr Ala Ala Asp Arg Ala Thr Tyr Phe Cys
                 85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 56
<211> LENGTH: 111
<212> TYPE: PRT
<213> ORGANISM: Artificial Sequence
<220> FEATURE:
<223> OTHER INFORMATION: anti-ROR1 R12 VL domain

<400> SEQUENCE: 56

Glu Leu Val Leu Thr Gln Ser Pro Ser Val Ser Ala Ala Leu Gly Ser
1               5                  10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr
            100                 105                 110

<210> SEQ ID NO 57
<211> LENGTH: 247
<212> TYPE: PRT
<213> ORGANISM: Artificial Sequence
<220> FEATURE:
<223> OTHER INFORMATION: anti-ROR1 scFv (VH-VL) from R12

<400> SEQUENCE: 57

Gln Glu Gln Leu Val Glu Ser Gly Gly Arg Leu Val Thr Pro Gly Gly
1               5                  10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Gly Gly Gly Gly Ser Gly Gly
            115                 120                 125

Gly Gly Ser Gly Gly Gly Ser Glu Leu Val Leu Thr Gln Ser Pro
        130                 135                 140
```

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
            165                 170                 175

Gly Glu Ala Pro Arg Tyr Leu Met Gln Val Gln Ser Asp Gly Ser Tyr
        180                 185                 190

Thr Lys Arg Pro Gly Val Pro Asp Arg Phe Ser Gly Ser Ser Ser Gly
    195                 200                 205

Ala Asp Arg Tyr Leu Ile Ile Pro Ser Val Gln Ala Asp Glu Ala
    210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr
                245

<210> SEQ ID NO 58
<211> LENGTH: 858
<212> TYPE: DNA
<213> ORGANISM: Artificial Sequence
<220> FEATURE:
<223> OTHER INFORMATION: secretory signal peptide-[anti-CD19 scFv
      (Tag-VH-VL)]

<400> SEQUENCE: 58
atgctgctgc tggtgaccag cctgctgctg tgcgagctgc ccacccccgc ctttctgctg        60
atccccaatt ggagccaccc gcagttcgaa aaaggaggtg aggttcagg tggtggaggc       120 tctgacatcc agatgaccca gaccacctcc agcctgagcg ccagcctggg cgaccgggtg      180
accatcagct gccgggccag ccaggacatc agcaagtacc tgaactggta tcagcagaag      240
cccgacggca ccgtcaagct gctgatctac cacaccagcc ggctgcacag cggcgtgccc      300
agccggttta gcggcagcgg ctccggcacc gactacagcc tgaccatctc caacctggaa      360
caggaagata tcgccaccta cttttgccag cagggcaaca cactgcccta cacctttggc      420
ggcggaacaa agctggaaat caccggcagc acctccggca gcggcaagcc tggcagcggc      480
gagggcagca ccaagggcga ggtgaagctg caggaaagcg gccctggcct ggtggccccc      540
agccagagcc tgagcgtgac ctgcaccgtg agcggcgtga gcctgcccga ctacggcgtg      600
agctggatca gcagcccccc caggaagggc ctggaatggc tgggcgtgat ctggggcagc      660
gagaccacct actacaacag cgccctgaag agccggctga ccatcatcaa ggacaacagc      720
aagagccagg tgttcctgaa gatgaacagc ctgcagaccg acgacaccgc catctactac      780
tgcgccaagc actactacta cggcggcagc tacgccatgg actactgggg ccagggcacc      840
agcgtgaccg tgagcagc                                                    858

<210> SEQ ID NO 59
<211> LENGTH: 807
<212> TYPE: DNA
<213> ORGANISM: Artificial Sequence
<220> FEATURE:
<223> OTHER INFORMATION: secretory signal peptide-[anti-CD19 scFv
      (VH-Tag-VL)]

<400> SEQUENCE: 59
atgctgctgc tggtgaccag cctgctgctg tgcgagctgc ccacccccgc ctttctgctg        60
atccccgaca tccagatgac ccagaccacc tccagcctga gcgccagcct gggcgaccgg      120
gtgaccatca gctgccgggc cagccaggac atcagcaagt acctgaactg gtatcagcag      180

| | | |
|---|---|---|
| aagcccgacg gcaccgtcaa gctgctgatc taccacacca gccggctgca cagcggcgtg | 240 | |
| cccagccggt ttagcggcag cggctccggc accgactaca gcctgaccat ctccaacctg | 300 | |
| gaacaggaag atatcgccac ctactttgc cagcagggca acacactgcc ctacaccttt | 360 | |
| ggcggcggaa caaagctgga aatcaccgga ggttcaggat ctggcaattg agccacccg | 420 | |
| cagttcgaaa aaggctctgg atcaggtgag gtgaagctgc aggaaagcgg ccctggcctg | 480 | |
| gtggccccca gccagagcct gagcgtgacc tgcaccgtga cggcgtgag cctgcccgac | 540 | |
| tacggcgtga gctggatcag cagcccccc aggaagggcc tggaatggct gggcgtgatc | 600 | |
| tggggcagcg agaccaccta ctacaacagc ccctgaaga gccggctgac catcatcaag | 660 | |
| gacaacagca agagccaggt gttcctgaag atgaacagc tgcagaccga cgacaccgcc | 720 | |
| atctactact gcgccaagca ctactactac ggcggcagct acgccatgga ctactggggc | 780 | |
| cagggcacca gcgtgaccgt gagcagc | 807 | |

<210> SEQ ID NO 60
<211> LENGTH: 807
<212> TYPE: DNA
<213> ORGANISM: Artificial Sequence
<220> FEATURE:
<223> OTHER INFORMATION: secretory signal peptide-anti-ROR1 scFv (VH-VL)

<400> SEQUENCE: 60

| | | |
|---|---|---|
| atgctgctgc tggtgacaag cctgctgctg tgcgagctgc ccaccccgc ctttctgctg | 60 | |
| atccccagg aacagctcgt cgaaagcggc ggcagactgg tgacacctgg cggcagcctg | 120 | |
| accctgagct gcaaggccag cggcttcgac ttcagcgcct actacatgag ctgggtccgc | 180 | |
| caggcccctg gcaagggact ggaatggatc gccaccatct accccagcag cggcaagacc | 240 | |
| tactacgcca cctgggtgaa cggacggttc accatctcca gcgacaacgc cagaacacc | 300 | |
| gtggacctgc agatgaacag cctgacagcc gccgaccggg ccacctactt ttgcgccaga | 360 | |
| gacagctacg ccgacgacgg cgccctgttc aacatctggg gccctggcac cctggtgaca | 420 | |
| atctctagcg gcggaggcgg atcggtggc ggaggaagtg gcggcggagg atctgagctg | 480 | |
| gtgctgaccc agagccccc tgtgtctgct gccctgggaa gccctgccaa gatcacctgt | 540 | |
| accctgagca gcgcccacaa gaccgacacc atcgactggt atcagcagct gcagggcgag | 600 | |
| gcccccagat acctgatgca ggtgcagagc gacggcagct acaccaagag gccaggcgtg | 660 | |
| cccgaccggt tcagcggatc tagctctggc gccgaccgct acctgatcat ccccagcgtg | 720 | |
| caggccgatg acgaggccga ttactactgt ggcgccgact acatcggcgg ctacgtgttc | 780 | |
| ggcggaggca cccagctgac cgtgacc | 807 | |

<210> SEQ ID NO 61
<211> LENGTH: 30
<212> TYPE: DNA
<213> ORGANISM: Artificial Sequence
<220> FEATURE:
<223> OTHER INFORMATION: (G4S)2

<400> SEQUENCE: 61

| | |
|---|---|
| ggaggtggag gttcaggtgg tggaggctct | 30 |

<210> SEQ ID NO 62
<211> LENGTH: 45
<212> TYPE: DNA
<213> ORGANISM: Artificial Sequence
<220> FEATURE:
<223> OTHER INFORMATION: (G4S)3

<400> SEQUENCE: 62
ggcggaggcg gatctggtgg cggaggaagt ggcggcggag gatct                45

<210> SEQ ID NO 63
<211> LENGTH: 66
<212> TYPE: DNA
<213> ORGANISM: Artificial Sequence
<220> FEATURE:
<223> OTHER INFORMATION: secretory signal peptide

<400> SEQUENCE: 63
atgctgctgc tggtgaccag cctgctgctg tgcgagctgc cccaccccgc ctttctgctg    60
atcccc                                                              66

<210> SEQ ID NO 64
<211> LENGTH: 66
<212> TYPE: DNA
<213> ORGANISM: Artificial Sequence
<220> FEATURE:
<223> OTHER INFORMATION: secretory signal peptide

<400> SEQUENCE: 64
atgctgctgc tggtgacaag cctgctgctg tgcgagctgc cccaccccgc ctttctgctg    60
atcccc                                                              66

<210> SEQ ID NO 65
<211> LENGTH: 6
<212> TYPE: PRT
<213> ORGANISM: Artificial Sequence
<220> FEATURE:
<223> OTHER INFORMATION: linker

<400> SEQUENCE: 65

Gly Gly Ser Gly Ser Gly
1               5

<210> SEQ ID NO 66
<211> LENGTH: 5
<212> TYPE: PRT
<213> ORGANISM: Artificial Sequence
<220> FEATURE:
<223> OTHER INFORMATION: linker

<400> SEQUENCE: 66

Gly Ser Gly Ser Gly
1               5

<210> SEQ ID NO 67
<211> LENGTH: 10
<212> TYPE: PRT
<213> ORGANISM: Artificial Sequence
<220> FEATURE:
<223> OTHER INFORMATION: linker

<400> SEQUENCE: 67

Gly Gly Gly Gly Ser Gly Gly Gly Gly Ser
1               5                   10

<210> SEQ ID NO 68
<211> LENGTH: 8
<212> TYPE: PRT
<213> ORGANISM: Artificial Sequence
<220> FEATURE:
<223> OTHER INFORMATION: linker

```
<400> SEQUENCE: 68

Gly Gly Gly Ser Gly Gly Gly Ser
1               5

<210> SEQ ID NO 69
<211> LENGTH: 11
<212> TYPE: PRT
<213> ORGANISM: Artificial Sequence
<220> FEATURE:
<223> OTHER INFORMATION: linker

<400> SEQUENCE: 69

Gly Gly Gly Ser Gly Gly Gly Ser Gly Gly Ser
1               5                   10

<210> SEQ ID NO 70
<211> LENGTH: 28
<212> TYPE: PRT
<213> ORGANISM: Artificial Sequence
<220> FEATURE:
<223> OTHER INFORMATION: modified CD28 transmembrane domain

<400> SEQUENCE: 70

Met Phe Trp Val Leu Val Val Val Gly Gly Val Leu Ala Cys Tyr Ser
1               5                   10                  15

Gly Gly Val Thr Val Ala Phe Ile Ile Phe Trp Val
            20                  25

<210> SEQ ID NO 71
<211> LENGTH: 4
<212> TYPE: PRT
<213> ORGANISM: Artificial Sequence
<220> FEATURE:
<223> OTHER INFORMATION: linker

<400> SEQUENCE: 71

Gly Gly Gly Ser
1

<210> SEQ ID NO 72
<211> LENGTH: 9
<212> TYPE: PRT
<213> ORGANISM: Artificial Sequence
<220> FEATURE:
<223> OTHER INFORMATION: linker

<400> SEQUENCE: 72

Gly Gly Gly Ser Gly Gly Gly Gly Ser
1               5

<210> SEQ ID NO 73
<211> LENGTH: 7
<212> TYPE: PRT
<213> ORGANISM: Artificial Sequence
<220> FEATURE:
<223> OTHER INFORMATION: linker

<400> SEQUENCE: 73

Gly Gly Gly Ser Gly Gly Ser
1               5
```

TAGGED CHIMERIC EFFECTOR MOLECULES AND RECEPTORS THEREOF

CROSS REFERENCE TO RELATED APPLICATION

This application is a continuation application of U.S. Nonprovisional application Ser. No. 15/106,657 filed on Jun. 20, 2016, which is a 371 application of International Application No. PCT/US2014/072007 filed on Dec. 22, 2014, which claims the benefit under 35 U.S.C. § 119(e) to U.S. Provisional Application No. 61/919,201 filed on Dec. 20, 2013, which applications are incorporated by reference herein in their entirety.

STATEMENT OF GOVERNMENT INTEREST

This invention was made with government support under CA136551 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_426C1_SEQUENCE_LISTING.txt. The text file is 31.8 KB, was created on Oct. 24, 2019, and is being submitted electronically via EFS-Web.

BACKGROUND

Technical Field

The present disclosure relates to fusion proteins containing a tag cassette and, more particularly, to tagged chimeric effector molecules (Key-ChEMs) and tagged chimeric antigen receptor molecules (T-ChARMs), and recombinant host cells producing such fusion proteins, wherein the recombinant host cells can be identified, isolated, sorted, induced to proliferate, tracked, eliminated, and/or used as a therapeutic (e.g., in adoptive immunotherapy).

Description of the Related Art

T cell-based immunotherapies began to be developed when tumor-reactive T cells were found among a population of tumor-infiltrating lymphocytes (TILs) (Clark et al., *Cancer Res.* 29:705, 1969). One strategy, known as adoptive T cell transfer, involves the isolation of tumor infiltrating lymphocytes pre-selected for tumor-reactivity, clonal expansion of the tumor-reactive T cells induced by anti-CD3 and anti-CD28 antibodies in the presence of IL-2, and finally infusing the expanded cell population back to the tumor-bearing patient (together with chemotherapy and repetitive administration of IL-2) (Dudley et al., *Science* 298:850, 2002). This form of adoptive T cell therapy with tumor infiltrating lymphocytes is technically cumbersome and leads to complete remission in only a minor fraction of patients with melanoma and is rarely effective in other cancers (Besser et al., *Clin. Cancer Res.* 16:2646, 2010).

Isolation of tumor-reactive T cell clones led to the development of another immunotherapeutic approach—the generation of recombinant T cell receptors (TCRs) specific for particular antigens, which are introduced into T cells using a vector delivery system to confer specificity for a tumor-associated peptide presented by an MHC molecule expressed on a tumor cell. A similar approach introduces a synthetic receptor, termed a chimeric antigen receptor (CAR), which contains an antigen-binding domain, which, e.g., in the context of anti-tumor therapy can bind to a tumor-specific or associated antigen, linked to one or more intracellular component comprising an effector domains, such as a TCR and/or costimulatory signaling domains. Unlike TILs, the basic procedure for TCR or CAR T cell immunotherapy is to genetically modify human T cells with a transgene encoding a tumor targeting moiety, ex vivo expansion of the recombinant T cells, and transfusing the expanded recombinant T cells back into patients. In the case of adoptive therapy with CAR T cells, the composition of the synthetic CAR structure, as well as the quality and purity of the genetically engineered T cells, will determine therapeutic efficacy against tumors in vivo. But, there are challenges to expanding and selecting the recombinant cell populations, as well as making sure the cells are effective and specific enough in vivo to avoid serious autoimmune side effects.

Currently, there remains a need in the immunotherapy field for compositions and methods for identifying, efficiently isolating/sorting, selectively expanding, in vivo tracking and controlling or eliminating engineered cells, such as engineered immune cells (e.g., T cells).

BRIEF SUMMARY

In certain aspects, the present disclosure is directed to a single chain fusion protein, comprising an extracellular component and an intracellular component connected by a hydrophobic portion, wherein the extracellular component comprises a binding domain that specifically binds a target, a tag cassette, and a connector region comprising a hinge, and wherein the intracellular component comprises an effector domain.

In some aspects, the present disclosure is directed to a chimeric antigen receptor molecule, comprising a fusion protein having one or more extracellular tag cassettes (a) located at the amino-terminus of an extracellular binding domain, (b) imbedded within an extracellular binding domain, or (c) disposed between and connecting an extracellular binding domain and an intracellular component comprising an effector domain.

In further aspects, the present disclosure is directed to a single chain fusion protein, comprising a hydrophobic portion disposed between and connecting an extracellular component and an intracellular component, wherein the extracellular component comprises a tag cassette and a connector region comprising a hinge, and wherein the intracellular component comprises an effector domain.

In still further aspects, the present disclosure is directed to a method for activating a cell, such as a T cell (e.g., a non-natural T cell), comprising contacting a cell with a binding domain specific for a tag cassette, wherein the cell comprises a nucleic acid molecule encoding a fusion protein according to this disclosure and the binding domain specific for the tag cassette is attached to a solid surface.

In yet further aspects, the present disclosure is directed to a method for promoting cell proliferation, such as T cell proliferation, comprising contacting a cell (e.g., a non-natural T cell) with a binding domain specific for a tag cassette and a growth factor cytokine for a time sufficient to allow cell growth, wherein the cell comprises a nucleic acid molecule encoding a fusion protein according to this disclosure and the binding domain specific for the tag cassette is attached to a solid surface.

In certain other aspects, the present disclosure is directed to a method for identifying cell, such as a T cell, comprising contacting a sample comprising a cell, such as a T cell (e.g., a non-natural T cell) with a binding domain specific for a tag cassette, wherein the cell comprises a nucleic acid molecule encoding a fusion protein according to this disclosure and the binding domain specific for the tag cassette comprises a detectable moiety, and detecting the presence of the cell expressing a fusion protein in the sample.

In certain further aspects, the present disclosure is directed to a method for sorting a T cell, comprising contacting a sample comprising a non-natural T cell with a binding domain specific for a tag cassette, wherein the non-natural T cell comprises a nucleic acid molecule encoding a fusion protein according to this disclosure and the binding domain specific for the tag cassette comprises a detectable moiety, and sorting the non-natural T cell expressing a fusion protein from other cells not expressing a fusion protein in the sample.

In certain aspects, the present disclosure is directed to a method for enriching or isolating a T cell, comprising contacting a sample comprising a non-natural T cell with a binding domain specific for a tag cassette, wherein the non-natural T cell comprises a nucleic acid molecule encoding a fusion protein according to this disclosure and the binding domain specific for the tag cassette comprises a detectable moiety, and enriching for or isolating the non-natural T cell expressing a fusion protein away from other cells not expressing a fusion protein in the sample.

In further aspects, the present disclosure is directed to a method for depleting certain T cells, comprising contacting a non-natural T cell with a binding domain specific for a tag cassette, wherein the non-natural T cell comprises a nucleic acid molecule encoding a fusion protein according to this disclosure and wherein binding of the binding domain specific for the tag cassette leads to cell death of the T cells expressing a fusion protein.

These and other aspects of the present disclosure will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A-1H show illustrations of various single chain chimeric effector molecules containing one or more affinity tag cassettes (A-D, referred to herein as a Key-ChEMs), and optionally containing one or more specific binding domains (E G, referred to herein as a T-ChARMs). The single chain ChEMs and ChARMs contain an intracellular domain. The tag cassettes may be any type of affinity tag, such as Strep Tag® II (SEQ ID NO.:1), Myc tag (SEQ ID NO.:7), V5 tag (SEQ ID NO.:8), Flag® tag (SEQ ID NO.:3), His tag, or other peptides or molecules, which are recognized by a non-endogenous cognate binding partner (e.g., receptor, protein, antibody). As shown, a Key-ChEM may contain (A, B) one tag cassette, (C) two tag cassettes (Key-ChEM$^2$), (D) three tag cassettes (Key-ChEM$^3$), or more. In addition, the chimeric molecules may have multiple effector domains (e.g., the molecules of A and C-G have two, while the molecule shown in B has three effector domains), and the tag cassettes may be placed in various different areas of a Key-ChEM or T-ChARM molecule. In these particular examples, T-ChARMs have one tag cassette located between the specific binding domain and the effector domain (E), at the distal end (e.g., amino-terminus) of the specific binding domain (F), integrated within the specific binding domain (G) (e.g., located within the flexible linker between the VH and VL chains of an scFv), and having two different tags—one C-terminal of the binding domain and one N-terminal of the binding domain (H). The T-ChARMs may also have two, three or more tag cassettes as shown for the Key-ChEMs. As is evident in these illustrations, a tag cassette may be connected to another Key-ChEM or T-ChARM component or another tag via a linker module (e.g., a flexible $(Gly_xSer)_n$ linker module). The linker length may be tailored to be longer or shorter to achieve the best interaction of a specific binding domain with a target ligand or antigen, and to achieve the best interaction between the cell expressing the ChEM or T-ChARM and the target cell.

FIGS. 2A-2D show the cytolytic activity of human effector T cells expressing various kinds of anti-CD19 T-ChARMs and conventional anti-C19 CARs (lacking a tag cassette and with short, intermediate, and long spacer domains) against K562 leukemia cells transfected to express CD19 or ROR1 (control), CD19$^+$/ROR1$^+$ Raji lymphoma cells, and EBV transformed B cells that express a membrane bound anti-CD3 mAb single chain antibody (OKT3 scFv) to activate all effector T cells.

FIGS. 3A-3F show the results of a multiplex cytokine assay (Luminex®) of supernatants obtained 24 hours after T cells expressing various anti-CD19 T-ChARMs (A C) and conventional anti-C19 CARs (D F) were co-cultured with K562 cells expressing either CD19 (A and D) or ROR1 (negative control; B and E), and with PMA/ionomycin (positive control; C and F).

FIGS. 6A-6E show that anti-CD19 human T cells expressing either a T-ChARM (containing one, two or three tag cassettes) or conventional CARs (containing short or intermediate connector regions) can eradicate established Raji tumors in NSG mice. In these experiments, the Raji cells are transfected to express the firefly luciferase gene, and tumor growth is measured by injecting the mice with luciferin and bioluminescence imaging.

FIG. 9 shows that T-ChARM expressing T cells can be sorted by flow cytometry from low purity (15% in the example) to high purity (99% in the example) with a tag-specific binding agent linked to a fluorochrome. In the example, the tag is Strep Tag® II and the tag-specific binding agent is anti STII mAb linked to a fluorochrome.

FIGS. 19A-19D show that anti-CD19 T-ChARM¹ T cells that were expanded by stimulation with Strep-Tactin® microbeads retain a comparable or superior ability to produce cytokines (GM-CSF, interferon-γ, IL-2, and TNF-α) upon re-stimulation with CD19 positive tumor cells (A. K562/CD19; B− Raji) as control T cells that express the anti-CD19 CAR (short) (CD19-S). K562 cells (C) and PMA-ionomycin (D) served as negative and positive controls, respectively.

FIGS. 23A and 23B show the cytolytic activity of T cells expressing (A) anti CD19 short, T-ChARM¹, T-ChARM², T-ChARM³ with a CD28/CD3ζ effector domain, and (B) having an anti-ROR1 R12 short and T-ChARM¹ with a 41BB/CD3ζ effector domain. The cells were tested for cytolytic activity against K562 cells transduced with CD19 (K562/CD19), or ROR1 (K562/ROR1) or CD19+ Raji tumor cells (targets). E/T=Effector/target ratio.

FIGS. 27A-27D show FACS sorted EGFR+ anti-CD19 ChARM (A) CD8+ T cells (CD19-Hi/4-1BB, ST-CD19/4-1BB, CD19(VH-ST-VL)/4-1BB; CD19-1ST/4-1BB, CD19-2ST/4-1BB, CD19-3ST/4-1BB CAR); (B) CD4+ T cells (CD19-Hi/4-1BB, ST-CD19/4-1BB, CD19(VH-ST-VL)/4-1BB; CD19-1ST/4-1BB, CD19-2ST/4-1BB, CD19-3 ST/4-

1BB CAR); (C) anti-CD19 ChARM CD8+ T cells (CD19-Hi/CD28, CD19-1ST/CD28, CD19-2ST/CD28, CD19-3ST/CD28 CAR); and (D) anti-ROR1 R12 ChARM T cells (R12-Hi/4-1BB, R12-1ST/4-1BB), which were stimulated with Strep-Tactin® coated microbeads (Strep-Tactin®-MB), anti-Strep Tag® antibody or anti-Strep Tag®/anti-CD28 antibody coated microbeads (αStrep tag-MB and αStrep tag/CD28-MB) in the culture with IL2. After 48 hours of stimulation, the cells were harvested and T cell activation marker CD25 was assessed by flow cytometry. Untreated cells (medium) were used as controls.

Figure 28:
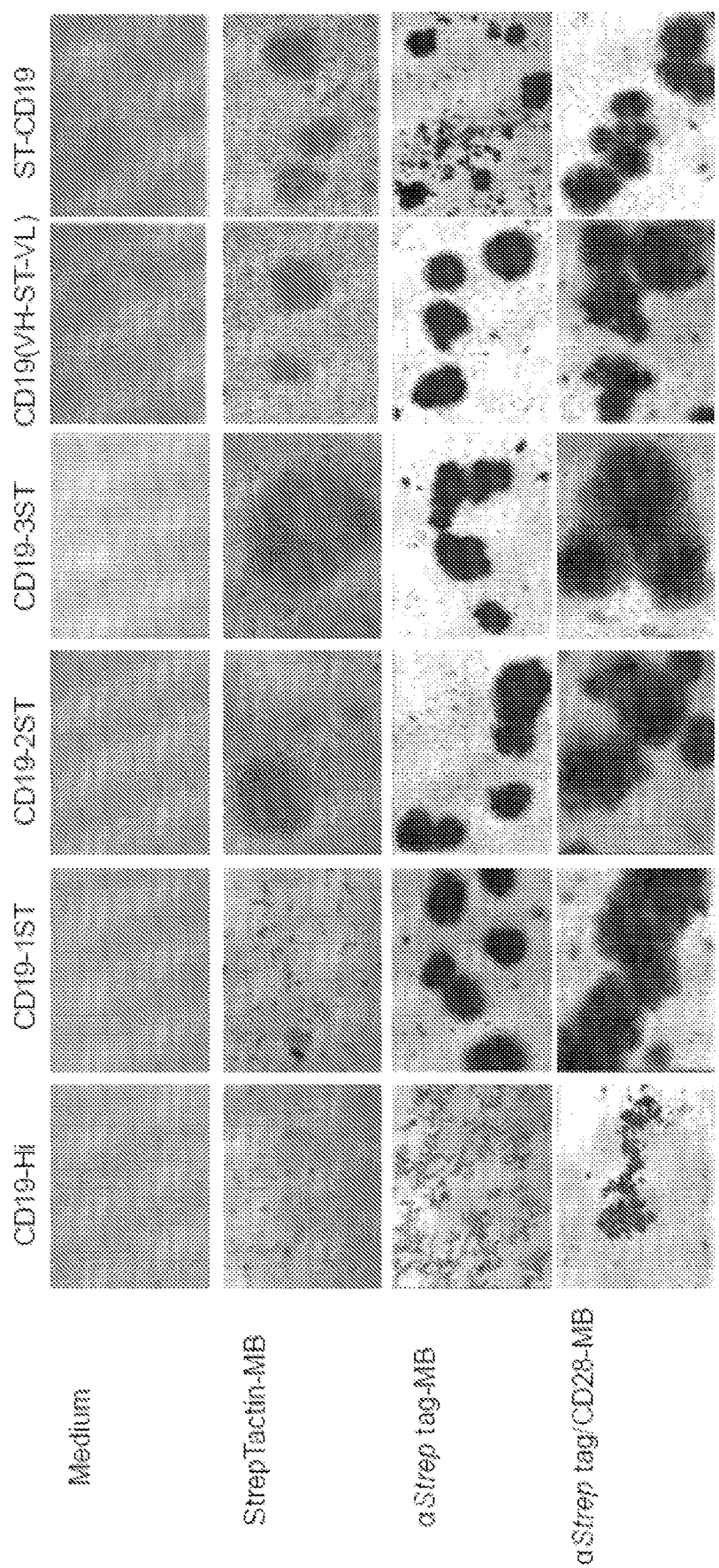

FIG. 28 shows representative microscopic images of FACS sorted EGFR+ anti CD19 4 1BB ChARM T cells (CD8+) that were stimulated with Strep-Tactin®-MB, αStrep tag-MB and αStrep tag/CD28-MB in presence of IL2. Untreated cells (medium) were used as control. Microscopic images were taken after 48 h of stimulation.

Figures 29A, 29B:
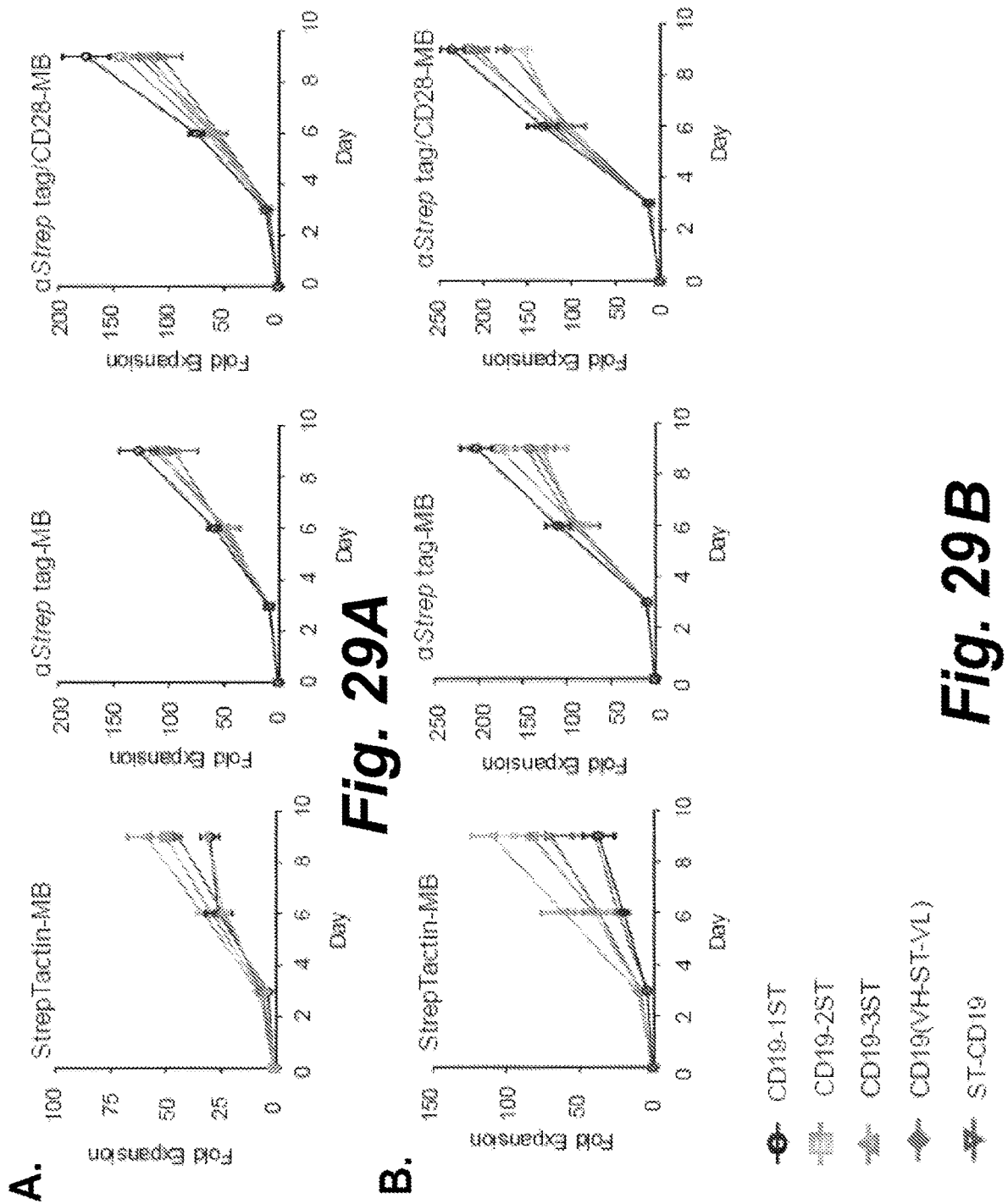

FIGS. 29A and 29B show growth curves of ChARM T cells. FACS sorted EGFR+ anti-CD19 ChARM (A) CD8+ and (B) CD4+ T cells were cultured in CTL medium with Strep-Tactin®-MB, αStrep tag-MB and αStrep tag/CD28-MB in presence of IL2.

FIGS. 30A-30F show anti-CD3/anti-CD28 microbead-stimulated CD8+ T cells transduced with anti-CD19-1ST/4-1BB or CD19-1ST/CD28 CAR; after EGFR staining and sorting, pure CAR T cells were expanded with TM-LCL or αStrep tag-MB or αStrep tag/CD28-MB for 8 days. In vitro functionality tests were carried out to evaluate CAR T cell function before (αCD3/CD28-MB) or after expansion (TM-LCL or αStrep tag-MB or αStrep tag/CD28-MB). (A) chromium release assays were carried out to examine cytolytic effect of ChARM T cells against target cells (K562/CD19) or control cells (K562/ROR1). E/T: Effector/target ratio; (B) cytokine production was measured by ELISA to evaluate IFN-γ and IL2 in supernatants obtained after 24 hours from co-cultures of $5\times10^4$ anti CD19 ChARM T cells with target cells (K562/CD19), or control cells (K562/ROR1). PMA/Ionomycin stimulated T cells were used as positive control. (n=3; *P<0.05); (C) CFSE proliferation assay of ChARM T cells 5 days after stimulation with target cells (K562/CD19) (solid grey), or control cells (K562/ROR1) (grey lines) without addition of exogenous cytokines. For analysis, triplicate wells were pooled and the proliferation of live (PI−), EGFR-positive CAR T cells was analyzed; (D) flow detection of CD45RO, CD62L, CD28 and CD27 expression on the ChARM T cells before (αCD3/CD28-MB) or after expansion (TM-LCL or αStrep tag-MB or αStrep tag/CD28-MB); (E) cohorts of mice were inoculated with Raji-ffluc via tail vein injection at day 1, and then $5\times10^6$ CD8+ ChARM T cells (CD19-Hi/4-1BB and CD19-1ST/4-1BB), which were expanded on either CD19+ B LCL or αStrep tag/CD28-MB were administered 7 days after tumor engraftment. Tumor progression and distribution was evaluated by serial bioluminescence imaging after injection of luciferin substrate; and (F) persistence of anti-CD19 ChARM T cells following adoptive transfer into NSG/Raji mice. Flow cytometric analysis of ChARM T cells in the peripheral blood (eye bleeds) of the cohort of mice treated with various ChARM transduced T cells at different time points after T cell infusion. The frequency of CD8+ tEGFR+ and ChARM+ T cells was used as the percentage of live peripheral blood cells.

Figure 31:
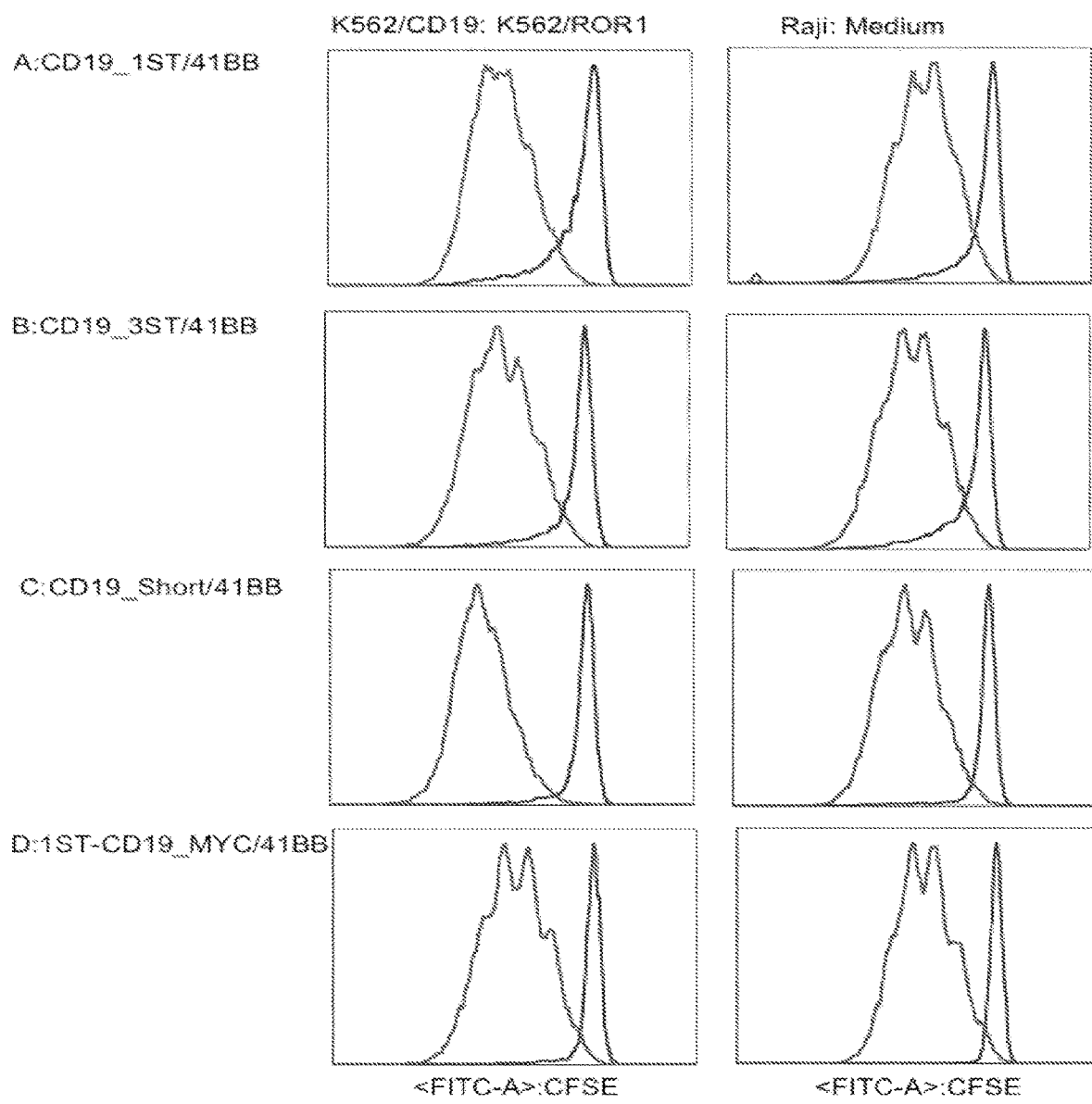

FIG. 31 shows CFSE dye dilution used to measure proliferation of anti CD19 CAR-Short, T-ChARM$^1$, T-ChARM$^3$, and Myc-ChARM with 4 1BB T cells 5 days after stimulation with CD19 (K562/CD19), ROR1 (K562/ROR1), medium alone, or CD19+ Raji tumor cells without addition of exogenous cytokines.

Figure 32:
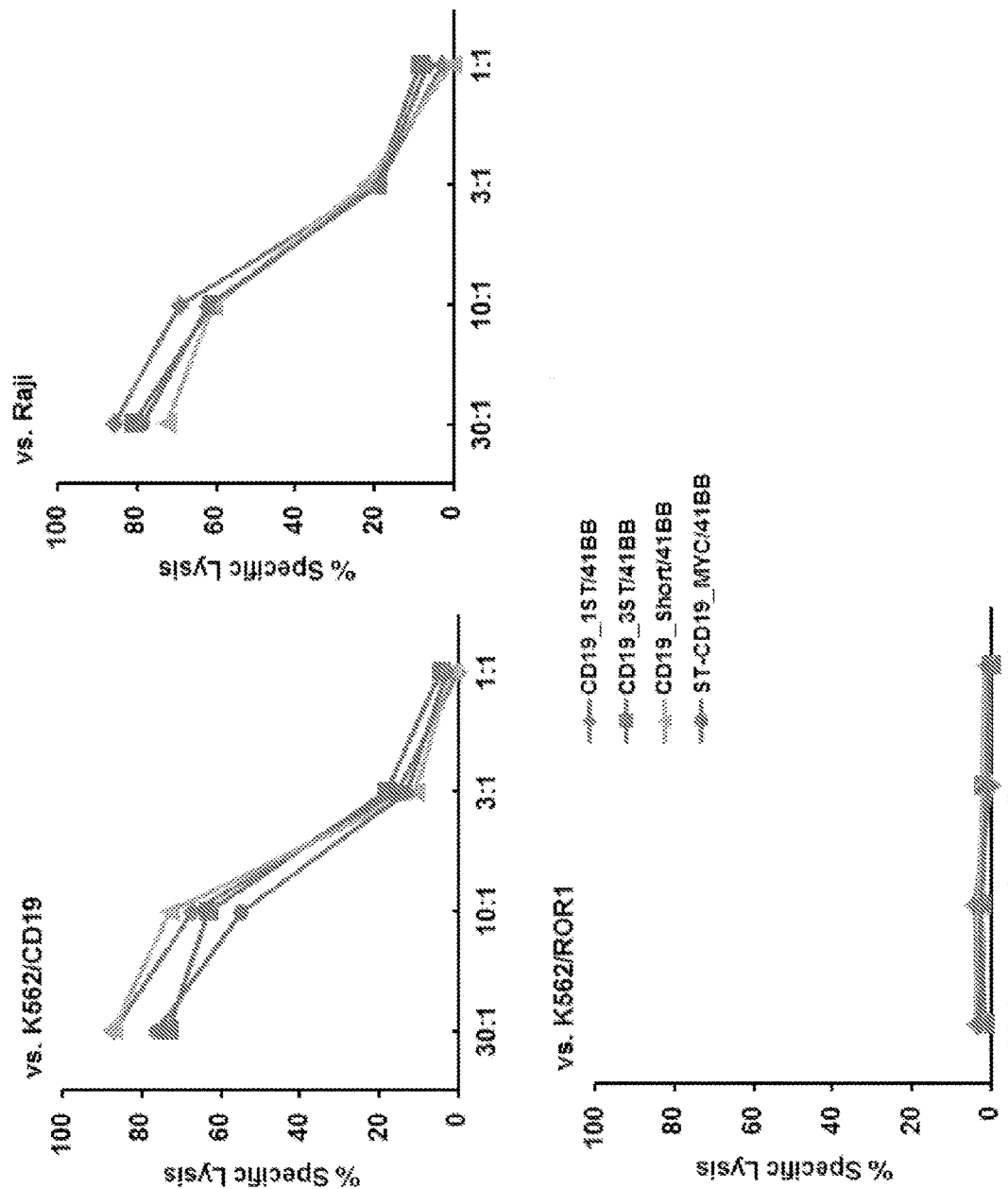

FIG. 32 shows chromium release assays carried out to examine cytolytic effect of anti CD19 CAR-Short, T-ChARM$^1$, T-ChARM$^3$, and Myc-ChARM with 4 1BB T cells against target cells (K562/CD19) or control cells (K562/ROR1). E/T: Effector/target ratio

DETAILED DESCRIPTION

The instant disclosure provides compositions and methods for generating various fusion proteins containing one or more affinity tag cassettes, which are chimeric effector molecules (ChEMs) that function like a "key" to access and manipulate (i.e., turn on or off or modulate) any of a variety of biological pathways. These chimeric effector molecules are referred to herein as a Key-ChEMs. Nucleic acid molecules encoding such fusion proteins can be used to generate modified host cells in which specific cellular responses, such as proliferation or killing, are elicited, controlled, or both. For example, certain types of progenitor cells may be obtained from a subject, modified to express a fusion protein comprising a tag cassette, induced to proliferate, and then infused back into the subject for a particular therapeutic effect (e.g., reconstitute a subject's depleted immune system). Alternatively, such fusion proteins containing a tag may further have a binding domain specific for a particular target (e.g., a tumor antigen). In such examples, these fusion proteins are tagged chimeric antigen receptor molecules (T-ChARMs) that can be introduced into a particular cell and then used to identify, sort, activate, or expand that modified cell. In certain embodiments, such tagged chimeric molecules are transduced into and expressed in cells, such as immune cells (e.g., T cells).

In certain aspects, the present disclosure further provides methods for selectively activating, promoting proliferation, identifying, sorting, enriching, isolating, tracking, or depleting cells (e.g., T cells) comprising a nucleic acid molecule encoding a fusion protein having one or more tag cassettes (Key-ChEMs or T-ChARMs). Additionally, this disclosure provides Key-ChEMs or T-ChARMs, as well as cells, compositions and methods for using the Key-ChEMs or T-ChARMs of this disclosure in various therapeutic applications, including the treatment of a disease in subject (e.g., cancer, infectious disease, inflammatory disease, immune disease, and aging-associated disease).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, module or cassette (e.g., a binding domain, hinge region, linker module, tag cassette) or a protein (which may have one or more domains, regions, modules or cassettes) "consists essentially of" a particular amino acid sequence when the amino acid sequence of a domain, region, module, cassette or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, cassette or protein and do not substantially affect (i.e., do not reduce the activity by more than 50%, such as no more than 40%, 30%, 25%, 20%, 15%, 10%, 5%, or 1%) the activity of the domain(s), region(s), module(s), cassette(s) or protein (e.g., the target binding affinity of a binding protein or tag cassette).

A "binding domain" (also referred to as a "binding region" or "binding moiety"), as used herein, refers to a molecule, such as a peptide, oligopeptide, polypeptide, or protein that possesses the ability to specifically and non-covalently associate, unite, or combine with a target molecule (e.g., CD19, CD20, CD22, ROR1, mesothelin, PD-L1, PD-L2, PSMA). A binding domain includes any naturally occurring, synthetic, semi-synthetic, or recombinantly produced binding partner for a biological molecule or other target of interest. In some embodiments, the binding domain is an antigen-binding domain, such as an antibody or T cell receptor (TCR) or functional binding domain or antigen-binding fragment thereof. Exemplary binding domains include single chain antibody variable regions (e.g., domain antibodies, sFv, scFv, Fab), receptor ectodomains (e.g., TNF-α), ligands (e.g., cytokines, chemokines), antigen-binding regions of T cell receptors (TCRs), such as single chain TCRs (scTCRs), or synthetic polypeptides selected for the specific ability to bind to a biological molecule.

As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., *Ann. N.Y. Acad. Sci.* 51:660, 1949; and U.S. Pat. Nos. 5,283,173, 5,468,614, or the equivalent).

As used herein, "heterologous" or "non-endogenous" or "exogenous" refers to any gene, protein, compound, molecule or activity that is not native to a host cell or a subject, or is any gene, protein, compound, molecule or activity native to a host or host cell but has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a molecule or activity found in or derived from a host cell, species or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species or a combination thereof.

As used herein, the term "endogenous" or "native" refers to a gene, protein, compound, molecule or activity that is normally present in a host or host cell.

As used herein, "tag cassette" refers to a unique peptide sequence affixed to, fused to, or that is part of a protein of interest, to which a heterologous or non-endogenous cognate binding molecule (e.g., receptor, ligand, antibody, or other binding partner) is capable of specifically binding where the binding property can be used to detect, identify, isolate or purify, track, enrich for, or target a tagged protein or cells expressing a tagged protein, particularly when a tagged protein is part of a heterogeneous population of proteins or other material, or when cells expressing a tagged protein are part of a heterogeneous population of cells (e.g., a biological sample like peripheral blood). In certain embodiments, a cell expressing a tagged protein can be contacted with a heterologous or non-endogenous cognate binding molecule and induce a biological response, such as promote cell activation, cell proliferation or cell death. In the provided fusion proteins, the ability of the tag cassette(s) to be specifically bound by the cognate binding molecule(s) is distinct from or in addition to the ability of the binding domain(s) to specifically bind to the target molecule(s). The tag cassette generally is not an antigen-binding molecule, for example, is not an antibody or TCR or an antigen-binding portion thereof.

As used herein, a "hinge region" or a "hinge" refers to (a) an immunoglobulin hinge sequence (made up of, for example, upper and core regions) or a functional fragment or variant thereof, (b) a type II C-lectin interdomain (stalk) region or a functional fragment or variant thereof, or (c) a cluster of differentiation (CD) molecule stalk region or a functional variant thereof. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a hinge region is human, and in particular embodiments, comprises a human IgG hinge region.

As used herein, a "connector region" refers to one or more proteins, polypeptides, oligopeptides, peptides, domains, regions, modules, cassettes, motifs or any combination thereof that join two or more proteins, polypeptides, oligopeptides, peptides, domains, regions, modules, cassettes, motifs or any combination thereof in a fusion protein. For example, a connector region may provide a spacer function to facilitate the interaction of two single chain fusion proteins, or positioning of one or more binding domains, so that the resulting polypeptide structure maintains a specific binding affinity to a target molecule or maintains signaling activity (e.g., effector domain activity) or both. In certain embodiments, a connector region may comprise a "linker module" that is an amino acid sequence having from about to two up to about 500 amino acids, which can provide flexibility and room for conformational movement between two regions, domains, motifs, cassettes or modules connected by a linker. Exemplary linker modules include those having from one to about ten repeats of $Gly_xSer_y$, wherein x and y are independently an integer from 0 to 10 provided that x and y are not both 0 (e.g., $(Gly_4Ser)_2$ (SEQ ID NO: 67), $(Gly_3Ser)_2$ (SEQ ID NO: 68), $Gly_2Ser$, or a combination thereof such as $(Gly_3Ser)_2Gly_2Ser$)(SEQ ID NO: 69). In certain other embodiments, a connector region may have a linker module that comprises one or more immunoglobulin heavy chain constant regions, such as a CH3 alone or a CH2CH3. In further embodiments, a connector region may comprise a hinge region or a tag cassette. Each such connector component is not mutually exclusive. For example, a connector region may comprise a hinge and one or more linker modules, or a connector region may comprise a hinge, one or more linker modules, and one or more tag cassettes. Exemplary connector regions can vary in length, for instance, from about five to about 500 amino acids, or from about ten to about 350 amino acids, or from about 15 to about 100 amino acids, or from about 20 to about 75 amino acids, or from about 25 to about 35 amino acids.

A "hydrophobic portion," as used herein, means any amino acid sequence having a three-dimensional structure that is thermodynamically stable in a cell membrane, and generally ranges in length from about 15 amino acids to about 30 amino acids. The structure of a hydrophobic domain may comprise an alpha helix, a beta barrel, a beta sheet, a beta helix, or any combination thereof.

As used herein, an "effector domain" is an intracellular portion of a fusion protein or receptor that can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response.

A "variable region linker" specifically refers to a five to about 35 amino acid sequence that connects a heavy chain immunoglobulin variable region to a light chain immunoglobulin variable region or connects T cell receptor $V_{\alpha/\beta}$ and $C_{\alpha/\beta}$ chains (e.g., $V_\alpha-C_\alpha$, $V_\beta-C_\beta$, $V_\alpha-V_\beta$) or connects each $V_\alpha-C_\alpha$, $V_\beta-C_\beta$, $V_\alpha-V_\beta$ pair to a hinge or hydrophobic domain, which provides a spacer function and flexibility sufficient for interaction of the two sub binding domains so that the resulting single chain polypeptide retains a specific binding affinity to the same target molecule as an antibody or T cell receptor. In certain embodiments, a variable region linker comprises from about ten to about 30 amino acids or from about 15 to about 25 amino acids. In particular embodiments, a variable region linker peptide comprises from one to ten repeats of $Gly_xSer_y$, wherein x and y are independently an integer from 0 to 10 provided that x and y are not both 0 (e.g., $Gly_4Ser$ (SEQ ID NO: 10), $Gly_3Ser$ (SEQ ID NO: 71), $Gly_2Ser$, or $(Gly_3Ser)_n(Gly_4Ser)_1$ (SEQ ID NO: 72), $(Gly_3Ser)_n(Gly_2Ser)_n$, (SEQ ID NO: 73) $(Gly_3Ser)_n(Gly_4Ser)_n$ (SEQ ID NO: 72), or $(Gly_4Ser)_n$ (SEQ ID NO: 10), wherein n is an integer of 1, 2, 3, 4, 5, 6, 7, 8, 9 or 10) and wherein linked variable regions form a functional immunoglobulin-like binding domain (e.g., scFv, scTCR). Exemplary variable region linkers include those amino acid sequences set forth in SEQ ID NOS.:44, 65-69, and 71-73, and $(Gly_4Ser)_n$ (SEQ ID NO: 10), wherein n is 3, as found in T-ChARM having the amino acid sequence set forth in SEQ ID NO.:57.

"Junction amino acids" or "junction amino acid residues" refer to one or more (e.g., about 2-20) amino acid residues between two adjacent motifs, regions or domains of a polypeptide, such as between a binding domain and an adjacent linker region or between a hydrophobic domain and an adjacent effector domain or on one or both ends of a linker region that links two motifs, regions or domains (e.g., between a linker and an adjacent binding domain and/or between a linker and an adjacent hinge). Junction amino acids may result from the construct design of a fusion protein (e.g., amino acid residues resulting from the use of a restriction enzyme site during the construction of a nucleic acid molecule encoding a fusion protein). For example, a single junction amino acid, asparagine, is encoded by the AAT codon found between the nucleic acid sequence encoding the secretory signal sequence (SEQ ID NO.:63) and the sequence encoding the tag cassette (SEQ ID NO.:38) in the T-ChARM encoded by the nucleic acid sequence set forth in SEQ ID NO.:58. Similarly, an asparagine (N) junction amino acid is found between the flexible linker amino acid sequence of GGSGSG (SEQ ID NO.:65) and the amino acid tag sequence WSHPQFEK (SEQ ID NO.:1) found in the T-ChARM having the amino acid sequence set forth in SEQ ID NO.:54.

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as an antigen-binding portion of an intact antibody that has or retains the capacity to bind a target molecule. A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "$V_L$" and "$V_H$" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

As used herein, "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In certain embodiments, an Fc region portion includes the CH2 and CH3 domains of an IgG, IgA, or IgD antibody or any combination thereof, or the CH3 and CH4 domains of an IgM or IgE antibody and any combination thereof. In other embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an immunoglobulin, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., *Nature* 337:525, 1989). In certain embodiments, an Fc region portion found in fusion proteins of the present disclosure will be capable of mediating one or more of these effector functions, or will lack one or more or all of these activities by way of, for example, one or more mutations known in the art.

In addition, antibodies have a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease,* 3rd Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form.

"Major histocompatibility complex molecules" (MHC molecules) refer to glycoproteins that deliver peptide antigens to a cell surface. MHC class I molecules are heterodimers consisting of a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where peptide: MHC complex is recognized by $CD8^+$ T cells. MHC class II molecules deliver peptides originating in the vesicular system to the cell surface, where they are recognized by $CD4^+$ T cells. An MHC molecule may be from various animal species, including human, mouse, rat, or other mammals.

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

A "hematopoietic progenitor cell" is a cell derived from hematopoietic stem cells or fetal tissue that is capable of further differentiation into mature cells types (e.g., cells of the T cell lineage). In certain embodiments, $CD24^{lo}$ $Lin^-$ $CD117^+$ hematopoietic progenitor cells are useful. As defined herein, hematopoietic progenitor cells may include embryonic stem cells, which are capable of further differentiation to cells of the T cell lineage. Hematopoietic progenitor cells may be from various animal species, including human, mouse, rat, or other mammals. A "thymocyte progenitor cell" or "thymocyte" is a hematopoietic progenitor cell present in the thymus.

"Hematopoietic stem cells" refer to undifferentiated hematopoietic cells that are capable of self-renewal either in vivo, essentially unlimited propagation in vitro, and capable of differentiation to other cell types including cells of the T cell lineage. Hematopoietic stem cells may be isolated, for example, but not limited to, from fetal liver, bone marrow, cord blood.

"Embryonic stem cells" or "ES cells" or "ESCs" refer to undifferentiated embryonic stem cells that have the ability to integrate into and become part of the germ line of a developing embryo. Embryonic stem cells are capable of differentiating into hematopoietic progenitor cells, and any tissue or organ. Embryonic stem cells that are suitable for use herein include cells from the J1 ES cell line, 129J ES cell line, murine stem cell line D3 (American Type Culture Collection), the R1 or E14K cell lines derived from 129/Sv mice, cell lines derived from Balb/c and C57Bl/6 mice, and human embryonic stem cells (e.g. from WiCell Research Institute, WI; or ES cell International, Melbourne, Australia).

"Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+$ $CD8^+$ double positive; single positive $CD4^+$ or $CD8+$; TCRαβ or TCR γδ; or mature and functional or activated T cells.

"Nucleic acid molecule", or polynucleotides, may be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Treat" or "treatment" or "ameliorate" refers to medical management of a disease, disorder, or condition of a subject (e.g., a human or non-human mammal, such as a primate, horse, dog, mouse, rat). In general, an appropriate dose or treatment regimen comprising a host cell expressing a Key-ChEM or T-ChARM of this disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a fusion protein or cell expressing a fusion protein of this disclosure (e.g., Key-ChEM, T-ChARM) refers to that amount of compound or cells sufficient to result in amelioration of one or more symptoms of the disease being treated in a statistically significant manner. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously. Another combination may be a cell expressing more than one active ingredient, such as two different T-ChARMs, a T-ChARM and a TCR, a T-ChARM and a CAR, or combinations thereof.

Additional definitions are provided throughout the present disclosure.

Key-ChEMs and T-ChARMs

In certain aspects, the present disclosure provides a single chain fusion protein, referred to as a Key-ChEM, which comprises an extracellular component and an intracellular component connected by a hydrophobic portion, wherein the extracellular component comprises a tag cassette and a connector region comprising a hinge, and wherein the intracellular component comprises an effector domain. In certain embodiments, a connector region further comprises a linker module, or one or more tag cassettes are located within the connector region. In certain other embodiments, one or more tag cassettes are linked to the connector region by a linker module.

In further Key-ChEM embodiments, the fusion protein comprises from amino-terminus to carboxy-terminus: a tag cassette, a connector region comprising a hinge, a hydrophobic portion, and an intracellular component comprising an effector domain (see, e.g., FIGS. 1A and 1B). In still further Key-ChEM embodiments, the fusion protein comprises from amino-terminus to carboxy-terminus: a first connector region, a tag cassette, a second connector region comprising a hinge, a hydrophobic portion, and an intracellular component comprising an effector domain. In yet further Key-ChEM embodiments, the fusion protein comprises from amino-terminus to carboxy-terminus: a first tag cassette, a first connector region, a second tag cassette, a second connector region comprising a hinge, a hydrophobic portion, and an intracellular component comprising an effector domain (see, e.g., FIG. 1C). In even further Key-ChEM embodiments, the fusion protein comprises from amino-terminus to carboxy-terminus: a first tag cassette, a first connector region, a second tag cassette, a second connector region, a third tag cassette, a third connector region comprising a hinge, a hydrophobic portion, and an intracellular component comprising an effector domain (see, e.g., FIG. 1D).

In certain other Key-ChEM embodiments, the fusion protein further comprises a non-covalently associated binding domain, such as a binding domain associated with the tag cassette (i.e., a multichain T-ChARM). In still other Key-ChEM embodiments, the non-covalently associated binding domain is bi-specific, wherein the first binding end is specific for the tag cassette and the second binding end is specific for a target other than the tag cassette, or the first and second binding ends are both specific for the tag cassette. In yet other Key-ChEM embodiments, the non-covalently associated binding domain is multispecific, wherein a first end binds to a tag cassette and a second end is specific for one or more targets other than the tag cassette. In such embodiments, a Key-ChEM comprises a multimer protein. In some embodiments, such Key-ChEMs comprising one or more non-covalently associated binding domains comprise heteromultimers.

In other aspects, the present disclosure provides a single chain fusion protein, referred to as a T-ChARM, which comprises an extracellular component and an intracellular component connected by a hydrophobic portion, wherein the extracellular component comprises a binding domain that specifically binds a target, a tag cassette, and a connector region comprising a hinge, and wherein the intracellular component comprises an effector domain. In certain embodiments, a T-ChARM binding domain is a scFv, scTCR, receptor ectodomain, or ligand.

In further T-ChARM embodiments, the fusion protein comprises from amino-terminus to carboxy-terminus: an extracellular binding domain, a tag cassette, a connector region comprising a hinge, a hydrophobic portion, and an intracellular component comprising an effector domain (see, e.g., FIG. 1E). In still further T-ChARM embodiments, the fusion protein comprises from amino-terminus to carboxy-terminus: an extracellular binding domain, a first connector region, a tag cassette, a second connector region comprising a hinge, a hydrophobic portion, and an intracellular component comprising an effector domain. In yet further T-ChARM embodiments, the fusion protein comprises from amino-terminus to carboxy-terminus: an extracellular binding domain, a first tag cassette, a first connector region, a second tag cassette, a second connector region comprising a hinge, a hydrophobic portion, and an intracellular component comprising an effector domain. In even further T-ChARM embodiments, the fusion protein comprises from amino-terminus to carboxy-terminus: an extracellular binding domain, a first tag cassette, a first connector region, a second tag cassette, a second connector region, a third tag cassette, a third connector region comprising a hinge, a hydrophobic portion, and an intracellular component comprising an effector domain.

In certain other T-ChARM embodiments, the fusion protein comprises from amino-terminus to carboxy-terminus: a tag cassette, an extracellular binding domain, a connector region comprising a hinge, a hydrophobic portion, and an intracellular component comprising an effector domain (see, e.g., FIG. 1F). In still other T-ChARM embodiments, the fusion protein comprises from amino-terminus to carboxy-terminus: an extracellular scFv or scTCR binding domain comprising a variable region linker containing a tag cassette disposed between the variable regions (e.g., at or closer to the N-terminal end of the variable region linker, at or closer to the C-terminal end of the variable region linker, or imbedded closer to the middle of the variable region linker), a connector region comprising a hinge, a hydrophobic portion, and an intracellular component comprising an effector domain. An exemplary tag cassette imbedded in a variable region linker comprises GGSGS-G(X)$_n$WSHPQFEKGSGSG (SEQ ID NO.:45), wherein X is optional, may be any amino acid and n is 0, 1, 2, 3, 4 or 5. In SEQ ID NO.:54, such a variable region linker having an imbedded tag is present, wherein n is 1 and X is asparagine (N).

A Key-ChEM or T-ChARM may be cell-bound (e.g., expressed on a cell surface) or in soluble form. In certain embodiments, nucleic acid molecules encoding Key-ChEM or T-ChARM fusion proteins may be codon optimized to enhance or maximize expression in certain types of cells, such as T cells (Scholten et al., *Clin. Immunol.* 119:135, 2006).

In other embodiments, Key-ChEM or T-ChARM may further comprise a cytotoxic component (e.g., chemotherapeutic drugs such as anti-mitotics (e.g., vindesine), antifolates, alkylating agents (e.g., temozolomide), bacterial toxins, ricin, anti-virals, radioisotopes, radiometals), which is useful for specific killing or disabling a cancer cell, infected cell or other diseased cell. In further embodiments, Key-ChEM or T-ChARM may further comprise a detectable component (e.g., biotin, fluorescent moiety, radionuclide), which is useful for tracking or imaging cancer cells, infected cells, or other tissues (e.g., tissue under autoimmune attack). In still further embodiments, Key-ChEM or T-ChARM may further comprise a functional component (e.g., an immunostimulatory moiety, cytokine, immune modulator, immunoglobulin protein, or the like).

Component parts of the fusion proteins of the present disclosure are further described in detail herein.

Tag Cassette

A tag cassette contained in a single chain fusion protein according to the present disclosure (e.g., Key-ChEM or T-ChARM) will be an extracellular component that can specifically bind to a cognate receptor or binding partner (e.g., antibody) with high affinity or avidity, wherein the cognate receptor or binding partner is heterologous or non-endogenous to a host or a cell expressing a Key-ChEM or T-ChARM. Within a single chain fusion protein structure, a tag cassette may be located (a) immediately amino terminal to a connector region, (b) interposed between and connecting linker modules, (c) immediately carboxy-terminal to a binding domain, (d) interposed between and connecting a binding domain (e.g., scFv) to an effector domain, (e) interposed between and connecting subunits of a binding domain, or (f) at the amino-terminus of a single chain fusion protein of this disclosure. In certain embodiments, one or more junction amino acids may be disposed between and connecting a tag cassette with a hydrophobic portion, or disposed between and connecting a tag cassette with a connector region, or disposed between and connecting a tag cassette with a linker module, or disposed between and connecting a tag cassette with a binding domain.

Exemplary tag cassettes include Strep Tag® (which refers the original Strep Tag®, Strep Tag® II, or any variant thereof; see, e.g., U.S. Pat. No. 7,981,632, which Strep tags are incorporated herein by reference), His tag, Flag® tag (SEQ ID NO.:3), Xpress tag (SEQ ID NO.:4), Avitag™ (SEQ ID NO.:5), Calmodulin tag (SEQ ID NO.:19), Polyglutamate tag, HA tag (SEQ ID NO.:6), Myc tag (SEQ ID NO.:7), Nus tag, S tag, SBP tag, SofTag® 1 (SEQ ID NO.:9), SofTag® 3 (SEQ ID NO.:32), V5 tag (SEQ ID NO.:8), CREB-binding protein (CBP), glutathione S-transferase (GST), maltose binding protein (MBP), green fluorescent protein (GFP), Thioredoxin tag, or any combination thereof. In certain embodiments, a tag cassette is a Strep Tag® having an amino acid sequence of Trp-Ser-His-Pro-Gln-Phe-Glu-Lys (SEQ ID NO.:1) or Trp-Arg-His-Pro-Gln-Phe-Gly-Gly (SEQ ID NO.:2). In other embodiments, a tag cassette may be a genetically engineered affinity site, such as a minimal chelation site (e.g., HGGHHG, SEQ ID NO.:33)

Tag cassettes may be present in multiple copies in fusion proteins of this disclosure. For example, a fusion protein of this disclosure can have one, two, three, four or five tag cassettes (e.g., Strep Tag®). In certain embodiments, a connector region of a Key-ChEM or T-ChARM includes one tag cassette, two tag cassettes, three tag cassettes, four tag cassettes, or five tag cassettes. Each of the plurality of tag cassettes may be the same or different. Exemplary embodiments include a Key-ChEM or T-ChARM having a Strep Tag® and a Strep Tag® cassette, or a His tag and a Strep Tag® cassette, or a HA tag and a Strep Tag® cassette, or a Myc tag and a Strep Tag® cassette. Alternatively, a Key-ChEM or T-ChARM will have multiple tag cassettes of the same type or same amino acid sequence, such as two, three, four or five Strep Tag® cassettes (e.g., Strep Tag® II).

For example, a Key-ChEM or T-ChARM may have at least two different tag cassettes. In some embodiments, a first tag cassette can provide a stimulation signal and a distinct second tag cassette might be used to associate with a detection reagent or associate with an antibody-toxin conjugate or with an antibody-imaging agent conjugate. In further embodiments, the two or more first tag cassettes may be located in different areas of a Key-ChEM or T-ChARM. In certain embodiments, a first tag cassette is located in the connector region and a second tag cassette is located at the amino-terminus or carboxy terminus or both of a Key-ChEM or T-ChARM (see, e.g., FIG. 1H).

In certain embodiments, a tag cassette comprises from about five to about 500 amino acids, or from about six to about 100 amino acids, or from about seven to about 50 amino acids, or from about eight to about 20 amino acids. In some embodiments, a tag cassette has seven to ten amino acids. Preferably, a tag cassette is non-immunogenic or minimally immunogenic. Essentially, a tag cassette can function as a handle or beacon to allow for the identification, enrichment, isolation, promotion of proliferation, activation, tracking, or elimination of cells expressing a Key-ChEM or T-ChARM.

In certain embodiments, a tag cassette is located within a connector region of a fusion protein of this disclosure. For example, a connector region may further comprise a linker module adjacent to a tag cassette, wherein the linker module with the tag cassette has an amino acid sequence of (Gly-Gly-Gly-Gly-Ser)$_2$-Trp-Ser-His-Pro-Gln-Phe-Glu-Lys (SEQ ID NO.:20), Trp-Ser-His-Pro-Gln-Phe-Glu-Lys-(Gly-Gly-Gly-Gly-Ser)$_2$ (SEQ ID NO.:21), (Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys (SEQ ID NO.:22), Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys-(Gly-Gly-Gly-Gly-Ser)$_2$ (SEQ ID NO.:23), (Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys-(Gly-Gly-Gly-Gly-Ser)$_2$-Trp-Ser-His-Pro-Gln-Phe-Glu-Lys (SEQ ID NO.:24), or Trp-Ser-His-Pro-Gln-Phe-Glu-Lys-(Gly-Gly-Gly-Gly-Ser)$_2$-Trp-Ser-His-Pro-Gln-Phe-Glu-Lys-(Gly-Gly-Gly-Ser)$_2$-Gly-Gly-Ser-Trp-Ser-His-Pro-Gln-Phe-Glu-Lys-(Gly-Gly-Gly-Gly-Ser)$_2$ (SEQ ID NO.:25).

A single chain fusion protein comprising one or more tag cassettes as described herein will be capable of associating with a cognate binding partner, wherein the cognate binding partner is heterologous to the host or cell expressing a fusion protein comprising a tag cassette as described herein. In certain embodiments, a tag cassette present in a single chain Key-ChEM or T-ChARM of this disclosure is a Strep Tag®, which has streptavidin, Strep-Tactin® (streptavidin mutein with improved binding capabilities compared to streptavidin), or both as a cognate binding partner, or is recognized by antibodies specific for a Strep Tag®. In certain embodiments, the cognate binding partner (e.g., receptor, protein, antibody) may be soluble, part of a matrix composition, or conjugated to a solid surface (e.g., plate, bead). Exemplary solid surfaces include beads and particles (e.g., micro and nano), such as magnetic beads and particles.

In single chain T-ChARM fusion protein embodiments, a protein complex can form between a fusion protein and a cognate tag cassette binding partner, which is a result of binding between the tag cassette and the binding partner. In certain embodiments, a T-ChARM comprises a scFv or scTCR binding domain where the tag cassette is located within the variable region linker (between the binding domain subunits). In other embodiments, a T-ChARM has a tag cassette located at the amino-terminus of the binding domain. In such protein complexes or fusion protein structures, a T-ChARM binding domain will retain its target specificity or its specific target binding affinity.

Connector Region and Hinge

A connector region comprising a hinge in a single chain fusion protein according to the present disclosure may be located (a) immediately amino-terminal to a hydrophobic portion, (b) interposed between and connecting a tag cassette (e.g., Strep Tag®) and an effector domain, (c) immediately carboxy-terminal to a binding domain, or (d) interposed between and connecting a linker module and an effector domain. A single chain fusion protein comprising a connector region with a hinge as described herein will be capable of associating with another single chain fusion protein to form a dimer (e.g., homodimer or heterodimer), wherein a Key-ChEM or T-ChARM dimer will contain one or more tag cassettes capable of binding a cognate binding partner, and a T-ChARM dimer will further comprise a binding domain that retains its target specificity or its specific target binding affinity.

A connector region can be comprised of a hinge only, linker modules only, a hinge and linker modules, or a hinge, one or more linker modules and one or more tag cassettes. In certain embodiments, linker modules include from about two to about 20 amino acids that form a flexible structure. Exemplary linker modules include an immunoglobulin CH2CH3, an immunoglobulin CH3, or one or more Gly$_x$Ser$_y$, wherein x and y are independently an integer from 0 to 10 provided that x and y are not both 0 (e.g., (Gly$_4$Ser)$_2$ (SEQ ID NO: 67), (Gly$_3$Ser)$_2$ (SEQ ID NO: 68), Gly$_2$Ser, or a combination thereof such as (Gly$_3$Ser)$_2$Gly$_2$Ser) (SEQ ID NO: 69). In further embodiments, a connector region comprises a tag cassette. For example, a connector region contains from one to five tag cassettes, wherein each tag cassette is connected to one or two linker modules comprising a (Gly$_x$Ser$_y$)$_n$, wherein n is an integer from 1 to 10, and x and y are independently an integer from 0 to 10 provided that x and y are not both 0. Exemplary linker modules have an amino acid sequence of Gly-Gly-Gly-Gly-Ser (SEQ ID NO.:10), (Gly-Gly-Gly-Gly-Ser)$_2$ (SEQ ID NO.:11), (Gly-Gly-Gly-Ser)$_2$-Gly-Gly-Ser (SEQ ID NO.:12), which may be present in any combination within a connector region.

In certain embodiments, a hinge present in a single chain Key-ChEM or T-ChARM of this disclosure may be an immunoglobulin hinge region, such as a wild type immunoglobulin hinge region or an altered immunoglobulin hinge region thereof. In certain embodiments, a hinge is a wild type human immunoglobulin hinge region. In certain other embodiments, one or more amino acid residues may be added at the amino- or carboxy-terminus of a wild type immunoglobulin hinge region as part of a fusion protein construct design. For example, one, two or three additional junction amino acid residues may be present at the hinge amino-terminus or carboxy-terminus, or a hinge may contain a terminal or internal deletion and have added back one, two or three additional junction amino acid residues.

In certain embodiments, a hinge is an altered immunoglobulin hinge in which one or more cysteine residues in a wild type immunoglobulin hinge region is substituted with one or more other amino acid residues. Exemplary altered immunoglobulin hinges include an immunoglobulin human IgG1, IgG2 or IgG4 hinge region having one, two or three cysteine residues found in a wild type human IgG1, IgG2 or IgG4 hinge substituted by one, two or three different amino acid residues (e.g., serine or alanine). In certain embodiments, a hinge polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to a wild type immunoglobulin hinge region, such as a wild type human IgG1 hinge, a wild type human IgG2 hinge, or a wild type human IgG4 hinge.

In further embodiments, a hinge present in a single chain Key-ChEM or T-ChARM of this disclosure may be a hinge that is not based on or derived from an immunoglobulin hinge (i.e., not a wild type immunoglobulin hinge or an altered immunoglobulin hinge). Examples of such hinges include peptides of about five to about 150 amino acids of the stalk region of type II C lectins or CD molecules, including peptides of about eight to about 25 amino acids or peptides of about seven to about 18 amino acids, or variants thereof.

A "stalk region" of a type II C-lectin or CD molecule refers to the portion of the extracellular domain of the type II C-lectin or CD molecule that is located between the C type lectin-like domain (CTLD; e.g., similar to CTLD of natural killer cell receptors) and the hydrophobic portion (transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule comprises amino acid residues 34-60, which are located between the hydrophobic portion (transmembrane domain) and CTLD (see Boyington et al., *Immunity* 10:75, 1999; for descriptions of other stalk regions, see also Beavil et al., *Proc. Nat'l. Acad. Sci.* USA 89:753, 1992; and Figdor et al., *Nat. Rev. Immunol.* 2:77, 2002). These type II C-lectin or CD molecules may also have junction amino acids between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an extracellular domain ranging from amino acids 94-233. The CTLD comprises amino acids 119-231, and the stalk region comprises amino acids 99 116, which may be flanked by additional junction amino acids. Other type II C-lectin or CD molecules, as well as their extracellular ligand-binding domains, stalk regions, and CTLDs are known in the art (see, e.g., GenBank Accession Nos. NP_001993.2; AAH07037.1; NP_001773.1; AAL65234.1; CAA04925.1; for the sequences of human CD23, CD69, CD72, NKG2A and NKG2D and their descriptions, respectively).

A "derivative" of a stalk region hinge, or fragment thereof, of a type II C-lectin or CD molecule includes about an eight to about 150 amino acid sequence in which one, two, or three amino acids of the stalk region of a wild type type II C-lectin or CD molecule have a deletion, insertion, substitution, or any combination thereof. For instance, a derivative can comprise one or more amino acid substitutions and/or an amino acid deletion. In certain embodiments, a derivative of a stalk region is more resistant to proteolytic cleavage as compared to the wild-type stalk region sequence, such as those derived from about eight to about 20 amino acids of NKG2A, NKG2D, CD23, CD64, CD72, or CD94.

In certain embodiments, stalk region hinges may comprise from about seven to about 18 amino acids and can form an α-helical coiled coil structure. In certain embodiments, stalk region hinges contain 0, 1, 2, 3, or 4 cysteines. Exemplary stalk region hinges include fragments of the stalk regions, such as those portions comprising from about ten to about 150 amino acids from the stalk regions of CD69, CD72, CD94, NKG2A and NKG2D.

Alternative hinges that can be used in single chain Key-ChEMs or T-ChARMs of this disclosure are from portions of cell surface receptors (interdomain regions) that connect immunoglobulin V-like or immunoglobulin C-like domains. Regions between Ig V-like domains where the cell surface receptor contains multiple Ig V-like domains in tandem and between Ig C-like domains where the cell surface receptor contains multiple tandem Ig C-like regions are also contemplated as hinges useful in single chain Key-ChEMs or T-ChARMs of this disclosure. In certain embodiments, hinge sequences comprised of cell surface receptor interdomain regions may further contain a naturally occurring or added motif, such as an IgG core hinge sequence to provide one or more disulfide bonds to stabilize the Key-ChEM or T-ChARM dimer formation. Examples of hinges include interdomain regions between the Ig V-like and Ig C-like regions of CD2, CD4, CD22, CD33, CD48, CD58, CD66, CD80, CD86, CD150, CD166, or CD244.

In certain embodiments, hinge sequences have from about 5 to about 150 amino acids, about 5 to about 10 amino acids, about 10 to about 20 amino acids, about 20 to about 30 amino acids, about 30 to about 40 amino acids, about 40 to about 50 amino acids, about 50 to about 60 amino acids, about 5 to about 60 amino acids, about 5 to about 40 amino acids, for instance, about 8 to about 20 amino acids or about 10 to about 15 amino acids. The hinges may be primarily flexible, but may also provide more rigid characteristics or may contain primarily α-helical structure with minimal β-sheet structure.

In certain embodiments, a hinge sequence is stable in plasma and serum, and is resistant to proteolytic cleavage. For example, the first lysine in an IgG1 upper hinge region may be mutated or deleted to minimize proteolytic cleavage, and hinges may include junction amino acids. In some embodiments, a hinge sequence may contain a naturally occurring or added motif, such as an immunoglobulin hinge core structure CPPCP (SEQ ID NO.:26) that confers the capacity to form a disulfide bond or multiple disulfide bonds to stabilize dimer formation.

Hydrophobic Portion

A hydrophobic portion contained in a single chain fusion protein of the present disclosure (e.g., Key-ChEM or T-ChARM) will allow a fusion protein of this disclosure to associate with a cellular membrane such that a portion of the fusion protein will be located extracellularly (e.g., tag cassette, connector domain, binding domain) and a portion will be located intracellularly (e.g., effector domain). A hydrophobic portion will generally be disposed within the cellular membrane phospholipid bilayer. In certain embodiments, one or more junction amino acids may be disposed between and connecting a hydrophobic portion with an effector domain, or disposed between and connecting a hydrophobic portion with a connector region, or disposed between and connecting a hydrophobic portion with a tag cassette.

In certain embodiments, a hydrophobic domain is a transmembrane domain, such as one derived from an integral membrane protein (e.g., receptor, cluster of differentiation (CD) molecule, enzyme, transporter, cell adhesion molecule, or the like). In particular embodiments, a hydrophobic portion is a transmembrane domain from CD4, CD8, CD27, or CD28. In certain embodiments, a transmembrane domain is a CD28 transmembrane domain having an amino acid as set forth in SEQ ID NO.:16.

Effector Domain

An effector domain contained in a single chain fusion protein of the present disclosure (e.g., Key-ChEM or T-ChARM) will be an intracellular component and capable of transmitting functional signals to a cell. In certain embodiments, a single chain Key-ChEM or T-ChARM will dimerize with a second single chain Key-ChEM or T-ChARM, respectively, wherein the dimerization allows the intracellular component comprising an effector domains to be in close proximity and promote signal transduction when exposed to the proper signal. In addition to forming such dimer protein complexes, the effector domains may further associate with other signaling factors, such as costimulatory factors, to form multiprotein complexes that produce an intracellular signal. In certain embodiments, an effector domain will indirectly promote a cellular response by associating with one or more other proteins that directly promote a cellular response. An effector domain may include one, two, three or more receptor signaling domains, costimulatory domains, or combinations thereof. Any intracellular component comprising an effector domain, costimulatory domain or both from any of a variety of signaling molecules (e.g., signal transduction receptors) may be used in the fusion proteins of this disclosure.

An effector domain useful in the fusion proteins of this disclosure may be from a protein of a Wnt signaling pathway (e.g., LRP, Ryk, ROR2), NOTCH signaling pathway (e.g., NOTCH1, NTOCH2, NOTCH3, NOTCH4), Hedgehog signaling pathway (e.g., PTCH, SMO), receptor tyrosine kinases (RTKs) (e.g., epidermal growth factor (EGF) receptor family, fibroblast growth factor (FGF) receptor family, hepatocyte growth factor (HGF) receptor family, Insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, muscle specific kinase (MuSK) receptor family); G protein-coupled receptors, GPCRs (Frizzled, Smoothened); serine/threonine kinase receptors (BMPR, TGFR); or cytokine receptors (IL1R, IL2R, IL7R, IL15R).

In certain embodiments, an effector domain comprises a lymphocyte receptor signaling domain or comprises an amino acid sequences having one or a plurality of immunoreceptor tyrosine-based activation motifs (ITAMs). In still further embodiments, an effector domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

Exemplary effector domains include those from 4-1BB (e.g., SEQ ID NO.:17), CD3ε, CD3δ, CD3ζ (e.g., SEQ ID NO.:18), CD27, CD28 (e.g., SEQ ID NO.:35), CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.

In particular embodiments, an effector domain of a Key-ChEM or T-ChARM of the instant disclosure is CD3ζ and CD28, is CD3ζ and 4-1BB, or is CD3ζ, CD28 and 4-1BB.

Binding Domain

As described herein, a T-ChARM single chain fusion protein of the present disclosure comprises a binding domain that specifically binds a target. Binding of a target by the binding domain may block the interaction between the target (e.g., a receptor or a ligand) and another molecule and, for example, interfere, reduce or eliminate certain functions of the target (e.g., signal transduction), or the binding of a target may induce certain biological pathways or identify the target for elimination.

A binding domain may be any peptide that specifically binds a target of interest. Sources of binding domains include antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci.* (USA) 95:11804, 1998), spotted ratfish (Nguyen et al., *Immunogen.* 54:39, 2002), or lamprey (Herrin et al., *Proc. Nat'l. Acad. Sci.* (USA) 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of binding domains of this disclosure includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:43 5, 2005 and Hackel et al. (2008) *J. Mol. Biol.* 381:1238-1252), cysteine-knot miniproteins (Vita et al. (1995) *Proc. Nat'l. Acad. Sci.* (USA) 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., *Proc. Nat'l. Acad. Sci.* (USA) 96:1898, 1999 and Schonfeld et al., *Proc. Nat'l. Acad. Sci.* (USA) 106:8198, 2009), V-like domains (see, e.g., US Patent Application Publication No. 2007/006543 1), C-type lectin domains (Zelensky and Gready, *FEBS J.* 272:6179, 2005; Beavil et al., *Proc. Nat'l. Acad. Sci.* (USA) 89:753, 1992 and Sato et al., *Proc. Nat'l. Acad. Sci.* (USA) 100:7779, 2003), mAb² or Fcab™ (see, e.g., PCT Patent Application Publication Nos. WO 2007/098934; WO 2006/072620), armadillo repeat proteins (see, e.g., Madhurantakam et al., *Protein Sci.* 21: 1015, 2012; PCT Patent Application Publication No. WO 2009/040338), affilin (Ebersbach et al., *J. Mol. Biol.* 372: 172, 2007), affibody, avimers, knottins, fynomers, atrimers, cytotoxic T-lymphocyte associated protein-4 (Weidle et al., *Cancer Gen. Proteo.* 10:155, 2013) or the like (Nord et al., *Protein Eng.* 8:601, 1995; Nord et al., *Nat. Biotechnol.* 15:772, 1997; Nord et al., *Euro. J. Biochem.* 268:4269, 2001; Binz et al., *Nat. Biotechnol.* 23:1257, 2005; Boersma and Plickthun, *Curr. Opin. Biotechnol.* 22:849, 2011).

Binding domains of this disclosure can be generated as described herein or by a variety of methods known in the art (see, e.g., U.S. Pat. Nos. 6,291,161 and 6,291,158). For example, binding domains of this disclosure may be identified by screening a Fab phage library for Fab fragments that specifically bind to a target of interest (see Hoet et al., *Nat. Biotechnol.* 23:344, 2005). Additionally, traditional strategies for hybridoma development using a target of interest as an immunogen in convenient systems (e.g., mice, HuMAb Mouse®, TC Mouse™, KM-Mouse®, llamas, chicken, rats, hamsters, rabbits, etc.) can be used to develop binding domains of this disclosure.

In some embodiments, a binding domain is a single chain Fv fragment (scFv) that comprises $V_H$ and $V_L$ regions specific for a target of interest. In certain embodiments, the $V_H$ and $V_L$ regions are human. Exemplary $V_H$ and $V_L$ regions include the segments of anti CD19 specific monoclonal antibody FMC63 (see, e.g., SEQ ID NOS.:51 and 52, respectively).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region ($V_L$) (e.g., from FMC63, SEQ ID NO.:52; from R12, SEQ ID NO.:56) or to a heavy chain variable region ($V_H$) (e.g., from FMC63, SEQ ID NO.:51; from R12, SEQ ID NO.:55), or both, wherein each CDR comprises zero changes or at most one, two, or three changes, from a monoclonal antibody or fragment or derivative thereof that specifically binds to target of interest (e.g., CD19, ROR1).

In certain embodiments, a binding domain $V_H$ region of the present disclosure can be derived from or based on a $V_H$ of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ of a known monoclonal antibody. An insertion, deletion or substitution may be anywhere in the $V_H$ region, including at the amino- or carboxy-terminus or both ends of this region, provided that each CDR comprises zero changes or at most one, two, or three changes and provided a binding domain containing the modified $V_H$ region can still specifically bind its target with an affinity similar to the wild type binding domain.

In further embodiments, a $V_L$ region in a binding domain of the present disclosure is derived from or based on a $V_L$ of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the $V_L$ of the known monoclonal antibody. An insertion, deletion or substitution may be anywhere in the $V_L$ region, including at the amino- or carboxy-terminus or both ends of this region, provided that each CDR comprises zero changes or at most one, two, or three changes and provided a binding domain containing the modified $V_L$ region can still specifically bind its target with an affinity similar to the wild type binding domain.

The $V_H$ and $V_L$ domains may be arranged in either orientation (i.e., from amino-terminus to carboxyl terminus, $V_H$-$V_L$ or $V_L$-$V_H$) and may be joined by an amino acid sequence (e.g., having a length of about five to about 35 amino acids) capable of providing a spacer function such that the two sub-binding domains can interact to form a functional binding domain. In certain embodiments, a variable region linker that joins the $V_H$ and $V_L$ domains includes those belonging to the (Gly$_n$Ser) family, such as (Gly$_3$Ser)$_n$ (Gly$_4$Ser)$_1$ (SEQ ID NO: 72), (Gly$_3$Ser)$_1$(Gly$_4$Ser)$_n$ (SEQ ID NO: 72), (Gly$_3$Ser)$_n$(Gly$_4$Ser)$_n$ (SEQ ID NO: 72), or (Gly$_4$Ser)$_n$ (SEQ ID NO: 10), wherein n is an integer of 1 to 5. In certain embodiments, the linker is (Gly-Gly-Gly-Gly-Ser)$_3$ (SEQ ID NO.:13) or Gly-Gly-Gly-Ser)$_4$ (SEQ ID NO.:14). In certain embodiments, these (Gly$_n$Ser)-based linkers are used to link the $V_H$ and $V_L$ domains in a binding domain, and these linkers may also be used to link the binding domain to a connector region or to a tag cassette, or to link a tag cassette to an effector domain. In certain other embodiments, a tag cassette is a part of or is located within a (Gly$_n$Ser)-based linker used to link the $V_H$ and $V_L$ domains of a binding domain. In still further embodiments, a (Gly$_n$Ser)-based linker may be used to connect one or more tag cassettes to the N-terminal end of a T-ChARM binding domain.

In some embodiments, a binding domain is a single chain T cell receptor (scTCR) comprising $V_{\alpha/\beta}$ and $C_{\alpha/\beta}$ chains (e.g., $V_\alpha$-$C_\alpha$, $V_\beta$-$C_\beta$, $V\alpha$-$V_\beta$) or comprising $V_\alpha$-$C_\alpha$, $V_\beta$-$C_\beta$, $V_\alpha$-$V_\beta$ pair specific for a target of interest (e.g., peptide-MHC complex).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to a target of interest.

In certain embodiments, a binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a V$\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type.

A target molecule, which is specifically bound by a binding domain contained in a T-ChARM single chain fusion protein of the present disclosure, may be found on or in association with a cell of interest ("target cell"). Exemplary target cells include a cancer cell, a cell associated with an autoimmune disease or disorder or with an inflammatory disease or disorder, and an infectious organism or cell (e.g., bacteria, virus, virus-infected cell). A cell of an infectious organism, such as a mammalian parasite, is also contemplated as a target cell.

In certain embodiments, binding domains of a T-ChARM single chain fusion protein of the present disclosure recognize a target selected from a tumor antigen, a B-cell target, a TNF receptor superfamily member, a Hedgehog family member, a receptor tyrosine kinase, a proteoglycan related molecule, a TGF-β superfamily member, a Wnt related molecule, a T cell target, a dendritic cell target, an NK cell target, a monocyte/macrophage cell target, or an angiogenesis target. In further embodiments, the binding domains of a T-ChARM single chain fusion protein of the present disclosure bind a receptor protein, such as peripheral membrane receptor proteins or transmembrane receptor proteins.

In certain embodiments, a T-ChARM single chain fusion protein of the present disclosure specifically binds a target, such as CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A, mesothelin, NY-ESO-1, PSMA, RANK, ROR1, TNFRSF4, CD40, CD137, TWEAK-R, HLA, tumor or pathogen derived peptides bound to HLA (such as from hTERT, tyrosinase, or WT-1), LTβR, LIFRβ, LRP5, MUC1, OSMRβ, TCRα, TCRβ, CD19, CD20, CD22, CD25, CD28, CD30, CD33, CD52, CD56, CD80, CD81, CD86, CD123, CD171, CD276, B7H4, TLR7, TLR9, PTCH1, PTCH1, Robo1, α-fetoprotein (AFP), Frizzled, OX40 (also referred to as CD134), or CD79b. In certain embodiments, a T-ChARM single chain fusion protein of the present disclosure specifically binds a pathogen specific molecule expressed on infected cells, such as molecules from an adenovirus, bunyavirus, herpesvirus (e.g., Epstein Barr Virus, cytomegalocvirus), papovavirus, papillomavirus (e.g., human papilloma virus, HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., human immunodeficiency virus, HIV), flavivirus (e.g., Hepatitis C virus, HCV; Hepatitis B virus, HBV).

Host Cells and Nucleic Acids

In certain aspects, the present disclosure provides nucleic acid molecules that encode any one or more of the Key-ChEM or T-ChARM described herein. Such nucleic acid molecules can be inserted into an appropriate vector (e.g., viral vector or non-viral plasmid vector) for introduction in a host cell of interest (e.g., hematopoietic progenitor cell, T cell).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be converted into a non-natural or recombinant cell (e.g., a non-natural or recombinant T cell) by introducing a nucleic acid that encodes a Key-ChEM or T-ChARM as described herein and whereby the cell expresses a cell surface located Key-ChEM or T-ChARM.

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous nucleic acid sequence encoding a Key-ChEM or a non-endogenous nucleic acid sequence encoding a T-ChARM specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising green fluorescent protein, an extracellular domain of human CD2, or a truncated human EGFR (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptide, or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g. green fluorescent protein, huEGFRt).

In certain embodiments, hematopoietic progenitor cells or embryonic stem cells are modified to comprise a non-endogenous nucleic acid molecule that encodes a Key-ChEM or T-ChARM of this disclosure. Hematopoietic progenitor cells may comprise thymocyte progenitor cells or induced pluripotent stem cells, which may be derived or originate from fetal liver tissue, bone marrow, cord blood, or peripheral blood. The hematopoietic progenitor cells may be from human, mouse, rat, or other mammals. In particular embodiments, $CD24^{lo}$ Lin$^-$ $CD117^+$ thymocyte progenitor cells are used.

In certain embodiments, culture conditions entail culturing hematopoietic progenitor cells expressing fusion proteins of this disclosure for a sufficient time to induce proliferation or differentiation. The cells are maintained in culture generally for about 3 days to about 5 days, or about 4 to about 10 days, or about 5 to about 20 days. It will be appreciated that the cells may be maintained for an appropriate amount of time required to achieve a desired result, i.e., a desired cellular composition or level of proliferation. For example, to generate a cellular composition comprising primarily immature and inactivated T cells, cells may be maintained in culture for about 5 to about 20 days. Cells may be maintained in culture for about 20 to about 30 days to generate a cellular composition comprising primarily mature T cells. Non-adherent cells may also be collected from culture at various time points, such as from about several days to about 25 days. In certain embodiments, hematopoietic stem cells are co-cultured on stromal cells lines (U.S. Pat. No. 7,575,925; Schmitt et al., *Nat. Immunol.* 5:410, 2004; Schmitt et al., *Immunity* 17:749, 2002).

One or more cytokines that promote commitment or differentiation of hematopoietic progenitor cells may be added to the culture. The cytokines may be human or non-human. Representative examples of cytokines that may be used include all members of the FGF family, including FGF-4 and FGF-2; Flt-3-ligand, stem cell factor (SCF), thrombopoietin (TPO), and IL-7. Cytokines may be used in combination with a glycosaminoglycan, such as heparin sulfate.

In some embodiments, cells capable of expressing a fusion protein of this disclosure on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., *Leukemia* 21:230, 2000. In certain embodiments, T cells that lack endogenous expression of TCR α and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In certain embodiments, cells capable of expressing a fusion protein of this disclosure on the cell surface are not T cells or cells of a T cell lineage, but cells that are progenitor cells, stem cells or cells that have been modified to express cell surface anti-CD3.

In certain embodiments, the host T cell transfected to express a Key-ChEM or T-ChARM of this disclosure is a functional T cell, such as a virus specific T cell, a tumor antigen specific cytotoxic T cell, a naïve T cell, a memory stem T cell, a central or effector memory T cell, or a CD4+CD25+ regulatory T cell.

One or more growth factor cytokines that promote proliferation of T cells expressing a Key-ChEM or T-ChARM of this disclosure may be added to the culture. The cytokines may be human or non-human. Exemplary growth factor cytokines that may be used promote T cell proliferation include IL2, IL15, or the like.

Uses

Diseases that may be treated with cells expressing Key-ChEM or T-ChARM as described in the present disclosure include cancer, infectious diseases (viral, bacterial, protozoan infections), immune diseases (e.g., autoimmune), or aging-related diseases (e.g., senescence). Adoptive immune and gene therapy are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLoS One* 4:38208, 2009; Rossi et al., *Nat. Biotechnol.* 25:1444, 2007; Zhang et al., *PLoS Pathog.* 6:e1001018, 2010; Luo et al., *J. Mol. Med.* 89:903, 2011).

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to Key-ChEM or T-ChARM therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-BarréSyndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, a method of treating a subject with the Key-ChEM or T-ChARM as disclosed herein include acute myelocytic leukemia, acute lymphocytic leukemia, and chronic myelocytic leukemia.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, infection with cytosolic pathogens whose antigens are processed and displayed with MHC Class I molecules, are treated with Key-ChEM or T-ChARM of this disclosure.

A Key-ChEM or T-ChARM of this disclosure may be administered to a subject in cell-bound form (e.g., gene therapy of target cell population (mature T cells (e.g., $CD8^+$ or $CD4^+$ T cells) or other cells of T cell lineage)). In a particular embodiment, cells of T cell lineage expressing Key-ChEM or T-ChARM administered to a subject are syngeneic, allogeneic, or autologous cells. In other embodiments, Key-ChEM or T-ChARM may be administered to a subject in soluble form. Soluble TCRs are known in the art (see, e.g., Molloy et al., *Curr. Opin. Pharmacol.* 5:438, 2005; U.S. Pat. No. 6,759,243).

Pharmaceutical compositions including Key-ChEM or T-ChARM of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. The present disclosure provides pharmaceutical compositions comprising cells expressing a Key-ChEM or T-ChARM as disclosed herein and a pharmaceutically acceptable carrier, diluents, or excipient. Suitable excipients include water, saline, dextrose, glycerol, or the like and combinations thereof.

An advantage of the instant disclosure is that Key-ChEM or T-ChARM expressing cells administered to a patient can be depleted using the cognate binding partner to a tag cassette. In certain embodiments, the present disclosure provides a method for depleting a T cell expressing a Key-ChEM or T-ChARM by using an antibody specific for the tag cassette, using a cognate binding partner specific for the tag cassette, or by using a second T cell expressing a CAR and having specificity for the tag cassette. In certain embodiments, a tag cassette allows for immunodepletion of a T cell expressing a Key-ChEM or T-ChARM of this disclosure. Elimination of engineered T cells may be accomplished using depletion agents specific for a tag cassette. For example, if a Strep Tag® is used, then an anti-Strep Tag® antibody, anti-Strep Tag® scFv, or Strep-Tactin® each fused to or conjugated to a cell-toxic reagent (such as a toxin, radiometal) may be used, or an anti-Strep Tag®/anti-CD3 bispecific scFv, or an anti-Strep Tag® CAR T cell may be used.

In certain other embodiments, cells expressing a Key-ChEM or T-ChARM of this disclosure can be identified, sorted, enriched or isolated by binding to antibodies having specificity to a tag cassette (e.g., anti-tag antibodies), or by other proteins that specifically bind a tag cassette (e.g., Strep-Tactin® binding to the Strep Tag®), which are conjugated to beads, a cell culture plate, agarose, or any other solid surface matrix. In certain embodiments, such cells are sorted, enriched or isolated by using an affinity column.

In certain embodiments, the present disclosure provides a method for selectively activating a T cell by contacting a non-natural or recombinant T cell expressing a Key-ChEM or T-ChARM with a binding domain specific for a tag cassette and attached to a solid surface or as part of a biocompatible matrix (e.g., alginate, basement membrane matrix (Matrigel®), biopolymer). The recombinant T cell comprises an exogenous nucleic acid molecule encoding a Key-ChEM or T-ChARM fusion protein of this disclosure. For example, a T cell expressing a Key-ChEM or T-ChARM may be activated with beads coated or conjugated with a cognate binding partner (e.g., antibody) specific for the tag cassette. For example, if the tag cassette is a Strep Tag®, then Strep-Tactin® (streptavidin mutein with improved binding capabilities compared to streptavidin) coated beads or anti-Strep Tag® antibody conjugated beads can be used to induce T cell activation. In certain embodiments, the method comprises activating ex vivo recombinant T cells expressing a Key-ChEM or T-ChARM of this disclosure and is optionally further expressing a chimeric antigen receptor (CAR). Such activated T cells are useful in the disease treatment methods described herein.

In another aspect, the present disclosure provides a method for selectively promoting proliferation of a recombinant T cell expressing a Key-ChEM or T-ChARM of this disclosure. In certain embodiments, the method comprises selective ex vivo proliferation of T cells expressing a Key-ChEM or T-ChARM using a tag binding partner, such as an antibody. In further embodiments, the method comprises expanding functional T cells (e.g., virus-specific, TAA (tumor-associated antigen) specific CTL, or specific T cell subsets, such as naïve T cells, memory stem T cells, central or effector memory T cells, CD4+CD25+ regulatory T cells) with a tag binding partner, such as an antibody, which may optionally be done in the presence of a costimulatory molecule binding partner (such as an anti-CD27 or antiCD28 antibody). In certain embodiments, anti-tag binding partners may be used to activate a Key-ChEM (e.g., a Wnt or Notch Key-ChEM) transduced hematopoietic stem cell, embryonic stem cell, or tissue stem cell (e.g., neural stem cell) to self-renew, proliferate or differentiate into one or more desired phenotype for therapeutic use.

In still further embodiments, a Key-ChEM or T-ChARM allows for selective promotion of T cell proliferation in vivo when expressing a Key-ChEM or T-ChARM of this disclosure. In certain embodiments, a T cell expressing a CAR comprising a tag cassette allows for expansion of the CAR T cells in vivo when contacting cells expressing a ligand (e.g., including T cell suppressor cell ligands PD-L1, PD-L2). Such expanded T cells are useful in the disease treatment methods described herein. In certain embodiments, proliferation or expansion of cells expressing Key-ChEM or T-ChARM as disclosed herein is induced in vivo, which may be induced with a tag cassette binding partner (such as an anti-tag antibody) and optionally a costimulatory molecule binding partner (such as an anti-CD27 or antiCD28 antibody).

In certain further embodiments, cells expressing Key-ChEM or T-ChARM as disclosed herein are activated in vivo, such as at the site of a tumor. For example, a composition (e.g., alginate, basement membrane matrix (Matrigel®), biopolymer, or other matrix) or a carrier (e.g., microbead, nanoparticle, or other solid surface) comprising a tag cassette binding partner (such as an anti-tag antibody) and a costimulatory molecule binding partner (such as an anti-CD27 or antiCD28 antibody) may be used to locally activate at the site of a tumor (e.g., a solid tumor) a T cell expressing a Key-ChEM or T-ChARM as disclosed herein.

In certain embodiments, recombinant cells expressing a Key-ChEM or T-ChARM may be detected or tracked in vivo by using antibodies that bind with specificity to a tag cassette (e.g., anti-Tag antibodies), or by other cognate binding proteins that specifically bind the tag cassette sequence (e.g., Strep-Tactin® binding to Strep Tag®), which binding partners for the tag cassette are conjugated to a fluorescent dye, radio-tracer, iron-oxide nanoparticle or other imaging agent known in the art for detection by X-ray, CT scan, MRI-scan, PET-scan, ultrasound, flow-cytometry, near infrared imaging systems, or other imaging modalities (see, e.g., Yu et al., *Theranostics* 2:3, 2012).

In further embodiments, cells expressing Key-ChEM or T-ChARM of the instant disclosure may be used in diagnostic methods or imaging methods, including methods used in relation to the indications or conditions identified herein.

EXAMPLES

Example 1

Key-Chimeric Effector Molecules (Key-ChEMs) and Tagged Chimeric Antigen Receptor Molecules (T-ChARMS), and Derivatives Thereof Exemplary chimeric fusion proteins containing one or more affinity tag cassettes are illustrated in FIG. 1. The tag cassettes are generally small (i.e., minimally immunogenic or non-immunogenic) and do not associate with or bind to any molecules endogenous to a host or host cell. The tags do specifically bind to a heterologous cognate receptor (e.g., ligand, antibody, or other binding partner), which binding can be used in the context of these chimeric effector molecules (ChEMs) as a "key" to access and manipulate (i.e., turn on or off or modulate) any of a variety of cellular pathways (referred to herein as a Key-ChEMs). These tagged chimeric fusion proteins may further comprise a binding domain specific for a particular target (e.g., a tumor antigen). For example, the tagged chimeric fusion proteins include chimeric antigen receptor molecules (referred to herein as T-ChARMs).

An exemplary nucleic acid molecule encoding a Key-ChEM (FIG. 1A) comprises the following elements (5' to 3'): Strep Tag® II (SEQ ID NO.:38 encoding peptide Trp-Ser-His-Pro-Gln-Phe-Glu-Lys as set forth in SEQ ID NO.: 1), a connector portion including a linker module (SEQ ID NO.:42 encoding peptide (Gly-Gly-Gly-Gly-Ser)$_2$ as set forth in SEQ ID NO.:11) and a modified IgG4 hinge (SEQ ID NO.:27 encoding peptide Glu-Ser-Lys-Tyr-Gly-Pro-Pro-Cys-Pro-Pro-Cys-Pro as set forth in SEQ ID NO.:15), a CD28 transmembrane domain (SEQ ID NO.:27 encoding a peptide as set forth in SEQ ID NO.:16), and an intracellular component comprising an effector domain comprising a 4-1BB portion (SEQ ID NO.:29 encoding a peptide as set forth in SEQ ID NO.:17) and a CD3ζ portion (SEQ ID NO.:30 encoding a peptide as set forth in SEQ ID NO.:18; Kowolik et al., *Cancer Res.* 66:10995, 2006). This Key-ChEM (single tag) encoding nucleic acid molecule was cloned into an epHIV7 lentiviral vector, as described by Yam et al. (*Mol. Ther.* 5:479, 2002) and Wang et al. (*Blood* 118:1255, 2011).

The epHIV7 lentiviral vector was derived from the pHIV7 vector by replacing the cytomegalovirus promoter of pHIV7 with an EF-1 promoter (Wang et al., 2011; Yam et al., 2002). The lentiviral vector also encodes a truncated human EGFR polypeptide (huEGFRt) that is devoid of extracellular N-terminal ligand binding domains and intracellular receptor tyrosine kinase activity but retains the native amino acid sequence, type I transmembrane cell surface localization, and a conformationally intact binding epitope for anti-EGFR monoclonal antibody, cetuximab (Wang et al., 2011). The lentiviral vectors coordinately express a Key-ChEM and huEGFRt separated by a self-cleaving T2A sequence (Szymczak et al., *Nat. Biotechnol.* 22:589, 2004), wherein the huEGFRt serves as an alternative selection epitope for Key-ChEM positive cells by using biotinylated cetuximab in conjunction with anti-biotin immunomagnetic microbeads.

An exemplary nucleic acid molecule encoding a T-ChARM (FIG. 1E) comprises the following elements: a scFv containing VH and VL gene segments of the CD19-specific FMC63 monoclonal antibody (SEQ ID NO.:36; Wang et al., 2011), a Strep Tag® II (SEQ ID NO.:38, encoding peptide Trp-Ser-His-Pro-Gln-Phe-Glu-Lys as set forth in SEQ ID NO.:1), a connector portion including a linker module (SEQ ID NO.:39, 40, or 41, encoding peptide (Gly-Gly-Gly-Gly-Ser)$_2$ as set forth in SEQ ID NO.:11) and an IgG4 hinge (SEQ ID NO.:27), a CD28 transmembrane domain (SEQ ID NO.:28), and an intracellular component comprising an effector domain comprising a 4-1BB portion (SEQ ID NO.:29) and a CD3ζ portion (SEQ ID NO.:30). An exemplary T-ChARM comprising two tags (T-ChARM$^2$) differs from the single tag T-ChARM (T-ChARM$^1$) by including a second linker module (encoding peptide (Gly-Gly-Gly-Ser)$_2$-Gly-Gly-Ser as set forth in SEQ ID NO.:12) between first and second Strep tags. An exemplary T-ChARM comprising three tags (T-ChARM$^3$) differs from the double tag T-ChARM by including a third linker module (encoding peptide (Gly-Gly-Gly-Gly-Ser)$_2$ as set forth in SEQ ID NO.:11) between second and third Strep tags. In certain embodiments, an scFv includes VH and VL regions of the ROR1-specific R12 monoclonal antibody (Yang et al., *PLoS One* 6:e21018, 2011) as set forth in SEQ ID NO.:57) and a variable domain linker as set forth in SEQ ID NO.:13. In addition, both anti-CD19 and anti-ROR1 T-ChARMs were alternatively constructed with an intracellular component comprising an effector domain comprising a CD28 portion (SEQ ID NO.:35) in place of a 4-1BB portion.

In certain embodiments, any of the fusion proteins described herein comprise from amino-terminus to carboxy-terminus: an extracellular scFv or scTCR binding domain, a tag cassette, a connector region comprising an IgG hinge, a transmembrane domain, and an intracellular component comprising an effector domain. In some embodiments, an effector domain comprises a pairing of 4-1BB and CD3π, CD27 and CD3ζ, CD28 and CD3ζ, OX40 and CD3ζ, CD28, 4-1BB and CD3ζ, OX40, 4-1BB and CD3ζ, or CD28, OX40 and CD3ζ. As defined herein, an effector domain for any of these molecules may the entire intracellular portion or may include only a effector portion of the selected molecule.

An exemplary nucleic acid molecule encoding a T-ChARM ($^{N1}$ChARM; FIG. 1F; SEQ ID NO.:58) having an N-terminal tag comprises the following elements: a secretory signal sequence (SEQ ID NO.:63, encoding peptide MLLLVTSLLLCELPHPAFLLIP as set forth in SEQ ID NO.:47, which is cleaved from the mature protein), an asparagine junction amino acid, a Strep Tag® II (SEQ ID NO.:38, encoding peptide Trp-Ser-His-Pro-Gln-Phe-Glu-Lys as set forth in SEQ ID NO.:1), a linker module (SEQ ID NO.:42, encoding peptide (Gly-Gly-Gly-Gly-Ser)$_2$ as set forth in SEQ ID NO.:11), scFv of the VH and VL gene segments of the CD19-specific FMC63 monoclonal antibody (SEQ ID NO.:36; Wang et al., 2011), an IgG4 hinge (SEQ ID NO.:27), a CD28 transmembrane domain (SEQ ID NO.:28), and an intracellular component comprising an effector domain comprising a 4-1BB portion (SEQ ID NO.:29) and a CD3ζ portion (SEQ ID NO.:30).

An exemplary nucleic acid molecule encoding a T-ChARM (Ch$^1$ARM; FIG. 1G; SEQ ID NO.:59) having a tag imbedded in the variable region linker comprises the following elements: a secretory signal sequence (SEQ ID NO.:63, encoding peptide MLLLVTSLLLCELPHPAFLLIP as set forth in SEQ ID NO.:47, which is cleaved from the mature protein), the VH gene segment of CD19-specific FMC63 monoclonal antibody (encoding the amino acid sequence as set forth in SEQ ID NO.:51), a first linker module (encoding peptide Gly-Gly-Ser-Gly-Ser-Gly as set forth in SEQ ID NO.:65), an asparagine junction amino acid, a Strep Tag® II (SEQ ID NO.:38, encoding peptide Trp-Ser-His-Pro-Gln-Phe-Glu-Lys as set forth in SEQ ID NO.: 1), a second linker module (encoding peptide Gly-Ser-Gly-Ser-Gly as set forth in SEQ ID NO.:66), the VL gene segment of CD19-specific FMC63 monoclonal antibody (encoding the amino acid sequence as set forth in SEQ ID NO.:52), an IgG4 hinge (SEQ ID NO.:27), a CD28 transmembrane domain (SEQ ID NO.:28), and an intracellular component comprising an effector domain comprising a 4-1BB portion (SEQ ID NO.:29) and a CD3ζ portion (SEQ ID NO.:30).

Nucleic acid molecules encoding each of these exemplary T-ChARM (e.g., single, double or triple tagged, N-terminal tagged, imbedded tag, indicated scFvs) were individually cloned into an epHIV7 lentiviral vector, as described by Yam et al. (*Mol. Ther.* 5:479, 2002), and used to transduce T cells as described in the examples herein. In certain embodiments, the nucleic acid molecules encoding Key ChARMs of the instant disclosure were codon optimized before cloning into the epHIV7 lentiviral vector. The T-ChARM-encoding lentivirus supernatants were produced in 293T cells co-transfected with each of the lentiviral vector plasmids and the packaging vectors pCHGP-2, pCMV-Rev2 and pCMV-G using Calphos transfection reagent (Clontech, Mountain View, Calif.). Medium was changed 16 hours post transfection, and lentivirus collected after 24, 48 and 72 hours.

Example 2

Production of Recombinant T Cells and Expression of T-ChARMs

CD8+ and CD4+ were isolated from PBMC of normal donors using CD8+/CD4+ T Cell Isolation Kit (Miltenyi Biotec), activated with anti-CD3/CD28 beads (Life Technologies) according to the manufacturer's instructions, and transduced with a lentiviral supernatant (as indicated in each Example) (MOI=3) supplemented with 0.8 µg/mL polybrene (Millipore, Bedford, Mass.) on day 3 after activation by centrifugation at 2,100 rpm for 45 min at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 hours. After expansion, an aliquot of each transduced T cell line was stained with biotin-conjugated anti-EGFR antibody and streptavidin-PE (Miltenyi, Auburn, Calif.). The tEGFR+ T cells were isolated by sorting on a FACS-Aria cell sorter (Becton Dickinson). The tEGFR+ T cell subset was then stimulated with irradiated (8,000 rad) CD19+B-LCL at a T cell:LCL ratio of 1:7, and expanded for 8 days in CTL medium with addition of 50 U/mL rh IL-2 every 48 hours or using a rapid expansion protocol for R12 T-ChARMs (Riddell and Greenberg, J. Immunol. Methods 128:189, 1990).

The following conjugated antibodies were used for flow cytometric phenotyping and analysis: CD4, CD8, CD25, CD137, CD45, Annexin V, CD62L, CD27, CD28 (BD Biosciences), anti-Strep Tag® II antibody (Genscript), EGFR antibody (ImClone Systems Incorporated, Branchburg, N.J.); strepTavidin-PE (BD Biosciences, San Jose, Calif.). Staining with propidium iodide (PI, BD Biosciences) was performed for live/dead cell discrimination as directed by the manufacturer. Flow analyses were done on a FACS Canto II, sort-purifications on a FACS AriaII (Becton Dickinson, Franklin Lakes, N.J.) and data analyzed using FlowJo software (Treestar, Ashland, Oreg.).

Figure 21:
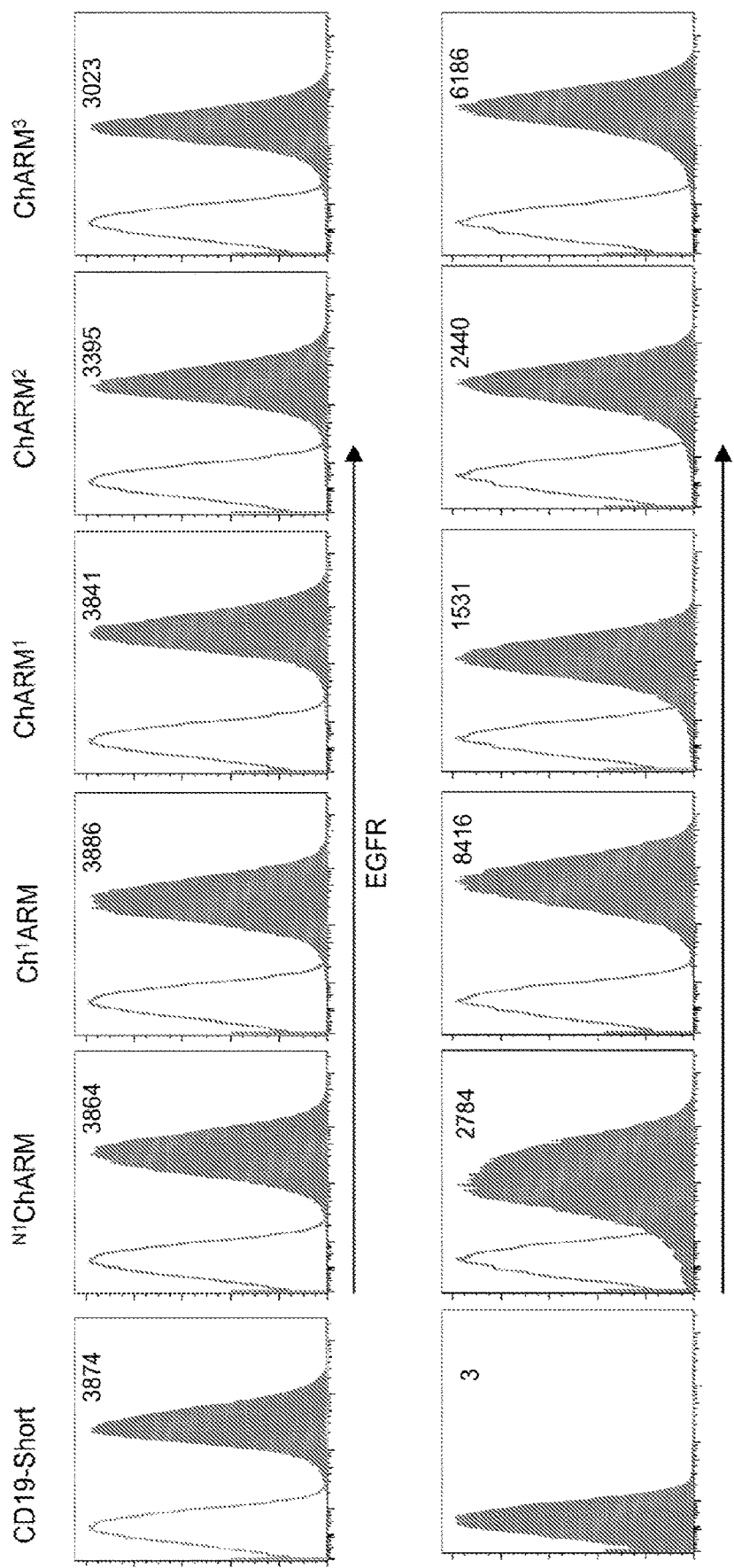
FIG. 21 shows flow cytometry analysis (MFI) of FACS sorted EGFR+ anti CD19 ChARM T cells after CD19+ immortalized B cell line (TM-LCL) expansion. Stained with anti-EGFR (upper row) and anti-Strep Tag® II (lower row) antibodies, respectively.

To examine cell surface expression of T-ChARMs, transduced T cells were sorted for EGFRt expression and evaluated by staining with fluorochrome labeled anti-Strep Tag® mAb. The mean fluorescence intensity (MFI) of EGFR staining was similar on T cells transduced with each of the T-ChARMs and the CD19-Short CAR, which indicates that introducing a tag into a CAR to produce a ChARM did not interfere with transgene expression (FIG. 21). An anti-Strep Tag® mAb specifically stained T cells transduced with the various T-ChARMs, independent of the position or number of tag sequences in each ChARM. The MFI of anti-Strep Tag® staining was higher for T cells transduced with T-ChARM$^2$ and T-ChARM$^3$ as compared to T-ChARM$^1$, presumably due to more sites on each T-ChARM$^2$ and T-ChARM$^3$ for binding the antibody-fluorochrome conjugate (FIG. 21).

Example 3

Cytolytic Activity of T Cells Expressing T-ChARMs

The in vitro effector function of CD8+ bulk T cells engineered to express anti-CD19 (scFv) T-ChARM$^1$, T-ChARM$^2$, or T-ChARM$^3$ were compared to the effector function of T cells engineered to express anti-CD19 CARs containing connector regions of different lengths—an IgG4 hinge only (short), an IgG4 CH3 and hinge (intermediate), and an IgG4 CH2CH3 and hinge (long), respectively—in a chromium release assay. Briefly, target cells were labeled with $^{51}$Cr (PerkinElmer, Norwalk, Conn.) overnight, washed and incubated in triplicate at 1-2×10$^3$ cells/well with effector T cells at various effector to target (E:T) ratios. Supernatants were harvested for γ-counting after incubating for 4 hours and specific lysis calculated using a standard formula. The target cells used were Raji/ROR1 (naturally CD19+, transduced to express unrelated antigen ROR1) and K562/CD19 (transduced to express CD19), with K562/ROR1 (naturally CD19-, transduced to express unrelated antigen ROR1) used as a negative control and LCL-OKT3 cells (transduced to express cell surface anti-CD3) used as a positive control. Lymphoblastoid cell line (LCL) cells engineered to express a membrane bound anti-CD3 scFv (LCL-OKT3) was used as a reference standard for the maximal activation potential of a T cell line since these OKT3 expressing cells activate T cells by binding the CD3 complex.

Figure 22:
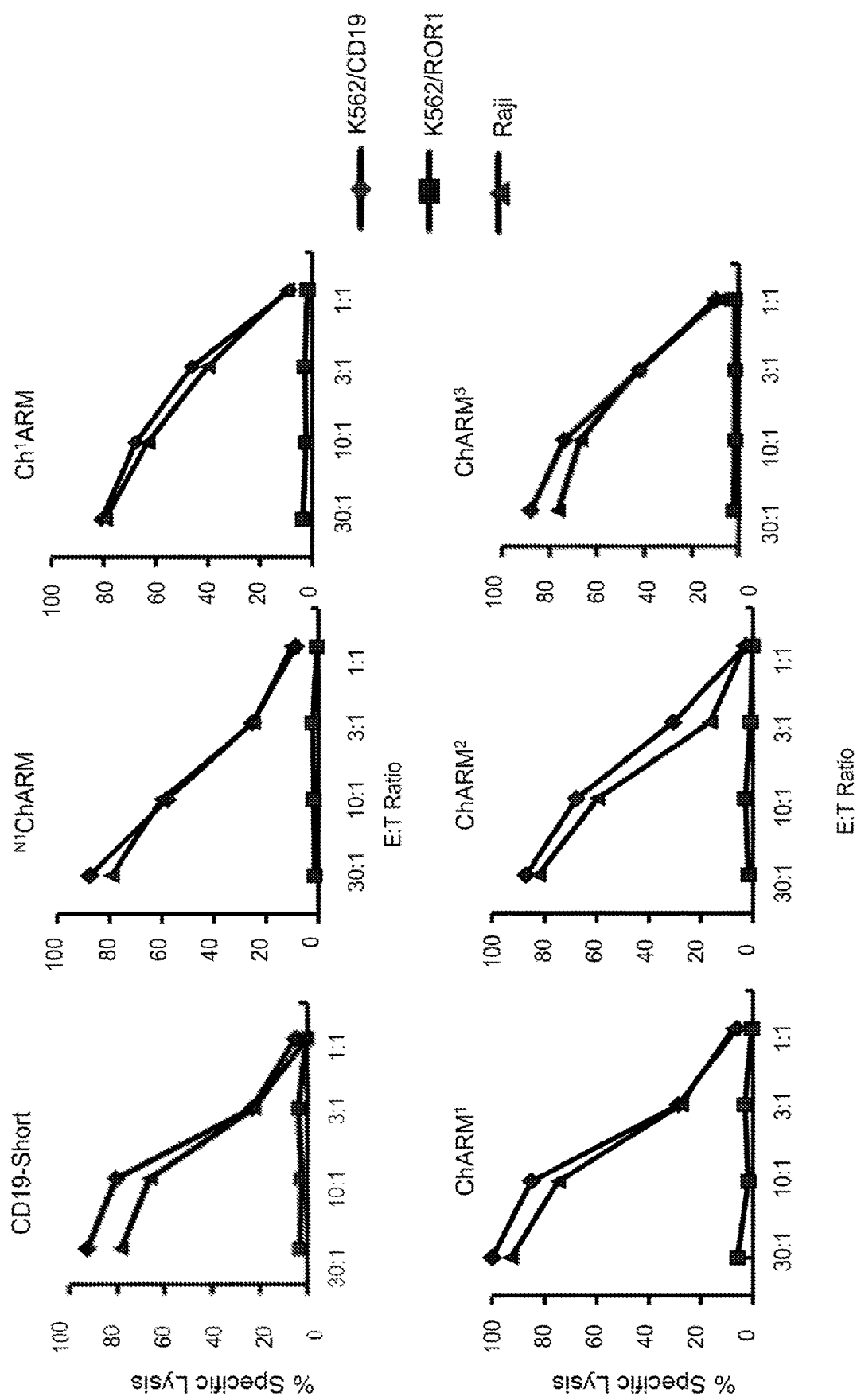
FIG. 22 shows chromium release assay results for examining the cytolytic effect of various anti CD19 ChARM transduced T cells (effectors) against the K562 cells transduced with CD19 (K562/CD19), or ROR1 (K562/ROR1) or CD19+ Raji tumor cells (targets). E/T=Effector/target ratio.

T cells expressing each of the different anti-CD19 T-ChARM and CAR constructs were not cytotoxic for K562/ROR1 cells (FIG. 2C), but were activated to be cytolytic in the presence of the anti-CD3 expressing LCL/OKT3 cells (FIG. 2D). Moreover, the T-ChARM or CAR expressing T cells conferred specific cytolytic activity against CD19+ cells, Raji cells (FIG. 2B) and K562/CD19 (FIG. 2A). Similar results were obtained when the tag was located at the amino-terminus of the T-ChARM ($^{N1}$ChARM) or imbedded in the scFv (VH-tag-VL; Ch$^1$ARM) (see FIG. 22). In addition, the efficiency of lysis was not affected by effector domain (CD28 instead of 4-1BB; see FIG. 23A), binding domain (anti-ROR1 instead of anti-CD19; see FIG. 23B), or the tag used (FIG. 32 shows the cytolytic effect of a Myc tagged ChARM). The T-ChARM expressing cells killed tumor cells as efficiently as the CARs containing the short, intermediate and long IgG4 Fc spacers.

Example 4

Cytokine Release by T Cells Expressing T-ChARMs Co-Cultured with K562 Cells

For analysis of cytokine secretion, effector (E) cells (T cells expressing anti-CD19 T-ChARMs and CARs) and target (T) cells (K562/CD19 and K562/ROR1, negative control) were co-cultured in triplicate at an E:T ratio of 4:1, incubated 24 hours, and then the supernatants were measured for GM CSF, IFN-γ, IL-2, and TNF-α levels using a multiplex cytokine immunoassay (Luminex®).

Figure 24:
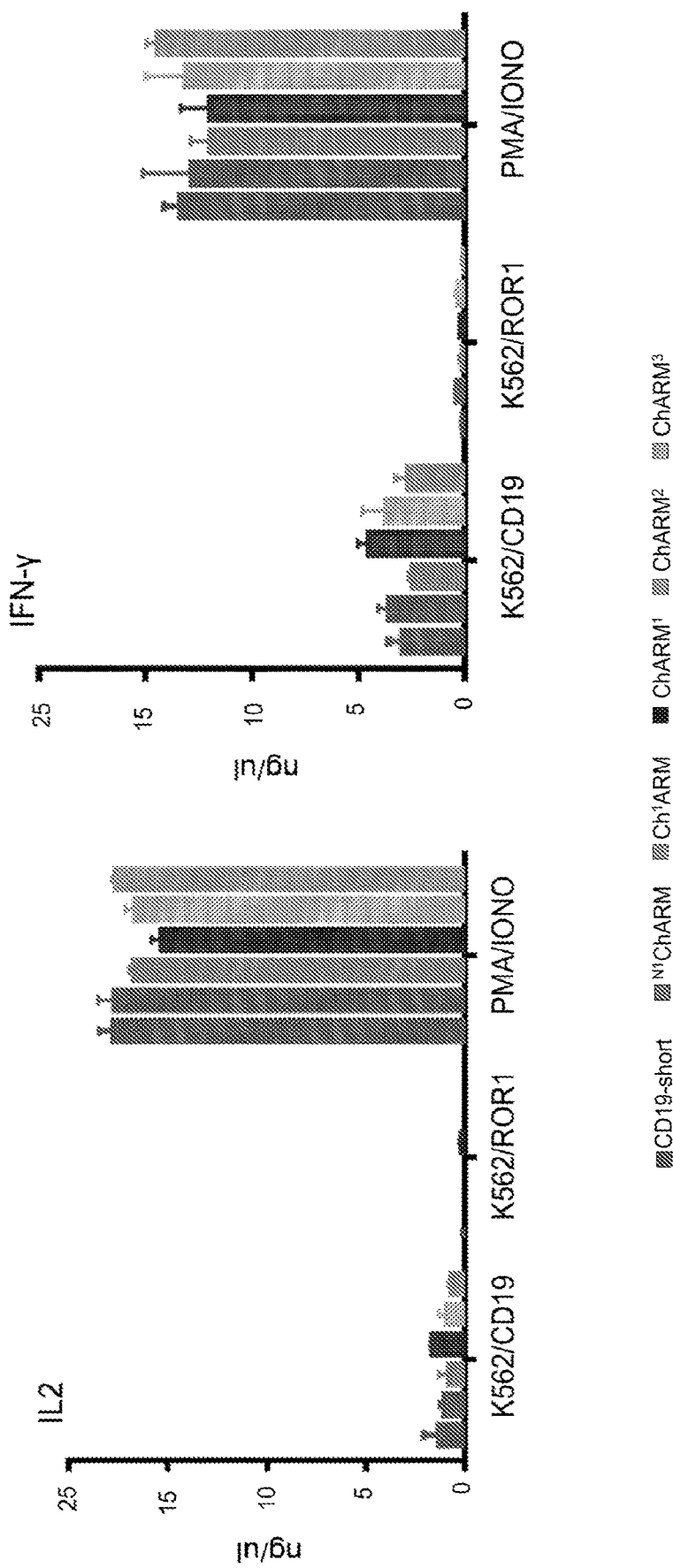
FIG. 24 shows IL2/IFN-γ production of various anti-CD19 T-ChARM transduced T cells (Effector) against K562 cells transduced with CD19 (K562/CD19), or ROR1 (K562/ROR1) or CD19+ Raji tumor cells (Target).
Figure 25A:
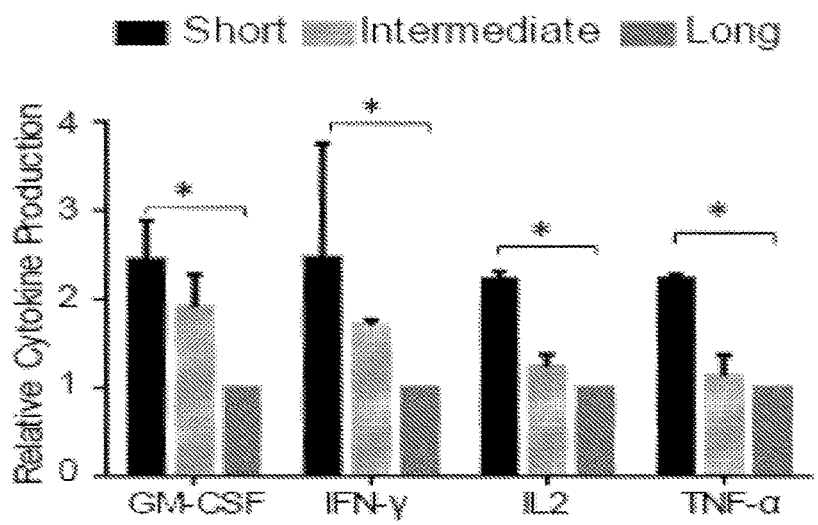
FIGS. 25A-25C show luminex multiplex cytokine analysis of triplicate co-culture supernatants of ChARM transduced T cells with CD19+ Raji cells (1:4 ratio) after 24 h. The data is derived from three independent experiments using T cells from different donors, and all data are expressed as means±SD. Student's t test was performed. *P<0.01. (A) Comparison of cytokine production by CD8+ T cells expressing the anti CD19 CAR with long (CH3-CH2-hinge), intermediate (CH3-hinge), and short (hinge only) spacers. Multiplex cytokine data from 3 independent experiments were normalized (cytokine release by CD19-CAR 'long/41BB'=1); (B) comparison of cytokine production by CD8+ T cells expressing anti CD19 T-ChARM¹ (1ST), T-ChARM² (2ST), T-ChARM³ (3ST) with a 4 1BB/CD3ζ effector domain as compared to anti-CD19 CAR-Short with 4 1BB/CD3ζ effector domain. Multiplex cytokine data from 3 independent experiments were normalized (cytokine release by CD19-CAR-Short: Hi/4-1BB=1); and (C) comparison of cytokine production by CD8+ T cells expressing anti CD19 T-ChARM¹ (1ST), T-ChARM² (2ST), T-ChARM³ (3ST) with a CD28/CD3ζ effector domain as compared to anti-CD19 CAR-Short with CD28/CD3ζ effector domain. Multiplex cytokine data from 3 independent experiments were normalized (cytokine release by CD19-CAR-Short: Hi/CD28=1).
Figure 25B:
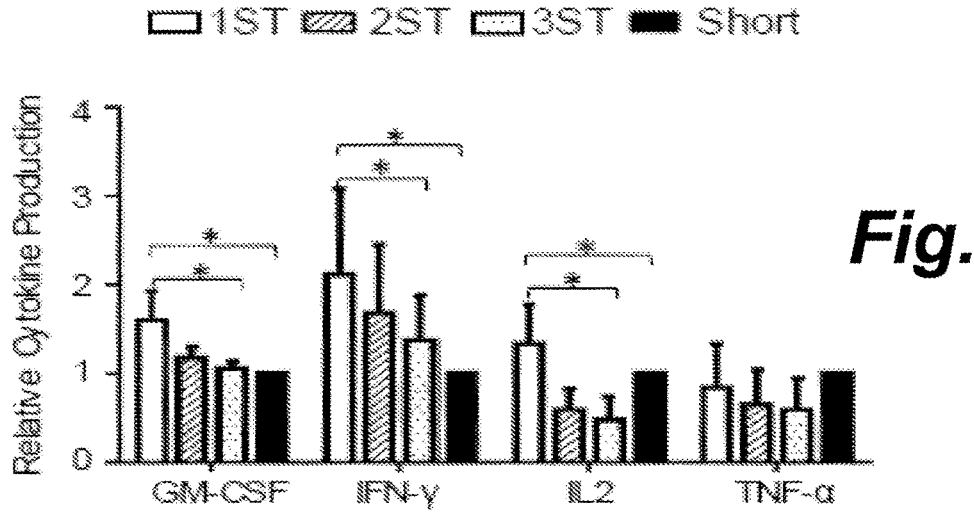
Figure 25C:
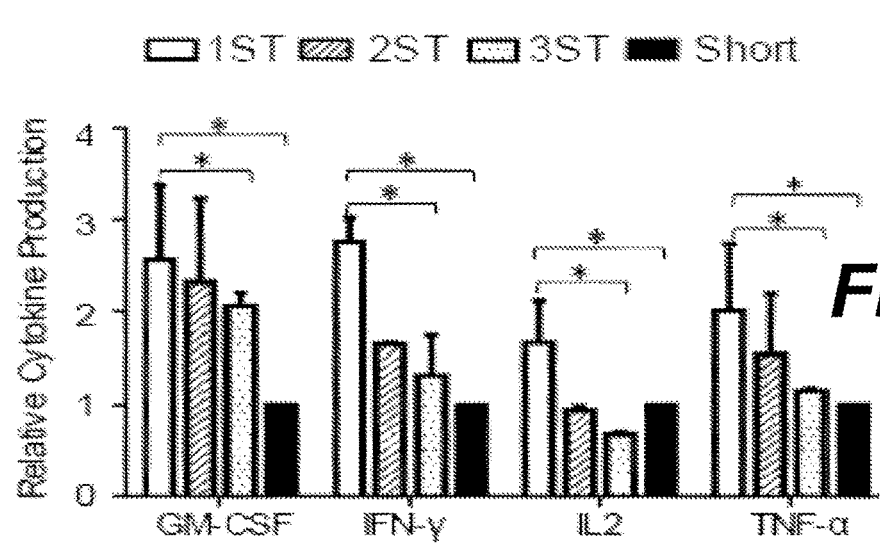

The results (FIG. 3D) show that cells expressing anti-CD19 CARs with a short connector region produce larger amounts of cytokine after engaging target cells than T cells expressing anti-CD19 CARs with intermediate or long connector regions. A similar pattern was observed with anti-CD19 T-ChARM expressing cells, wherein (FIG. 3A) T-ChARM$^1$ cells having a shorter linker and a single tag produce greater amounts of cytokine after engaging target cells than T-ChARM² or T-ChARM³ cells having two tags and three tags, respectively. The levels of cytokines produced were similar for the anti CD19 T-ChARM and anti CD19 CAR cells, although the T-ChARM expressing cells induced a significantly higher level of IFN-γ production than did the CAR expressing cells. FIGS. 3B and 3E show that cytokine production was not induced in K562 cells that do not express CD19. FIGS. 3C and 3F show the results from the positive control, which is stimulation with PMA/Ionomycin. Similar results were observed when examining $^{N1}$ChARM and Ch¹ARM constructs (see FIG. 24). In addition, the hierarchy of cytokine production and proliferation of T cells transduced with the anti-CD19 ChARM was independent of the co-stimulatory domain (4-1BB or CD28) used in the ChARM (FIG. 25).

Example 5

Cytokine Release by T Cells Expressing T-Charm Molecules Co-Cultured with Raji B Cell Lymphoma Cells T cells expressing various anti-CD19 T-ChARMs or CARs were co-cultured with CD19+ Raji cells for 24 hours and the supernatants were examined in a multiplex cytokine assay (Luminex®). For analysis of cytokine secretion, effector (E) cells (T cells expressing anti-CD19 T-ChARMs and CARs) and target (T) cells (Raji) were co-cultured in triplicate at an E:T ratio of 2:1, incubated 24 hours, and then the supernatants were measured for GM CSF, IFN-γ, IL-2, and TNF-α levels using a multiplex cytokine immunoassay (Luminex®).

Figure 4A:
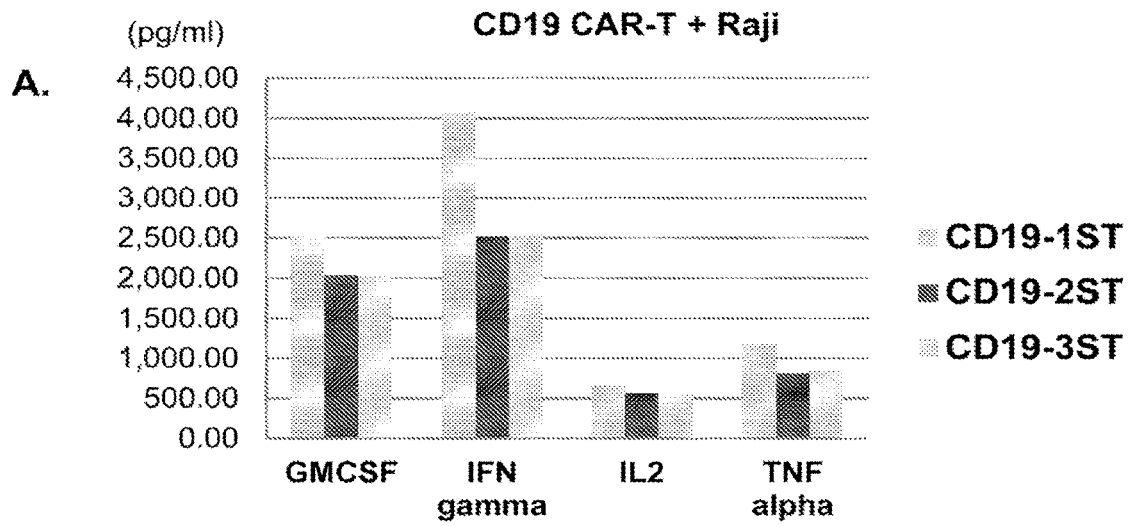
FIGS. 4A and 4B show the results of a multiplex cytokine assay (Luminex®) of supernatants obtained 24 hours after T cells expressing various anti-CD19 T-ChARMs (A) and CD19 CARs (B) after co-culture with CD19+ Raji cells.
Figure 4B:
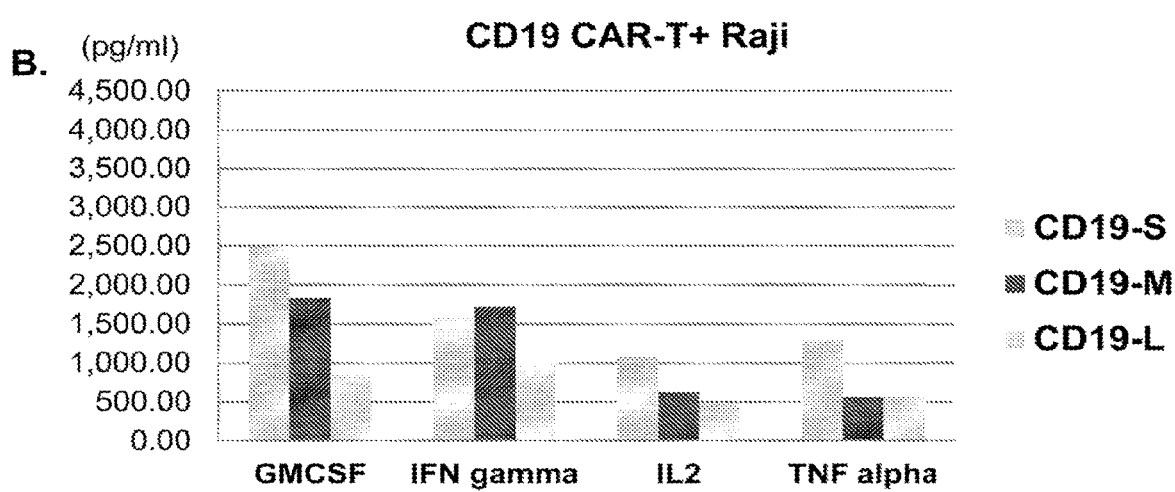

The results indicate that T cells expressing anti-CD19 T-ChARMs with one, two or three tag cassettes were able to produce much higher levels of IFN-γ and GM-CSF when co-cultured with Raji cells (FIG. 4A) as compared to T cells expressing any of the conventional anti-CD19 CARs (FIG. 4B).

Example 6

Proliferation of T Cells Expressing T-ChARM Molecules

For analysis of cell proliferation, T cells expressing anti-CD19 T-ChARMs or CARs were labeled with 0.2 µM carboxyfluorescein succinimidyl ester (CFSE, Invitrogen), which binds to intracellular proteins and makes the cells visible by flow cytometry in the FITC channel. After labeling, the cells were washed and plated in triplicate with stimulator cells at a ratio of 4:1 (K562/CD19 or K562/ROR1, negative control) in CTL medium without exogenous cytokines. After incubating 72 hours, cells were labeled with PI to exclude dead cells from the analysis. Samples were analyzed by flow cytometry and cell division of live CD3+ T cells was assessed by the degree of CFSE dilution (i.e., dye dilution is an indicator of proliferation since the strength of label is diluted by half with each cell division).

Figure 5:
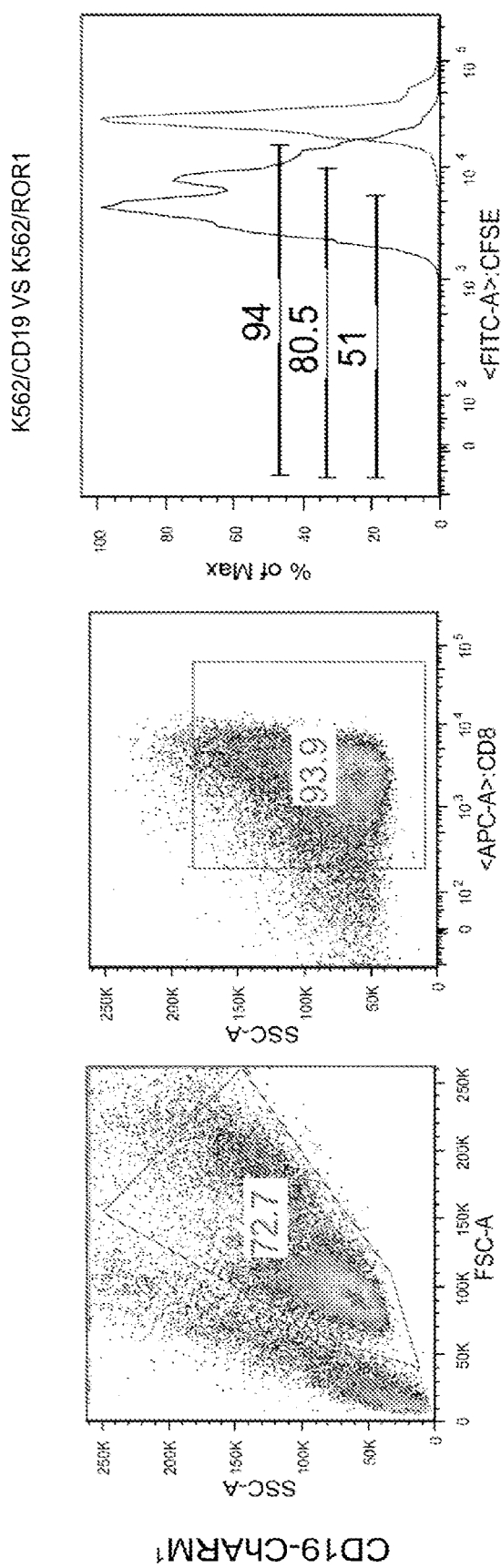
FIG. 5 shows results of a T cell proliferation assay, wherein carboxyfluorescein dye dilution indicates that anti-CD19 CD8$^+$ T cells expressing T-ChARMs (containing one, two or three tag cassettes) or a conventional CAR (CD19 (Long)) were proliferating in response to tumor cells expressing CD19 (left peak), while not proliferating in the presence of tumor cells expressing ROR1 (right peak).
Figure 5:
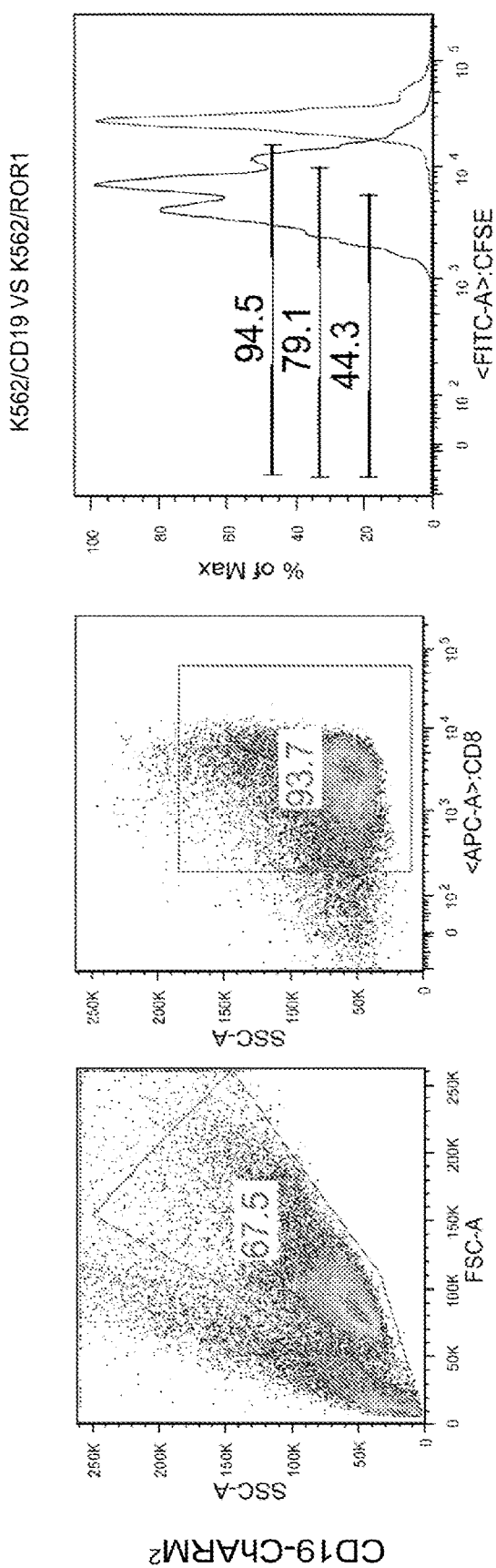
Figure 5:
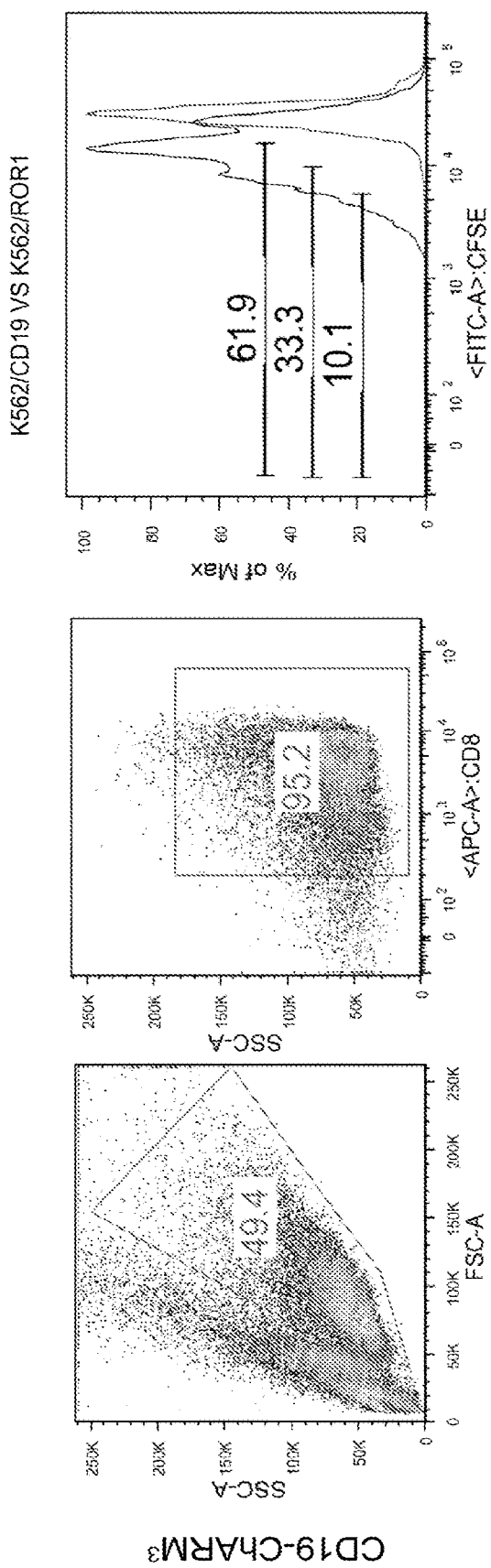
Figure 5:
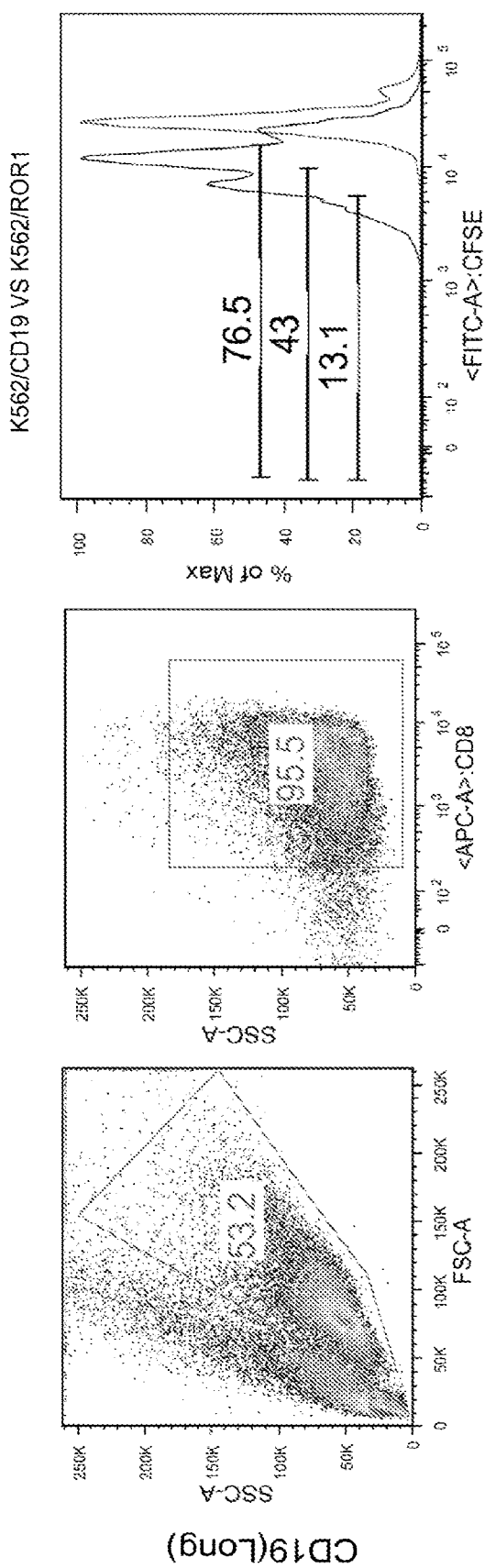
Figure 26:
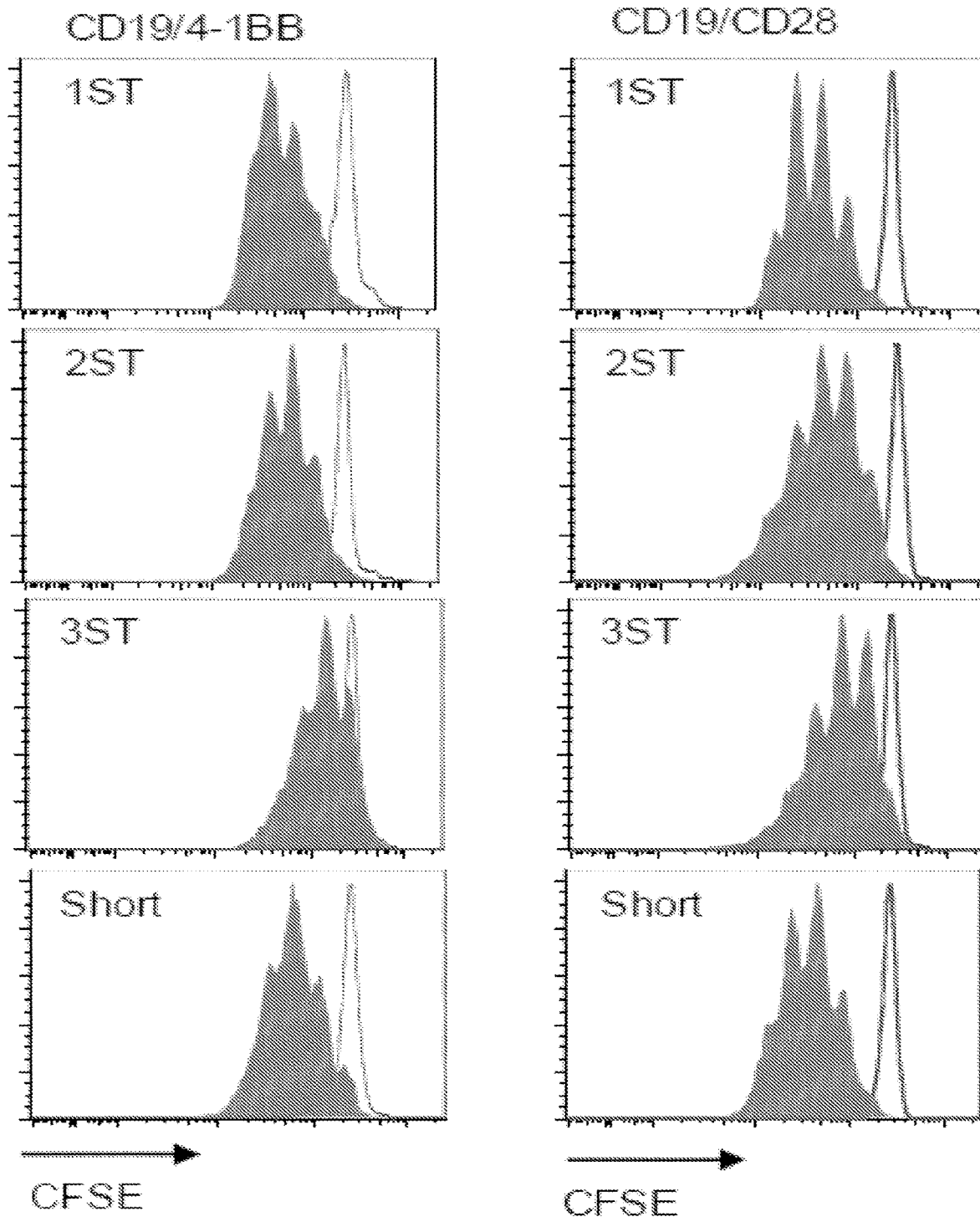
FIG. 26 shows CFSE dye dilution used to measure proliferation of anti CD19 4 1BB or CD28 ChARM expressing T cells 5 days after stimulation with CD19+ Raji tumor cells (solid grey) or medium only (grey lines) without addition of exogenous cytokines.

For analysis, triplicate wells were pooled and proliferation of live CD8+ T cells was measured. The left-most column is a forward scatter/side scatter plot of the total number of cells, the middle column is a plot gated on CD8⁺ T cells, and the right-most column is a histogram showing CFSE dilution in the CD8⁺ T cell subset (increased dilution to the left). The right peak in the right-most column indicates no cell division, and the left peaks represent indicate ≥3, 2, or 1 cell division and the three numbers in each of the histograms indicate the percent of cells that have diluted CFSE and undergone more than 3, 2, or 1 cell division, respectively. The histogram shows that T-ChARM and CAR expressing T cells proliferated vigorously during the 72 hours after co-culture stimulation with K562/CD19 cells (left peak), but not with the negative control cells K562/ROR1 (right peak) (FIG. 5, right column). The average number of cell divisions was higher in T-ChARM¹ and T-ChARM² expressing T cells as compared to either T-ChARM³ or CAR (long) expressing T cells. Similarly, the level of proliferation was independent of the co-stimulatory domain (4-1BB or CD28) used in the ChARM (FIG. 26) and independent of the tag used (FIG. 31 shows equal proliferation when a Myc tag is used).

Example 7

In Vivo Adoptive Transfer of T Cells Expressing T-ChARM Molecules

Figure 6B:
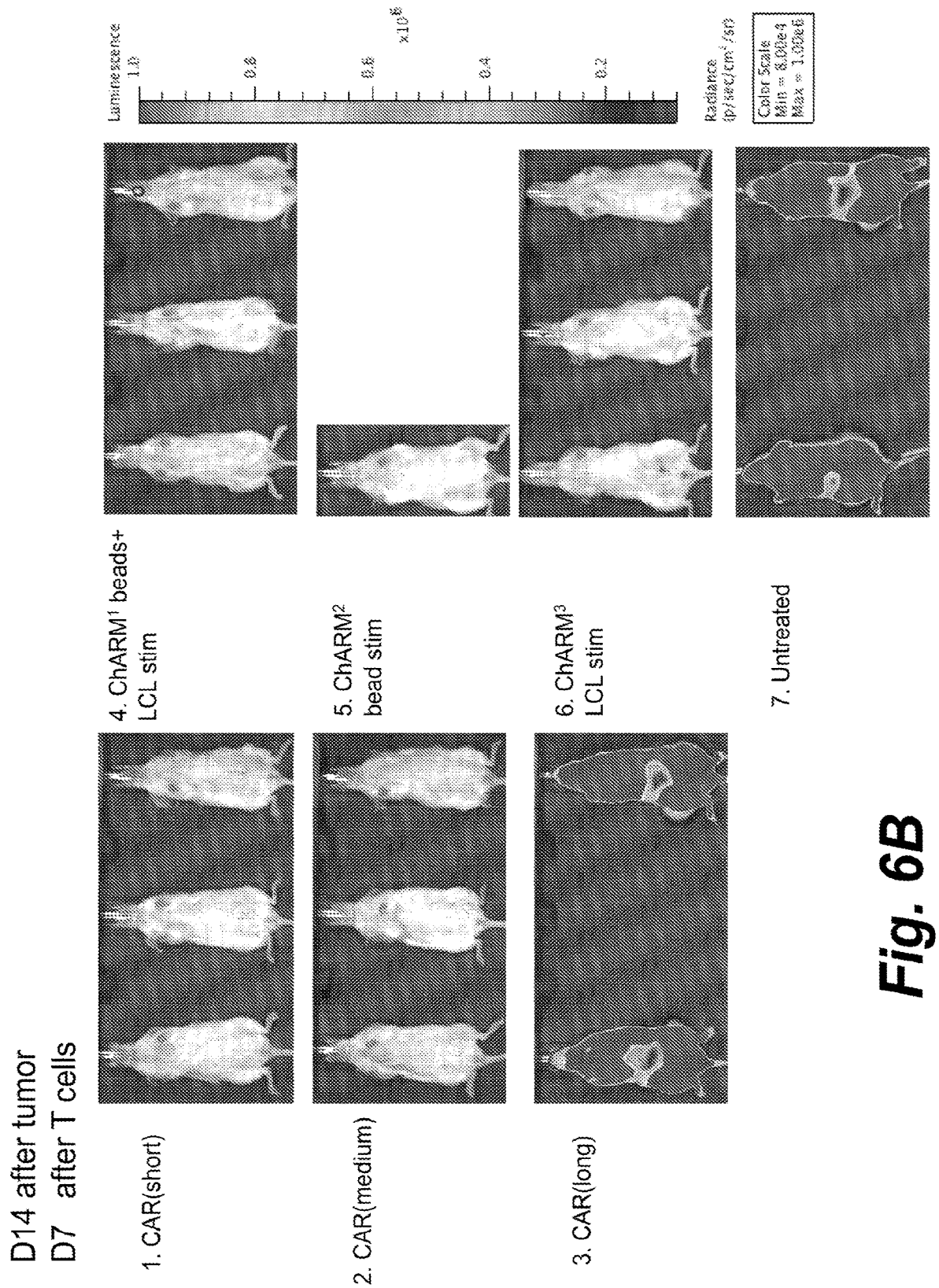
Figure 6C:
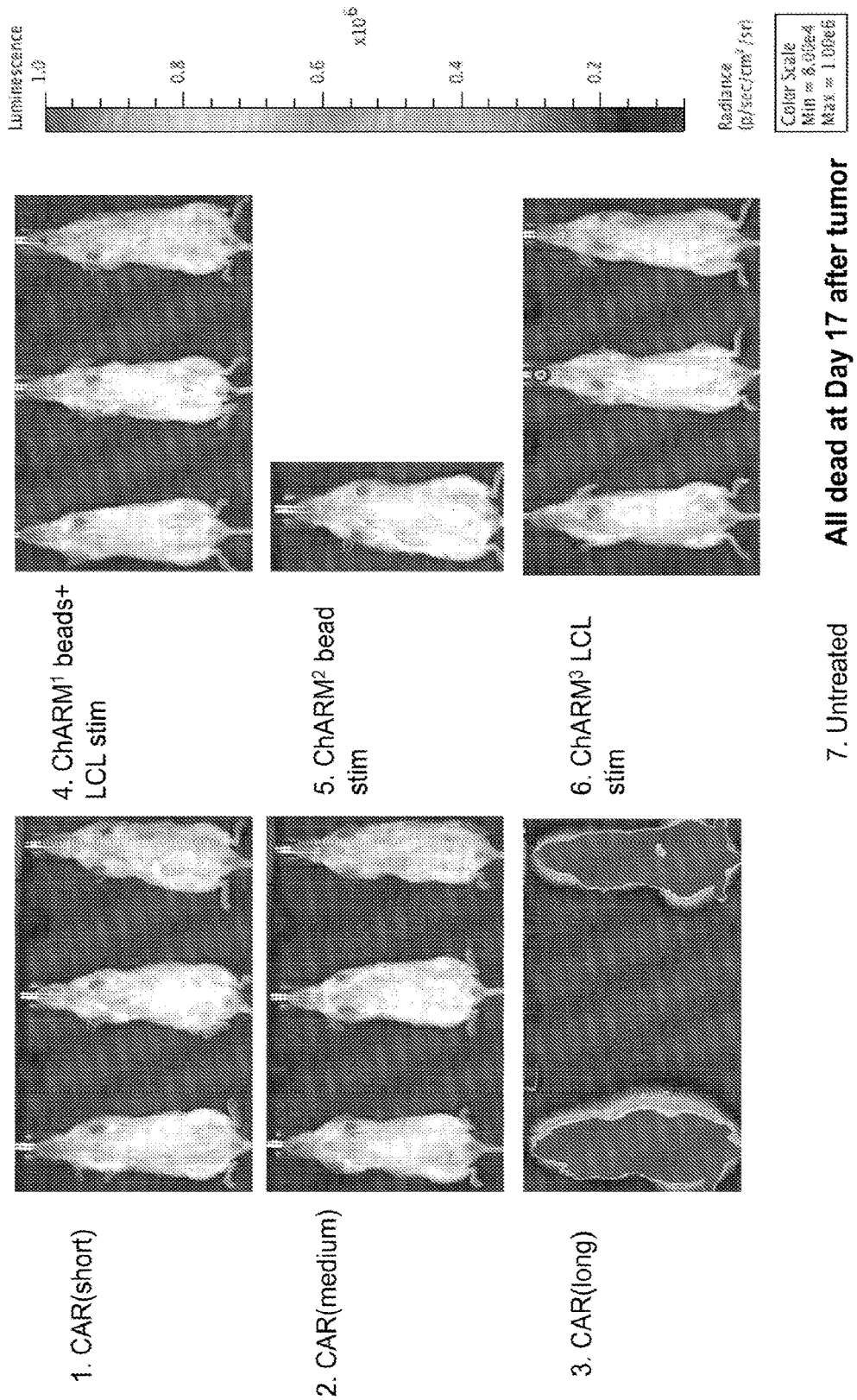
Figure 6D:
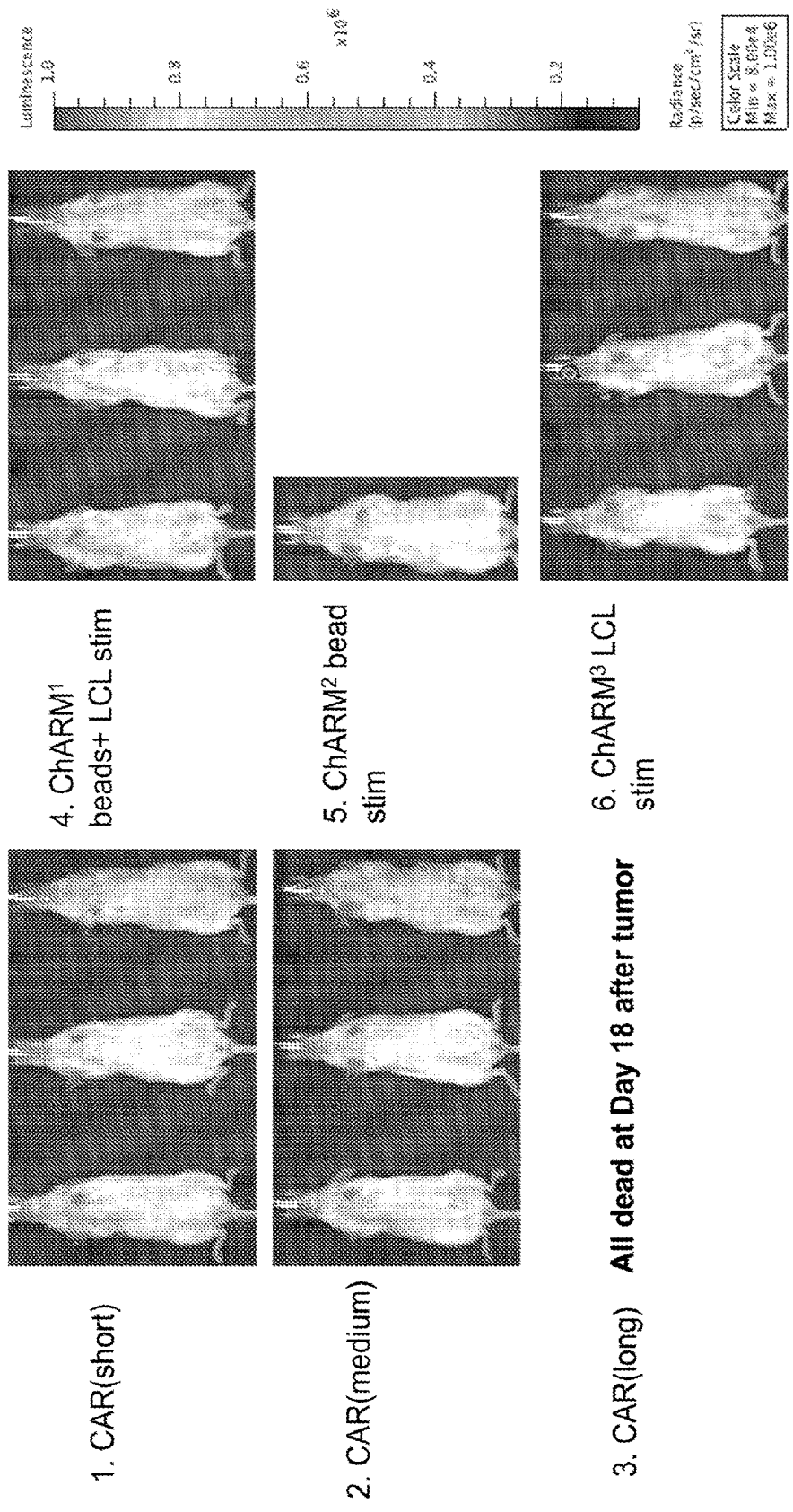
Figure 6E:
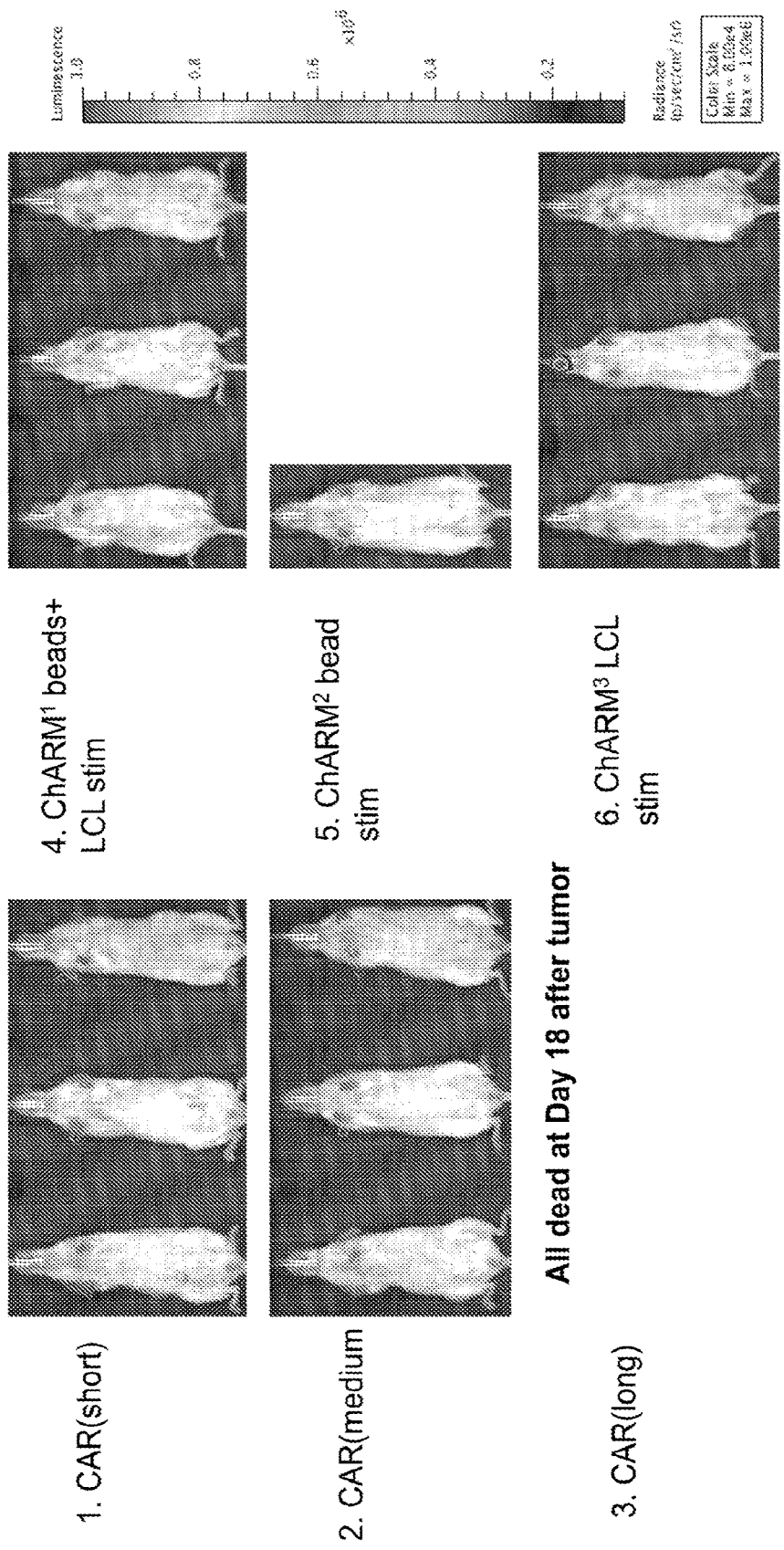

Six- to eight-week old female NOD.CB 17-Prkdcscid/J (NOD/SCID) or NOD.Cg Prkdc$^{scid}$Il2rg$^{tm1Wjl}$/SzJ (NSG) mice were obtained from Jackson Laboratory or bred in-house. Mice were injected intravenously (i.v.) with 0.5×10⁶ Raji lymphoma tumor cells transfected with firefly luciferase (Raji-ffluc) via the tail vein and tumor engraftment was allowed to occur for 6 days. On day 7, mice received a single intra-venous (i.v.) injection of 5×10⁶ of T cells transduced with one of anti-CD19 (scFv) T-ChARM¹, T-ChARM², T-ChARM³, CAR (short), CAR (medium), and CAR (long) human T cells. To verify tumor engraftment, bioluminescence imaging was performed on day 6 after Raji-ffluc inoculation (FIG. 6A). To monitor anti-tumor activity of the adoptive T cell therapy, bioluminescence imaging was performed on day 7 (FIG. 6B), day 11 (FIG. 6C), day 18 (FIG. 6D), and day 26 (FIG. 6E) after T cell administration.

For bioluminescence imaging of tumor cells, mice received intraperitoneal (i.p.) injections of luciferin substrate (CaliperLife Sciences, Hopkinton, Mass.) resuspended in PBS (15 µg/g body weight). Mice were anesthetized with isoflurane in an induction chamber and imaged using an Xenogen IVIS In vivo Imaging System (Caliper Life Sciences) 10, 12 and 14 minutes after the injection of luciferin in small binning mode at an acquisition time of 1 second-1 minute to obtain unsaturated images. Luciferase activity was analyzed using Living Image Software (Caliper Life Sciences) and photon flux was analyzed within regions of interest that encompassed the entire body of each individual mouse.

The bioluminescence images show that T cells expressing anti-CD19 T-ChARM¹, T-ChARM², or T-ChARM³ eradicated tumor as efficiently as T cells expressing anti CD19 CAR (short) or CAR (intermediate), while the T cells expressing CAR (long) were not very effective for this particular construct and/or target (FIG. 6).

Example 8

In Vivo Persistence of T Cells Expressing T-ChARM Molecules

A cohort of NSG mice bearing Raji tumors were treated with 5×10⁶ anti CD19 CAR/huEGFRt or T-ChARM/huEGFRt expressing human T cells, and 3 weeks later peripheral blood (eye bleeds) was analyzed by flow cytometry using anti huEGFR, anti human CD8, and anti human CD45 monoclonal antibodies. The frequency of CD8+ huEGFRt+

Figure 7:
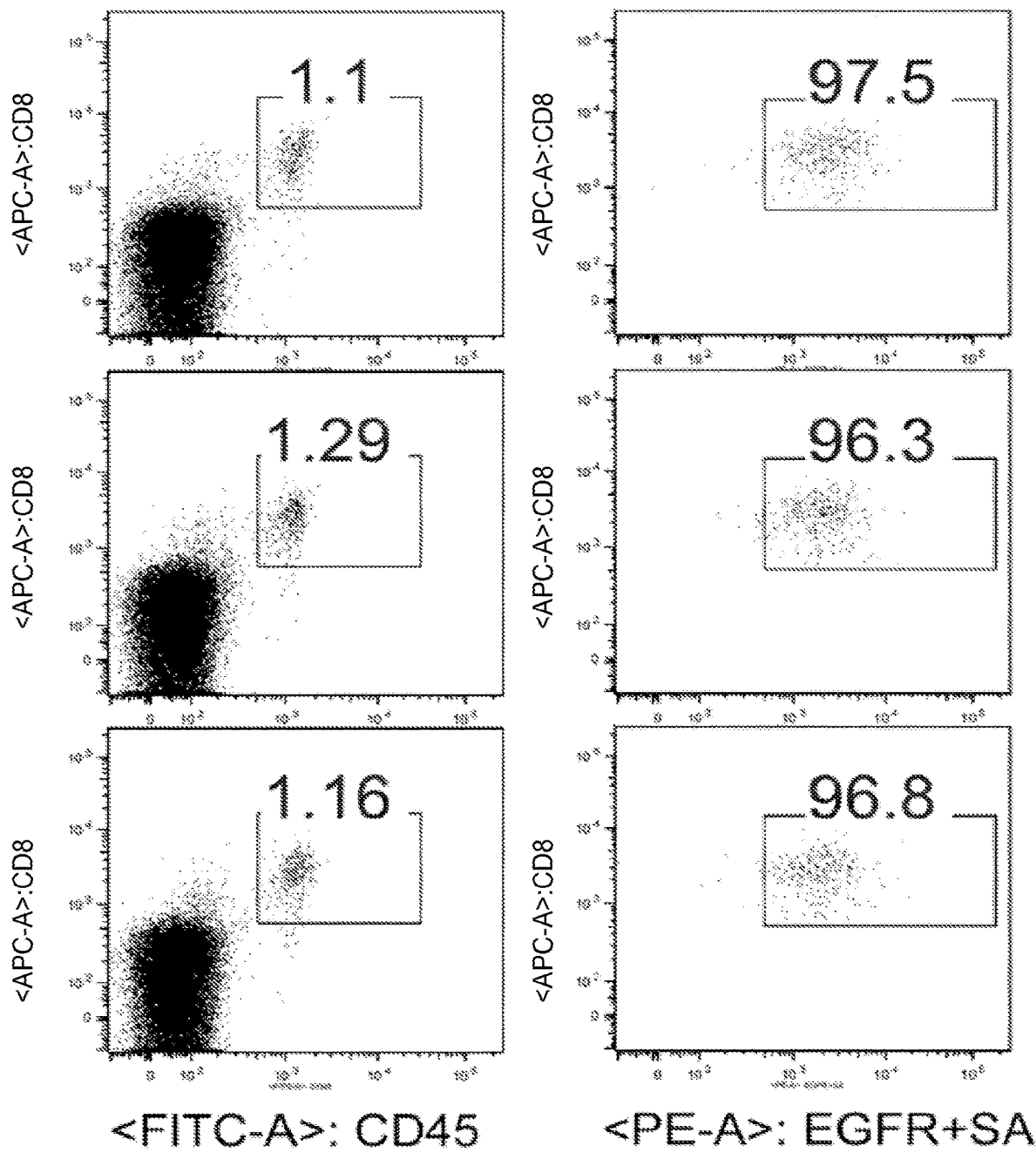
FIG. 7 shows that anti-CD19 CAR and T-ChARM expressing human T cells can persist in the blood following adoptive transfer into NSG mice that were inoculated with Raji lymphoma. Human T cells are distinguished by staining with monoclonal antibodies specific for the human CD8 and CD45 cell surface molecules.
Figure 7:
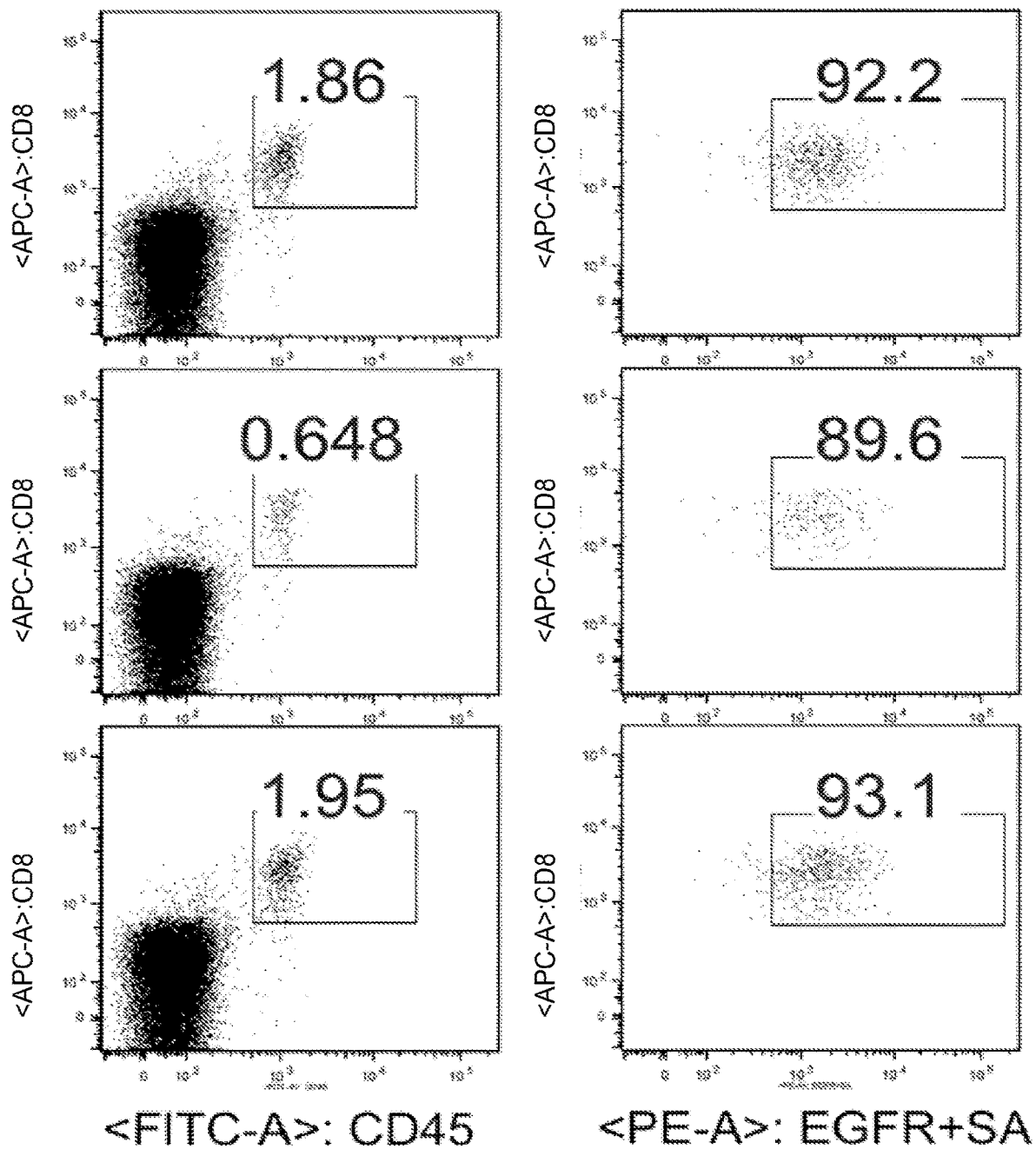
Figure 7:
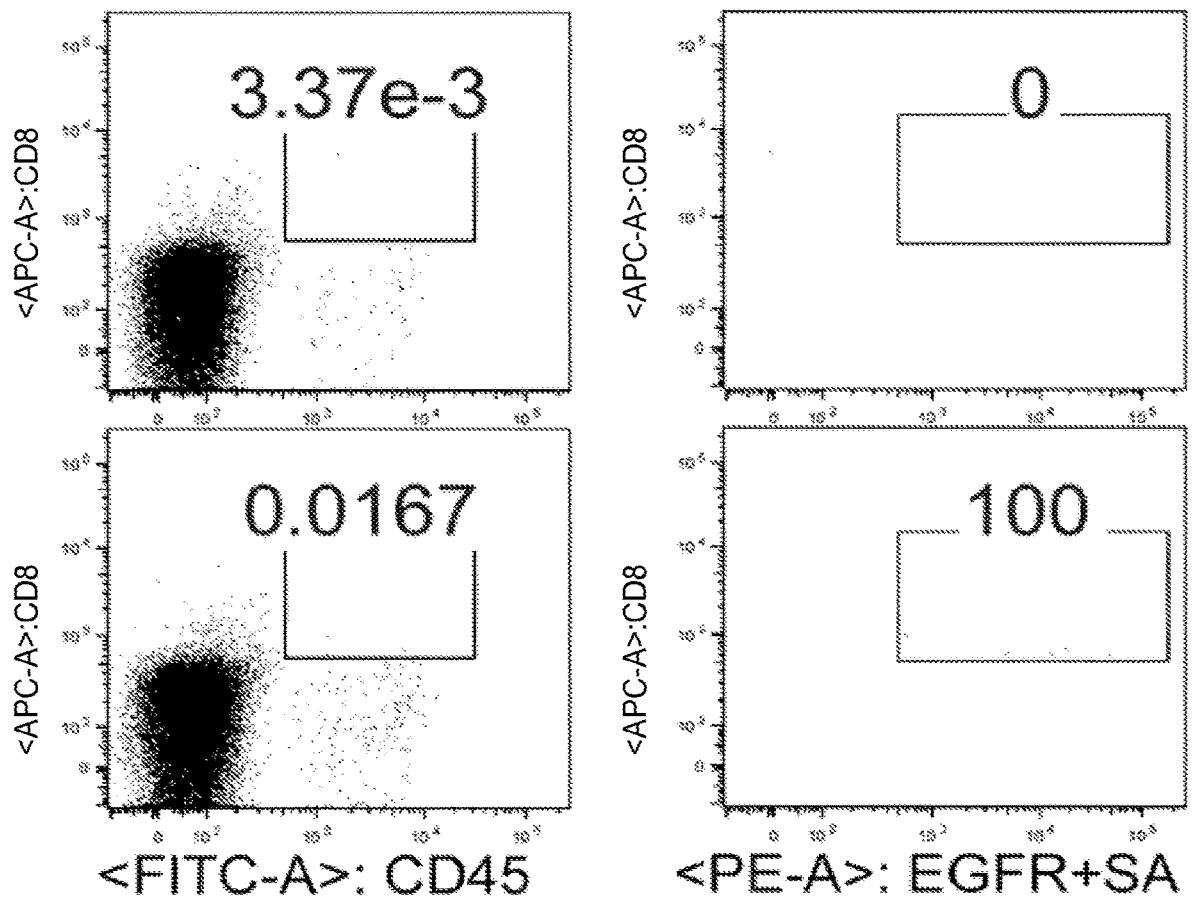
Figure 7:
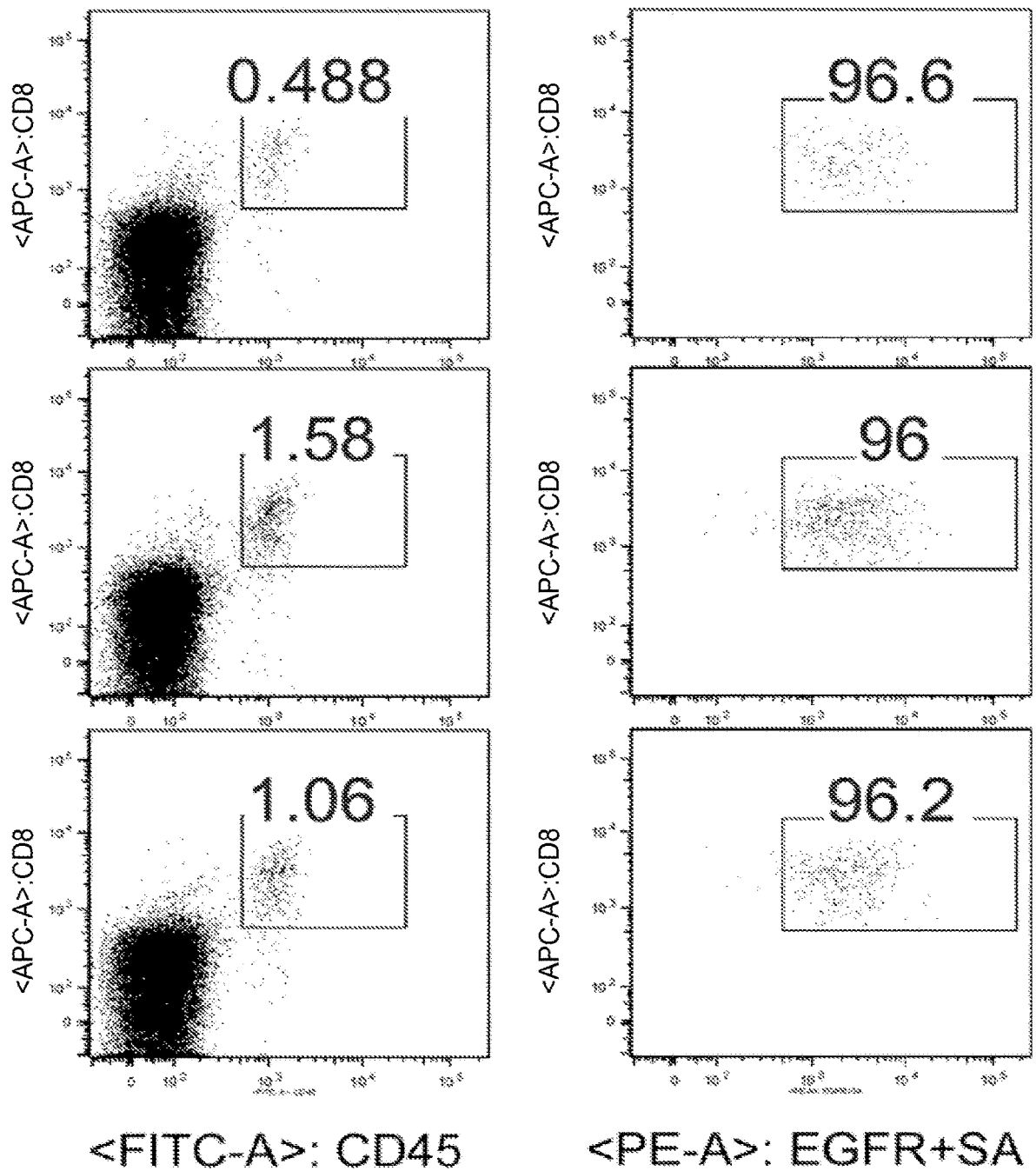
Figure 7:
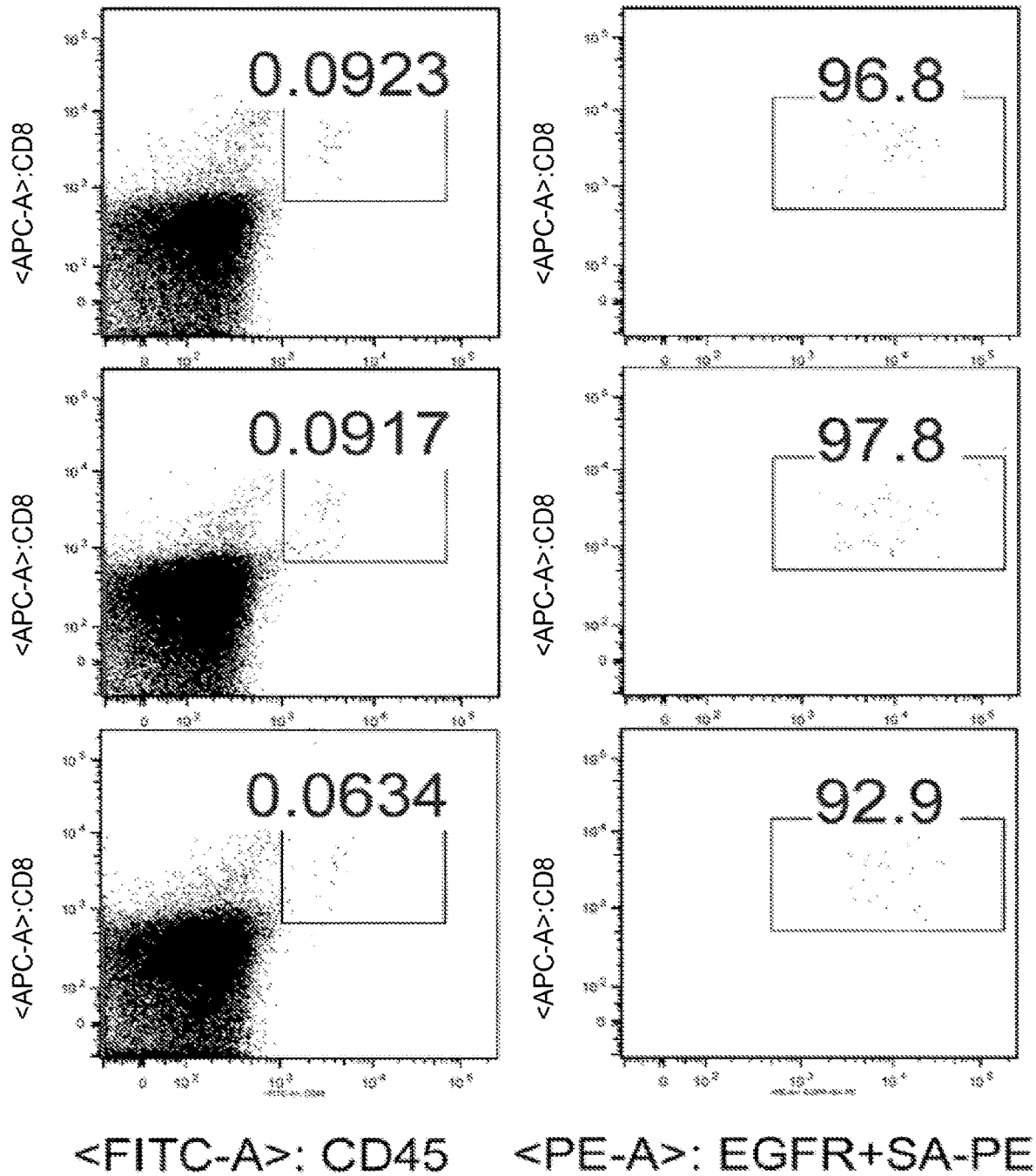
Figure 7:
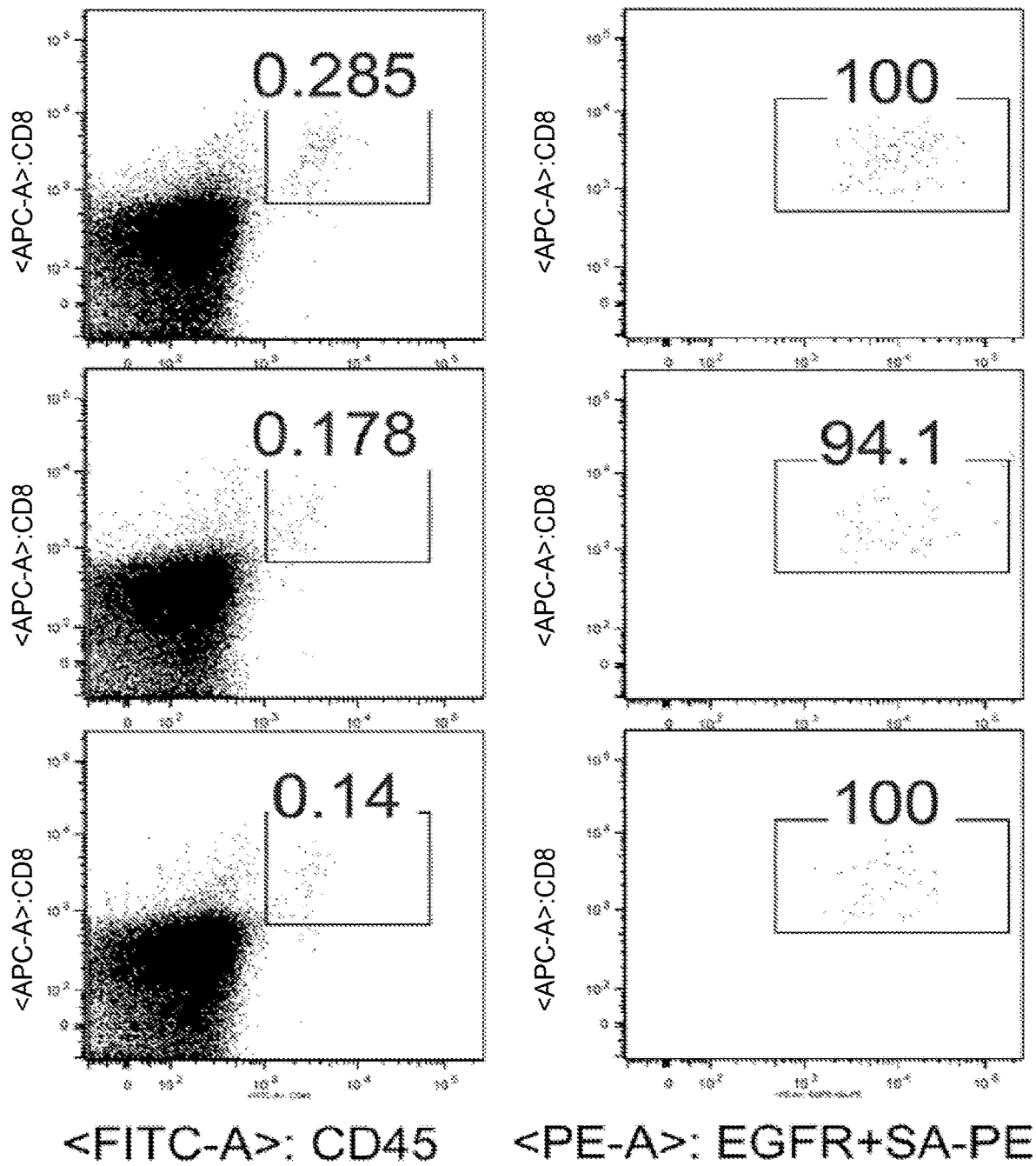
Figure 7:
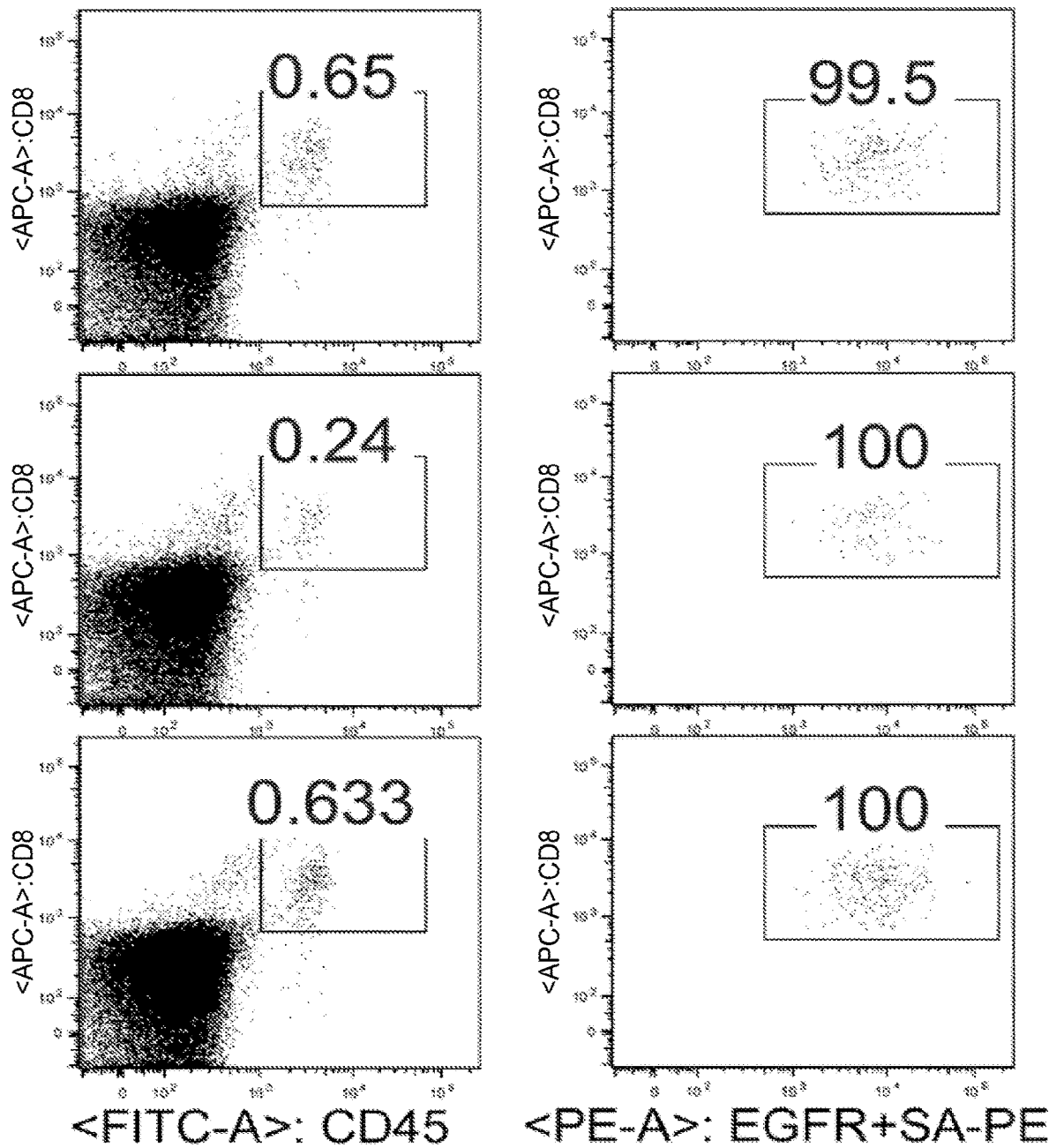

(Wang et al., 2011) T cells is shown as a percentage of live peripheral blood cells in FIG. 7. The level of detectable huEGFRt correlates to the level of T-ChARM expressing T cells.

Although anti-CD19 CAR (long) expressing T cells were not consistently prominent after 3 weeks, all other anti-CD19 CAR and T-ChARM expressing T cells were easily detected in the peripheral blood of NSG mice for at least 3 weeks after adoptive transfer and tumor eradication. These results indicate that anti-CD19 CAR and T-ChARM expressing T cells can persist for an extended period of time in vivo and mediate antitumor activity.

Example 9

Identification of T Cells Expressing T-ChARM Molecules

Figure 8A:
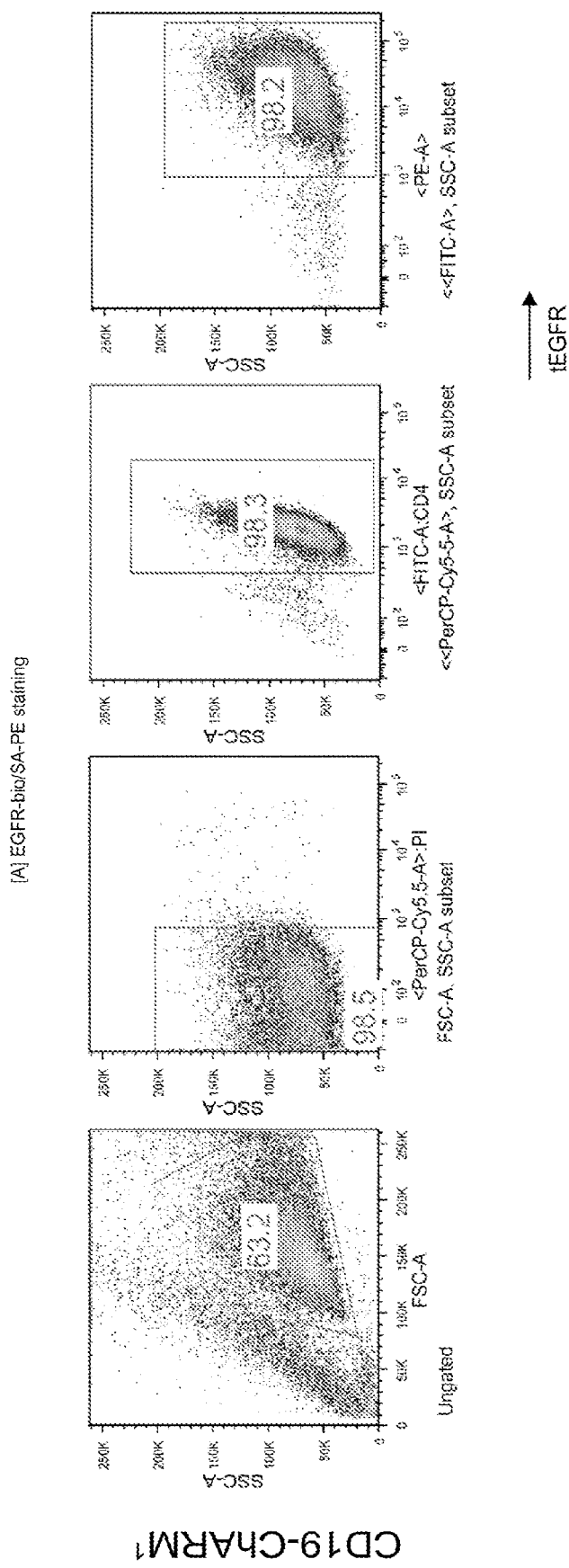
FIGS. 8A-8D show that T-ChARM expressing T cells can be identified by flow cytometry using a tag specific binding agent. In the examples, purified T-ChARM T cells are detected by the expression marker tEGFR (A), detected by anti-Strep Tag® II (STII) (B), or with Strep-Tactin® APC (C, D).
Figure 8A:
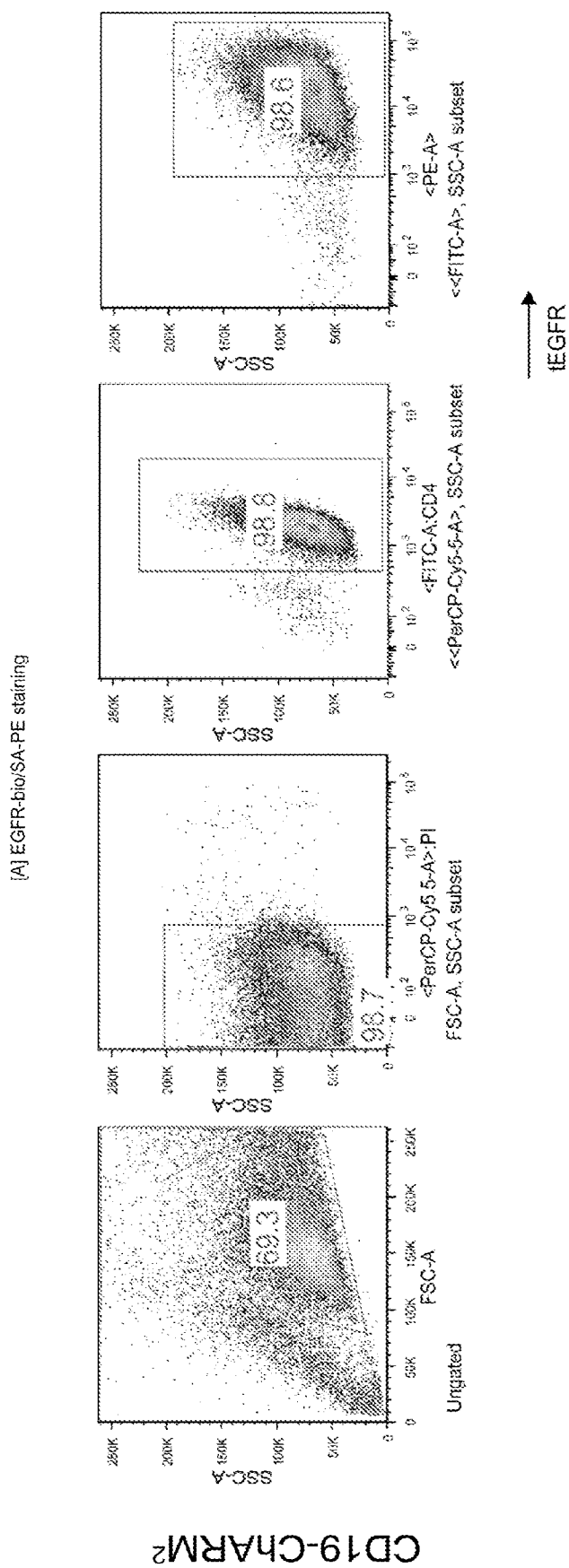
Figure 8A:
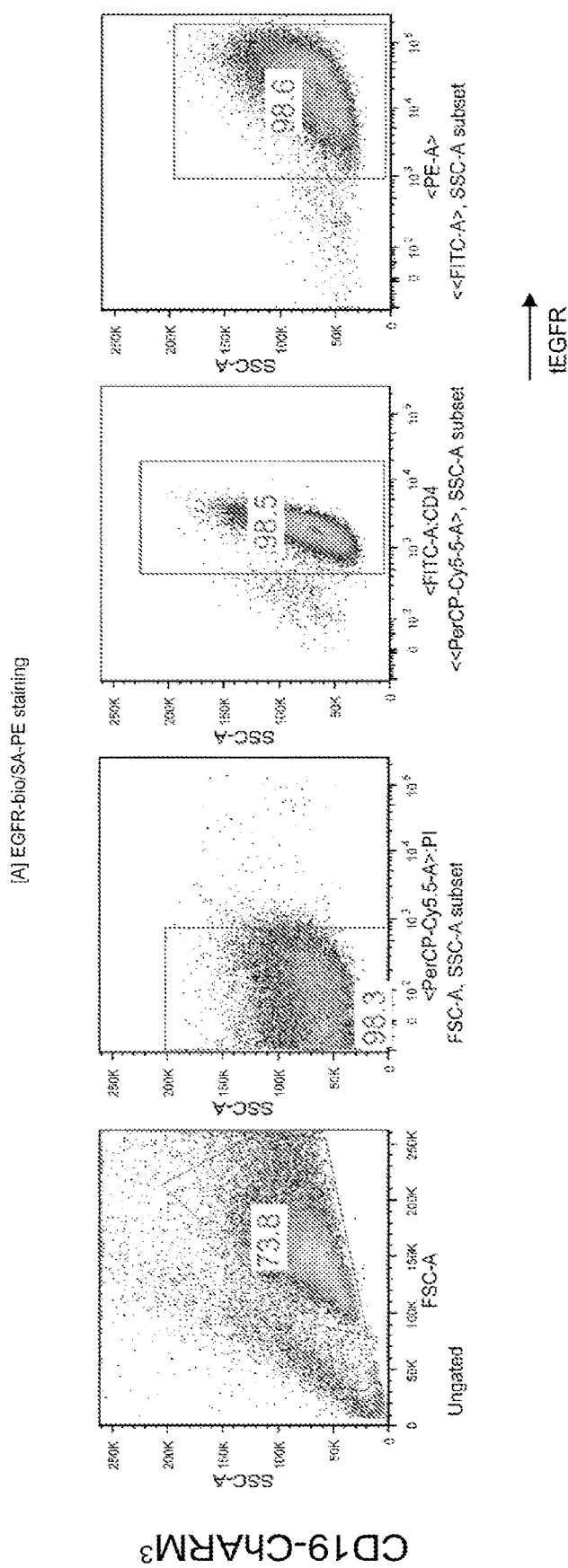
Figure 8A:
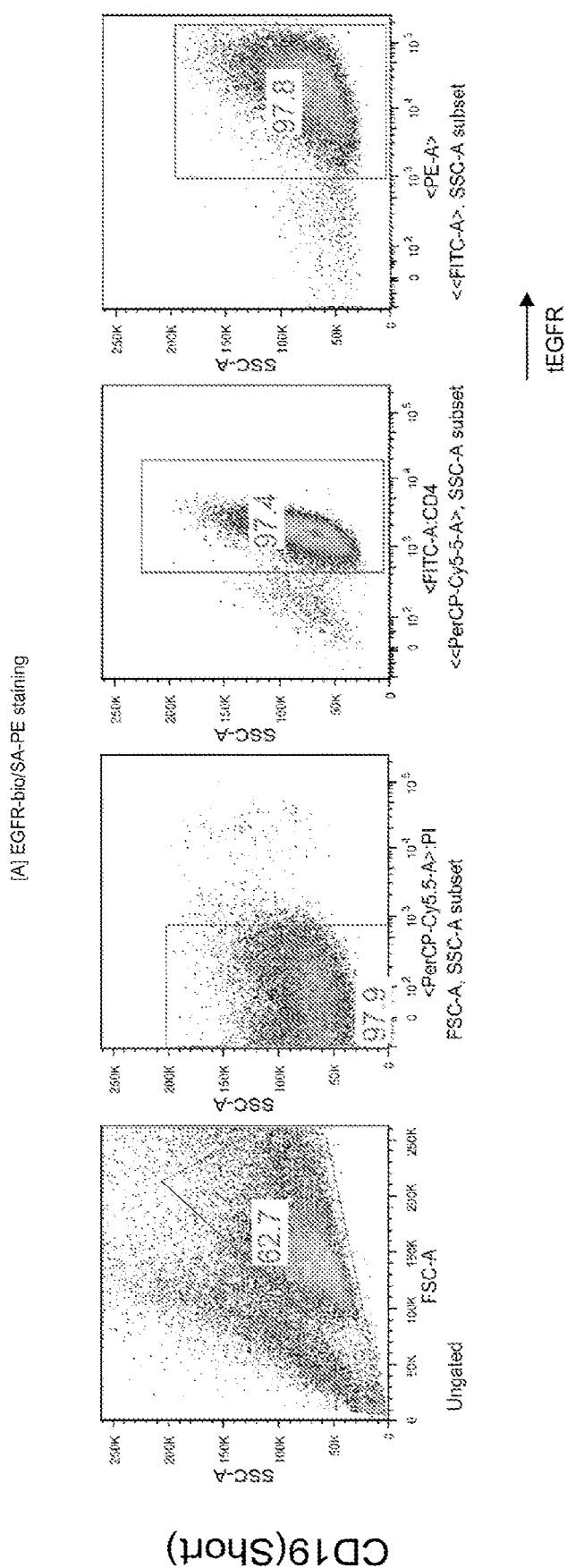

Anti-CD19 T-ChARM/huEFRt expressing T cells were stained with EGFR Ab-biotin/StrepTavidin-PE, anti-Strep Tag® II-FITC, Strep-Tactin®-APC (allophycocyanin), and then analyzed by flow cytometry. Anti-CD19 CAR (short) transduced T cells were used as a control. All of the transduced T-ChARM and anti-CD19 CAR (short) T cells stained positively with the anti-EGFR mAb indicating they were transduced and expressed the huEGFRT (FIG. 8A).

Figure 8B:
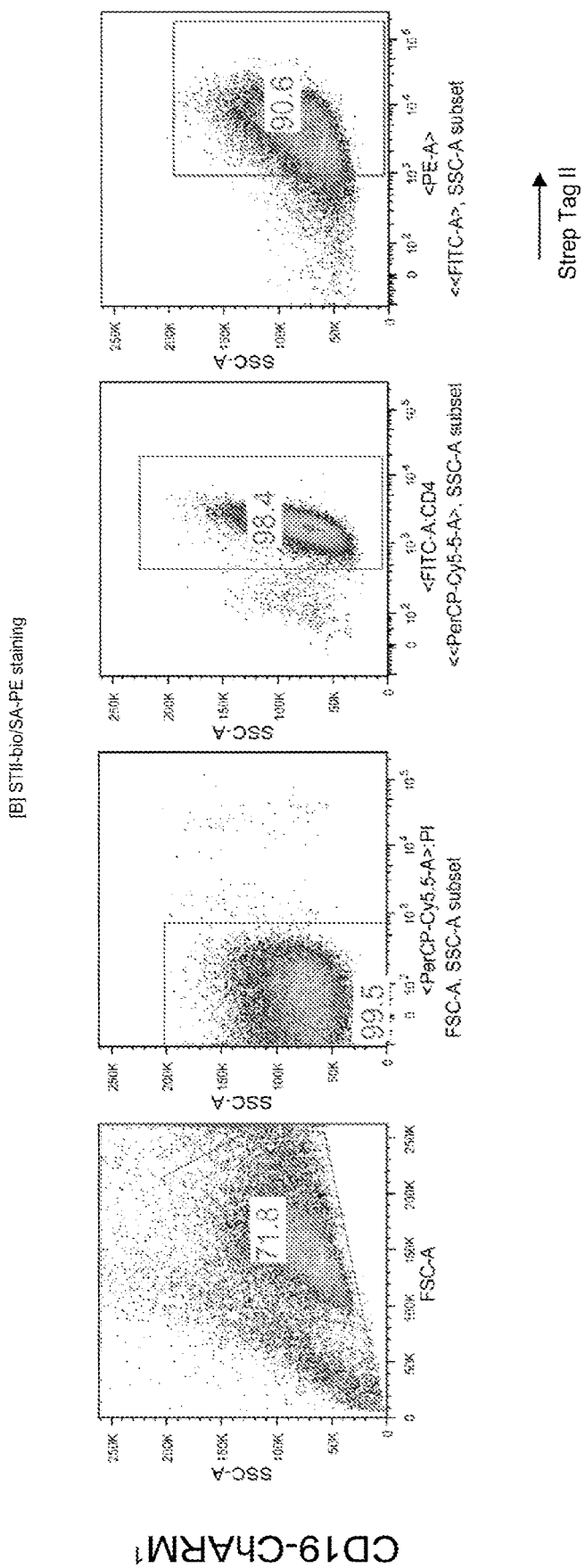
Figure 8B:
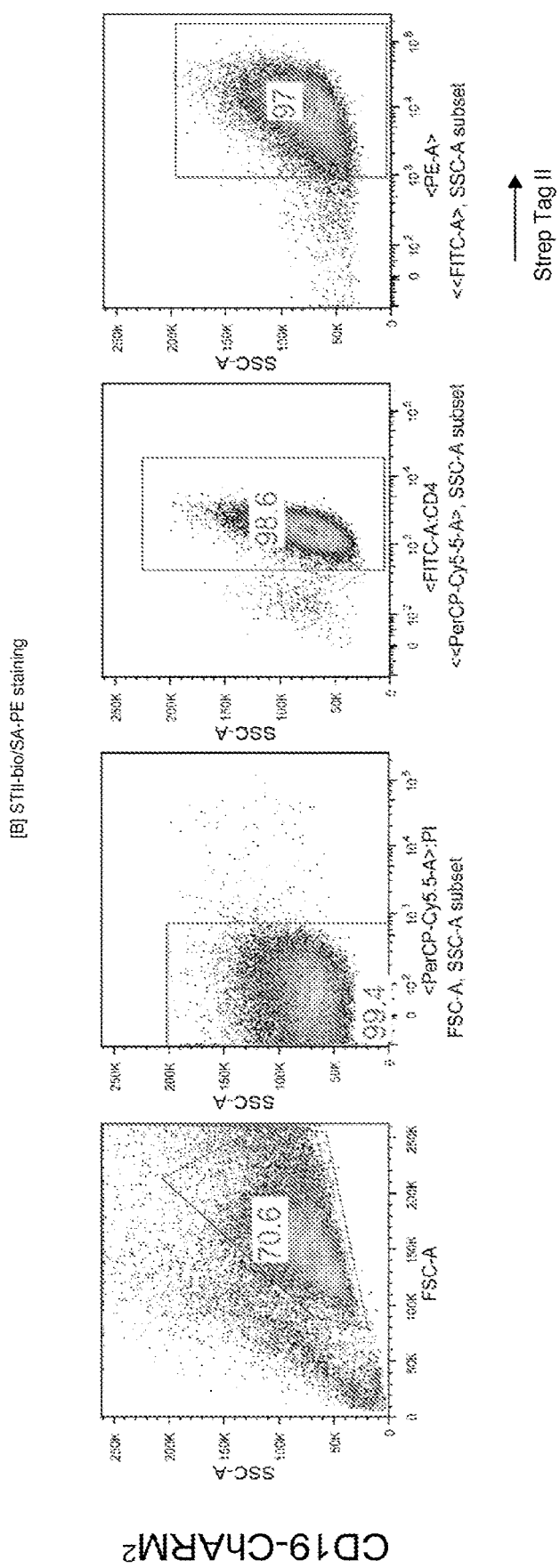
Figure 8B:
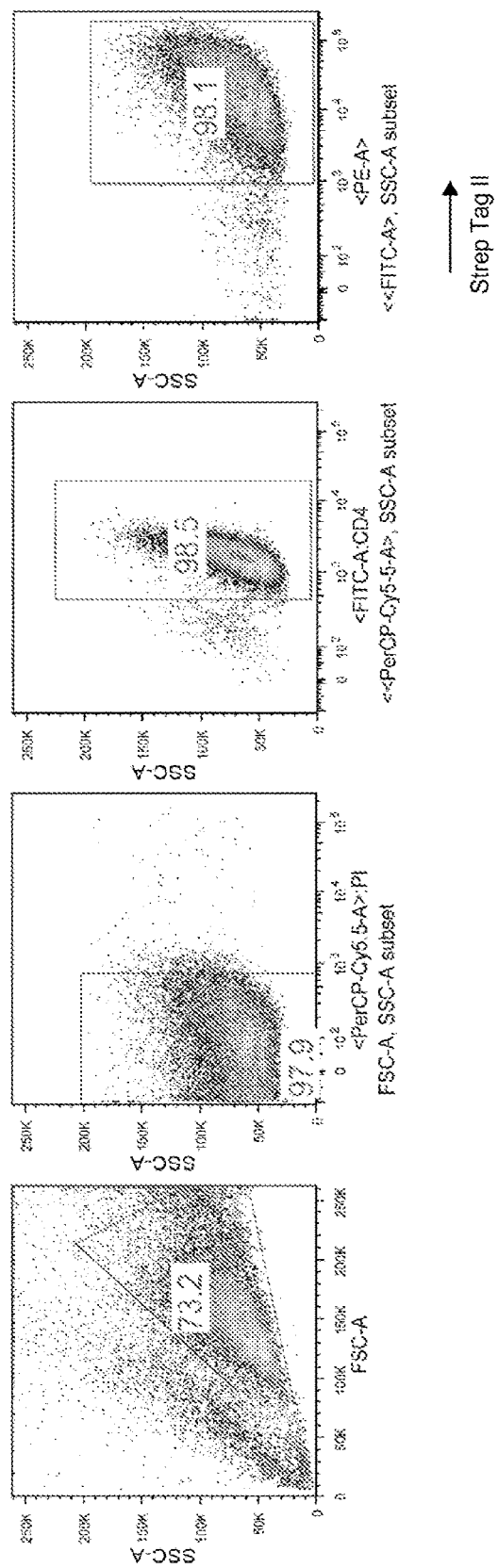
Figure 8B:
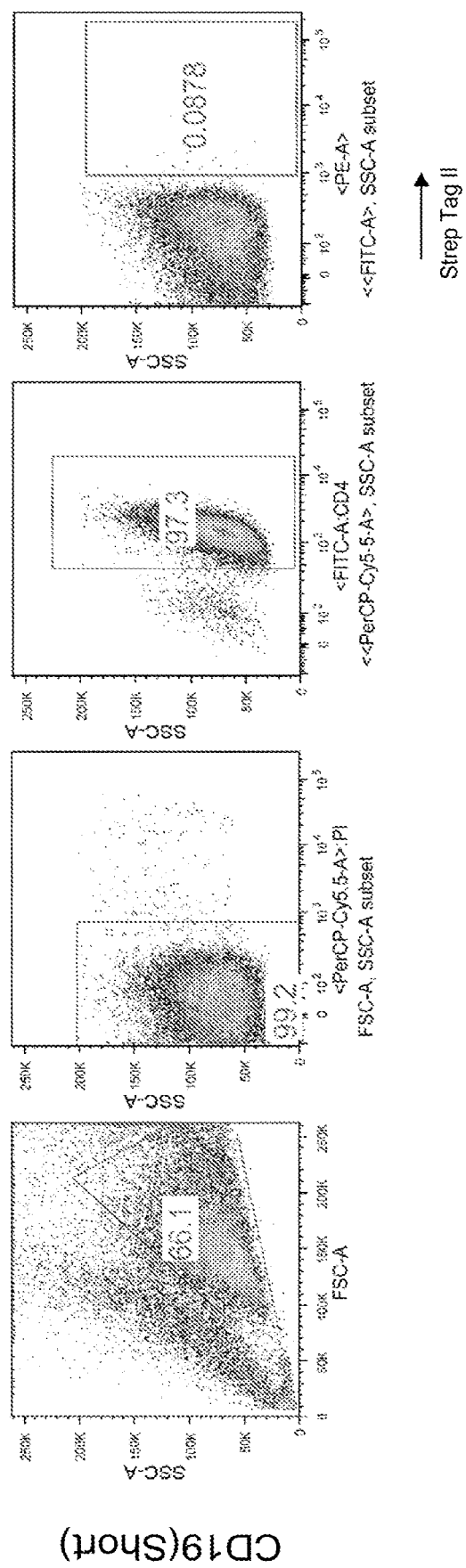
Figure 8C:
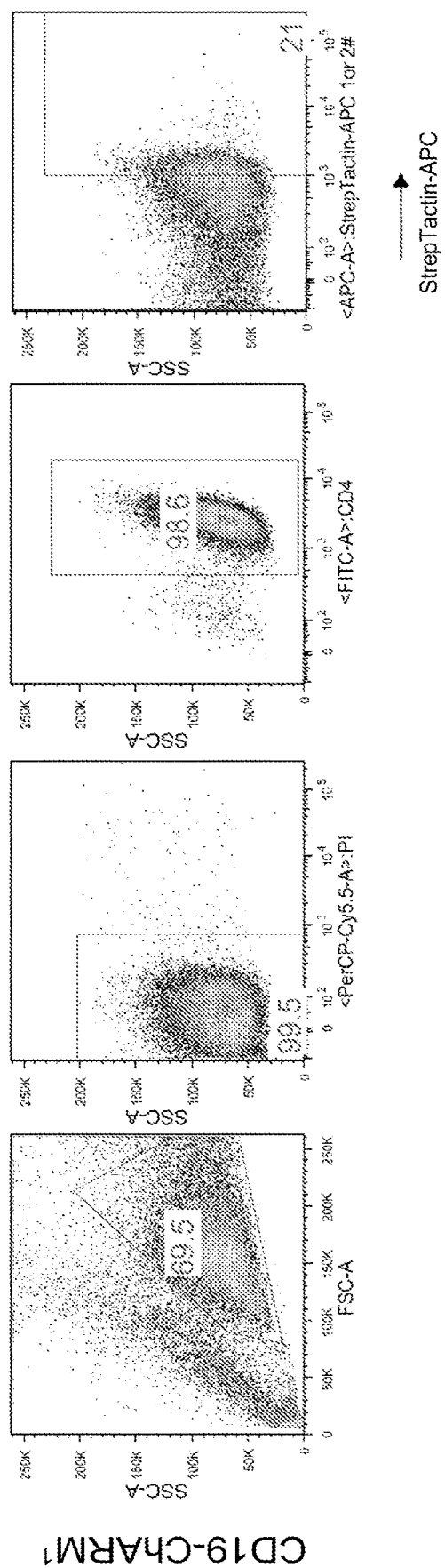
Figure 8C:
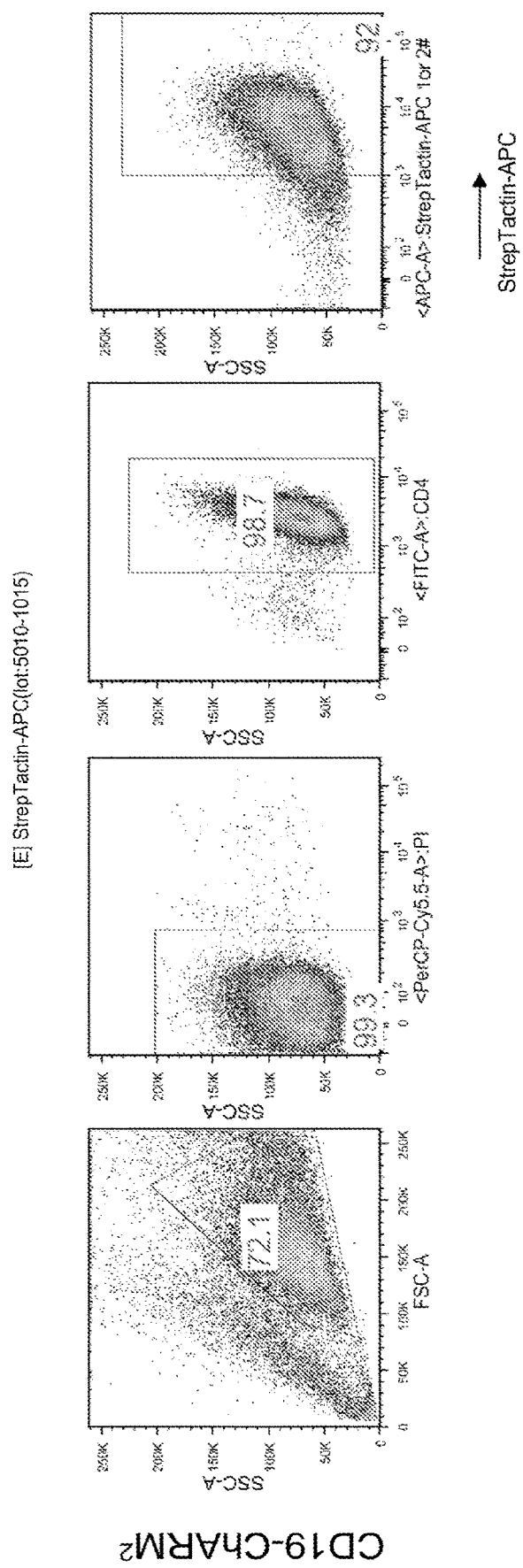
Figure 8C:
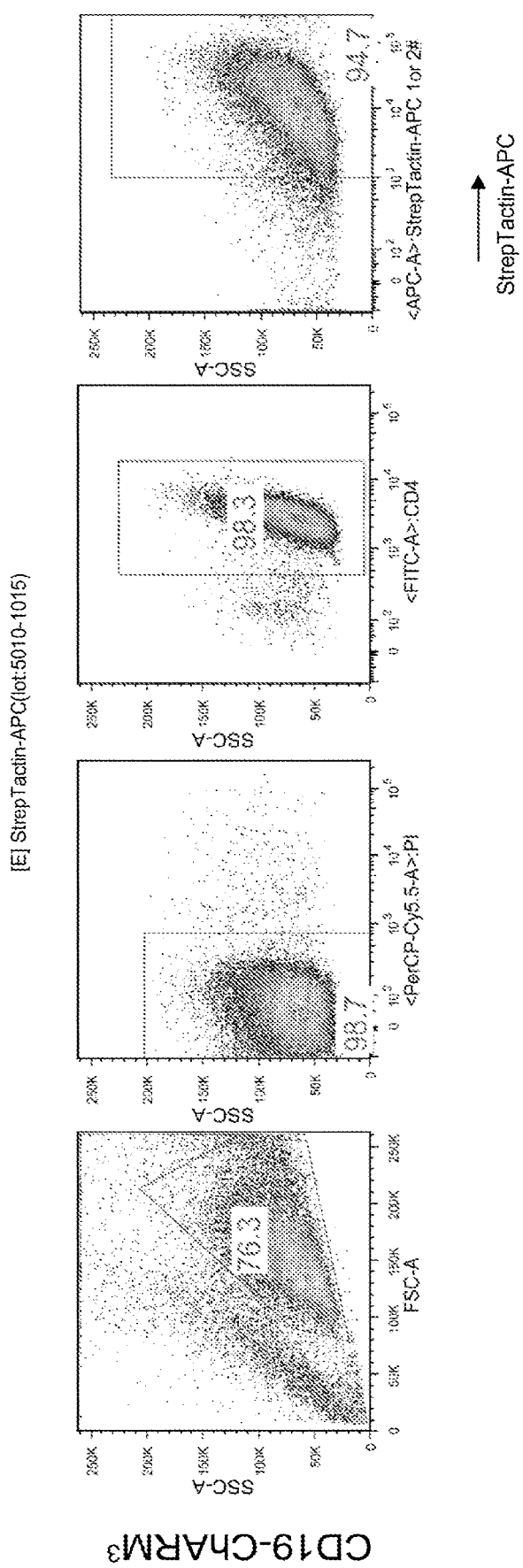
Figure 8C:
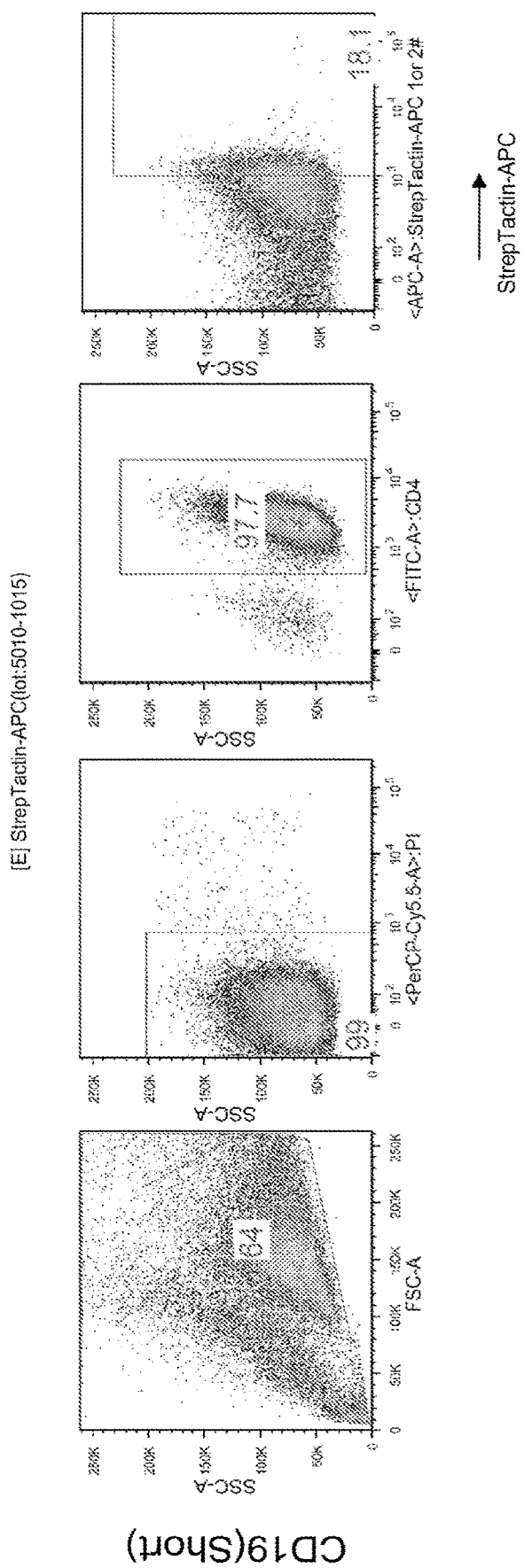
Figure 8D:
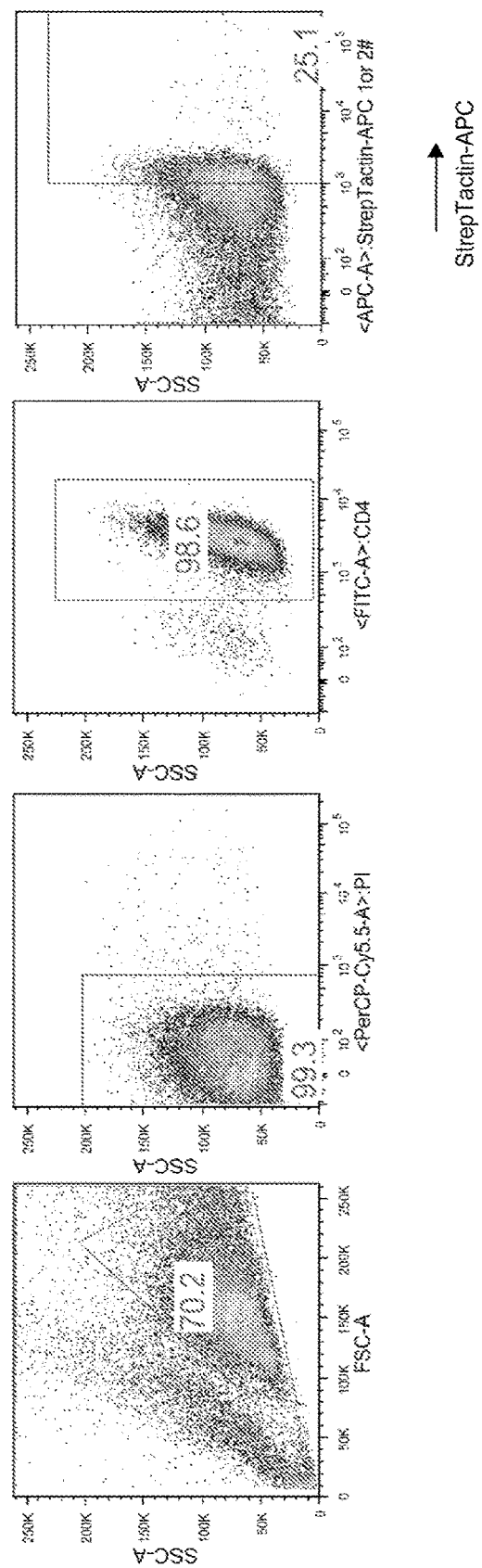
Figure 8D:
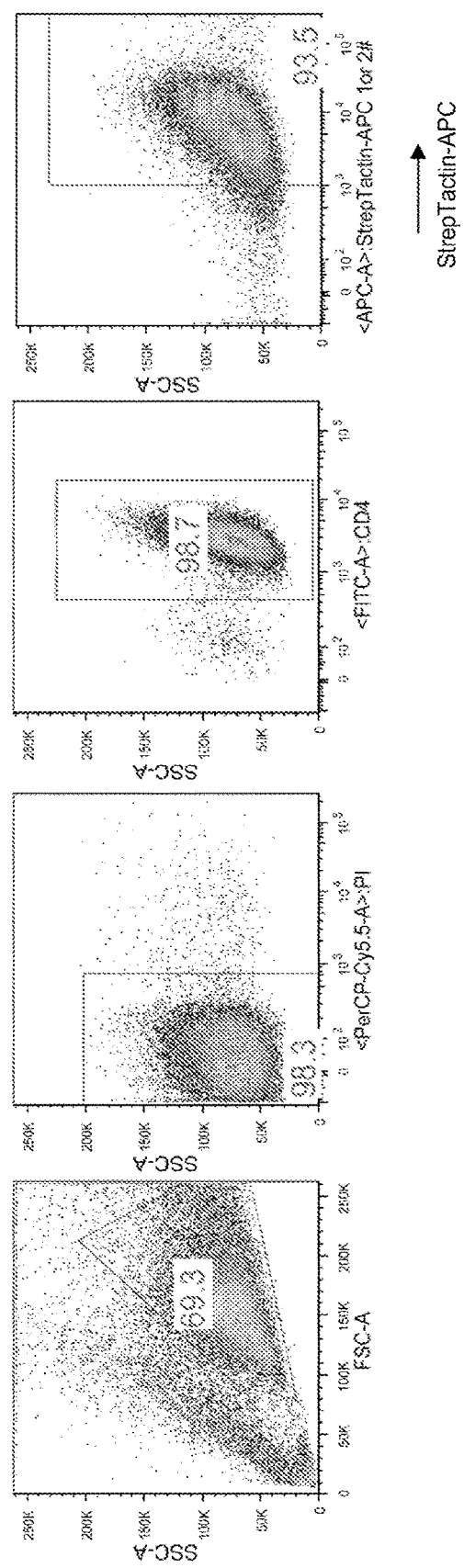
Figure 8D:
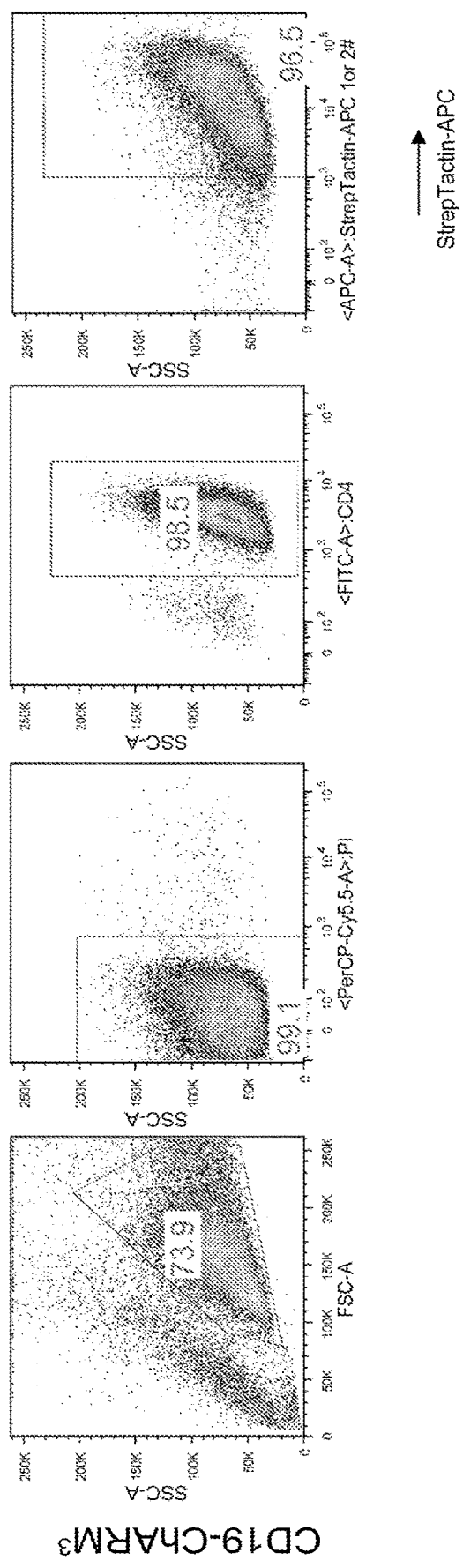
Figure 8D:
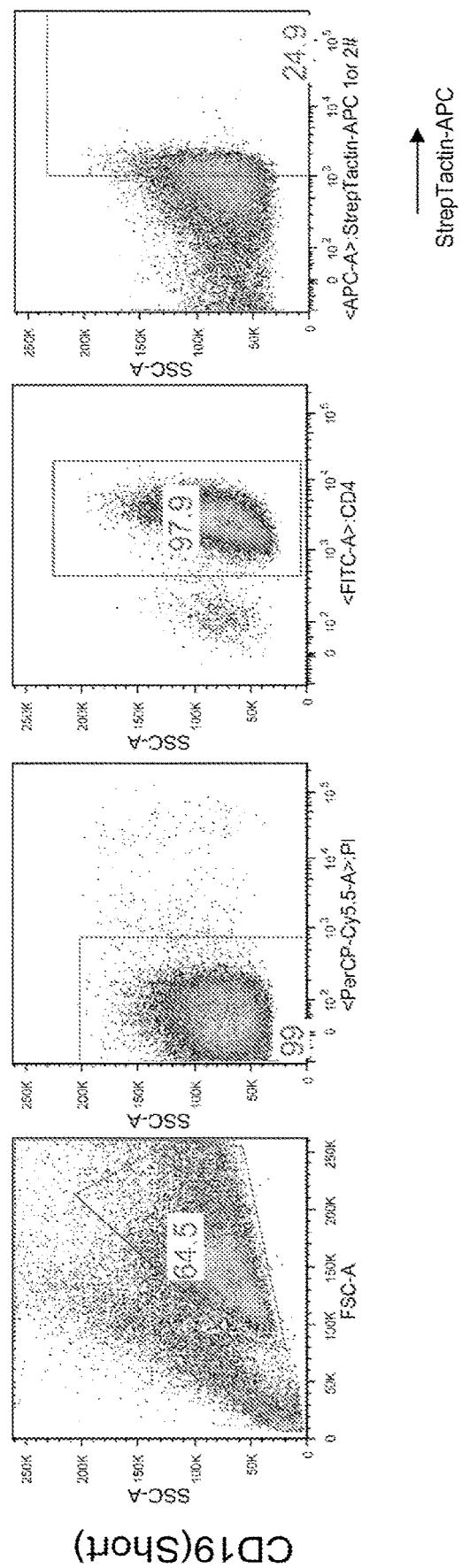

The results show that T-ChARM$^2$ and T-ChARM$^3$ transduced T cells could be easily distinguished from non-transduced cells with reagents that stained the tag sequence expressed in the T-ChARM cells (FIG. 8B,C). The T-ChARM$^1$, T-ChARM$^2$ and T-ChARM$^3$ transduced T cells, but not the anti-CD19 CAR (short), stained positive with the anti-Strep Tag® II-FITC antibody (FIG. 8B). Those with more copies of the tag sequence had an increased staining signal. The T-ChARM cells also stained with Strep-Tactin® APC (FIG. 8C), demonstrating that in the case of Strep Tag®, more than one staining reagent can be used to detect the T cells.

Example 10

Sorting T Cells Expressing T-ChARM Molecules

T-ChARM$^2$ transduced T cells were stained with anti-Strep Tag®-FITC labeled antibody and then sorted using a benchtop FACS cell sorter (BD FACSAria II cell sorter, BD Biosciences, San Jose, Calif.). FIG. 9 shows the cell populations before sorting (top row) and after sorting (bottom row). The furthest right panel (after sorting) shows that T-ChARM$^2$ expressing T cells were enriched from a cell population of 15.8% to a cell population that is greater than 99% T-ChARM$^2$ T cells.

Example 11

Enrichment of T Cells Expressing T-ChARM Molecules Using Immunomagnetic Selection Cells were incubated with Strep-Tactin®-microbeads or Nanobeads (IBA, Goettingen, Germany), then loaded onto a MACS column (Miltenyi Biotec) in a Magnetic separator. The column was washed 3 times with 3 ml MACS buffer. The column was then removed from the separator and the Strep-Tactin® magnetic beads with the attached T cells expressing the Strep Tag® were flushed out by firmly pushing a plunger into the column. T-ChARM$^3$ transduced T cells mixed with control T cells were labeled with one of the following types of beads: Strep-Tactin® Microbeads 1# (generally used for protein purification, size of about 0.5 to 1.5 µm); Strep-Tactin® Microbeads 2# (generally used for cell isolation with Fab Streptamers® [Strep-tagged Fab fragment], size of about 0.5 µm); Strep-Tactin® Nanobeads 3#(generally used for cell isolation with MHC I Streptamers [Strep-tagged MHCI monomer], size of about 100 nm); loaded onto a MACS® column (Miltenyi) and inserted into a magnetic separator. The direct effluent and retained fractions were individually stained with an anti-Strep Tag®-FITC labeled antibody and analyzed by flow cytometry.

Figure 10:
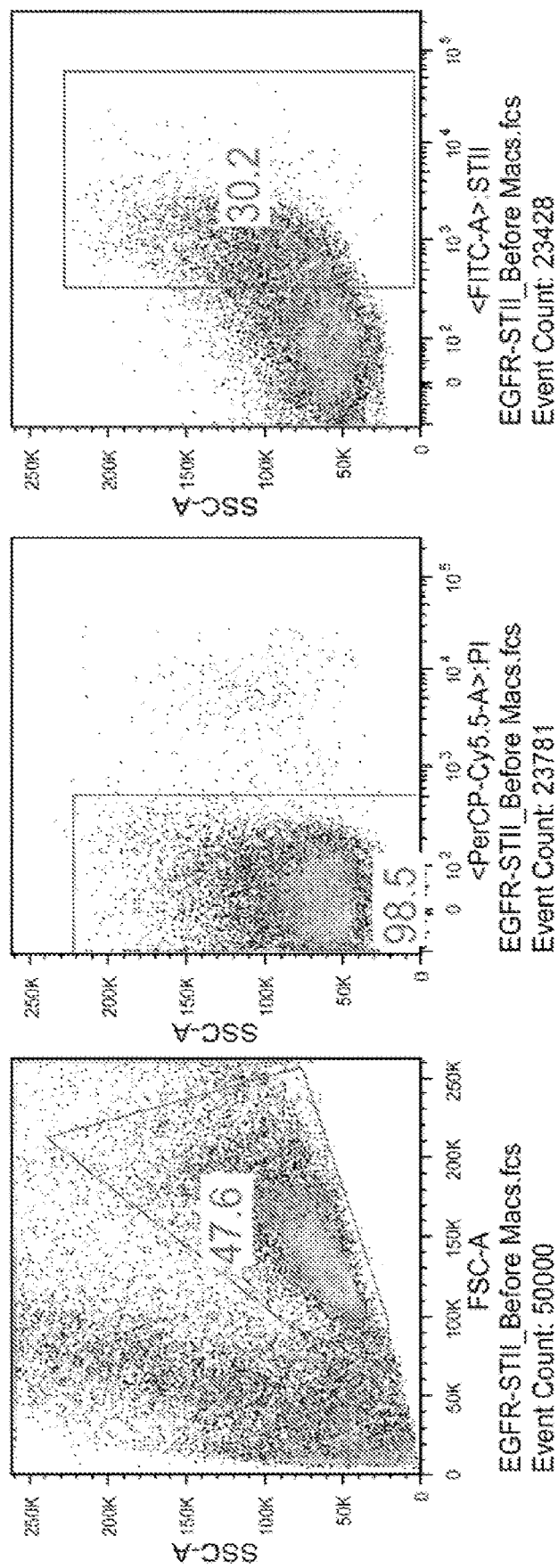
FIG. 10 shows direct enrichment of T-ChARM expressing T cells (containing three Strep-tag tag cassettes) by using Strep-Tactin® beads of various sizes. The panels on the left show staining of the enriched fraction and the panels on the right show the effluent (unenriched fraction).
Figure 10:
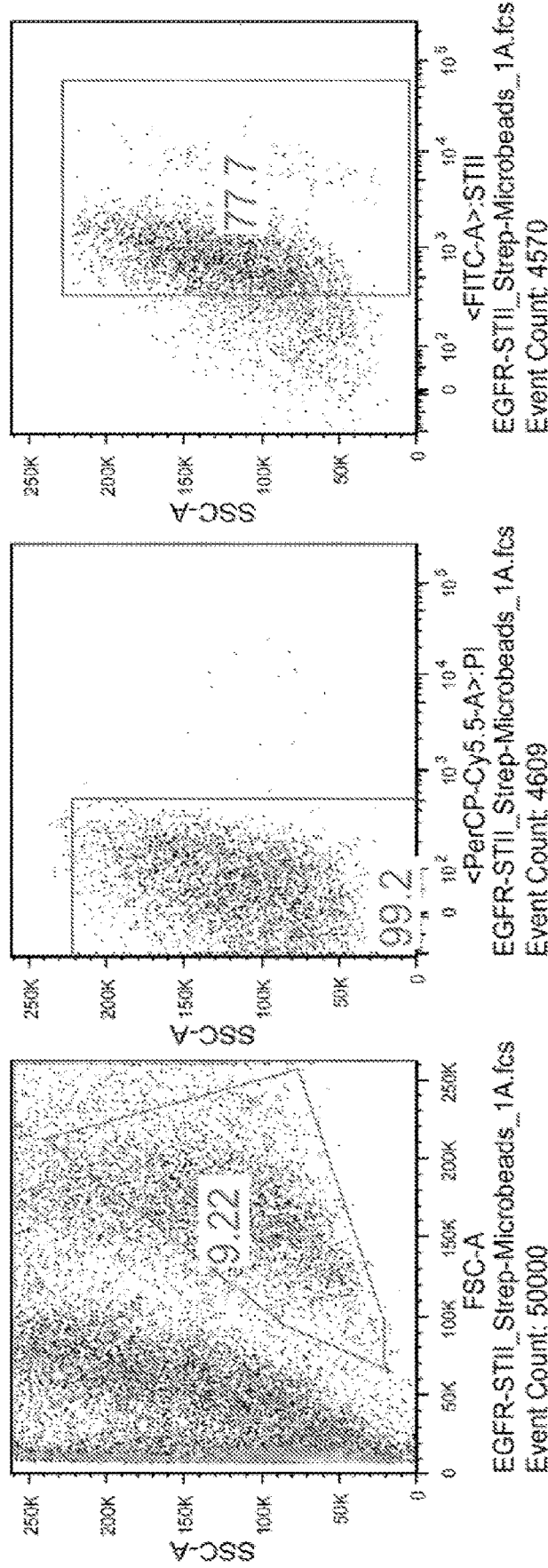
Figure 10:
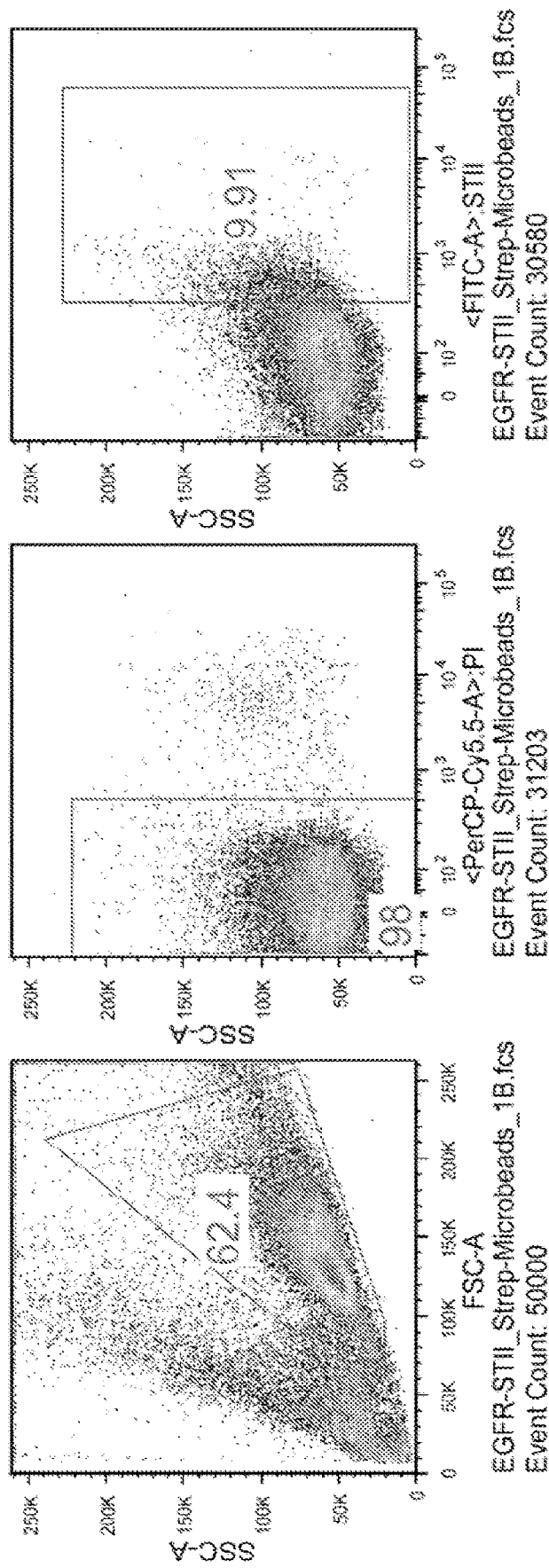
Figure 10:
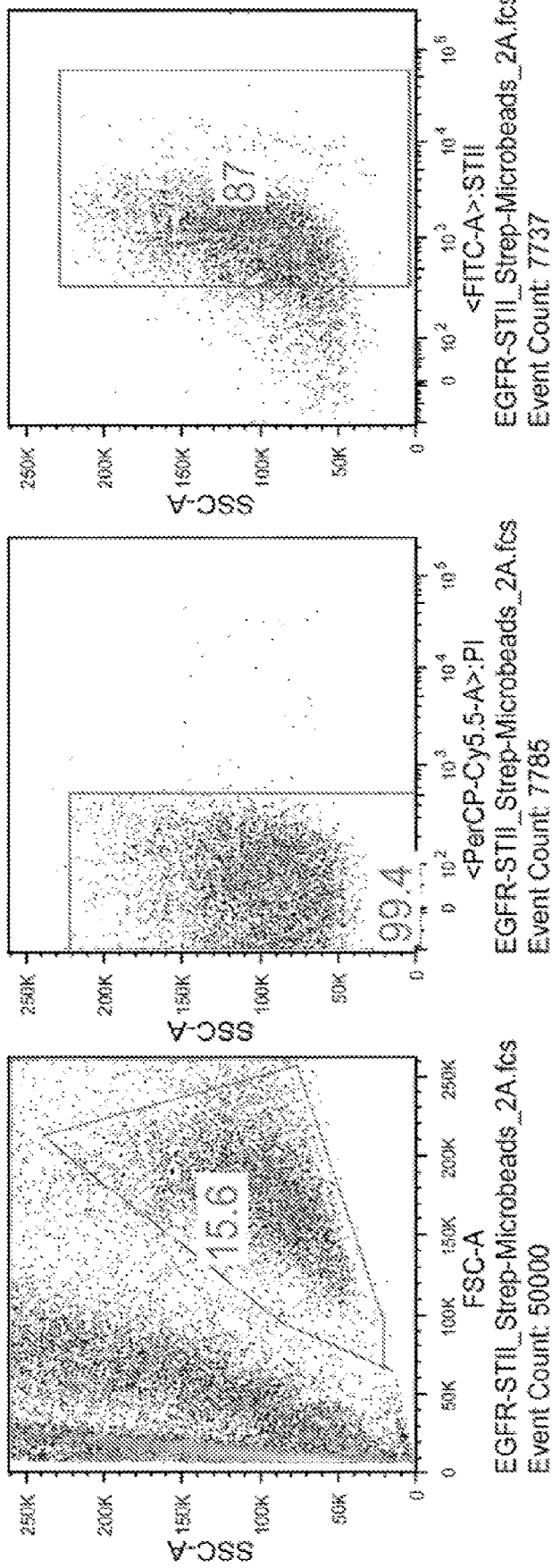
Figure 10:
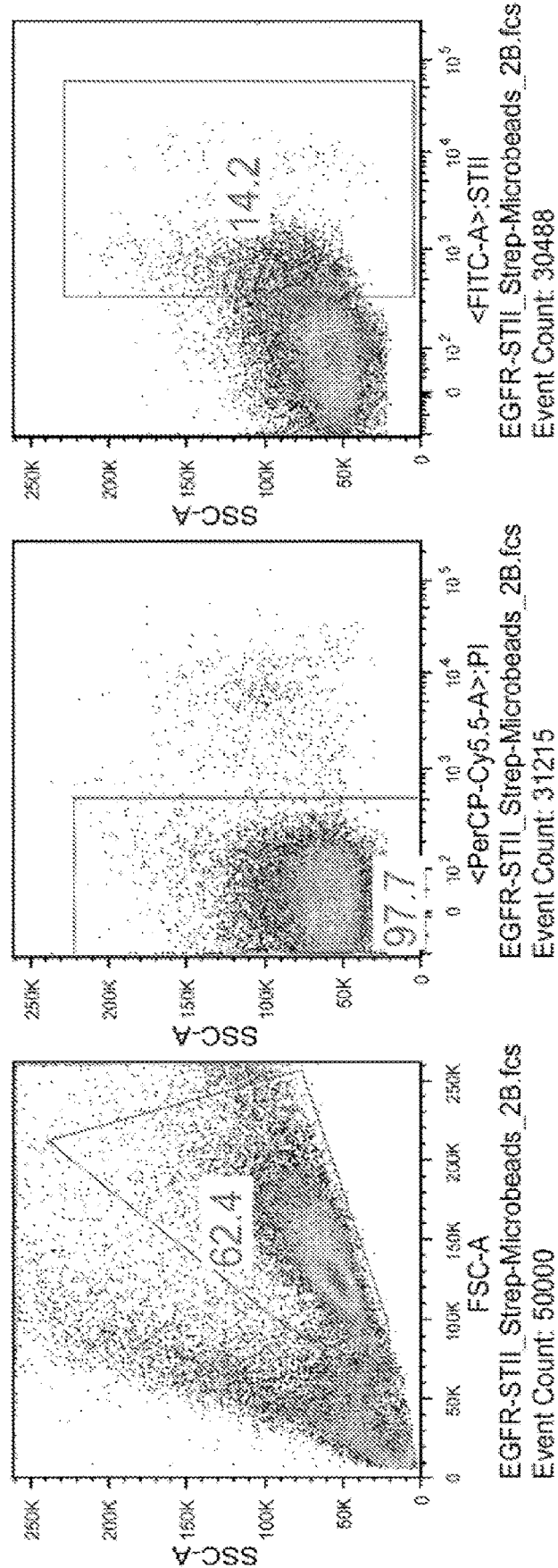
Figure 10:
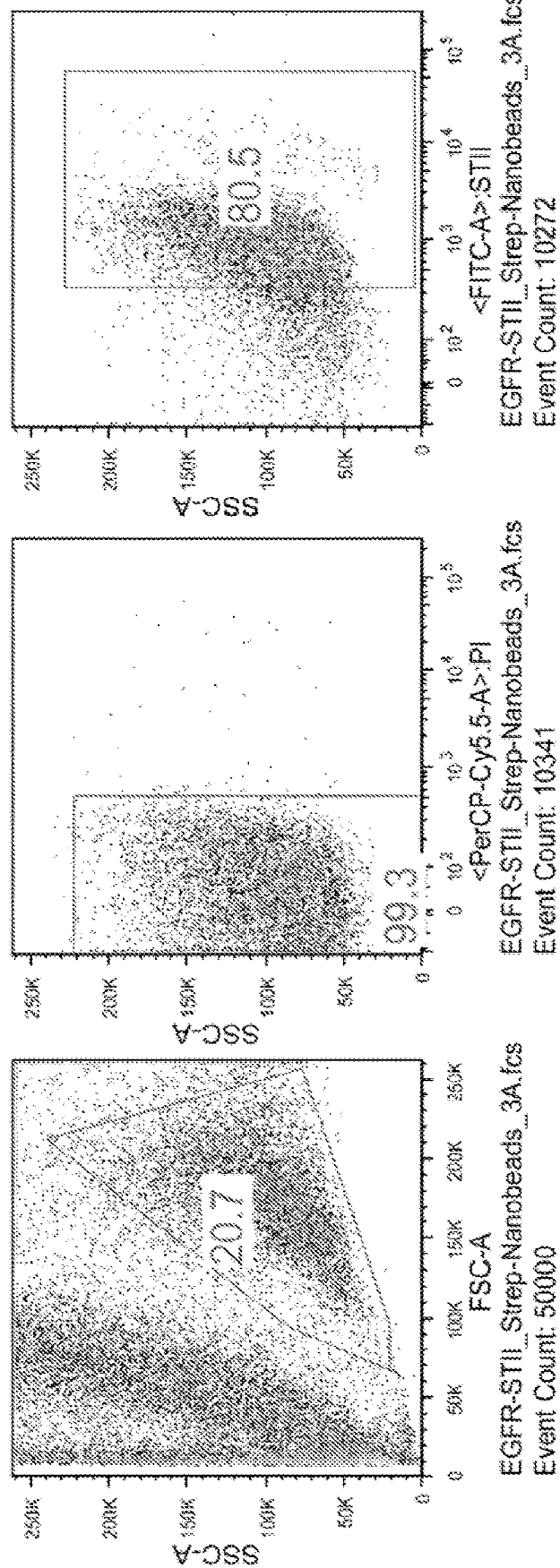
Figure 10:
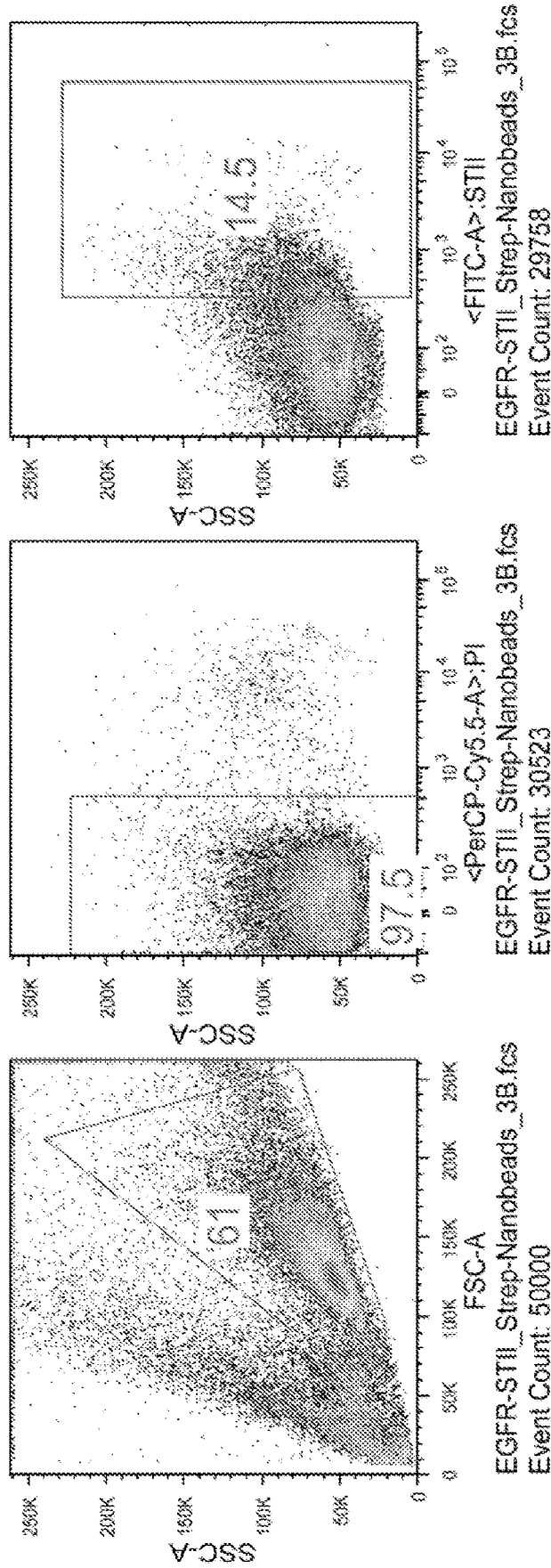

The first row of FIG. 10 shows cell populations before being applied to a Strep-Tactin® bead column, while the second, third and fourth rows of FIG. 10 show the cell populations from each sample after passage through bead column 1#, 2#, and 3#, respectively. The second row shows there was some cell loss, which may be due to the size of Strep-Tactin® Microbeads 1# not allowing some cells to pass through the column. Overall, the data show that any type of Strep-Tactin® bead tested was useful for directly enriching T-ChARM expressing T cells.

Example 12

Activation of T Cells Expressing Cell Surface T-ChARMs with Tag Binding Reagents T cell activation and proliferation requires two signals mediated through engagement of the T cell antigen-specific receptor (TCR) and a costimulatory signal, most typically binding of CD28 by CD80 and CD86 (Ledbetter et al., *Blood* 75:1531, 1990). Accordingly, anti-CD3/CD28 mAb coated microbeads have been developed to provide both requisite signals, and non-specifically activate and expand T cells for clinical applications (Riddell and Greenberg, 1990). Anti CD3/CD28 stimulation of T cells also facilitates transduction with retroviral or lentiviral vectors that encode CARs, but does not selectively expand transduced T cells.

T cells transduced with anti-CD19 T-ChARM$^3$ were cultured for 48 h in CTL medium with either no treatment (negative control) or with one of the following treatments: (a) Strep-Tactin® Microbeads 1#; (b) Strep-Tactin® Microbeads 2#; (c) Strep-Tactin® Nanobeads 3#; (d) anti-Strep Tag® antibody conjugated to protein G beads (size of about 2 µm); (e) anti-Strep Tag® antibody/anti-CD28 antibody dual conjugated protein G beads, or (f) co cultured with irradiated TM-LCL cells plus 50 U/ml IL2 (positive control). To determine whether the cells were being activated after culturing for 24 h and 48 h, cells were examined for the presence of CD25/CD69 using immunofluorescence staining and flow cytometry. T cells express de novo activation molecules, including CD69 and CD 25, after activation through the T cell surface receptor or by signaling through a CAR that expresses CD3ζ. CD69 is one of the earliest cell surface activation markers and may be involved with the ongoing activation process. CD25 synthesis (the IL2 receptor α chain), along with IL2 itself, is induced by T cell activation when initially encountering an antigen.

The data unexpectedly show that Strep Tag® binding of T-ChARM expressing T cells through either Strep-Tactin® or anti-Strep Tag® antibody coated beads significantly activated these T cells, and further show that bead size may also have an effect on the level of T cell activation (FIG. 13).

Figure 27C:
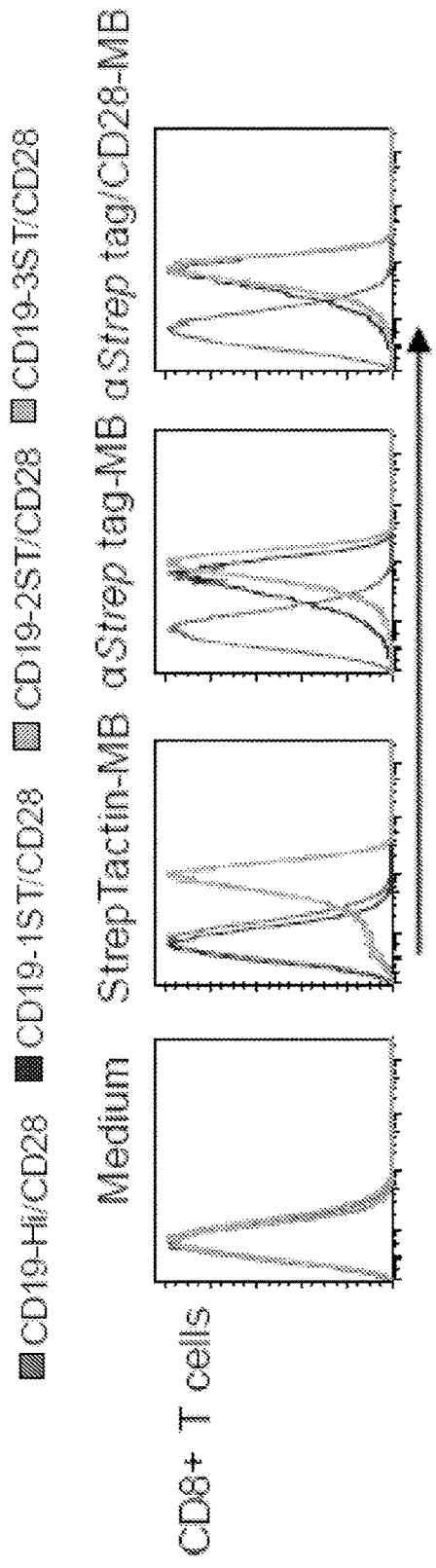
Figure 27D:
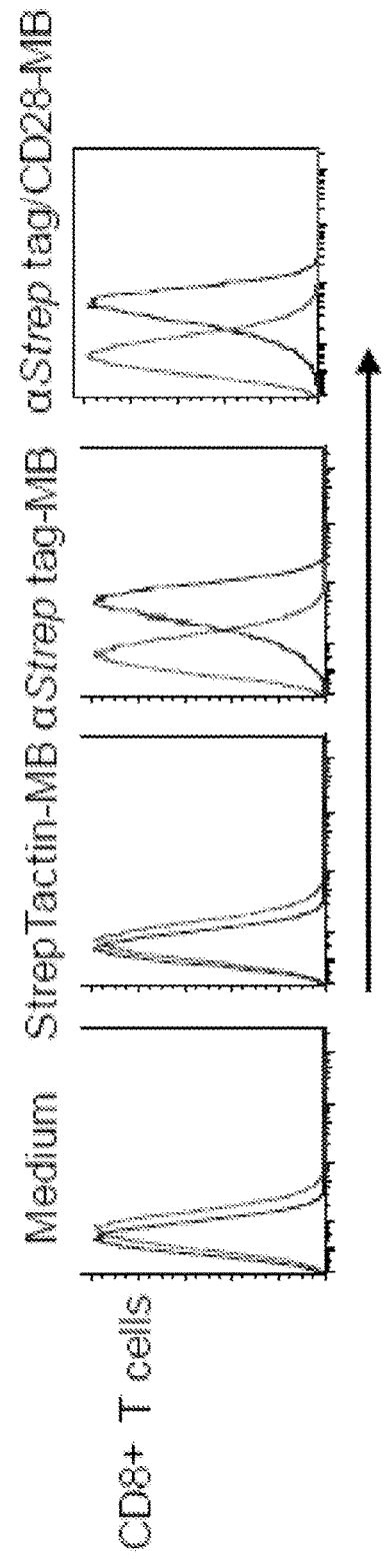

In further experiments with additional constructs, Strep-Tactin® microbeads induced CD25 upregulation on CD8+ (FIG. 27A) and CD4+(FIG. 27B) T cells that expressed ChARM$^2$ and ChARM$^3$, but not T cells that expressed ChARM[1] or CARs that lacked a tag, indicating thaT-ChARM[1] affinity for binding Strep-Tactin® microbeads is suboptimal in ChARM-based T cell activation. But, anti-Strep Tag® antibody-coated microbeads, which have a binding affinity to Strep Tag® ($K_D$=~10 nm) 100 fold higher than Strep-Tactin® ($K_D$=~1 uM), activated various ChARM T cells, independent of the copy number or location of the tag in the ChARM (FIGS. 27A and B). Notably, Strep-tag binding-mediated activation could be found in both 4 1BB and CD28 ChARM T cells (FIG. 27C) and non CD19 targeting ChARM T cells (FIG. 27D, ROR1-targeting R12 ChARM[1]).

Example 13

Figure 11:
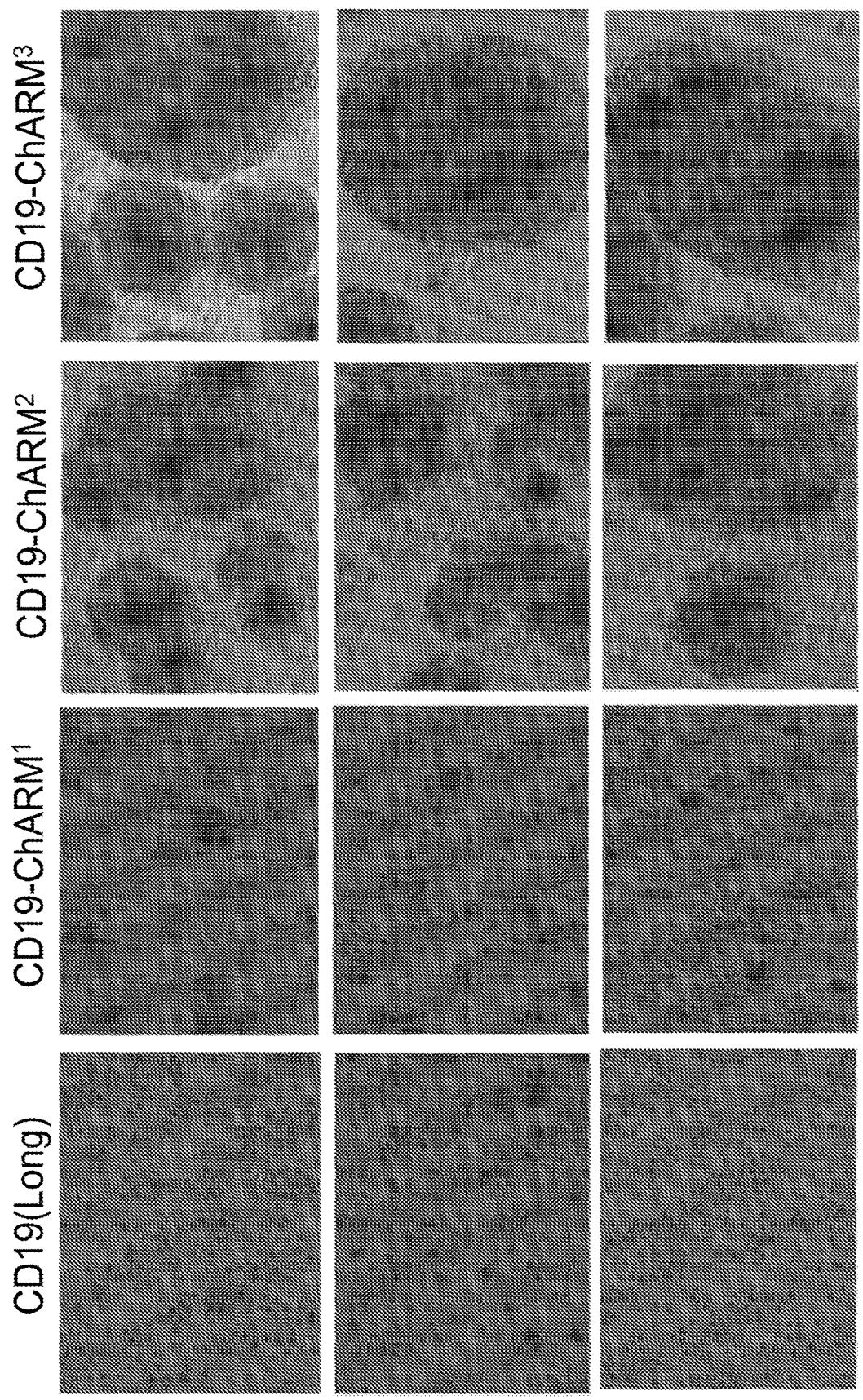
FIG. 11 shows light photomicrographs of T-ChARM (containing one, two or three tag cassettes) or conventional anti-CD19 CAR expressing T cells (CD19 Long) that have been co-cultured with beads linked to binding ligand (Strep-Tactin®) for the tag sequence. The photomicrographs demonstrate selective clustering and proliferation of T-ChARM T cells.

Proliferation of T Cells Expressing Cell Surface T-ChARMs with Tag Binding Reagents Anti CD19 T-ChARM[1], T-ChARM[2], T-ChARM[3] and CAR (long) (negative control) transduced T cells that were individually cultured in CTL medium with Strep-Tactin® microbeads and 50 U/ml IL2. Microscopy imaging on day 5 reveals that T-ChARM[2] and T-ChARM[3] expressing T cells surprisingly developed large clusters around the beads, indicative of cell proliferation on the Strep-Tactin® beads, which was not evident with the anti-CD19 CAR (long) expressing T cells (FIG. 11). The T-ChARM[1] expressing T cells showed less expansive cell clusters, but there was clearly cell expansion since there were more cells visible on the plate as compared to the negative control. In further experiments, various different T-ChARM expressing T cells (including [N1]ChARM and Ch[1]ARM) had proliferation clusters appear within just 48 hours after stimulation with either Strep-Tactin® microbeads or anti-Strep Tag® antibody microbeads (FIG. 28). The conventional short spacer CAR T cells (CD19-Hi) were used as negative control.

Figure 12:
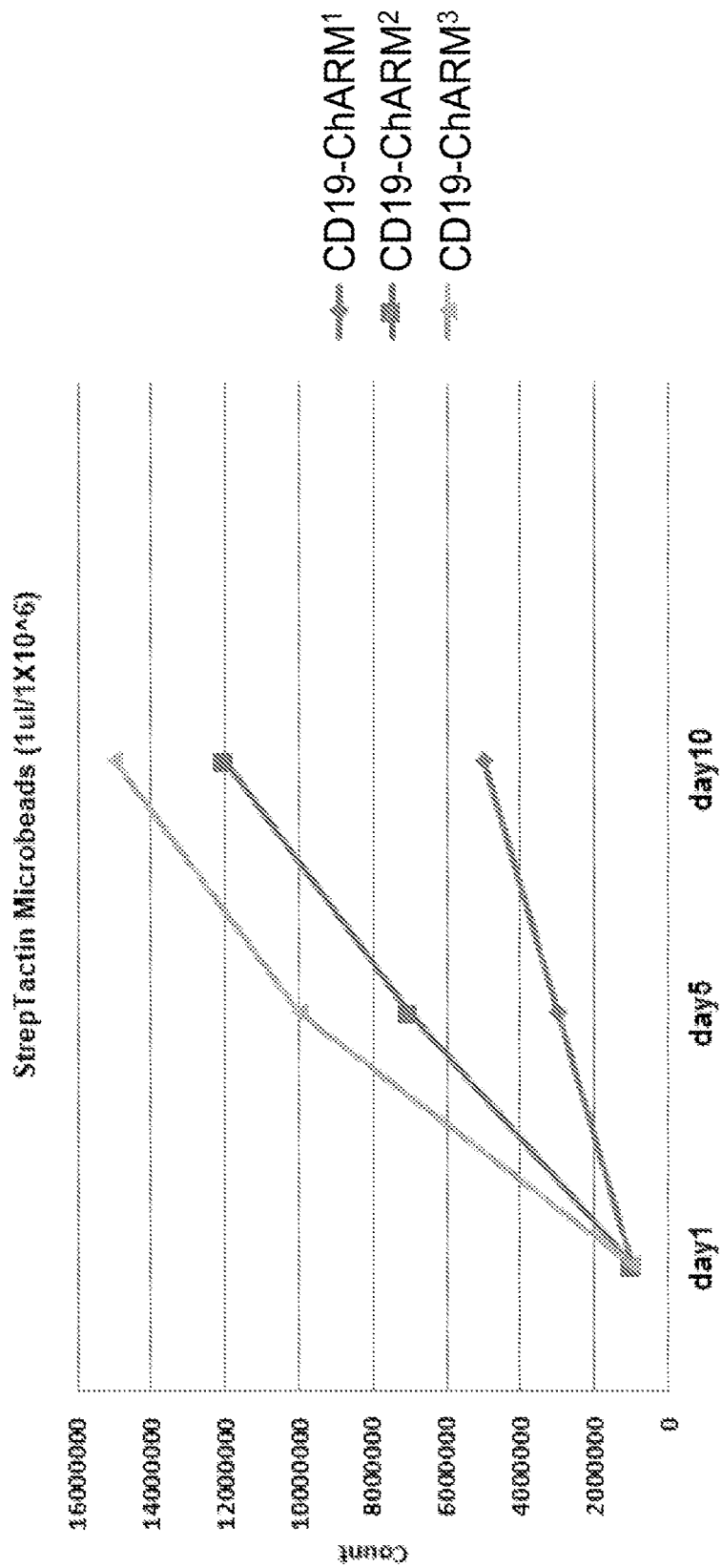
FIG. 12 shows the growth curve of T-ChARM expressing T cells (containing one, two or three tag cassettes) over 10 days of culture with Strep-Tactin® microbeads.
Figure 13A:
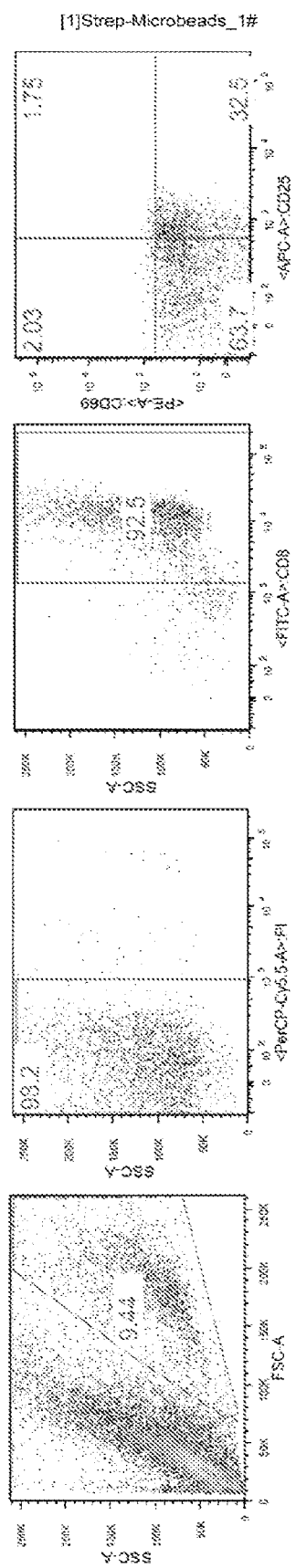
FIGS. 13A and 13B show activation of T-ChARM expressing T cells as determined by upregulation of CD25 and CD69 after binding of the tag cassette by either Strep-Tactin® microbeads, nanobeads or anti-Strep Tag® II mAb alone or in combination with anti-CD28 mAb. Data is shown after (A) 24 hours and (B) 48 hours of stimulation.
Figure 13A:
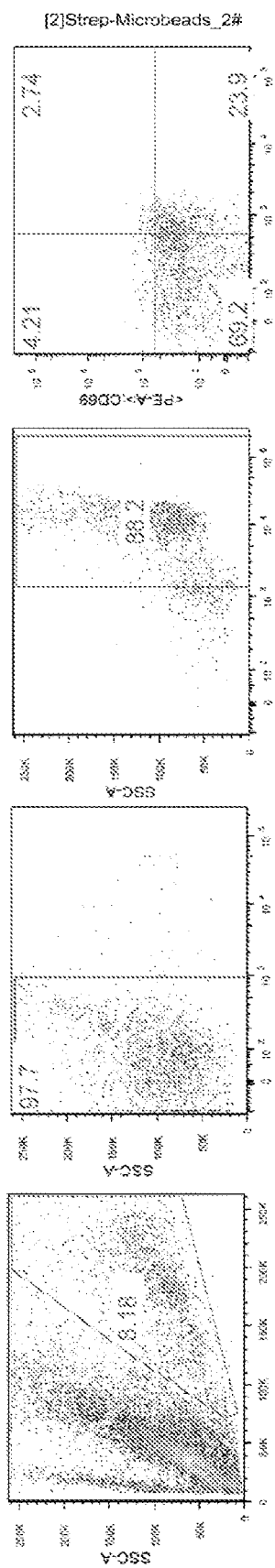
Figure 13A:
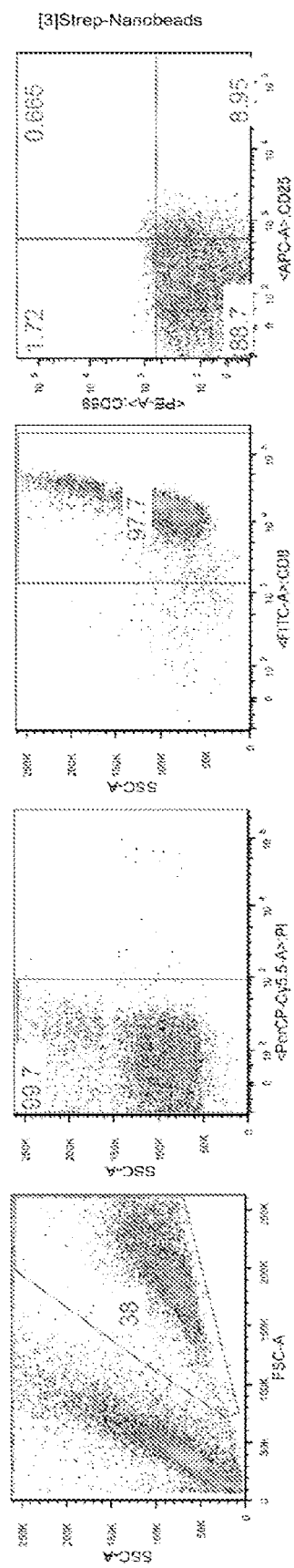
Figure 13A:
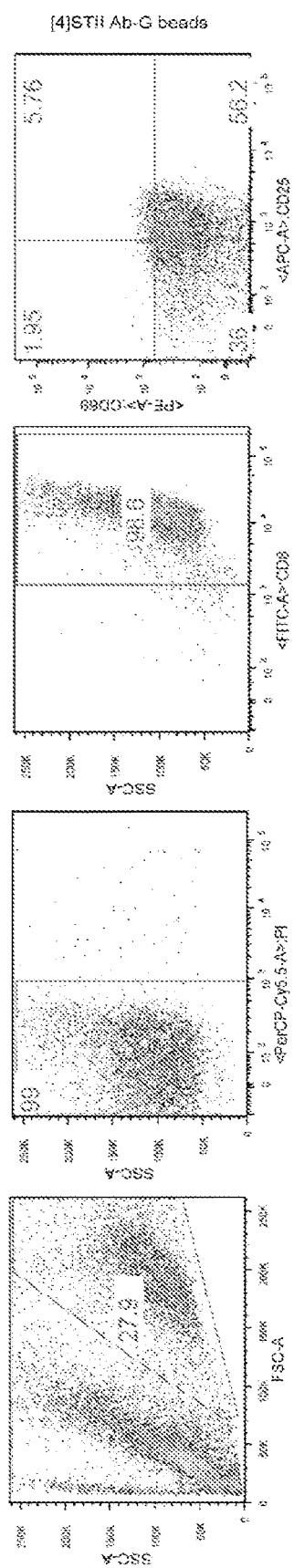
Figure 13A:
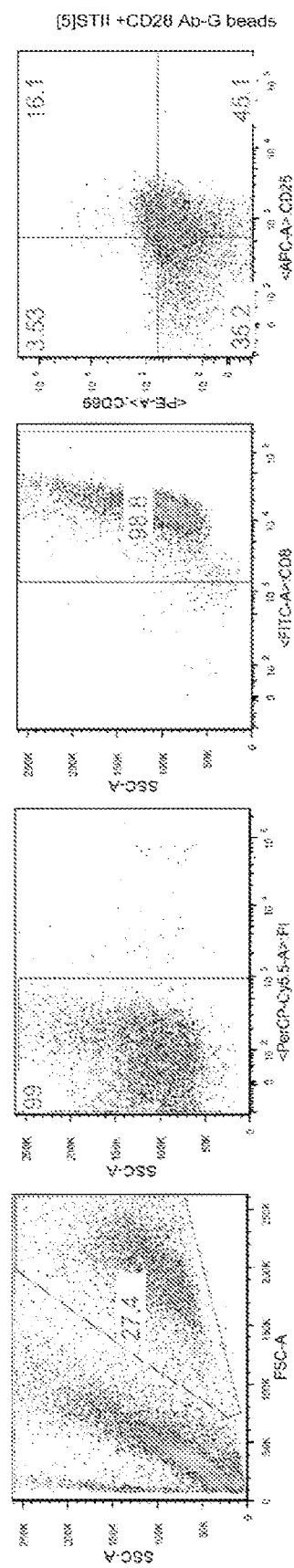
Figure 13A:
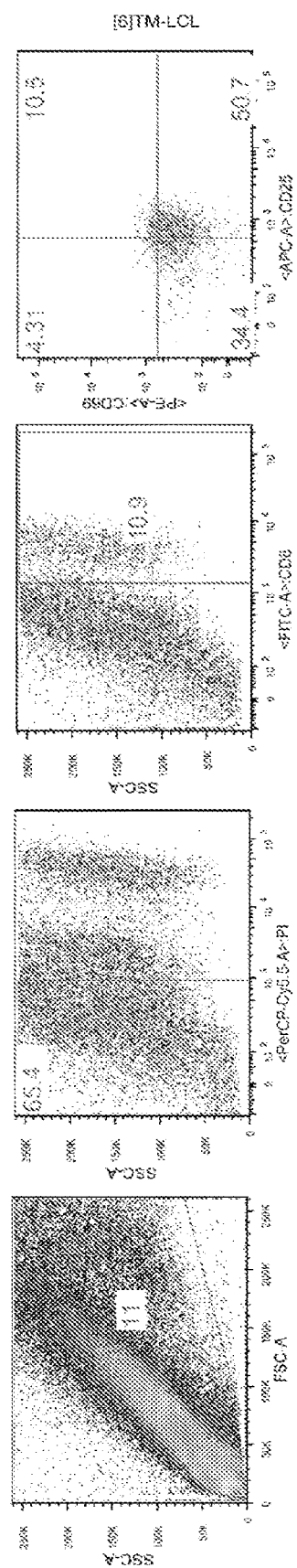
Figure 13A:
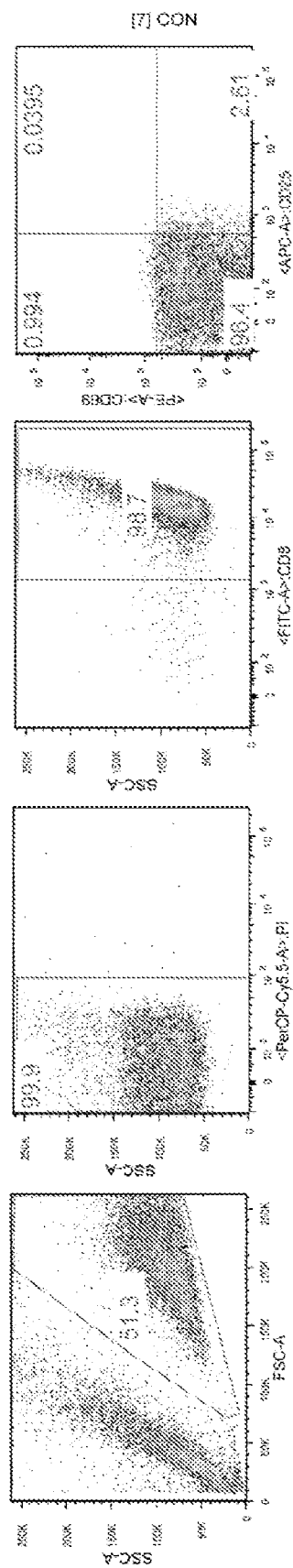
Figure 13B:
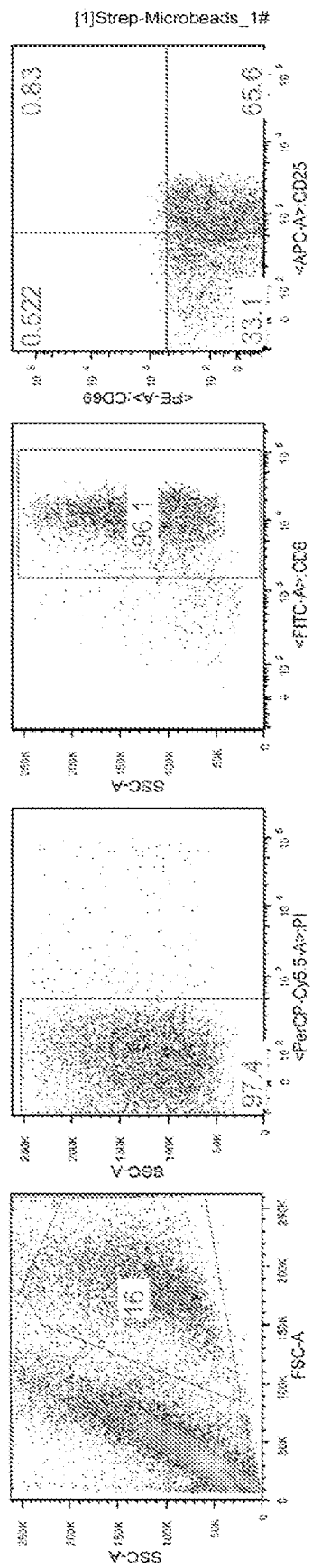
Figure 13B:
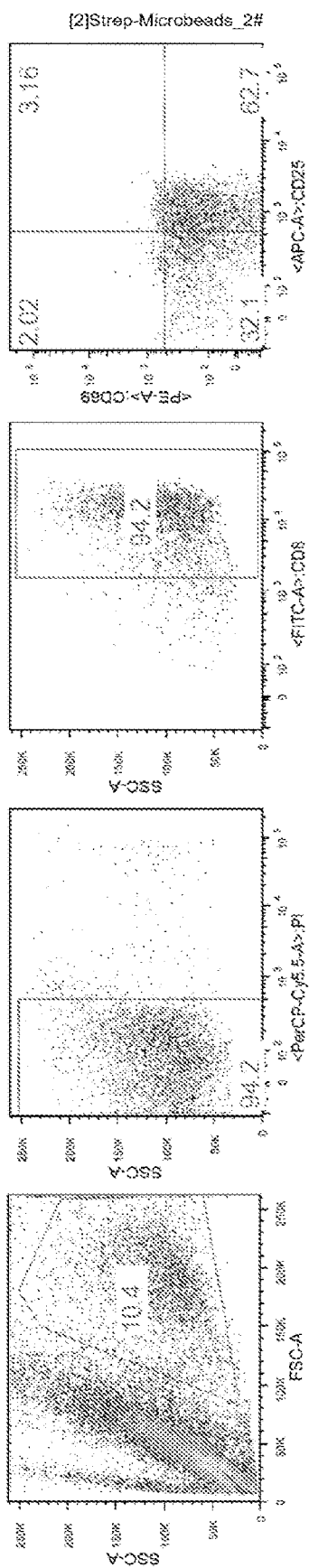
Figure 13B:
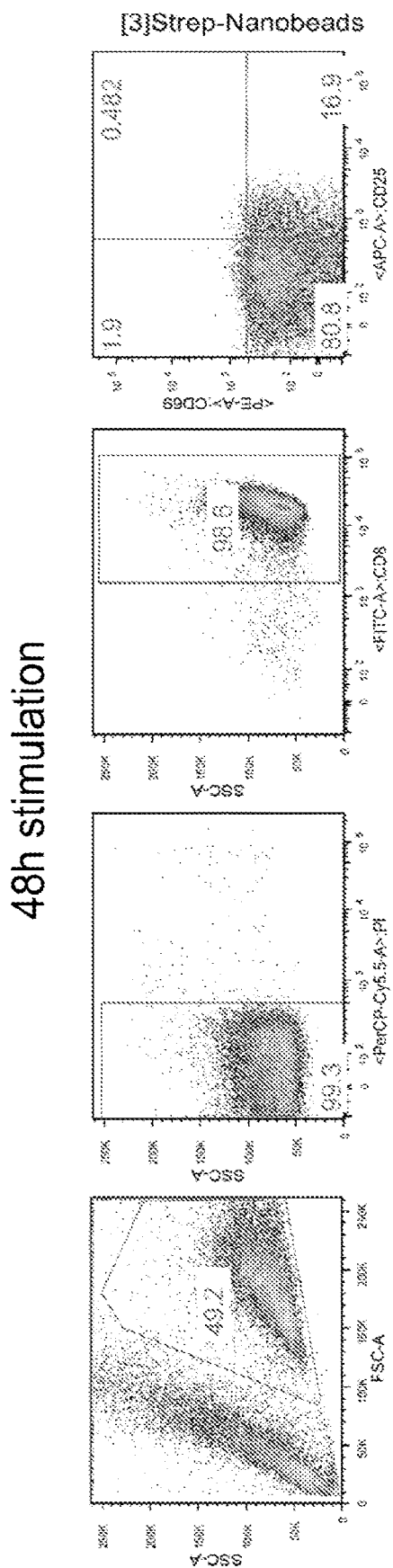
Figure 13B:
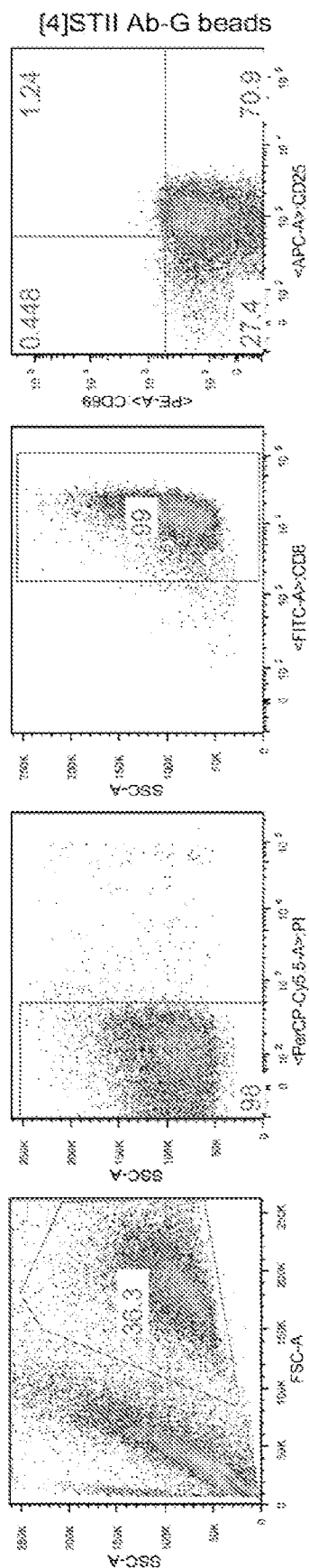
Figure 13B:
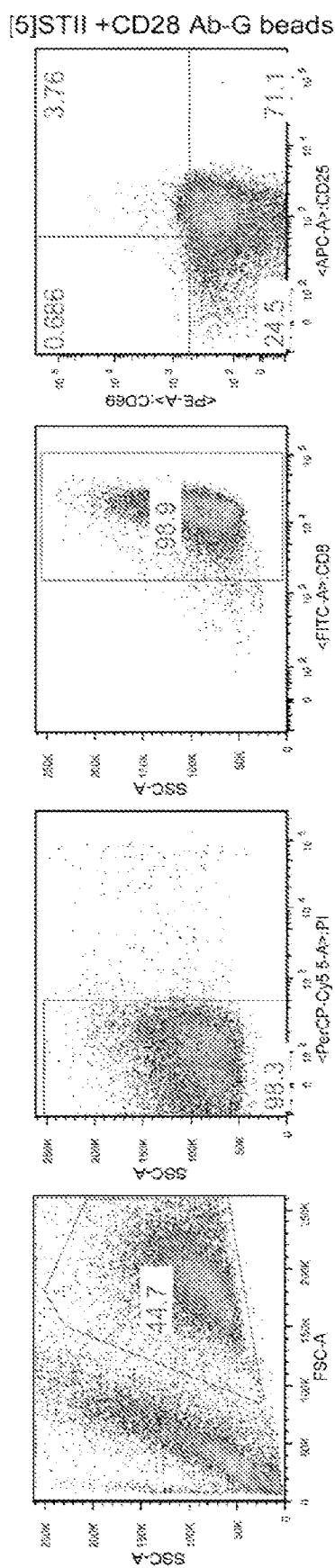
Figure 13B:
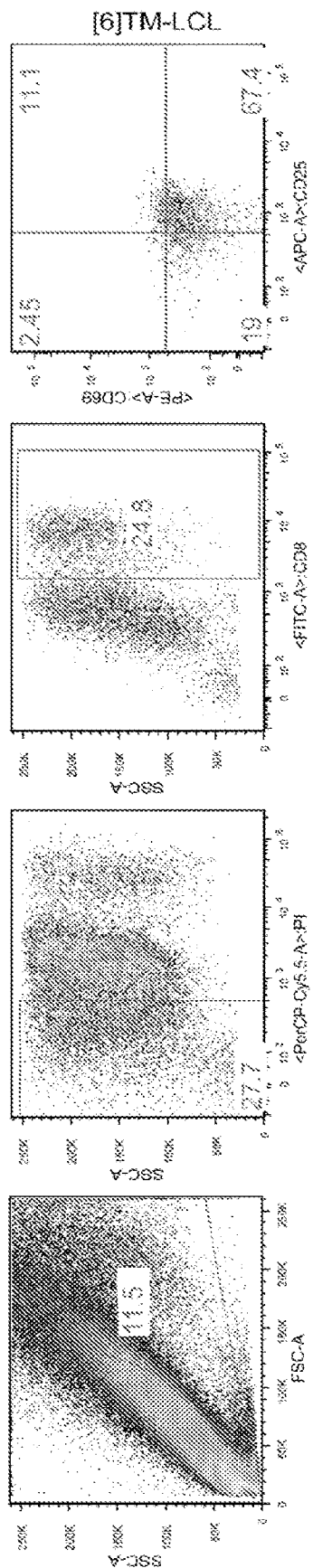
Figure 13B:
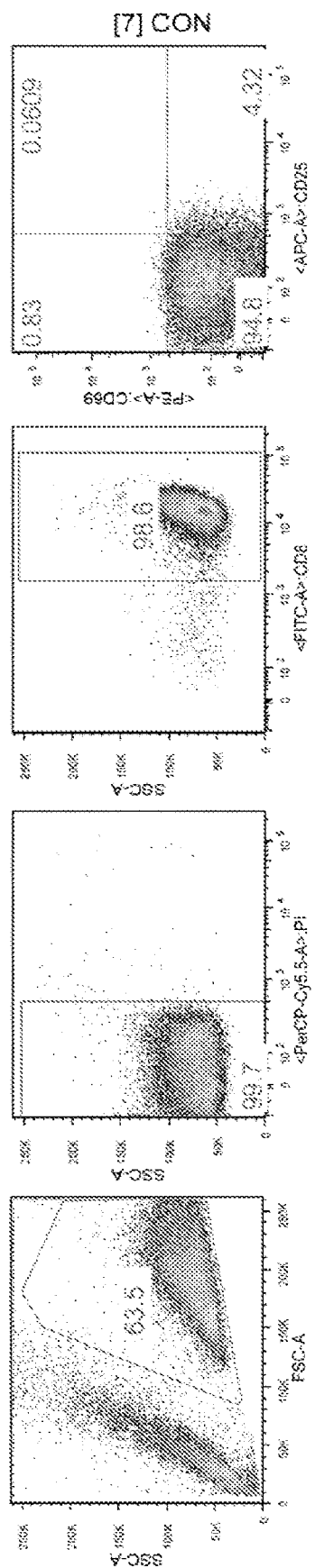

The growth curve of T-ChARM expressing T cells cultured on Strep-Tactin® microbeads was determined (see FIGS. 12 and 29). A total of about 1×10⁶ anti CD19 T-ChARM[1], T-ChARM[2], and T-ChARM[3] transduced T cells were individually plated in CTL medium with Strep-Tactin® microbeads, anti-Strep Tag® mAb, or anti-Strep Tag®/anti-CD28 mAb coated microbeads (FIG. 28) in the presence of 50 U/ml IL2 and 5 ng/ml IL15, and cultured for 10 days. Cell numbers for each well was counted at day 3, 6 and 9. The data show that T-ChARM[3] transduced T cells had the highest growth rate over 9 days when stimulated by Strep-Tactin® beads. With Strep-Tactin® bead stimulation, CD8⁺ or CD4⁺ anti-CD19 ChARM-T cells expanded about 20 to about 100 fold, and the greatest expansion was observed in ChARM[3] T cells (FIGS. 29A and B). Anti-Strep Tag® and anti-Strep Tag®/anti-CD28 mAb coated beads induced even greater expansion (100 to 250-fold) in total ChARM T cell numbers, and unlike Strep-Tactin® bead stimulation, CD8⁺ and CD4⁺ T cells expressing a ChARM[1] exhibited a trend towards greater expansion than T cells expressing ChARM[2] or ChARM[3]. T cells that expressed a CD28 ChARM or anti ROR1 ChARM were also effectively expanded with anti-Strep Tag®/anti-CD28 beads, demonstrating the applicability of this approach for expanding ChARM T cells with different co-stimulatory domains and specificity for different tumor targets (data not shown).

Figure 16:
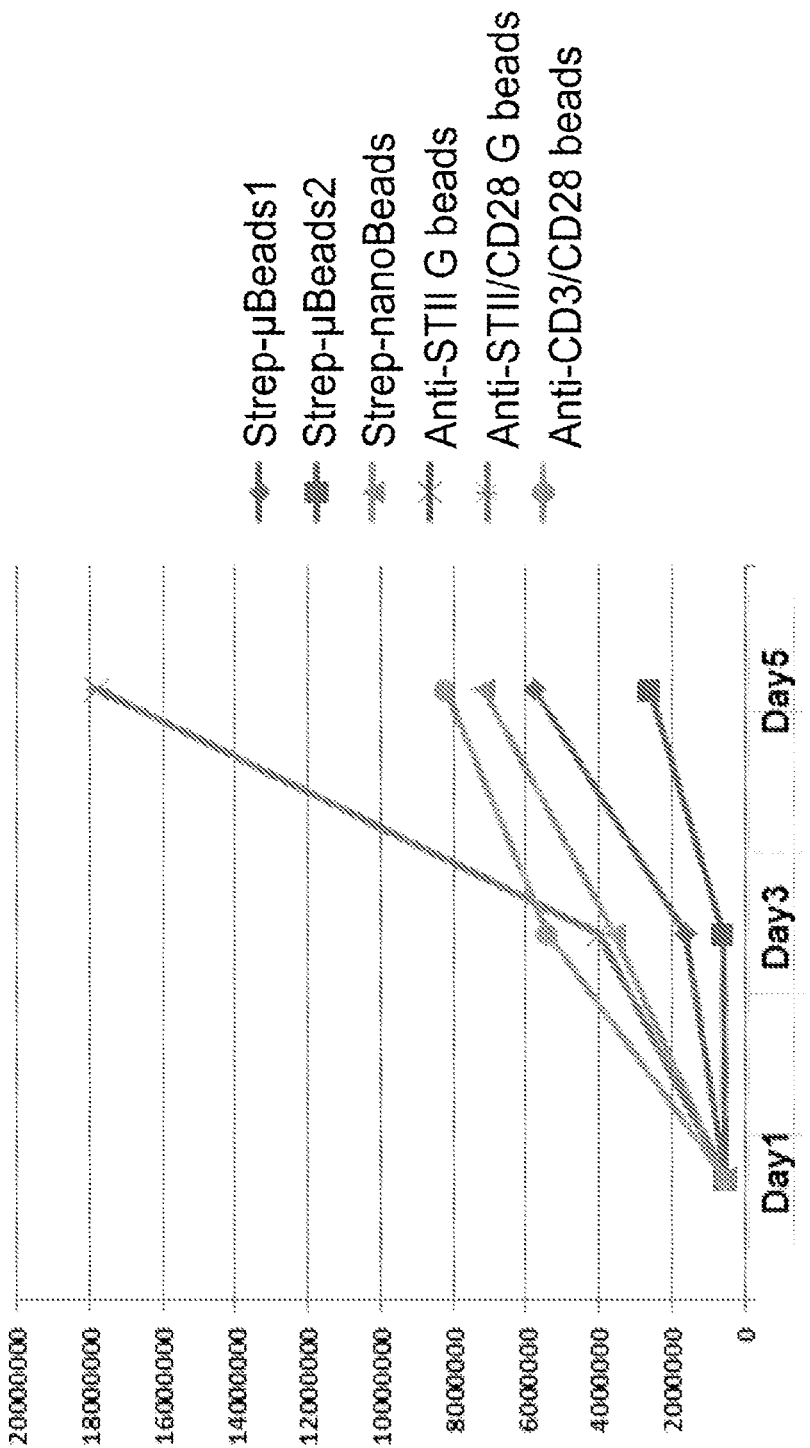
FIG. 16 shows the growth curve of T-ChARM expressing T cells cultured on different kinds of Strep-Tactin®, anti-Strep Tag® II or antiCD3/anti-CD28 conjugated beads.

In another growth curve assay, a total of about 5×10⁵ anti CD19 T-ChARM[3] transduced T cells were plated in CTL medium with 50 U/ml IL2; one of the following beads: (a) Strep-Tactin® Microbeads 1#, (b) Strep-Tactin® Microbeads 2#, (c) Strep-Tactin® Nanobeads 3#, (d) anti-Strep Tag® antibody conjugated to protein G beads, (e) anti-Strep Tag® antibody/anti CD28 antibody dual conjugated protein G beads, or (f) anti CD3/anti-CD28 dual antibody beads (positive control); and cultured for 7 days. Cell numbers for each well was counted at day 3, day 5 and day 7. The data show that anti Strep Tag® antibody/anti-CD28 antibody dual conjugated protein G beads promoted maximal T-ChARM[3] expressing T cell proliferation by day 5, which was significantly better that the anti-CD3/anti-CD28 positive control (FIG. 16). The Strep Tag® engaging reagents, other than Strep-Tactin® Microbeads 2#, promoted proliferation of T-ChARM expressing T cells to about the same level as the anti-CD3/anti-CD28 positive control.

To further verify proliferation of T-ChARM expressing T cells, the level of Ki-67 protein was measured as a surrogate measure of proliferation. Ki-67 is a nuclear protein associated with and possibly required for cellular proliferation. T cells transduced with anti-CD19 T-ChARM[3] were cultured for 5 days in CTL medium in the presence of one of the following treatments: (a) Strep-Tactin® Microbeads 1#; (b) Strep-Tactin® Microbeads 2#; (c) Strep-Tactin® Nanobeads 3#; (d) anti-Strep Tag® antibody conjugated to protein G beads; (e) anti-Strep Tag® antibody/anti-CD28 antibody dual conjugated protein G beads, or (f) anti CD3/anti-CD28 dual antibody beads (positive control). After culturing for 5 days, the cells were fixed, permeabilized, stained with anti-Ki-67-FITC conjugated antibody, and analyzed by flow cytometry.

Figure 14A:
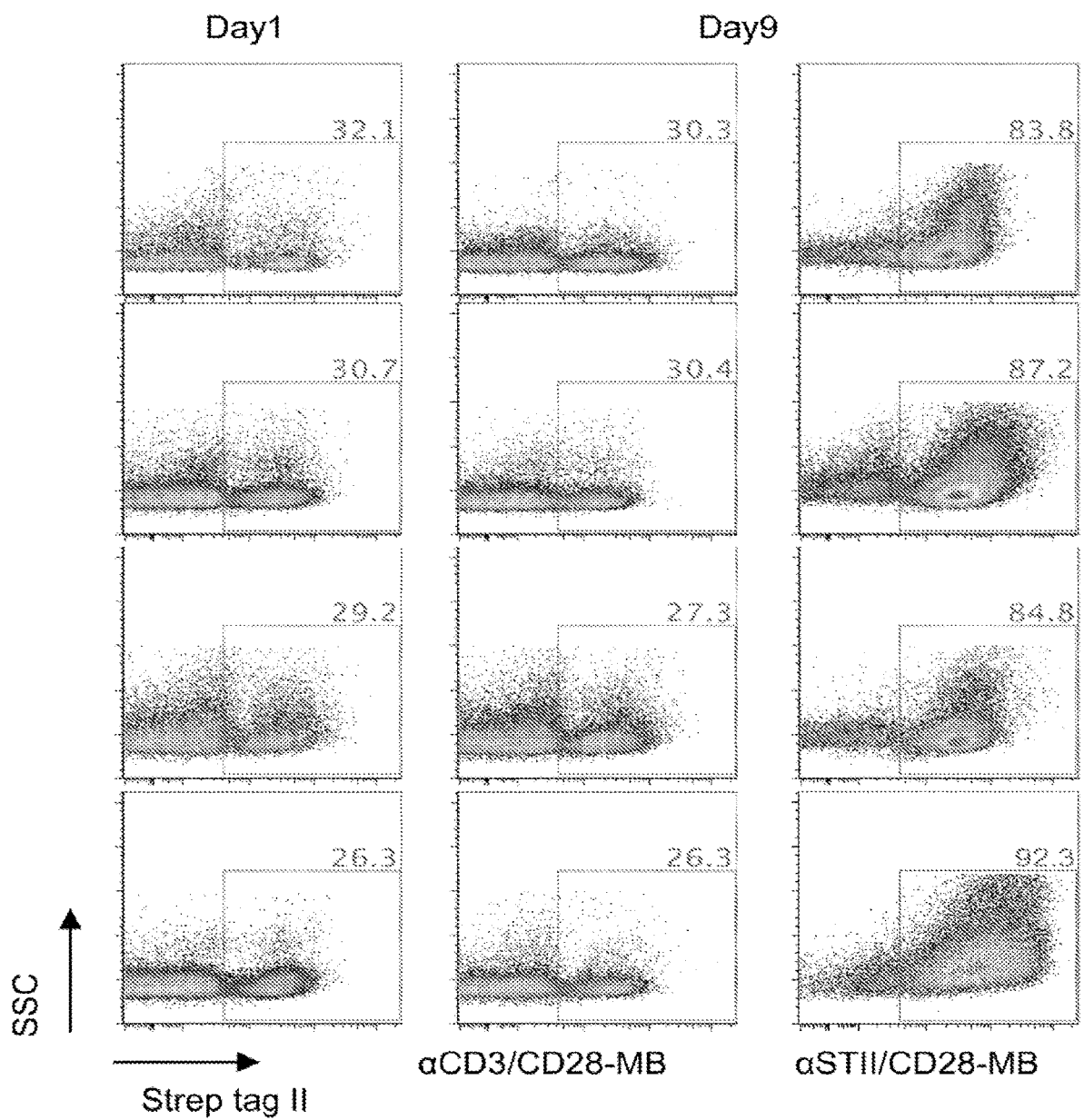
FIGS. 14A and 14B show the selective expansion of T-ChARM expressing T cells. Unsorted T-ChARM¹/4-1BB and T-ChARM¹/CD28 transduced T cells (CD8+ and CD4+) cultured with anti-Strep Tag®/anti-CD28-MB for 9 days. The percentage of T-ChARM cells was assessed by (A) flow detection of Strep Tag® expression on T cells before and after culture. Culture cells treated with anti-CD3/anti-CD28-MB alone were used as control. (B) FACS sorted EGFR+ anti CD19 ChARM T cells after CD19+ immortalized B cell line (TM-LCL) expansion. Stained with anti-EGFR (upper row) and anti-Strep Tag® II (lower row) antibodies, respectively
Figure 14B:
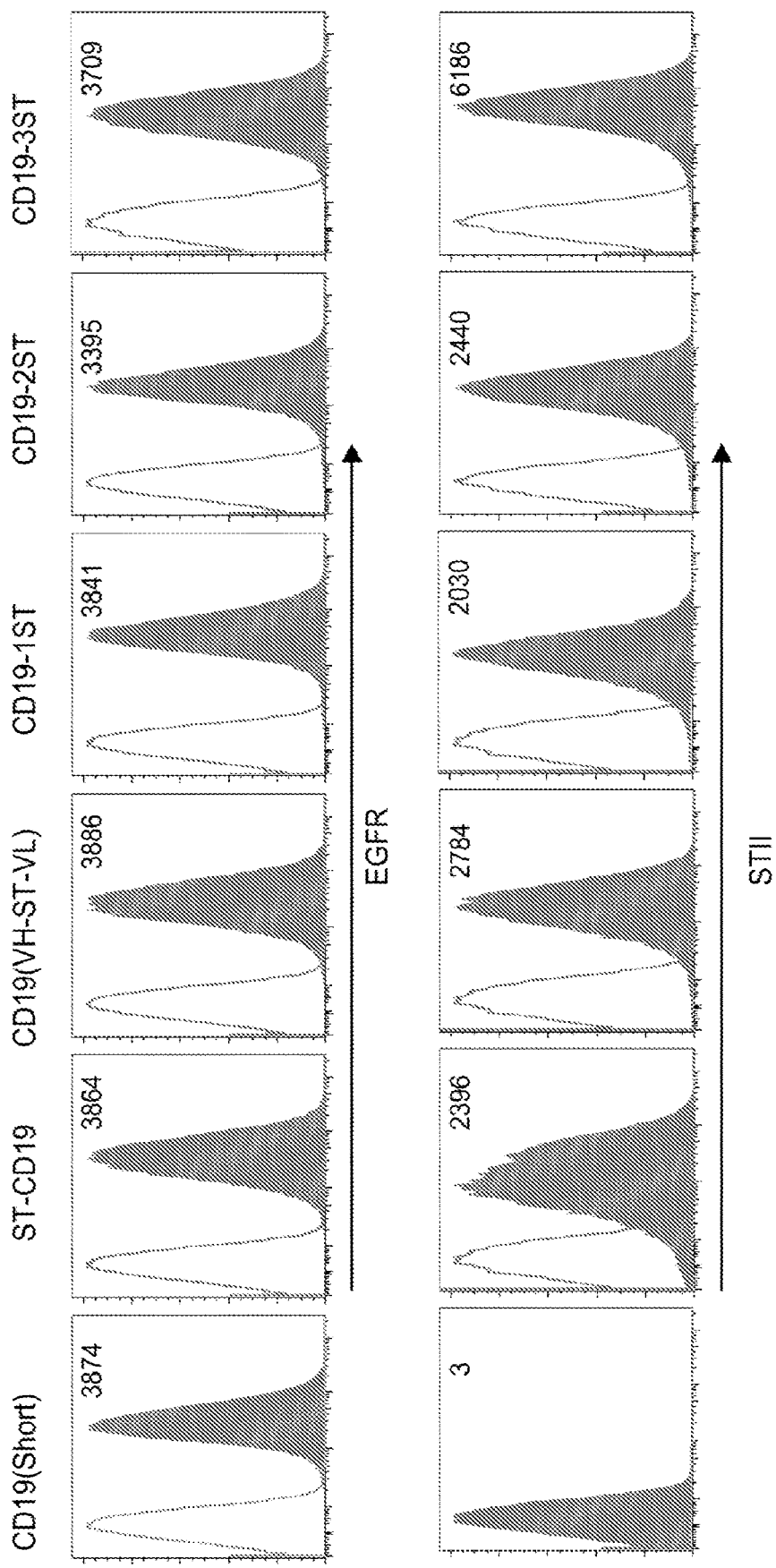

These data show that Strep-Tactin® beads or anti-Strep Tag® beads can promote selective cell proliferation and the proliferation as measured by Ki-67 staining was better than that observed with the anti-CD3/anti-CD28 positive control (FIG. 14).

Figure 15:
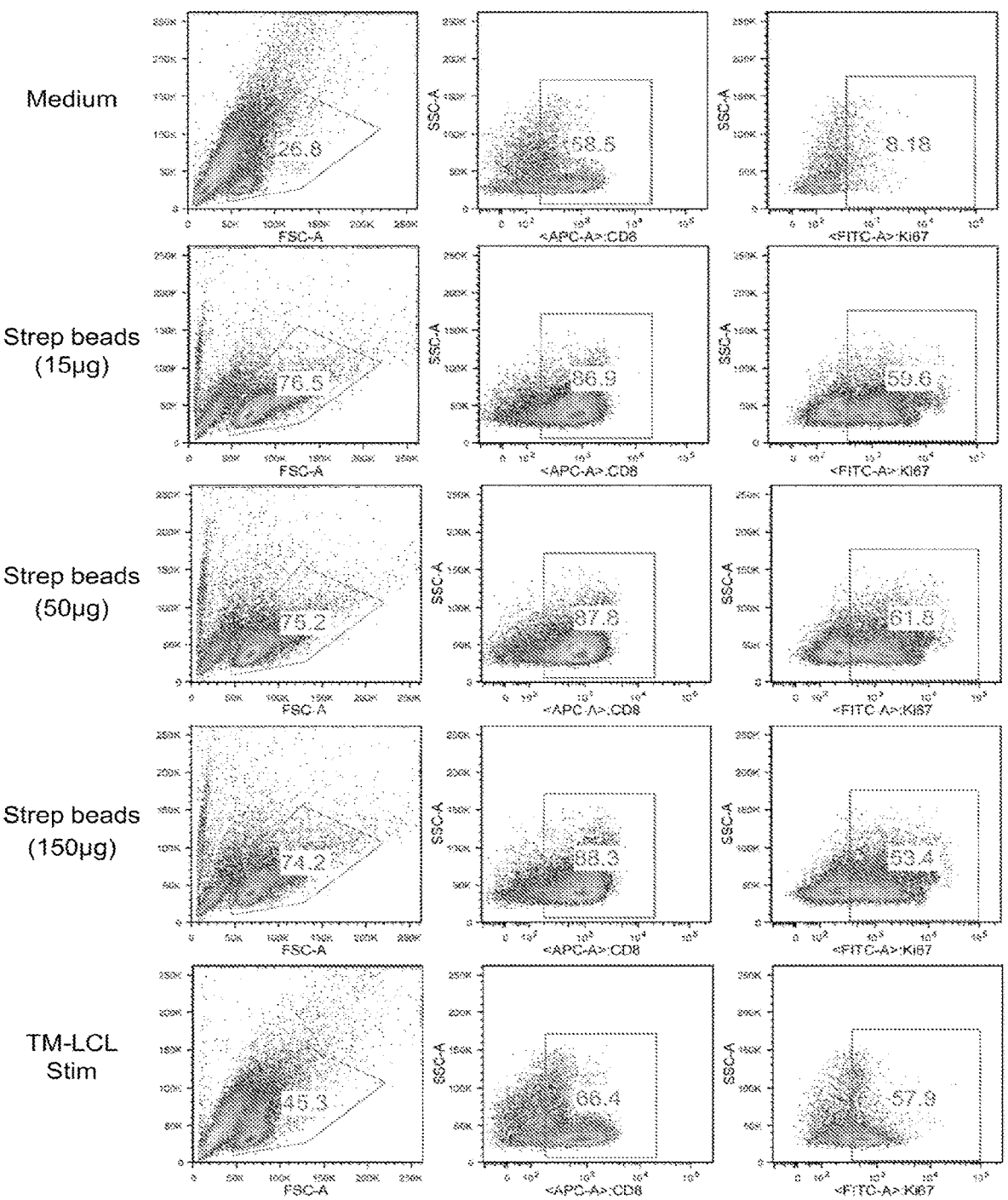
FIG. 15 shows proliferation of anti-CD19 T-ChARM expressing T cells (containing one, two or three tag cassettes) as measured by the level of Ki-67 protein 7 days after stimulation with varying amounts of Strep-Tactin® beads. In the bottom panels, the expression of Ki-67 in T-ChARM expressing T cells after stimulation through the anti CD19 binding component of the T-ChARM with CD19⁺ EBV-LCL (TM-LCL) is shown.
Figure 15:
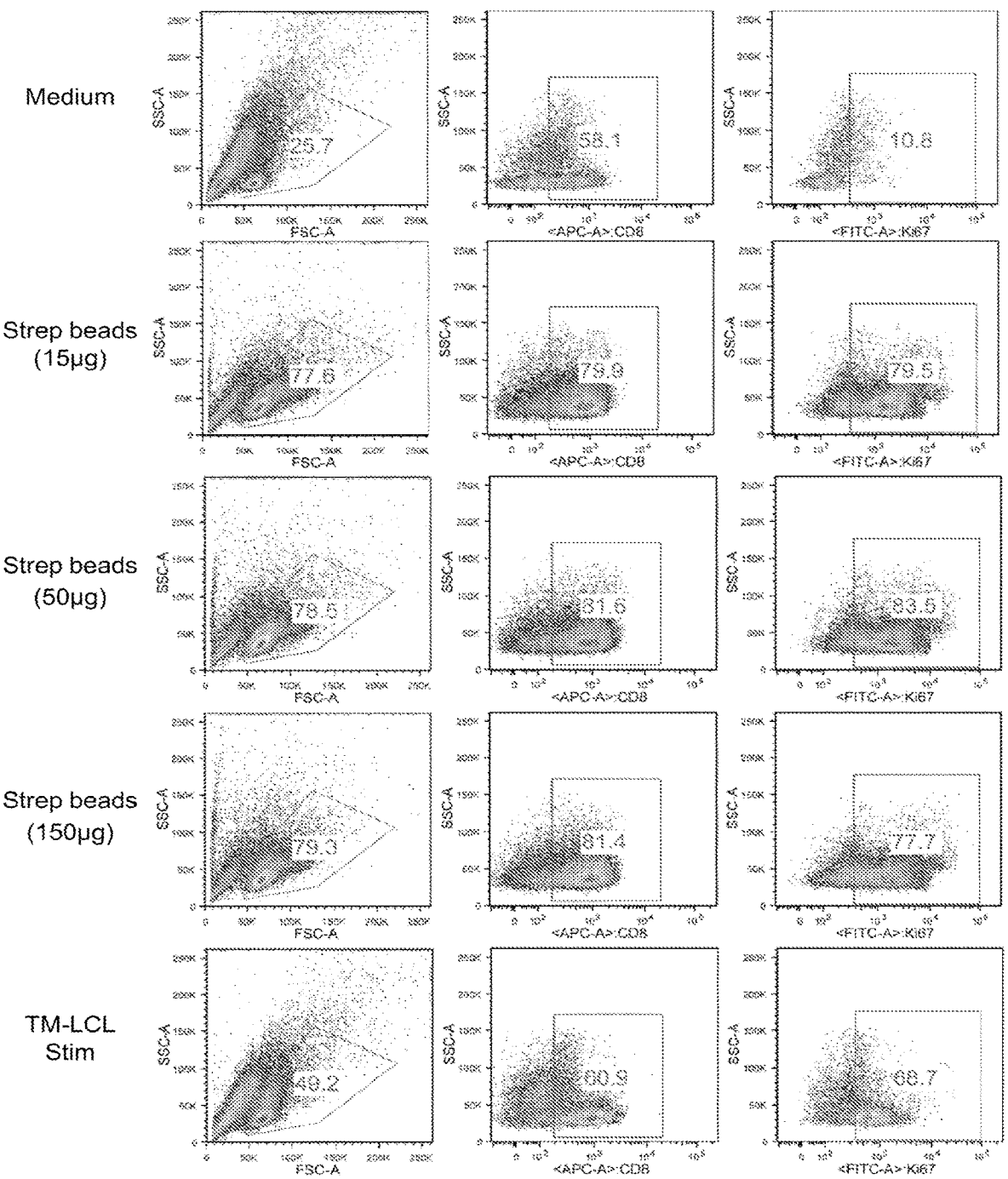
Figure 15:
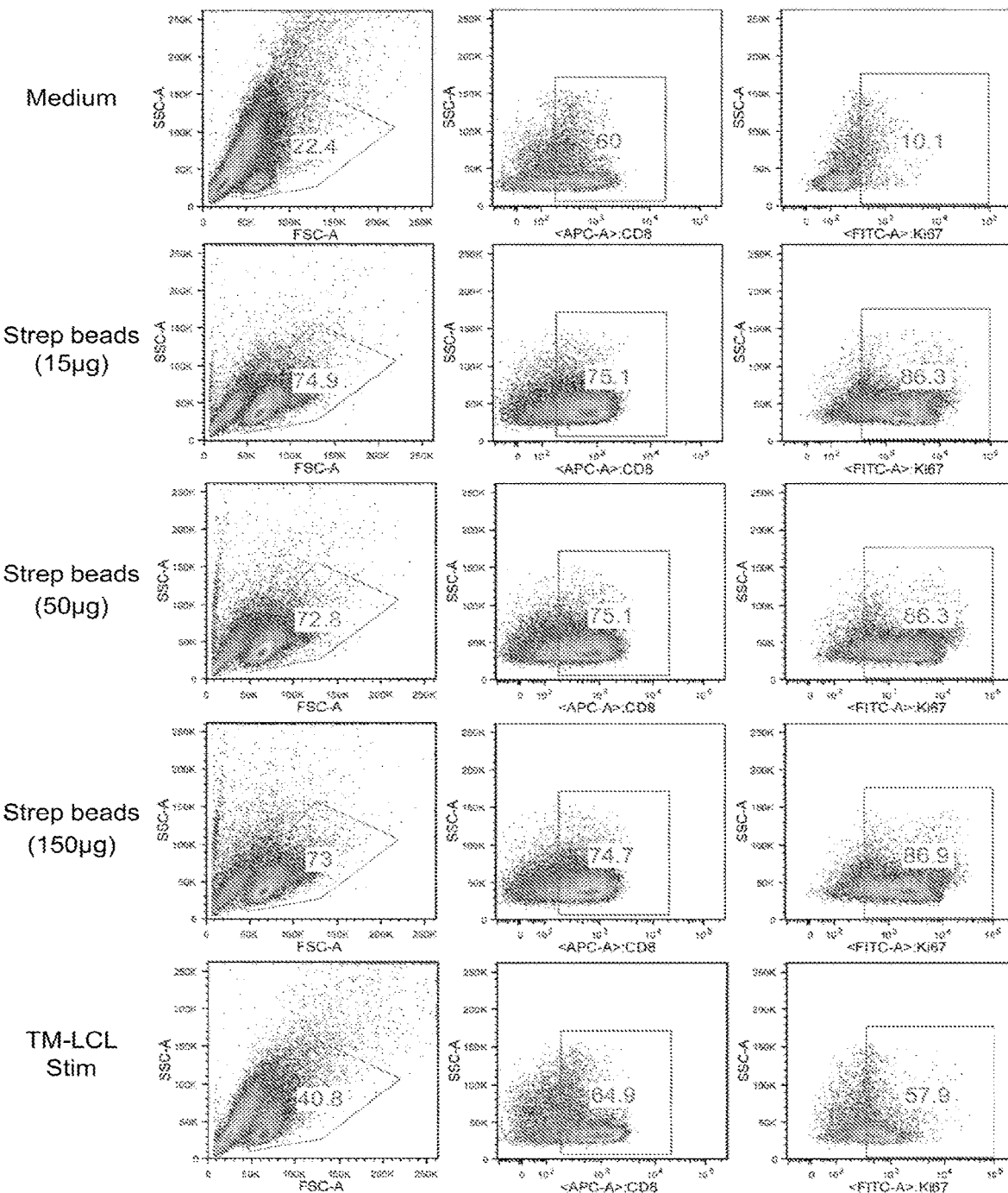

A further level of Ki-67 protein as was performed on T cells transduced with anti-CD19 T-ChARM[1], T-ChARM[2], or T-ChARM[3] and cultured for 7 days in CTL medium in the presence of: (a) no treatment; (b) Strep-Tactin® Microbeads 1# at a dose of 15 g, 50 g, or 150 g per 1×10⁶ cells; or (c) co cultured with irradiated TM-LCL cells plus 50 U/ml IL2 (positive control). After culturing for 7 days, the cells were fixed, permeabilized, stained with anti-Ki-67-FITC conjugated antibody, and analyzed by flow cytometry. These results also show that Strep-Tactin® beads can promote proliferation in T-ChARM expressing T cells regardless of the amount of the beads used, particularly for the T-ChARM[2] and T-ChARM[3] cells (FIG. 15). Moreover, each of the T-ChARM expressing T cells proliferated in the presence of Strep-Tactin® beads as well as or better than the TM LCL positive control stimulation.

Example 14

Selective Expansion of T Cells Expressing T-ChARM Molecules

Figure 17A:
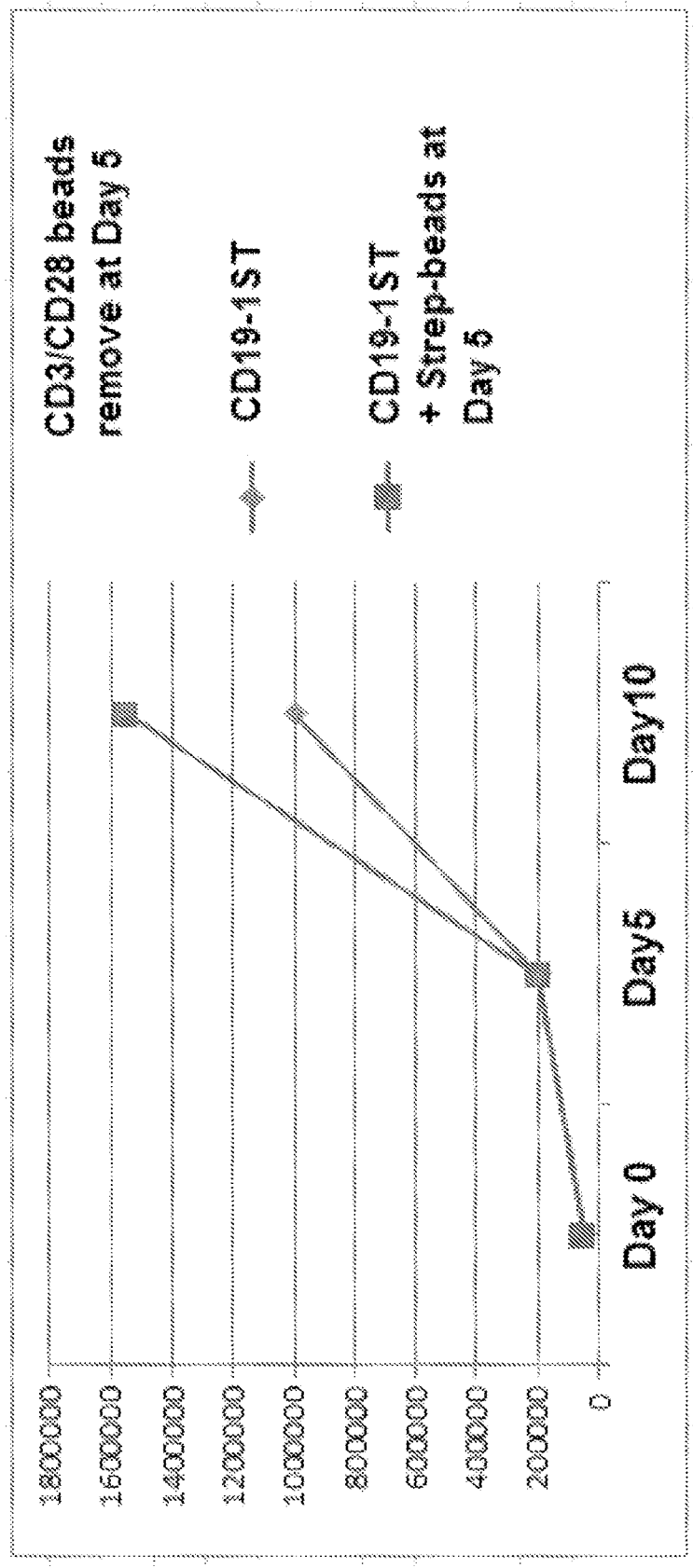
FIGS. 17A and 17B show the selective expansion of anti-CD19 T-ChARM expressing T cells on Strep-Tactin® beads (A). The anti-CD19 T-ChARM expressing T cells can subsequently be expanded by stimulation through the anti-CD19 chimeric receptor with CD19⁺ LCL (B).
Figure 17B:
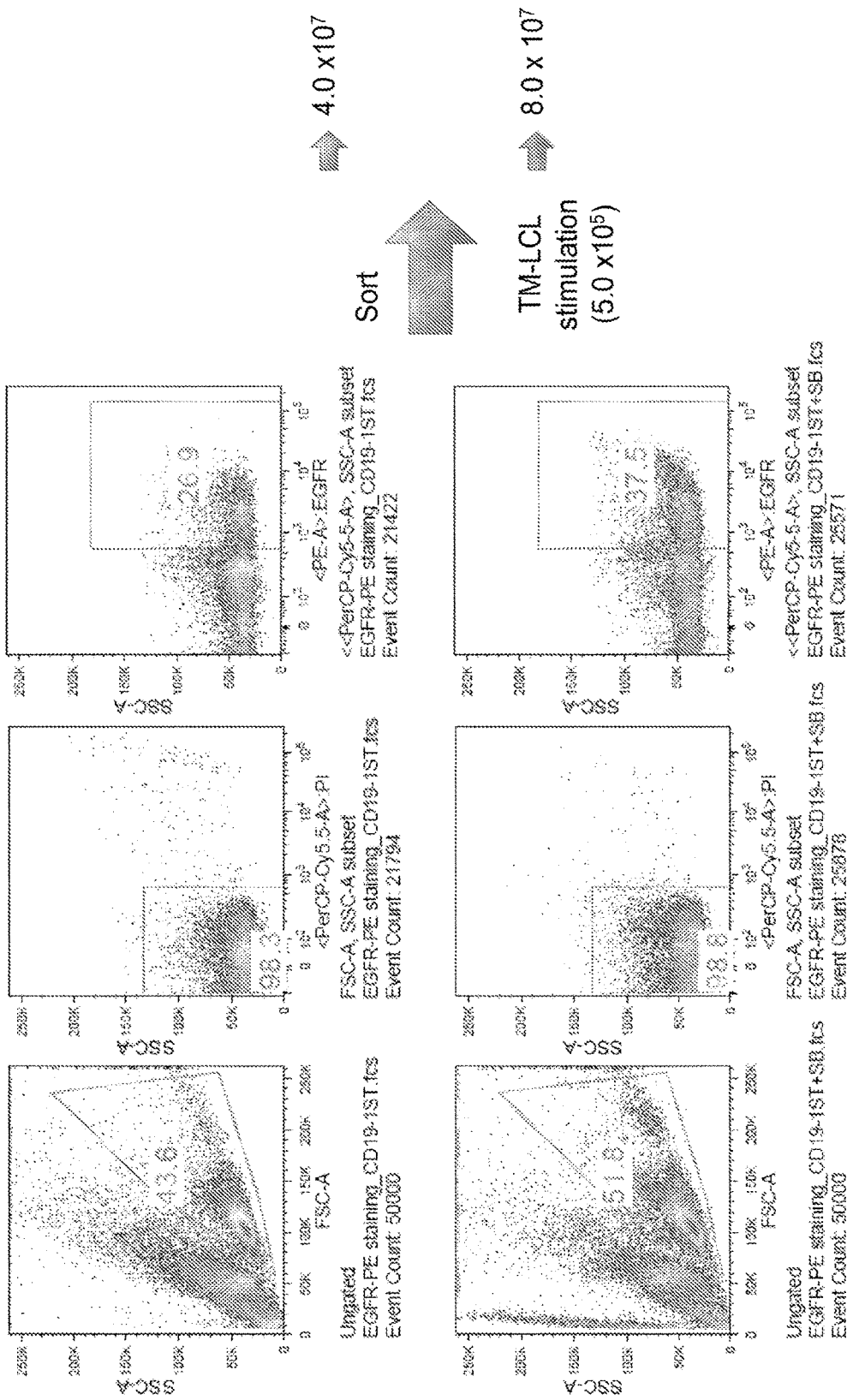

A total of about 5×10⁵ human CD8+ T cells were stimulated with anti CD3/anti CD28 beads. On day 2, the treated cells were transduced with a lentivirus containing a nucleic acid molecule encoding an anti CD19 T-ChARM/huEGFRt. On day 5, the anti CD3/anti CD28 beads were removed. At this point, the treated cells were split into two groups, one group was not treated any further and the other group was treated with Strep-Tactin® microbeads (about 0.5 μm to about 1.5 μm). On day 10, the cells from each group were harvested, stained with immunofluorescent anti-Strep Tag® antibody and analyzed by flow cytometry. The growth curve shows that, after the removal of the anti CD3/anti CD28 beads, the addition of Strep-Tactin® microbeads continued to promote significant T cell proliferation (FIG. 17A). The flow cytometry analysis shows that the cells that were proliferating were in fact T-ChARM expressing T cells since there was a significantly higher percentage of T-ChARM expressing T cells (as measured by huEGFRt staining) in the Strep-Tactin® microbead treated group (bottom panel) as compared to the control group (top panel) (FIG. 17B). The cells from each group were then further sorted using the huEGFRt marker, then $5.0 \times 10^5$ cells were expanded by stimulation with CD19+TM-LCL. The cells previously treated with the Strep-Tactin® microbeads underwent significant and quick proliferation to a level of about $8.0 \times 10^7$ cells in 7 days as compared to only $4.0 \times 10^6$ cells in the control group. This demonstrates that after Strep-Tactin® microbead stimulation through the tag sequence of the T-ChARM, subsequent re stimulation through the anti-CD19 scFv component of the T-ChARM is highly effective.

To determine whether anti CD3/anti CD28 bead stimulation was needed at all to expand T-ChARM expressing T cells, we examined whether T cells could be transduced to express the T-ChARM with cytokine stimulation alone and then selectively expanded by treatment with anti-Strep Tag® beads only. A total of about $5 \times 10^5$ human CD8+ T cells were cultured with 5 ng/mL IL 7 and 10 ng/mL IL 15 for 24 h and then transduced with the same titer of virus encoding two types of anti CD19 T-ChARM$^3$ (41BB or CD28 effector domains). The transduced cells were treated with anti-Strep Tag® antibody conjugated to protein G beads on day 2, and then on day 7 were harvested, stained with immunofluorescent anti-Strep Tag® II antibody, and analyzed by flow cytometry.

Figure 18A:
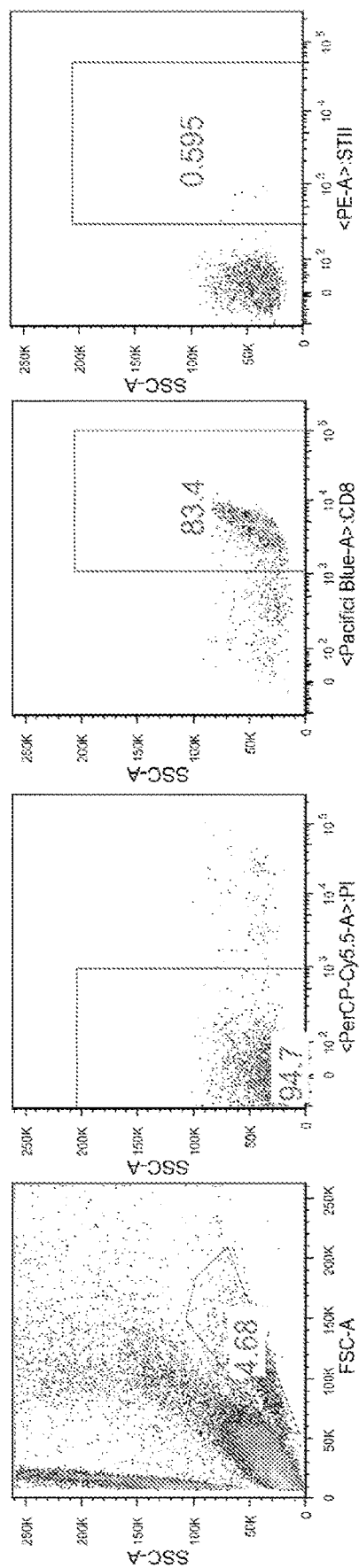
FIGS. 18A-18D show that T cells can be transduced with two types of T-ChARM (effector domain of 4-1BB/CD3ζ (A and B), or CD28/CD3ζ (C and D)) after culture in the presence of IL-7 and IL 15 without prior activation with anti-CD3/anti-CD28 beads. The transduced T-ChARM expressing T cells can be selectively expanded and enriched by adding anti-Strep Tag® II beads to the culture (B and D) (even in the absence anti CD3/anti CD28 bead stimulation), but are not expanded when anti-Strep Tag® II beads are not added to the culture (A and C).
Figure 18B:
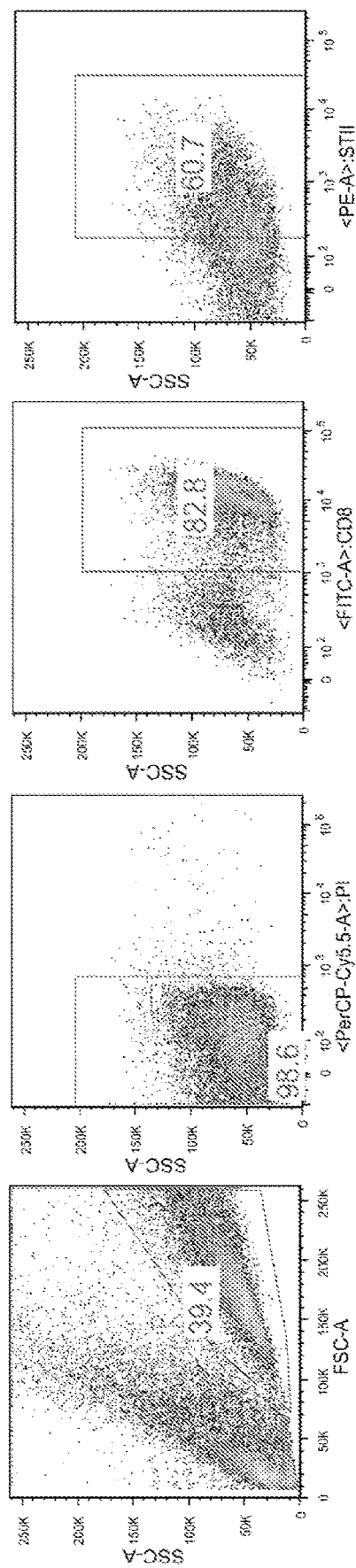
Figure 18C:
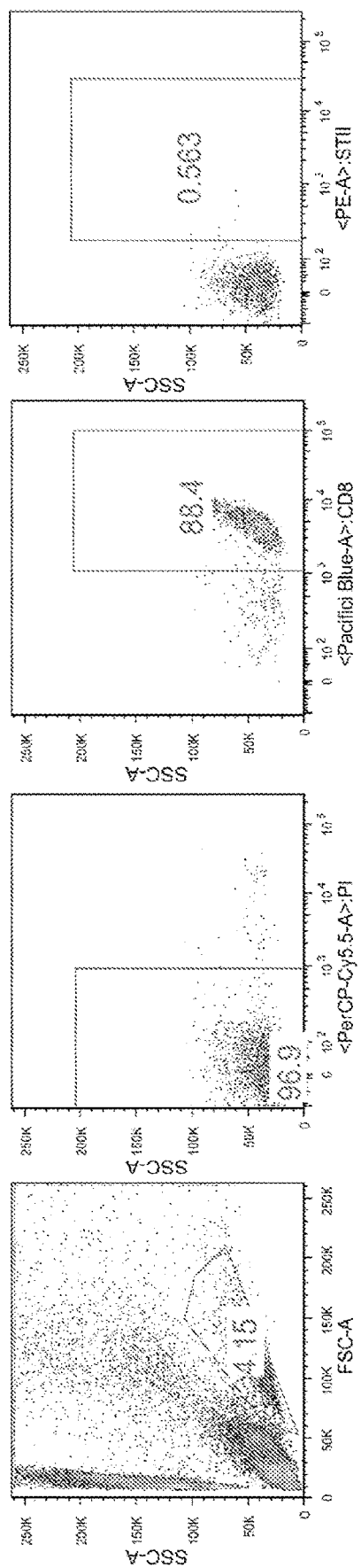
Figure 18D:
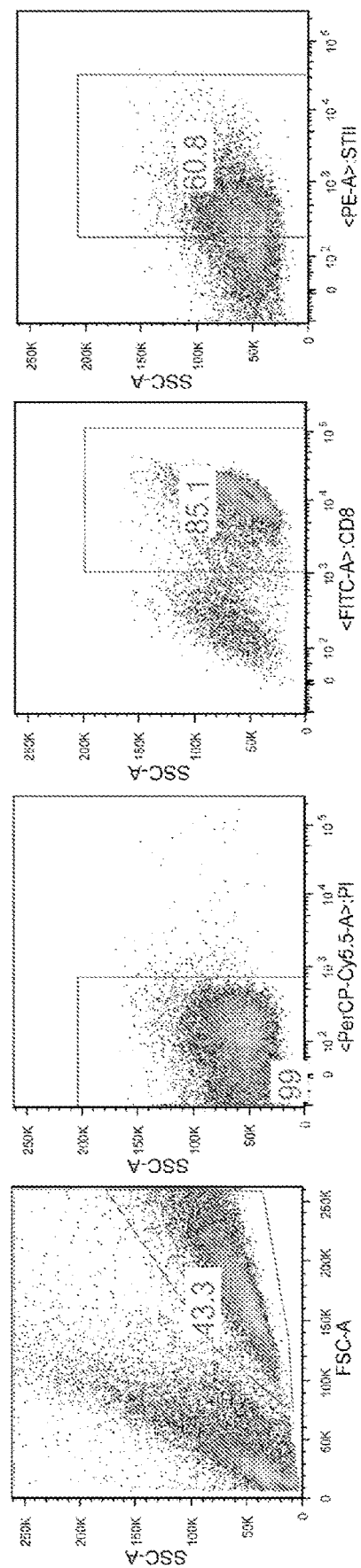

The data show that anti-Strep Tag® antibody conjugated to protein G beads promoted proliferation of T-ChARM expressing T cells to greater than 60% of the cells in the culture (FIGS. 18B and 18D) in the absence of anti CD3/anti CD28 bead stimulation. When transduced cells were not exposed to anti-Strep Tag® antibody beads, then less than 1% of the transduced cells would proliferate (FIGS. 18A and 18C).

Figure 30A:
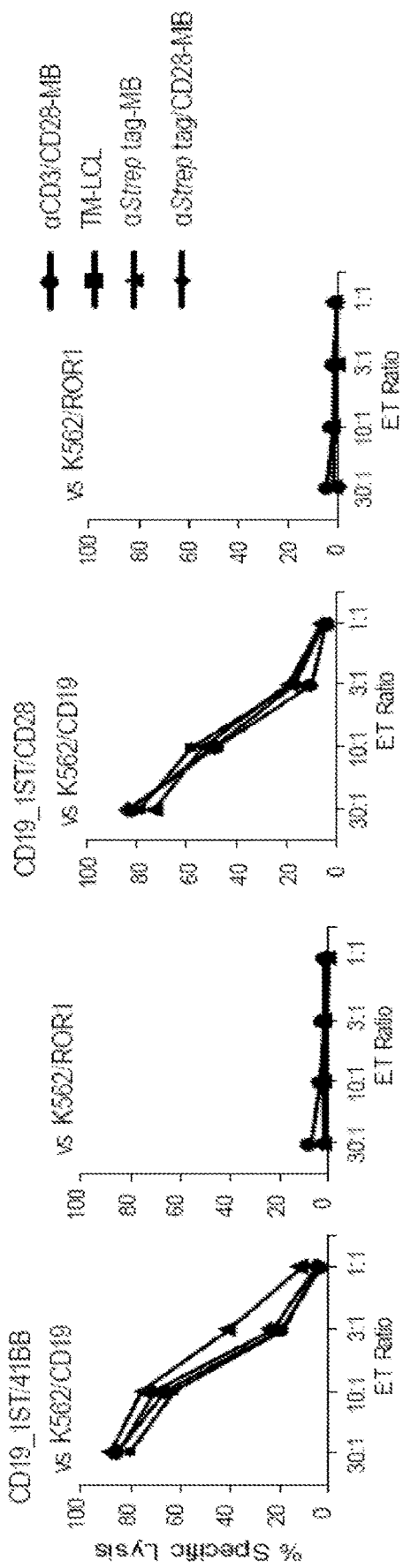
Figure 30B:
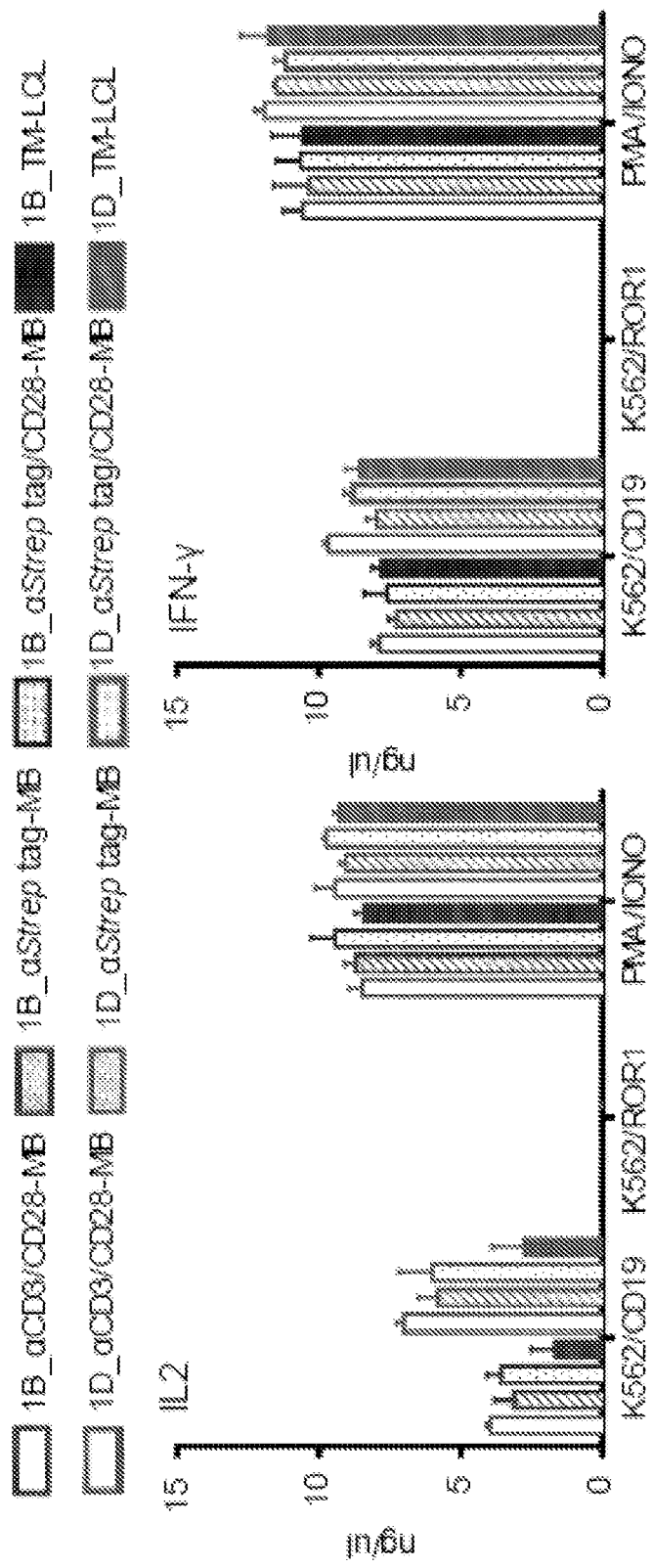
Figure 30C:
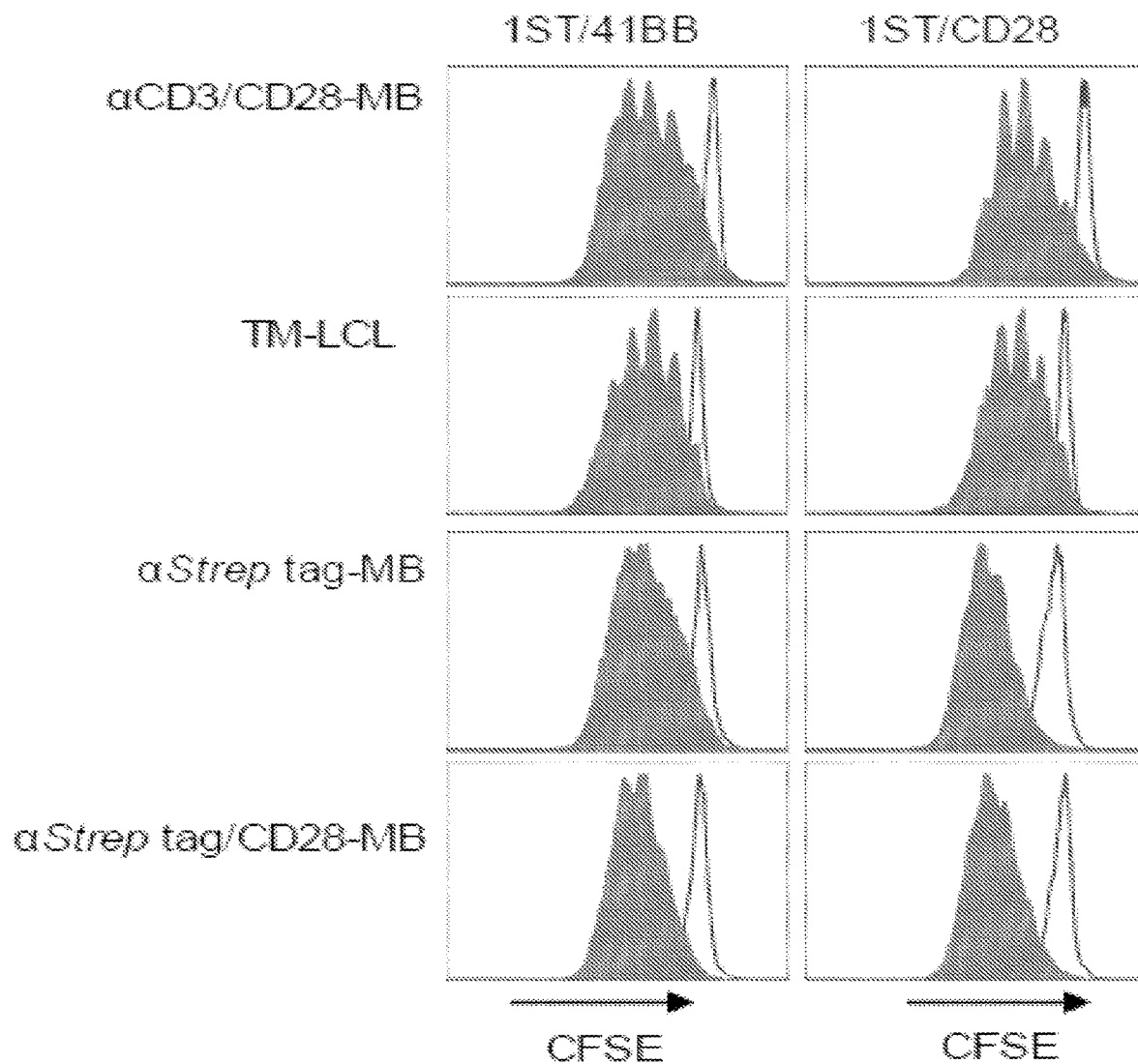
Figure 30D:
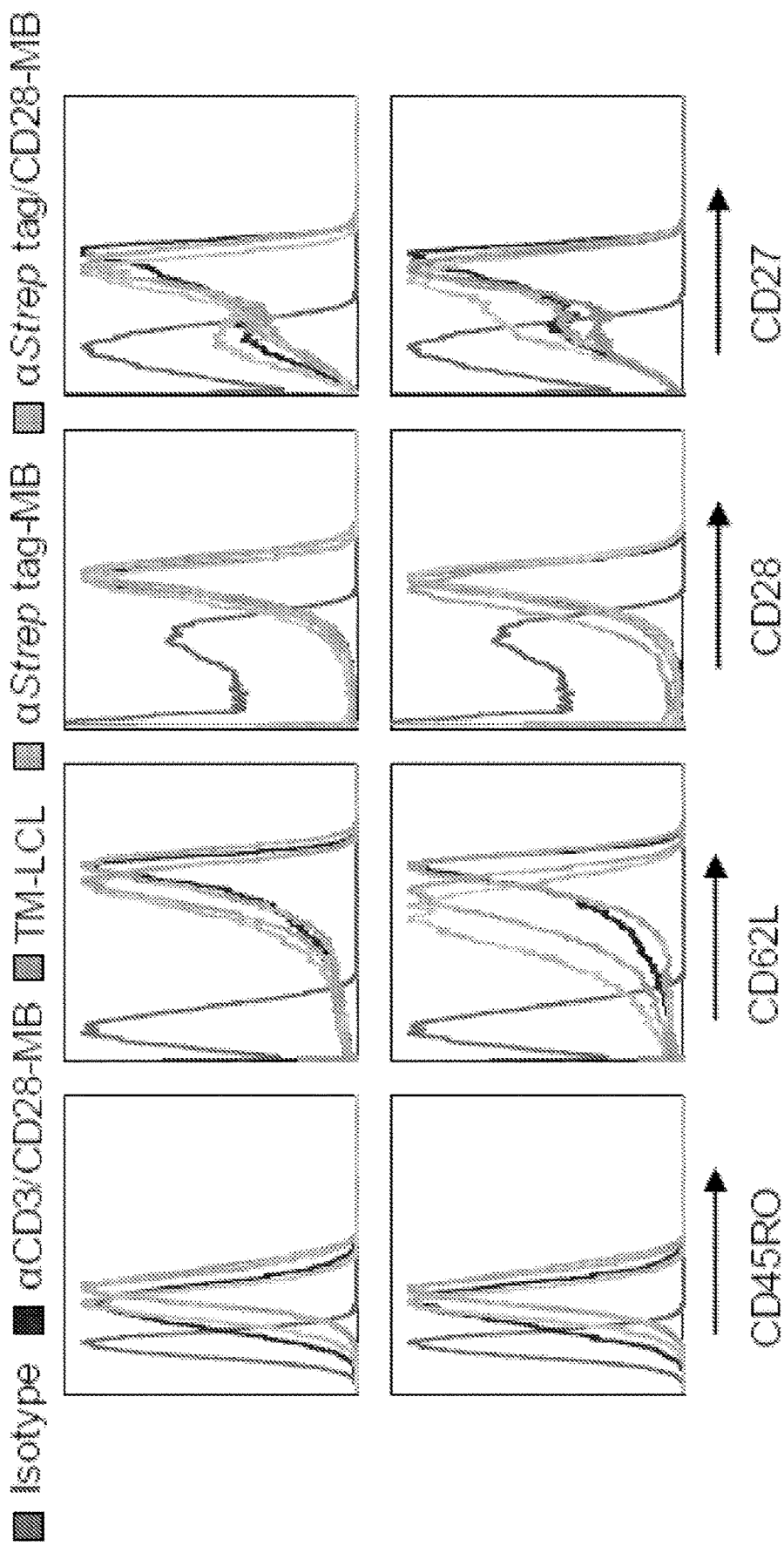
Figure 30E:
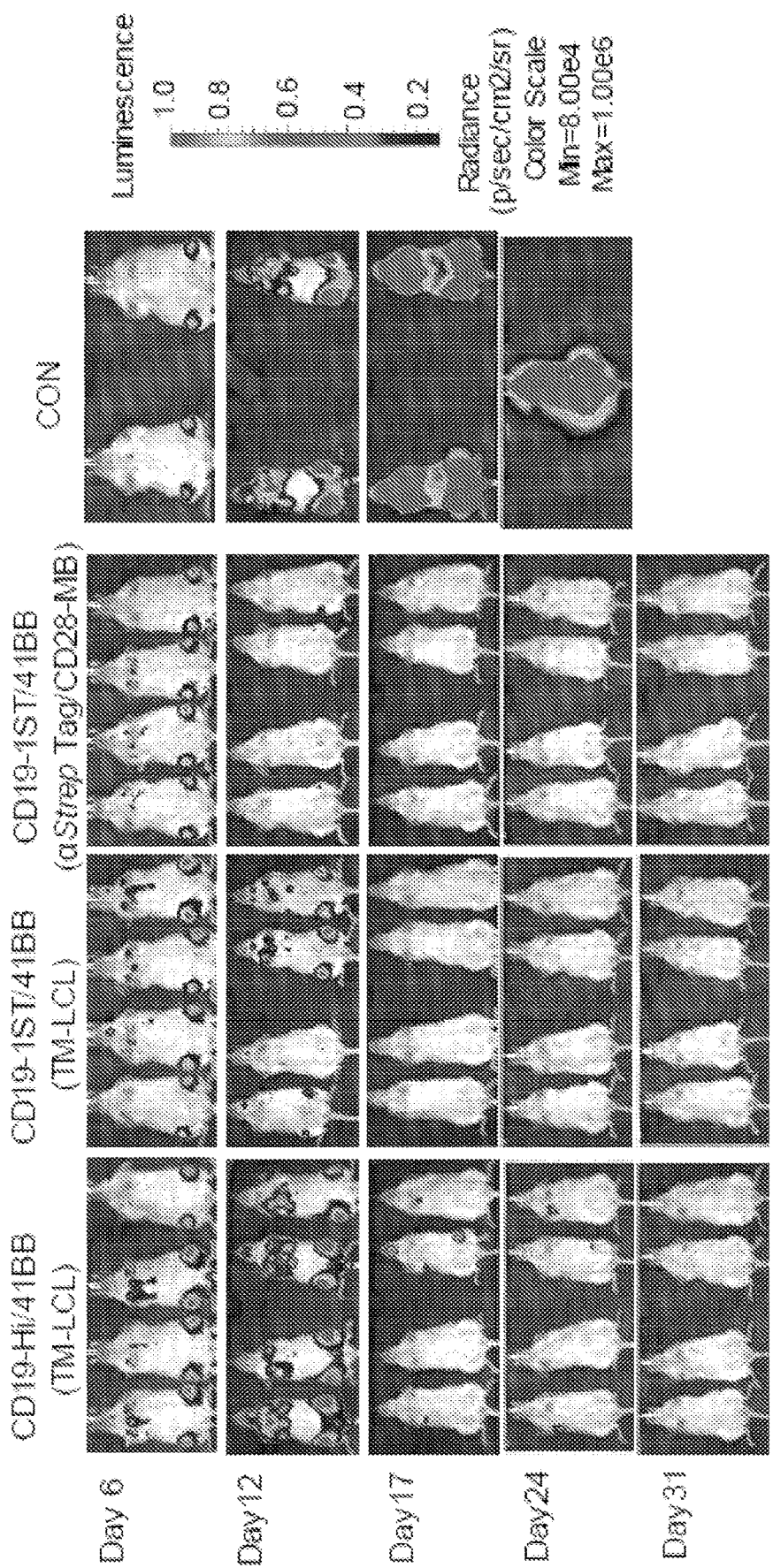
Figure 30F:
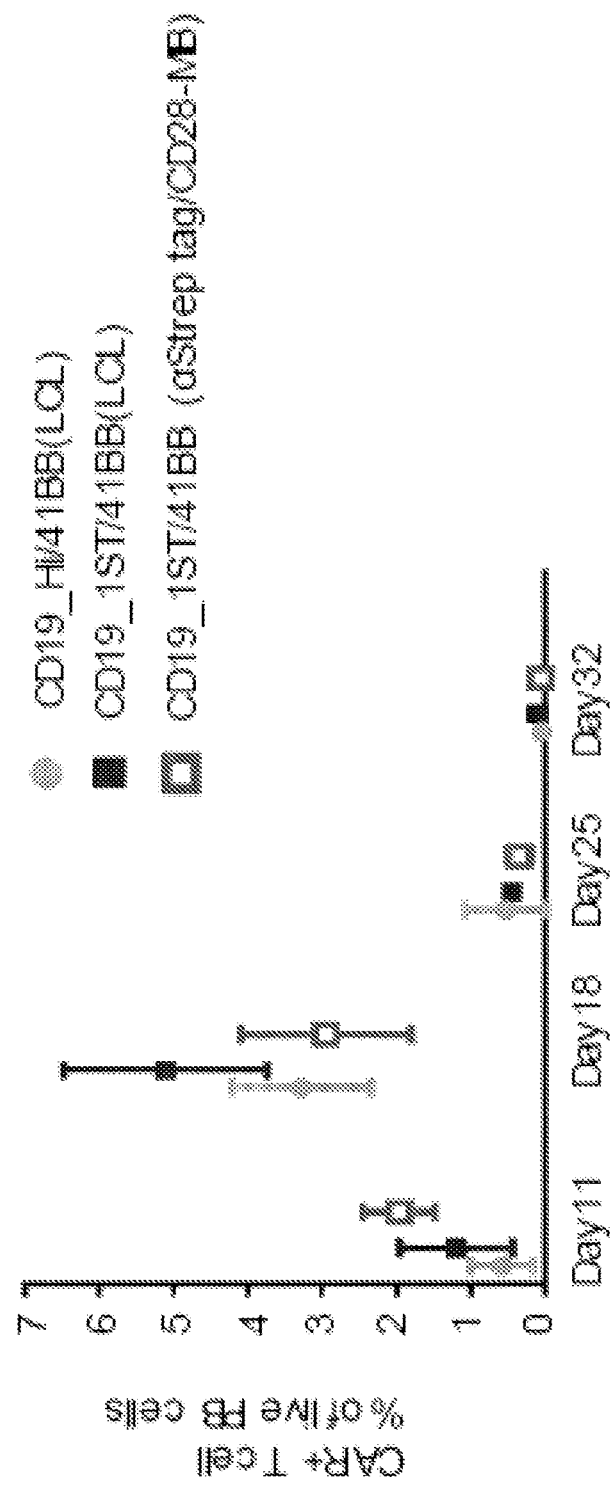

The functionality of ChARM T cells after expansion on anti-Strep Tag® alone or anti-Strep Tag®/anti-CD28 mAb coated microbeads was tested to ensure that stimulation through the ChARM would not have detrimental effects on tumor recognition in vitro or in vivo. Independent of the co-stimulatory domain in the design, ChARM T cells expanded on anti-Strep Tag® microbeads displayed potent cytolytic activity, efficiently release cytokines and retained extensive proliferation capacity among antigen stimulation compared the cells before expansion or after antigen-driven expansion (TM-LCL) (FIGS. 30A-30C). After selective expansion, the ChARM T cells had high viability (>90%), a large proportion retained expression of co-stimulatory receptors (CD27/CD28) and central memory T cell markers CD45RO and CD62L (FIG. 30D), were able to eliminated Raji tumors in NSG mice (FIG. 30E), and were able to persist as well as CAR T cells expanded by stimulation with CD19$^+$ B cells (FIG. 30F).

Example 15

Effect of Engagement of Tag Binding Reagents on Cytokine Release by T Cells Expressing T-ChARM$^1$ Anti-CD19 CAR (short) (expanded by TM-LCL stimulation) or T-ChARM$^1$ expressing T cells (expanded by TM-LCL or Strep-Tactin® microbead stimulation) were co cultured for 24 hours with Raji cells (FIG. 19C) or K562 cells expressing either CD19 (FIG. 19A) or ROR1 (negative control) (FIG. 19B). PMA/Ionomycin were used as the positive control (FIG. 19D). Supernatants were harvested and analyzed using a multiplex cytokine assay (Luminex®). The level of cytokine release by the anti-CD19 T-ChARM$^1$ expressing T cells cultured on Strep-Tactin® microbeads was higher (except for IFN-γ) than observed for T-ChARM$^1$ expressing T cells stimulated with TM-LCL cells (FIGS. 19A, C, and D). Regardless of conditions, the K562/ROR1 cell co-culture group (negative control) did not produce any detectable cytokines (FIG. 19B). Interestingly, there was a significantly higher level of IL2 production in the Strep-Tactin® bead induced cultures (more than a 10 fold increase) as compared to the TM LCL stimulated group.

Example 16

Proliferation Enhanced with Anti-Strep Tag® Antibody Combined with Anti-Cd27 or Anti-Cd28 Antibodies Purified anti-CD19 T-ChARM$^3$ expressing T cells ($5 \times 10^5$) were placed in CTL medium plus 50 U/ml IL2 at day 0, and then 2 μg G protein Magnetic Beads (NEB), anti-Strep Tag® II (0.5 μg)/anti-CD27 antibody (0.5 μg) conjugated G protein beads, or anti-Strep Tag® II (0.5 μg)/anti-CD28 antibody (0.5 μg) conjugated G protein beads, were added to the cell culture. The cells in culture medium only were used as a negative control. At day 5, the cells were examined under a microscope.

Figure 20:
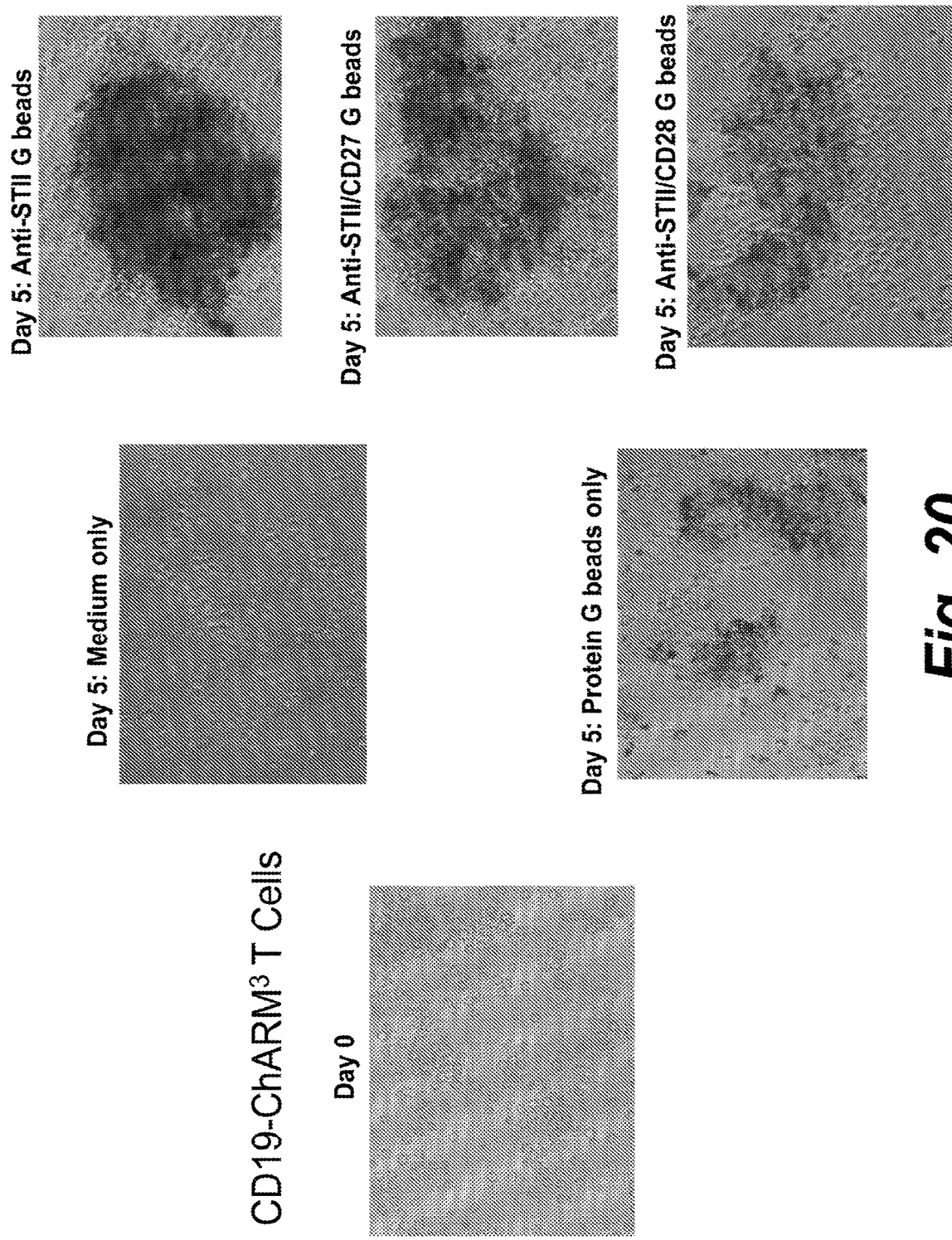
FIG. 20 shows that T-ChARM expressing T cells can be induced to form clusters and to proliferate with anti-Strep Tag® beads alone or with beads containing anti-Strep Tag® and anti-CD27 antibodies or containing anti-Strep Tag® and anti-CD28 antibodies.

FIG. 20 shows that anti-Strep Tag® II antibody conjugated protein G beads promoted expansion of T-ChARM expressing T cells, and that combining anti-Strep Tag® II with either anti-CD28 or anti-CD27 antibodies would promote T-ChARM expressing T cell expansion even more efficiently.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A single chain fusion protein comprising an extracellular component and an intracellular component connected by a hydrophobic portion,
wherein the extracellular component comprises a plurality of tag cassettes and a connector region comprising a hinge,
wherein the intracellular component comprises an effector domain, and
wherein the plurality of tag cassettes comprises two tag cassettes, wherein each of the two tag cassettes independently (a) comprises a peptide having a length of up to 20 amino acids that includes the amino acid sequence of SEQ ID NO.:1 or 2 and/or (b) is recognized by an antibody specific for the amino acid sequence of SEQ ID NO.:1 or 2.

2. The single chain fusion protein of claim 1, wherein the plurality of tag cassettes comprises three tag cassettes, wherein each of the three tag cassettes independently (a) comprises a peptide having a length of up to 20 amino acids that includes the amino acid sequence of SEQ ID NO.:1 or 2 and/or (b) is recognized by an antibody specific for the amino acid sequence of SEQ ID NO.:1 or 2.

3. The single chain fusion protein of claim 1, wherein each of the plurality of tag cassettes independently (a) comprises a peptide having a length of up to 20 amino acids that includes the amino acid sequence of SEQ ID NO.:1 or 2 and/or (b) is recognized by an antibody specific for the amino acid sequence of SEQ ID NO.:1 or 2.

4. The single chain fusion protein according to claim 1, wherein the connector region further comprises a linker module.

5. The single chain fusion protein according to claim 4, wherein the linker module is a $(Gly_xSer_y)_n$, wherein n is an integer from 1 to 10, and x and y are independently an integer from 0 to 10 provided that x and y are not both 0; or wherein the linker module comprises an immunoglobulin CH2CH3 or an immunoglobulin CH3.

6. The single chain fusion protein according to claim 1, wherein:
one or more of the plurality of tag cassettes are located within the connector region; or
one or more of the plurality of tag cassettes are located within the connector region, wherein each tag cassette is connected to one or two linker modules comprising a $(Gly_xSer_y)_n$, wherein n is an integer from 1 to 10, and x and y are independently an integer from 0 to 10 provided that x and y are not both 0; or
one or more of the plurality of tag cassettes are located within the connector region, wherein each tag cassette is connected to one or two linker modules having the amino acid sequence of Gly-Gly-Gly-Gly-Ser (SEQ ID NO:10), (Gly-Gly-Gly-Gly-Ser)$_2$ (SEQ ID NO:11), (Gly-Gly-Gly-Ser)$_2$-Gly-Gly-Ser (SEQ ID NO:12), or any combination thereof; or
the plurality of tag cassettes comprises five tag cassettes and one to five of the plurality of tag cassettes are located within the connector region; or
the plurality of tag cassettes comprises five tag cassettes and one to five of the plurality of tag cassettes are located within the connector region, wherein each tag cassette is connected to one or two linker modules comprising a $(Gly_xSer_y)_n$, wherein n is an integer from 1 to 10, and x and y are independently an integer from 0 to 10 provided that x and y are not both 0; or
the plurality of tag cassettes comprises five tag cassettes and the connector region comprises from one to five tag cassettes, wherein each tag cassette is connected to one or two linker modules having the amino acid sequence of Gly-Gly-Gly-Gly-Ser (SEQ ID NO:10), (Gly-Gly-Gly-Gly-Ser)$_2$ (SEQ ID NO:11), (Gly-Gly-Gly-Ser)$_2$-Gly-Gly-Ser (SEQ ID NO:12), or any combination thereof.

7. The single chain fusion protein according to claim 1, wherein the single chain fusion protein further comprises a His tag, a tag of SEQ ID NO.:3, an Xpress tag, a tag of SEQ ID NO.:5, a Calmodulin tag, a Polyglutamate tag, an HA tag, a Myc tag, a Nus tag, an S tag, an SBP tag, a tag of SEQ ID NO.:9 or 32, a V5 tag, a CBP, a GST, an MBP, a GFP, a Thioredoxin tag, or any combination thereof.

8. The single chain fusion protein according to claim 1, wherein one or more of the plurality of tag cassettes consists of the amino acid sequence of Trp-Ser-His-Pro-Gln-Phe-Glu-Lys (SEQ ID NO.:1) or Trp-Arg-His-Pro-Gln-Phe-Gly-Gly (SEQ ID NO.:2).

9. The single chain fusion protein according to claim 1, wherein the hydrophobic portion is a transmembrane domain and the transmembrane domain comprises a CD4, CD8, CD28 or CD27 transmembrane domain.

10. The single chain fusion protein according to claim 1, wherein the effector domain or an effector portion thereof is from one or more of the group consisting of a 4-1BB (CD137), a CD3ε, a CD3δ, a CD3ζ, a CD25, a CD27, a CD28, a CD79A, a CD79B, a CARD11, a DAP10, a FcRα, a FcRβ, a FcRγ, a Fyn, a HVEM, an ICOS, a Lck, a LAG3, a LAT, a LRP, a NKG2D, a NOTCH1, a NOTCH2, a NOTCH3, a NOTCH4, an OX40 (CD134), a ROR2, a Ryk, a SLAMF1, a Slp76, a pTα, a TCRα, a TCRβ, a TRIM, a Zap70, and a PTCH2.

11. The single chain fusion protein according to claim 1, comprising an effector domain or an effector portion thereof of (a) a CD3ζ and (b) one or more of 4-1BB (CD137), CD27, CD28, and OX40 (CD134).

12. The single chain fusion protein according to claim 1, wherein the fusion protein comprises, from amino-terminus to carboxy-terminus:
(a) an extracellular binding domain, the first tag cassette, a first connector region, the second tag cassette, a second connector region comprising a hinge, the hydrophobic portion, and the intracellular component comprising an effector domain; or
(b) an extracellular binding domain, the first tag cassette, a first connector region, the second tag cassette, a second connector region, a third tag cassette, a third connector region comprising a hinge, the hydrophobic portion, and the intracellular component comprising an effector domain; or
(c) the first tag cassette, an extracellular binding domain, the second tag cassette, the connector region comprising a hinge, a hydrophobic portion, and the intracellular component comprising an effector domain; or
(d) an extracellular binding domain, two to five of the plurality of tag cassettes, the connector region comprising a hinge, a hydrophobic portion, and the intracellular component comprising an effector domain; or
(e) an extracellular scFv or scTCR binding domain comprising a variable region linker disposed between the variable regions and containing the first tag cassette, a first connector region, the second tag cassette, the second connector region comprising a hinge, a hydrophobic portion, and the intracellular component comprising an effector domain; or (f) an extracellular scFv or scTCR binding domain, the first tag cassette, a first connector region, the second tag cassette, the second connector region comprising an IgG hinge, a transmembrane domain, and the intracellular component comprising an effector domain, wherein the effector domain (A) comprises, or comprises an effector domain of, each of 4 1BB and CD3ζ, (B) comprises, or comprises an effector domain of, each of CD27 and CD3ζ, (C) comprises, or comprises an effector domain of, each of CD28 and CD3ζ, (D) comprises or comprises an effector domain of each of OX40 and CD3ζ, (E) comprises, or comprises an effector domain of, each of CD28, 4-1BB and CD3ζ, (F) comprises, or comprises an effector domain of, each of OX40, 4-1BB and CD3ζ, or (G) comprises, or comprises an effector domain of, each of CD28, OX40 and CD3ζ; or (g) an extracellular binding domain comprising a receptor ectodomain, the first tag cassette, a first connector region, the second tag cassette, the connector region comprising a hinge, a hydrophobic portion, and the intracellular component comprising an effector domain, wherein the effector domain comprises, or comprises an effector domain of a 4-1BB, CD27, CD28, or OX40.

13. The single chain fusion protein according to claim 1, wherein:
the extracellular component comprises from two to five of the plurality of tag cassettes; and/or
the fusion protein further comprises: (i) one or more linker modules comprising a $(Gly_zSer_y)_m$, wherein m is an integer from 1 to 10, and z and y are independently an integer from 0 to 10 provided that z and y are not both 0; (ii) a $(Gly_xSer)_n$ linker module disposed between an extracellular binding domain and one or more of the plurality of tag cassettes, wherein x is an integer from 2 to 4 and n is an integer from 1 to 3; (iii) an extracellular $(Gly_xSer)_n$ linker module disposed between one or more of the plurality of tag cassettes and the intracellular component comprising an effector domain, wherein x is an integer from 2 to 4 and n is an integer from 1 to 3; and/or (iv) two extracellular $(Gly_xSer)_n$ linker modules, wherein x is an integer from 2 to 4 and n is an integer from 1 to 3, and wherein the first linker module is amino-terminal to one or more of the plurality of tag cassettes and the second linker module is carboxy-terminal to one or more of the plurality of tag cassettes; and/or
the extracellular component comprises the two tag cassettes and the fusion protein further comprises two extracellular $(Gly_xSer)_n$ linker modules, wherein x is an integer from 2 to 4 and n is an integer from 1 to 3, and wherein a first of the two tag cassettes is disposed between an extracellular binding domain and the first linker module, a second of the two tag cassettes is disposed between the first and second linker modules, and the second linker module is disposed between the second tag cassette and the effector domain, optionally wherein the fusion protein further comprises a third tag cassette and a third extracellular $(Gly_xSer)_n$ linker module, wherein x is an integer from 2 to 4 and n is an integer from 1 to 3, and wherein the third tag cassette is disposed between the second linker module and the third linker module, and the third linker module is disposed between the third tag cassette and the effector domain.

14. The single chain fusion protein of claim 1, wherein the extracellular component further comprises a binding domain that specifically binds a target.

15. The single chain fusion protein of claim 1, wherein the fusion protein is non-covalently associated with a binding domain that specifically binds a target.

16. The single chain fusion protein of claim 15, wherein:
the non-covalently associated binding domain is associated with one or more of the plurality of tag cassettes of the fusion protein; and/or
the non-covalently associated binding domain is multi-specific, optionally bi-specific, with at least a first binding end and a second binding end, wherein (i) the first binding end is specific for one or more of the plurality of tag cassettes of the fusion protein and the second binding end is specific for the target, which is a target other than the plurality of tag cassettes; and/or (ii) the first and the second binding ends are specific for one or more of the plurality of tag cassettes; and/or
the non-covalently associated binding domain is multi-specific, with a first end that binds to one or more of the plurality of tag cassettes and one or more additional ends that are specific for one or more targets other than the plurality of tag cassettes.

17. The single chain fusion protein of claim 14, wherein the binding domain is a scFv, a scTCR, a receptor ectodomain, or a ligand of a receptor.

18. The single chain fusion protein of claim 14, wherein the target comprises CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A, mesothelin, NY-ESO-1, PSMA, RANK, ROR1, TNFRSF4, CD40, CD137, TWEAK-R, HLA, tumor or pathogen associated peptide bound to HLA, hTERT peptide bound to HLA, tyrosinase peptide bound to HLA, WT-1 peptide bound to HLA, LTβR, LIFRβ, LRP5, MUC1, OSMRβ, TCRα, TCRβ, CD19, CD20, CD22, CD25, CD28, CD30, CD33, CD52, CD56, CD80, CD81, CD86, CD123, CD171, CD276, B7H4, TLR7, TLR9, PTCH1, WT-1, Robo1, α-fetoprotein (AFP), Frizzled, OX40, or CD79b.

19. The single chain fusion protein of claim 14, wherein the binding domain comprises:
(a) one or more of the plurality of tag cassettes; or
(b) a scFv or scTCR comprising a variable region linker, wherein the variable region comprises one or more of the plurality of tag cassettes; or
(c) one or more of the plurality of tag cassettes, wherein the one or more tag cassettes is located amino-terminal to the binding domain, carboxy-terminal to the binding domain, or both.

20. A nucleic acid molecule encoding a single chain fusion protein, the encoded single chain fusion protein comprising an extracellular component and an intracellular component connected by a hydrophobic portion,
wherein the extracellular component comprises a plurality of tag cassettes and a connector region comprising a hinge,
wherein the intracellular component comprises an effector domain, and
wherein the plurality of tag cassettes comprises two tag cassettes, wherein each of the two tag cassettes independently (a) comprises a peptide having a length of up to 20 amino acids that includes the amino acid sequence of SEQ ID NO.:1 or 2 and/or (b) is recognized by an antibody specific for the amino acid sequence of SEQ ID NO.:1 or 2.

21. A vector comprising a nucleic acid molecule according to claim 20.

22. The vector according to claim 21, wherein the vector is a viral vector.

23. The vector according to claim 22, wherein the viral vector is a retroviral vector or lentiviral vector.

24. A host cell, comprising the nucleic acid molecule according to claim 20.

25. The host cell according to claim 24, wherein the host cell is a T cell.

26. A method for activating a cell and/or promoting cell proliferation, comprising contacting a cell expressing the single chain fusion protein of claim 1 with a cognate binding partner specific for one or more of the plurality of tag cassettes, thereby activating and/or promoting proliferation of the cell expressing the single chain fusion protein.

27. The method of claim 26 further comprising contacting the cell with a growth factor cytokine for a time sufficient to allow cell growth.

28. A method for identifying a cell or a population of cells, the method comprising:

contacting a sample, or a subject, comprising a cell or a population of cells expressing the single chain fusion protein of claim 1 with a binding domain specific for one or more of the plurality of tag cassettes, wherein the binding domain specific for one or more of the plurality of tag cassettes comprises a detectable moiety, and detecting the presence of the cell or the population of cells expressing the single chain fusion protein in the sample or the subject.

29. A method for enriching for or isolating a cell or a population thereof, the method comprising contacting a sample comprising a cell expressing the single chain fusion protein of claim 1 with a cognate binding partner specific for one or more of the plurality of tag cassettes, and enriching for or isolating a cell bound by the cognate binding partner from other cells not bound by the cognate binding partner in the sample.

30. A method for depleting cells, comprising contacting a cell expressing the single chain fusion protein of claim 1 with a cognate binding partner specific for one or more of the plurality of tag cassettes, wherein binding between the cognate binding partner and the one or more of the plurality of tag cassettes leads to cell death and/or depletion of the cell expressing the single chain fusion protein.

31. A method of treating a disease in a subject, comprising administering to a subject a host cell expressing the single chain fusion protein according to claim 1.

32. The method of claim 31, wherein the extracellular component further comprises a binding domain that specifically binds a target, wherein the target is associated with the disease.

33. The method of claim 31, wherein the fusion protein is non-covalently associated with a binding domain that specifically binds a target, wherein the target is associated with the disease.

34. A chimeric antigen receptor molecule comprising a fusion protein having a plurality of extracellular tag cassettes disposed between and connecting an extracellular binding domain which specifically binds to an antigen and an intracellular component comprising an effector domain, wherein the plurality of extracellular tag cassettes comprises two tag cassettes, wherein each of the two tag cassettes independently (a) comprises a peptide having a length of up to 20 amino acids that includes the amino acid sequence of SEQ ID NO.:1 or 2 and/or (b) is recognized by an antibody specific for the amino acid sequence of SEQ ID NO.:1 or 2.

* * * * *